United States Patent
Witt et al.

(10) Patent No.: US 11,912,687 B2
(45) Date of Patent: Feb. 27, 2024

(54) 3,4,5-TRISUBSTITUTED-1,2,4-TRIAZOLES AND 3,4,5-TRISUBSTITUTED-3-THIO-1,2,4-TRIAZOLES AND USES THEREOF

(71) Applicant: Board of Trustees of the Southern Illinois University, Edwardsville, IL (US)

(72) Inventors: Kenneth A. Witt, Edwardsville, IL (US); Albert M. Crider, Maryville, IL (US); William Neumann, St. Louis, MO (US); Audrey Hospital, Robbinsville, NJ (US); Karin Sandoval, Edwardsville, IL (US); Maria Kontoyianni, Glen Carbon, IL (US)

(73) Assignee: Board of Trustees of the Southern Illinois University, Edwardsville, IL (US)

( * ) Notice: Subject to any disclaimer, the term of this patent is extended or adjusted under 35 U.S.C. 154(b) by 159 days.

(21) Appl. No.: 17/466,480

(22) Filed: Sep. 3, 2021

(65) Prior Publication Data

US 2022/0002274 A1 Jan. 6, 2022

Related U.S. Application Data

(63) Continuation-in-part of application No. 16/613,086, filed as application No. PCT/US2018/032368 on May 11, 2018, now Pat. No. 11,136,312.

(60) Provisional application No. 62/505,384, filed on May 12, 2017.

(51) Int. Cl.
*C07D 401/14* (2006.01)
*C07D 403/06* (2006.01)
*C07D 403/14* (2006.01)

(52) U.S. Cl.
CPC ......... *C07D 403/14* (2013.01); *C07D 401/14* (2013.01); *C07D 403/06* (2013.01)

(58) Field of Classification Search
CPC ... C07D 401/14; C07D 403/06; C07D 403/14
See application file for complete search history.

(56) References Cited

U.S. PATENT DOCUMENTS

| | | | |
|---|---|---|---|
| 5,885,988 A | 3/1999 | Neumann et al. |
| 7,019,144 B2 | 3/2006 | Cho et al. |
| 8,778,974 B2 | 7/2014 | MacDonald et al. |
| 2005/0154039 A1 | 7/2005 | Glacera Contour et al. |
| 2012/0283298 A1 | 11/2012 | Crider et al. |
| 2015/0232478 A1 | 8/2015 | Ishida et al. |

FOREIGN PATENT DOCUMENTS

| | | |
|---|---|---|
| WO | 1999052875 | 10/1999 |
| WO | 2005033124 A1 | 4/2005 |
| WO | 2007021941 A2 | 2/2007 |
| WO | 2011047165 A1 | 4/2011 |
| WO | 2014184275 A1 | 11/2014 |
| WO | 2016075240 A1 | 5/2016 |

OTHER PUBLICATIONS

Chemical Abstracts Registry No. 1997819-71-2, indexed in the Registry file on STN CAS Online Sep. 22, 2016. (Year: 2016).*
Chemical Abstracts Registry No. 2008658-00-0, indexed in the Registry file on STN CAS Online Oct. 9, 2016. (Year: 2016).*
Liu S et al., Nonpeptide Somatostatin Agonists with sst4 Selectivity: Synthesis and Structure-Activity Relationships of Thioureas, Journal of Medicinal Chemistry, 1998, pp. 4693-4705, vol. 41, No. 24.
Liu S et al., 2-Pyridylthioureas: Novel Nonpeptide Somatostatin Agonists with SST4 Selectivity, Current Pharmaceutical Design, 1999, pp. 255-263, vol. 5, No. 4.
Liu Z et al., A Structure-Based Approach to Understanding Somatostatin Receptor-4 Agonism (sst4), Journal of Chemical Information and Modeling, 2012, pp. 171-186, vol. 52, No. 1.
Mancuso C et al., Pharmacologists and Alzheimer Disease Therapy: To Boldly Go Where No. Scientist Has Gone Before, Expert Opinion on Investigational Drugs, 2011, pp. 1243-1261, vol. 20, No. 9.
Moller LN et al., Somatostatin Receptors, Biochimica et Biophysica Acta, 2003, pp. 1-84, vol. 1616, No. 1.
Moulin A et al., Toward Potent Ghrelin Receptor Ligands Based on Trisubstituted 1,2,4-Triazole Structure. 2. Synthesis and Pharmacological in Vitro and in Vivo Evaluations, Journal of Medicinal Chemistry, 2007, pp. 5790-5806, vol. 50, No. 23.
Moulin A et al., Trisubstituted 1,2,4-Triazoles as Ligands for the Ghrelin Receptor: On the Significance of the Orientation and Substitution at Position 3, Bioorganic & Medicinal Chemistry Letters, 2008, pp. 164-168, vol. 18, No. 1.
Moulin A et al., Synthesis of 3,4,5-Trisubstituted-1,2,4-Triazoles, Chemical Reviews, 2010, pp. 1809-1827, vol. 110, No. 4.

(Continued)

*Primary Examiner* — Laura L Stockton
(74) *Attorney, Agent, or Firm* — STINSON LLP

(57) ABSTRACT

The present disclosure describes novel compounds that are somatostatin receptor type 4 agonists. The present disclosure is also directed to a compound of Formula (II):

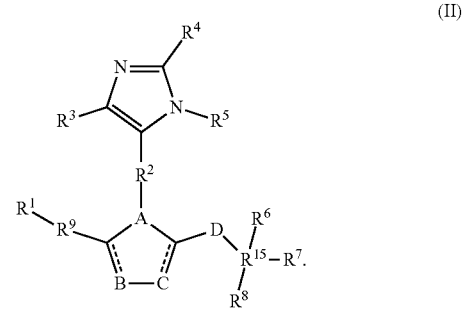

20 Claims, No Drawings

(56) References Cited

OTHER PUBLICATIONS

Nalivaeva NN et al., The Alzheimer's Amyloid-Degrading Peptidase, Neprilysin: Can We Control It?, International Journal of Alzheimer's Disease, 2012 article 383796, vol. 2012.
Nalivaeva NN et al., Are Amyloid-Degrading Enzymes Viable Therapeutic Targets in Alzheimer's Disease?, Journal of Neurochemistry, 2012, pp. 167-185, vol. 120, No. s1 (Supplement 1).
Neelamkavil S et al., Replacement of Phe6, Phe7, and Phe11 of D-Trp8-Somatostatin-14 with L-Pyrazinylalanine. Predicted and Observed Effects on Binding Affinities at hSST2 and hSST4. An Unexpected Effect of the Chirality of Trp8 on NMR Spectra in Methanol, Journal of Medicinal Chemistry, 2005, pp. 4025-4030, vol. 48, No. 12.
Nikiforovich GV et al., Molecular Modeling Suggests Conformational Scaffolds Specifically Targeting Five Subtypes of Somatostatin Receptors, Chemical Biology & Drug Design, 2007, pp. 163-169, vol. 69, No. 3.
Papageorgiou C et al., Design, Synthesis, and Binding Affinity of a Nonpeptide Mimic of Somatostatin, Bioorganic & Medicinal Chemistry Letters, 1992, pp. 135-140, vol. 2, No. 2.
Papageorgiou C and Borer X, A Non-Peptide Ligand for the Somatostatin Receptor Having a Benzodiazepinone Structure, Bioorganic & Medicinal Chemistry Letters, 1996, pp. 267-272, vol. 6, No. 3.
Qiu C et al., Somatostatin Receptor Subtype 4 Couples to the M-Current to Regulate Seizures, The Journal of Neuroscience, 2008, pp. 3567-3576, vol. 28, No. 14.
Rohrer SP et al., Rapid Identification of Subtype-Selective Agonists of the Somatostatin Receptor through Combinatorial Chemistry, Science, 1998, pp. 737-740, vol. 282, No. 5389.
Rohrer SP and Schaeffer JM, Identification and Characterization of Subtype Selective Somatostatin Receptor Agonists, Journal of Physiology, Paris, 2000, pp. 211-215, vol. 94, No. 3-4.
Saito T et al., Somatostatin Regulates Brain Amyloid Beta Peptide Abeta42 through Modulation of Proteolytic Degradation, Nature Medicine, 2005, pp. 434-439, vol. 11, No. 4.
Sandoval KE et al., Chronic Peripheral Administration of Somatostatin Receptor Subtype-4 Agonist NNC 26-9100 Enhances Learning and Memory in SAMP8 Mice, European Journal of Pharmacology, 2011, pp. 53-59, vol. 654, No. 1.
Sandoval KE et al., Somatostatin Receptor Subtype-4 Agonist NNC 26-9100 Decreases Extracellular and Intracellular AB1-42 Trimers, European Journal of Pharmacology, 2012, pp. 116-124, vol. 683, No. 1-3.
Sandoval KE et al., Somatostatin Receptor Subtype-4 Agonist NNC 26-9100 Mitigates the Effect of Soluble AB(42) Oligomers Via a Metalloproteinase-Dependent Mechanism, Brain Research, 2013, pp. 145-156, vol. 1520.
Sandoval KE et al., Somatostatin Receptor-4 Agonists as Candidates for Treatment of Alzheimer's Disease, in Frontiers in Drug Design & Discovery, 2014, pp. 566-597, vol. 6, Bentham Science.
Scheich B et al., Somatostatin Receptor Subtype 4 Activation Is Involved in Anxiety and Depression-Like Behavior in Mouse Models, Neuropharmacology, 2016, pp. 204-215, vol. 101.
Schreff M et al., Distribution, Targeting, and Internalization of the sst4 Somatostatin Receptor in Rat Brain, The Journal of Neuroscience, 2000, pp. 3785-3797, vol. 20, No. 10.
Schuelert N et al., The Somatostatin Receptor 4 Agonist J-2156 Reduces Mechanosensitivity of Peripheral Nerve Afferents and Spinal Neurons in an Inflammatory Pain Model, European Journal of Pharmacology, 2015, pp. 274-281, vol. 746.
Selkoe DJ, Resolving Controversies on the Path to Alzheimer's Therapeutics, Nature Medicine, 2011, pp. 1060-1065, vol. 17, No. 9.
Serrano-Pozo A et al., Neuropathological Alterations in Alzheimer Disease, Cold Spring Harbor Perspectives in Medicine, 2011, article a006189, vol. 1, No. 1.
Somvanshi RK and Kumar U, Delta-Opioid Receptor and Somatostatin Receptor-4 Heterodimerization: Possible Implications in Modulation of Pain Associated Signaling, PLoS One, 2014, article e85193, vol. 9, No. 1.
Stevens GJ et al., In Vitro Metabolism of N-(5-Chloro-2-Methylphenyl)-N'-(2-Methylpropyl)Thiourea: Species Comparison and Identification of a Novel Thiocarbamide-Glutathione Adduct, Chemical Research in Toxicology, 1997, pp. 733-741, vol. 10, No. 7.
Szokoloczi O et al., TT232, a Novel Signal Transduction Inhibitory Compound in the Therapy of Cancer and Inflammatory Diseases, Journal of Receptor and Signal Transduction Research, 2005, pp. 217-235, vol. 25, No. 4-6.
Szolcsanyi J et al., Analgesic Effect of TT-232, a Heptapeptide Somatostatin Analogue, in Acute Pain Models of the Rat and the Mouse and in Streptozotocin-Induced Diabetic Mechanical Allodynia, European Journal of Pharmacology, 2004, pp. 103-109, vol. 498, No. 1-3.
Szolcsanyi J et al., Inhibition of the Function of TRPV1-Expressing Nociceptive Sensory Neurons by Somatostatin 4 Receptor Agonism: Mechanism and Therapeutical Implications, Current Topics in Medicinal Chemistry, 2011, pp. 2253-2263, vol. 11, No. 17.
Tejada M et al., Antitumor Activity of the Somatostatin Structural Derivative (TT-232), Against Mouse and Human Melanoma Tumor Models, Anticancer Research, 2007, pp. 4015-4019, vol. 27, No. 6B.
Verdonk ML et al., Improved Protein-Ligand Docking Using GOLD, Proteins, 2003, pp. 609-623, vol. 52, No. 4.
Verdonk ML et al., Modeling Water Molecules in Protein-Ligand Docking Using GOLD, Journal of Medicinal Chemistry, 2005, pp. 6504-6515, vol. 48, No. 20.
Viollet C et al., Somatostatinergic Systems in Brain: Networks and Functions, Molecular and Cellular Endocrinology, 2008, pp. 75-87, vol. 286, No. 1-2.
Wang D-S et al., Decreased Neprilysin Immunoreactivity in Alzheimer Disease, but Not in Pathological Aging, Journal of Neuropathology and Experimental Neurology, 2005, pp. 378-385, vol. 64, No. 5.
Wang X et al., Synthesis of 2-Thiohydantoins as Somatostatin Subtype 4 Receptor Ligands, Letters in Drug Design & Discovery, 2012, pp. 655-662, vol. 9, No. 7.
Yamamoto J et al., Regulation of Somatostatin Receptor 4-Mediated Cytostatic Effects by CD26 in Malignant Pleural Mesothelioma, British Journal of Cancer, 2014, pp. 2232-2245, vol. 110, No. 9.
Yang L et al., Spiro[1H-Indene-1,4'-Piperidine] Derivatives as Potent and Selective Non-Peptide Human Somatostatin Receptor Subtype 2 (sst2) Agonists, Journal of Medicinal Chemistry, 1998, pp. 2175-2179, vol. 41, No. 13.
Yang L et al., Synthesis and Biological Activities of Potent Peptidomimetics Selective for Somatostatin Receptor Subtype 2, Proceedings of the National Academy of Sciences of the United States of America, 1998, pp. 10836-10841, vol. 95, No. 18.
Yasojima K et al., Relationship between Beta Amyloid Peptide Generating Molecules and Neprilysin in Alzheimer Disease and Normal Brain, Brain Research, 2001, pp. 115-121, vol. 919, No. 1.
Yasojima K et al., Reduced Neprilysin in High Plaque Areas of Alzheimer Brain: A Possible Relationship to Deficient Degradation of Beta-Amyloid Peptide, Neuroscience Letters, 2001, pp. 97-100, vol. 297, No. 2.
Chemical Abstracts Registry No. 627055-02-1, indexed in the Registry file on STN CAS Online Dec. 15, 2003. (Year: 2003).
Chemical Abstracts Registry No. 1543337-39-8, indexed in the Registry file on STN CAS Online Feb. 14, 2014. (Year: 2014).
International Search Report and Written Opinion for PCT/US2018/032368, dated Aug. 13, 2018, 8 pages.
Alzheimer's Association, 2016 Alzheimer's Disease Facts and Figures, Alzheimer's & Dementia, 2016, pp. 459-509, vol. 12, No. 4.
Ankersen M et al., Discovery of a Novel Non-Peptide Somatostatin Agonist with SST4 Selectivity, Journal of the American Chemical Society, 1998, pp. 1368-1373, vol. 120, No. 7.
Bibian M et al., Multi-Gram Scale Mercury-Free Synthesis of Optically Pure 3,4,5-Trisubstituted 1,2,4-Triazoles Using Silver Benzoate, Tetrahedron Letters, 2010, pp. 2660-2663, vol. 51, No. 19.

(56) References Cited

OTHER PUBLICATIONS

Blurton-Jones M and Laferla FM, Pathways by Which Abeta Facilitates Tau Pathology, Current Alzheimer Research, 2006, pp. 437-448, vol. 3, No. 5.

Boeglin D et al., Solution and Solid-Supported Synthesis of 3,4,5-Trisubstituted 1,2,4-Triazole-Based Peptidomimetics, Organic Letters, 2003, pp. 4465-4468, vol. 5, No. 23.

Bruno JF et al., Molecular Cloning and Functional Expression of a Brain-Specific Somatostatin Receptor, Proceedings of the National Academy of Sciences of the United States of America, 1992, pp. 11151-11155, vol. 89, No. 23.

Carpentier M et al., Declining Expression of Neprilysin in Alzheimer Disease Vasculature: Possible Involvement in Cerebral Amyloid Angiopathy, Journal of Neuropathology & Experimental Neurology, 2002, pp. 849-856, vol. 61, No. 10.

Castanedo GM et al., Rapid Synthesis of 1,3,5-Substituted 1,2,4-Triazoles from Carboxylic Acids, Amidines, and Hydrazines, The Journal of Organic Chemistry, 2011, pp. 1177-1179, vol. 76, No. 4.

Chagnault V et al., Synthesis of Somatostatin Mimetics Based on 1-Deoxynojirimycin, ChemMedChem, 2008, pp. 1071-1076, vol. 3, No. 7.

Chen H et al., Fiber Tracts Anomalies in APPxPS1 Transgenic Mice Modeling Alzheimer's Disease, Journal of Aging Research, 2011, article 281274, vol. 2011.

Contour-Galcera M-O et al., 3-Thio-1,2,4-Triazoles, Novel Somatostatin sst2/sst5 Agonists, Bioorganic & Medicinal Chemistry Letters, 2005, pp. 3555-3559, vol. 15, No. 15.

Crider A, Recent Advances in the Development of Nonpeptide Somatostatin Receptor Ligands, Mini Reviews in Medicinal Chemistry, 2002, pp. 507-517, vol. 2, No. 5.

Crider AM et al., Somatostatin Receptor Subtype 4 (sst4) Ligands: Synthesis and Evaluation of Indol-3-yl- and 2-Pyridyl-Thioureas, Letters in Drug Design & Discovery, 2004, pp. 84-87, vol. 1, No. 1.

Crider AM and Witt KA, Somatostatin sst4 Ligands: Chemistry and Pharmacology, Mini Reviews in Medicinal Chemistry, 2007, pp. 213-220, vol. 7, No. 3.

Daryaei I, Trisubstituted-1,2,4-Triazoles: Novel Scaffolds for the Development of Somatostatin Subtype-4 Receptor (sst4) Ligands, A Thesis Submitted in Partial Fulfillment of the Requirements for the Master of Science Degree, Department of Chemistry in the Graduate School, Southern Illinois University Edwardsville, Aug. 2011.

Daryaei I et al., Synthesis of Trisubstituted-1,2,4-Triazoles as Somatostatin Subtype-4 Receptor (sst4) Ligands, abstract presented at the 243rd American Chemical Society National Meeting, Mar. 25-29, 2012, San Diego, California.

Davies P et al., Reduced Somatostatin-Like Immunoreactivity in Cerebral Cortex from Cases of Alzheimer Disease and Alzheimer Senile Dementia, Nature, 1980, pp. 279-280, vol. 288, No. 5788.

Demange L et al., Synthesis and Pharmacological in Vitro and in Vivo Evaluations of Novel Triazole Derivatives as Ligands of the Ghrelin Receptor 1, Journal of Medicinal Chemistry, 2007, pp. 1939-1957, vol. 50, No. 8.

Engstrom M et al., Superagonism at the Human Somatostatin Receptor Subtype 4, The Journal of Pharmacology and Experimental Therapeutics, 2005, pp. 332-338, vol. 312, No. 1.

Epelbaum J, Somatostatin in the Central Nervous System: Physiology and Pathological Modifications, Progress in Neurobiology, 1986, pp. 63-100, vol. 27, No. 1.

Epelbaum J et al., Somatostatin, Alzheimer's Disease and Cognition: An Old Story Coming of Age?, Progress in Neurobiology, 2009, pp. 153-161, vol. 89, No. 2.

Friesner RA et al., Glide: A New Approach for Rapid, Accurate Docking and Scoring. 1. Method and Assessment of Docking Accuracy, Journal of Medicinal Chemistry, 2004, pp. 1739-1749, vol. 47, No. 7.

Friesner RA et al., Extra Precision Glide: Docking and Scoring Incorporating a Model of Hydrophobic Enclosure for Protein-Ligand Complexes, Journal of Medicinal Chemistry, 2006, pp. 6177-6196, vol. 49, No. 21.

Gastambide F et al., Hippocampal SSTR4 Somatostatin Receptors Control the Selection of Memory Strategies, Psychopharmacology, 2009, pp. 153-163, vol. 202, No. 1-3.

Gastambide F et al., Cooperation Between Hippocampal Somatostatin Receptor Subtypes 4 and 2: Functional Relevance in Interactive Memory Systems, Hippocampus, 2010, pp. 745-757, vol. 20, No. 6.

Gouin SG and Murphy PV, Synthesis of Somatostatin Mimetics Based on the 1-Deoxymannojirimycin Scaffold, The Journal of Organic Chemistry, 2005, pp. 8527-8532, vol. 70, No. 21.

Grace CR et al., Novel sst(4)-Selective Somatostatin (SRIF) Agonists. 4. Three-Dimensional Consensus Structure by NMR, Journal of Medicinal Chemistry, 2003, pp. 5606-5618, vol. 46, No. 26.

Hayashi M et al., Somatostatin and Brain-Derived Neurotrophic Factor mRNA Expression in the Primate Brain: Decreased Levels of mRNAs During Aging, Brain Research, 1997, pp. 283-289, vol. 749, No. 2.

Helyes Z et al., TT-232: Somatostatin sst1/sst4 Agonist, Treatment of Neuropathic Pain, Treatment of Inflammation, Drugs of the Future, 2005, pp. 558-566, vol. 30, No. 6.

Helyes Z et al., Effects of the Somatostatin Receptor Subtype 4 Selective Agonist J-216 on Sensory Neuropeptide Release and Inflammatory Reactions in Rodents, British Journal of Pharmacology, 2006, pp. 405-415, vol. 149, No. 4.

Hirschmann R et al., Nonpeptidal Peptidomimetics with .Beta.-D-Glucose Scaffolding. A Partial Somatostatin Agonist Bearing a Close Structural Relationship to a Potent, Selective Substance P Antagonist, Journal of the American Chemical Society, 1992, pp. 9217-9218, vol. 114, No. 23.

Hirschmann R et al., De Novo Design and Synthesis of Somatostatin Non-Peptide Peptidomimetics Utilizing Beta-D-Glucose as a Novel Scaffolding, Journal of the American Chemical Society, 1993, pp. 12550-12568, vol. 115, No. 26.

Hitotsuyanagi Y et al., A Cis Amide Bond Surrogate Incorporating 1,2,4-Triazole, The Journal of Organic Chemistry, 2002, pp. 3266-3271, vol. 67, No. 10.

Ho B et al., Synthesis of 2-Piperidinecarboxylic Acid Derivatives as Potential Anticonvulsants, European Journal of Medicinal Chemistry, 1998, pp. 23-31, vol. 33, No. 1.

Howell S et al., Neutral Endopeptidase Can Hydrolyze Beta-Amyloid(1-40) but Shows No Effect on Beta-Amyloid Precursor Protein Metabolism, Peptides, 1995, pp. 647-652, vol. 16, No. 4.

Huang SM et al., Neprilysin-Sensitive Synapse-Associated Amyloid-Beta Peptide Oligomers Impair Neuronal Plasticity and Cognitive Function, The Journal of Biological Chemistry, 2006, pp. 17941-17951, vol. 281, No. 26.

Isaacs MG et al., Structure-Based Design of Novel Groups for Use in the P1 Position of Thrombin Inhibitor Scaffolds. Part 1: Weakly Basic Azoles, Bioorganic & Medicinal Chemistry Letters, 2006, pp. 338-342, vol. 16, No. 2.

Iwata N et al., Identification of the Major Abeta1-42-Degrading Catabolic Pathway in Brain Parenchyma: Suppression Leads to Biochemical and Pathological Deposition, Nature Medicine, 2000, pp. 143-150, vol. 6, No. 2.

Iwata N et al., Metabolic Regulation of Brain Abeta by Neprilysin, Science, 2001, pp. 1550-1552, vol. 292, No. 5521.

Iwata N et al., Presynaptic Localization of Neprilysin Contributes to Efficient Clearance of Amyloid-Beta Peptide in Mouse Brain, The Journal of Neuroscience, 2004, pp. 991-998, vol. 24, No. 4.

Iwata N et al., Metabolism of Amyloid-Beta Peptide and Alzheimer's Disease, Pharmacology & Therapeutics, 2005, pp. 129-148, vol. 108, No. 2.

Jones G et al., Development and Validation of a Genetic Algorithm for Flexible Docking, Journal of Molecular Biology, 1997, pp. 727-748, vol. 267, No. 3.

Kanemitsu H et al., Human Neprilysin Is Capable of Degrading Amyloid Beta Peptide Not Only in the Monomeric Form but Also the Pathological Oligomeric Form, Neuroscience Letters, 2003, pp. 113-116, vol. 350, No. 2.

Kumar U, Expression of Somatostatin Receptor Subtypes (SSTR1-5) in Alzheimer's Disease Brain: An Immunohistochemical Analysis, Neuroscience, 2005, pp. 525-538, vol. 134, No. 2.

Kumar U and Grant M, Somatostatin and Somatostatin Receptors, in Results and Problems in Cell Differentiation, Cellular Peptide

(56) References Cited

OTHER PUBLICATIONS

Hormone Synthesis and Secretory Pathways, Rehfeld J and Bundgaard, eds, 2010, pp. 137-184, vol. 50, Springer, Heidelberg.
Leissring MA et al., Enhanced Proteolysis of Beta-Amyloid in APP Transgenic Mice Prevents Plaque Formation, Secondary Pathology, and Premature Death, Neuron, 2003, pp. 1087-1093, vol. 40, No. 6.
Lewis I et al., A Novel Somatostatin Mimic with Broad Somatotropin Release Inhibitory Factor Receptor Binding and Superior Therapeutic Potential, Journal of Medicinal Chemistry, 2003, pp. 2334-2344, vol. 46, No. 12.
Li J and Sha Y, A Convenient Synthesis of Amino Acid Methyl Esters, Molecules, 2008, pp. 1111-1119, vol. 13, No. 5.
Liu C and Iwanowicz EJ, A Novel One-Pot Synthesis of 1,2,4-Triazoles-3,5,-Diamine Derivatives from Isothiocyanates and Mono-Substituted Hydrazines, Tetrahedron Letters, 2003, pp. 1409-1411, vol. 44, No. 7.

\* cited by examiner

3,4,5-TRISUBSTITUTED-1,2,4-TRIAZOLES AND 3,4,5-TRISUBSTITUTED-3-THIO-1,2,4-TRIAZOLES AND USES THEREOF

REFERENCE TO RELATED APPLICATIONS

This application is a continuation-in-part of U.S. application Ser. No. 16/613,086, filed Nov. 12, 2019, which is the U.S. 371 National Stage Application of PCT/US2018/032368, filed May 11, 2018, which claims benefit of U.S. Provisional Application 62/505,384, filed May 12, 2017, the contents of which are incorporated herein by reference.

GOVERNMENTAL RIGHTS

This invention was made with government support under grant number AG047858 awarded by the National Institutes of Health. The government has certain rights in the invention.

TECHNICAL FIELD

The present disclosure relates to compounds that are somatostatin receptor type 4 agonists.

BACKGROUND

Somatostatin, also known as somatostatin release inhibitory factor (SRIF) is a cyclic peptide distributed throughout the human body, and is involved in numerous physiological processes. SRIF occurs as a tetradecapeptide and an N-terminally extended form (SST-28).

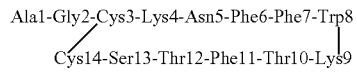

There are six somatostatin receptor (SSTR) subtypes; SSTR 1-5, including the alternatively spliced SSTR2A and SSTR2B receptors. The somatostatin receptors were originally divided into two families based on binding studies with iodinated synthetic analogues of somatostatin; a high affinity family (SRIF-1) and a lower affinity family (SRIF-2). When SRIF binds to its receptors, it produces changes in intracellular signaling pathways. SSTRs are all G-protein coupled receptors (GPCRs). Through receptor action, SRIF produces primarily inhibitory effects on endocrine and exocrine secretions throughout the body, regulates cellular differentiation and proliferation, and acts as a neurotransmitter/neuromodulator in the central nervous system. Given SRIF has shown to exhibit inhibitory actions on endocrine and exocrine secretions, as well as numerous modulatory effects on neuronal activity in the periphery and central nervous system (CNS), the respective receptors have become primary therapeutic targets.

SUMMARY

One aspect of the disclosure encompasses a compound comprising Formula I):

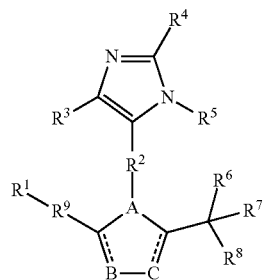

wherein
- ⸜ are independently a single bond or is absent;
- A, B, and C are independently C, N, O, or S;
- $R^1$ and $R^7$ are independently hydrogen, substituted or unsubstituted aryl, substituted or unsubstituted heteroaryl, substituted or unsubstituted $C_1$-$C_6$ alkyl, substituted or unsubstituted cycloalkyl, or substituted or unsubstituted fused ring system;
- $R^2$ is substituted or unsubstituted $C_1$-$C_6$ alkyl;
- $R^3$, $R^4$, and $R^5$ are independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide;
- $R^6$ and $R^8$ are independently hydrogen, F, Cl, Br, I, substituted or unsubstituted $C_1$-$C_6$ alkyl, substituted or unsubstituted aryl, substituted or unsubstituted heteroaryl, or substituted or unsubstituted cycloalkyl; and
- $R^9$ is a substituted or unsubstituted $C_1$-$C_3$ alkyl;
- with the proviso that when $R^9$ is $C_2$ alkyl, $R^7$ is not a 3,4-dichlorobenzene; or a pharmaceutically acceptable salt thereof.

Another aspect of the disclosure encompasses a compound of Formula (II):

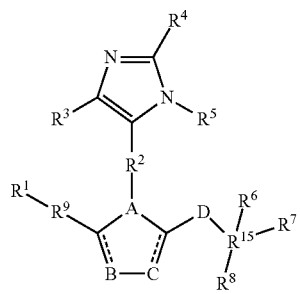

wherein
- ⸜ E are independently a bond or is absent;
- A, B, and C are independently C, N, O, or S;
- D is S, O, $NR^{16}$, P, sulfone, or sulfoxide;
- $R^1$ and $R^7$ are independently hydrogen, substituted or unsubstituted aryl, substituted or unsubstituted heteroaryl, substituted or unsubstituted $C_1$-$C_6$ alkyl, substituted or unsubstituted cycloalkyl or substituted or unsubstituted fused ring system;
- $R^2$ is substituted or unsubstituted $C_1$-$C_6$ alkyl;
- $R^3$, $R^4$, and $R^5$ are independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide;

$R^6$ and $R^8$ are independently hydrogen, F, Cl, Br, I, substituted or unsubstituted $C_1$-$C_6$ alkyl, substituted or unsubstituted aryl, substituted or unsubstituted heteroaryl, or substituted or unsubstituted cycloalkyl;

$R^9$ and $R^{15}$ are independently substituted or unsubstituted $C_1$-$C_6$ alkyl, substituted or unsubstituted aryl, substituted or unsubstituted heteroaryl, or substituted or unsubstituted cycloalkyl; and $R^{16}$ is hydrogen, $C_1$-$C_6$ alkyl, aryl, or benzyl;

or a pharmaceutically acceptable salt thereof.

DETAILED DESCRIPTION

The present disclosure provides compounds of Formula (I) and Formula (II), which have been found to be somatostatin receptor type 4 agonists.

Various aspects of the disclosure are described in greater detail below.

I. Compounds of Formula (I)

Provided herein are compounds comprising Formula (I)

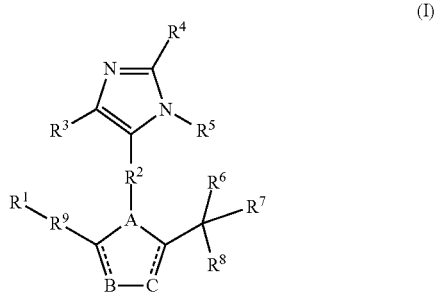

(I)

wherein $\backslash$ are independently a single bond or is absent;

A, B, and C are independently C, N, O, or S;

$R^1$ and $R^7$ are independently hydrogen, substituted or unsubstituted aryl, substituted or unsubstituted heteroaryl, substituted or unsubstituted $C_1$-$C_6$ alkyl, substituted or unsubstituted cycloalkyl, or substituted or unsubstituted fused ring system;

$R^2$ is substituted or unsubstituted $C_1$-$C_6$ alkyl;

$R^3$, $R^4$, and $R^5$ are independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide;

$R^6$ and $R^8$ are independently hydrogen, F, Cl, Br, I, substituted or unsubstituted $C_1$-$C_6$ alkyl, substituted or unsubstituted aryl, substituted or unsubstituted heteroaryl, or substituted or unsubstituted cycloalkyl; and $R^9$ is a substituted or unsubstituted $C_1$-$C_3$ alkyl;

with the proviso that when $R^9$ is $C_2$ alkyl, $R^7$ is not a 3,4-dichlorobenzene; or a pharmaceutically acceptable salt thereof.

In one aspect, a compound of Formula (I) comprises any of the preceding compounds of Formula (I), wherein $\backslash$ are each a single bond and A, B, and C are N.

In another aspect, a compound of Formula (I) comprises any of the preceding compounds of Formula (I), wherein $R^6$ and $R^8$ are independently hydrogen or substituted or unsubstituted $C_1$-$C_3$ alkyl.

In another aspect, a compound of Formula (I) comprises any of the preceding compounds of Formula (I), wherein $R^6$ and $R^8$ are hydrogen.

In another aspect, a compound of Formula (I) comprises any of the preceding compounds of Formula (I), wherein $R^6$ and $R^8$ are substituted or unsubstituted $C_1$-$C_2$ alkyl.

In another aspect, a compound of Formula (I) comprises any of the preceding compounds of Formula (I), wherein $R^1$ and $R^7$ are independently substituted or unsubstituted aryl or substituted or unsubstituted fused ring system.

In another aspect, a compound of Formula (I) comprises any of the preceding compounds of Formula (I), wherein $R^1$ is substituted or unsubstituted fused ring system.

In another aspect, a compound of Formula (I) comprises any of the preceding compounds of Formula (I), wherein $R^1$ is substituted or unsubstituted indole.

In another aspect, a compound of Formula (I) comprises any of the preceding compounds of Formula (I), wherein $R^9$ is substituted or unsubstituted aryl.

In another aspect, a compound of Formula (I) comprises any of the preceding compounds of Formula (I), wherein $R^9$ is

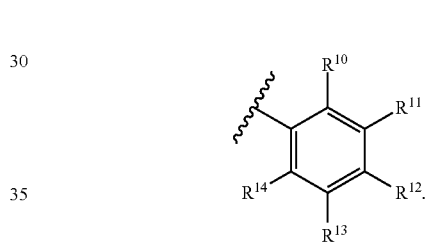

In another aspect, a compound of Formula (I) comprises any of the preceding compounds of Formula (I), wherein $R^{10}$, $R^{11}$, $R^{12}$, $R^{13}$, and $R^{14}$ is independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide.

In another aspect, a compound of Formula (I) comprises any of the preceding compounds of Formula (I), wherein $R^{10}$, $R^{11}$, $R^{12}$, $R^{13}$, and $R^{14}$ is independently hydrogen, F, Cl, Br, I, $CF_3$, $OCH_3$, $NO_2$, $OCH_2(C_6H_4)$, $C_6H_4$, $SO_2CH_3$, or $OCF_3$.

In another aspect, a compound of Formula (I) comprises any of the preceding compounds of Formula (I), wherein $R^2$ is substituted or unsubstituted $C_1$-$C_3$ alkyl.

In another aspect, a compound of Formula (I) comprises any of the preceding compounds of Formula (I), wherein $R^2$ is substituted or unsubstituted propyl.

In another aspect, a compound of Formula (I) comprises any of the preceding compounds of Formula (I), wherein $R^2$ is unsubstituted propyl.

In another aspect, a compound of Formula (I) comprises any of the preceding compounds of Formula (I), wherein $R^3$, $R^4$, and $R^5$ are independently hydrogen, F, Cl, Br, I, substituted or unsubstituted alkyl.

In another aspect, a compound of Formula (I) comprises any of the preceding compounds of Formula (I), wherein $R^3$, $R^4$, and $R^5$ are hydrogen.

In another aspect, a compound of Formula (I) comprises any of the preceding compounds of Formula (I), wherein R⁹ is methyl.

In another aspect, a compound of Formula (I) comprises any of the preceding compounds of Formula (I), wherein R⁹ is ethyl.

In another aspect, a compound of Formula (I) comprises any of the preceding compounds of Formula (I), may be selected from the group consisting of:

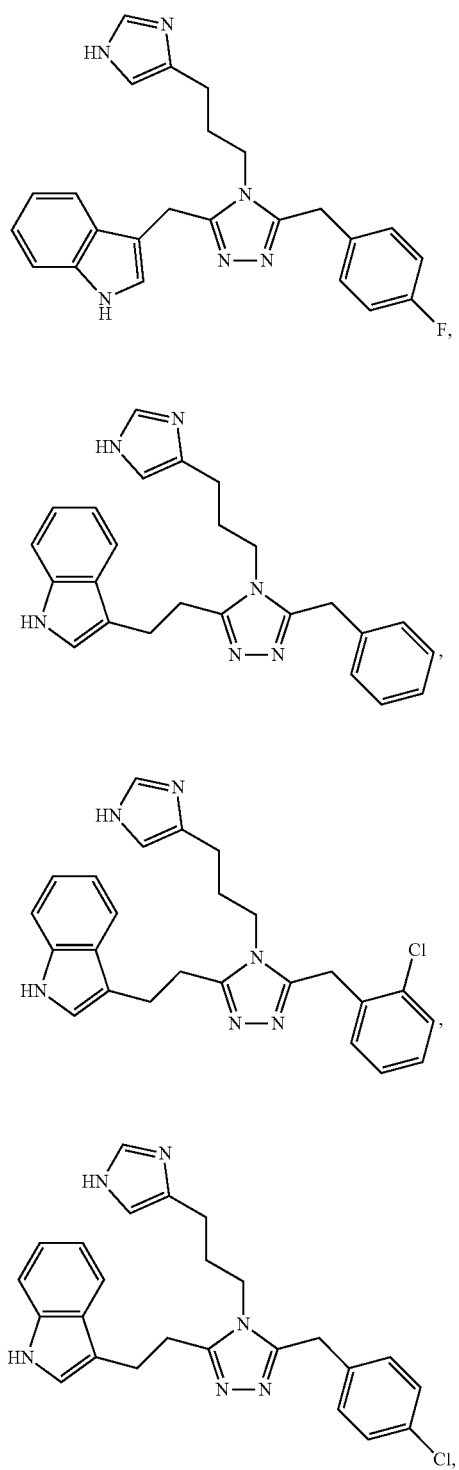

-continued

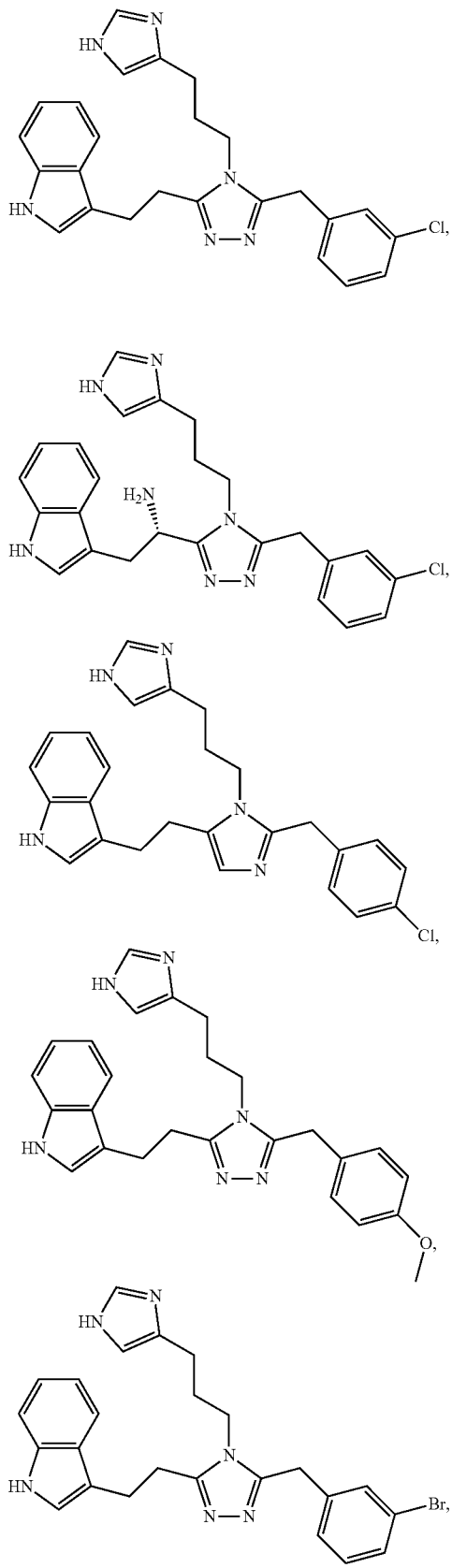

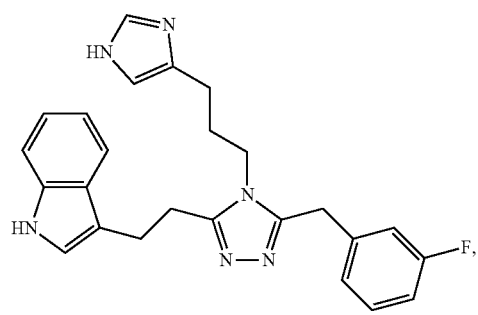
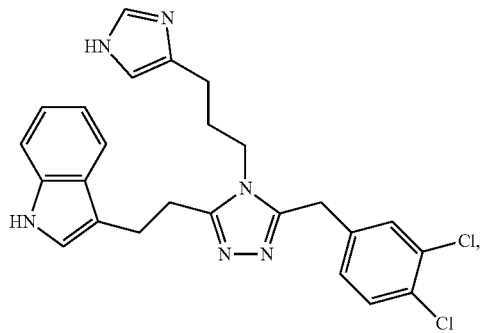
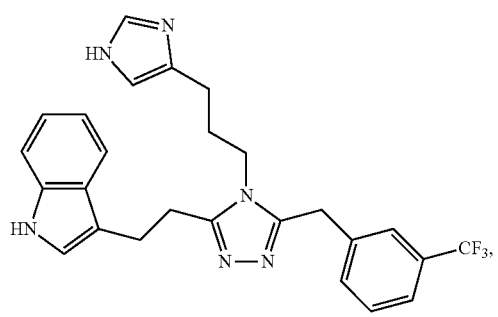
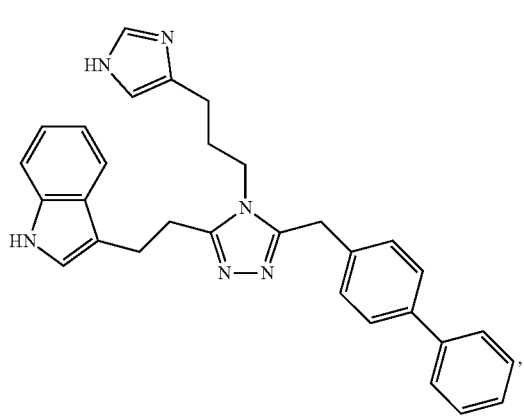
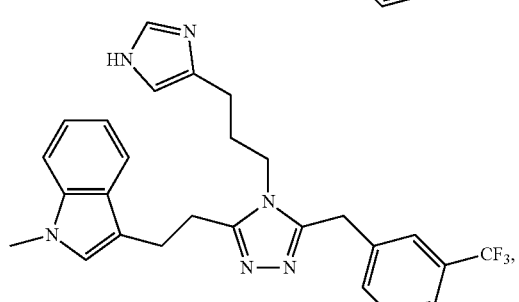
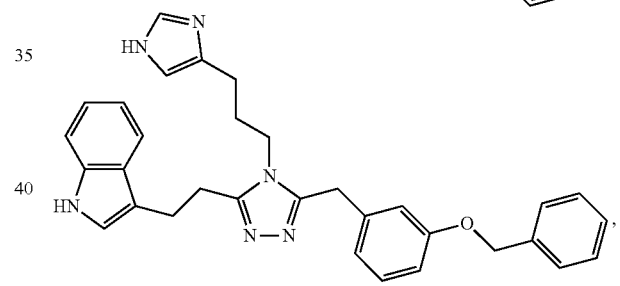
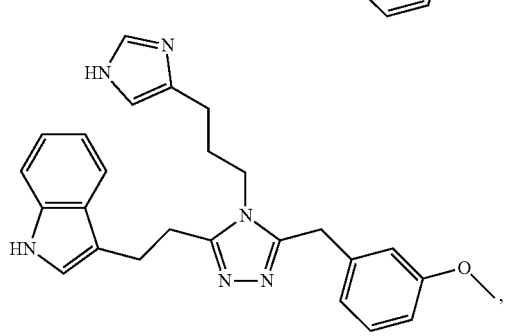
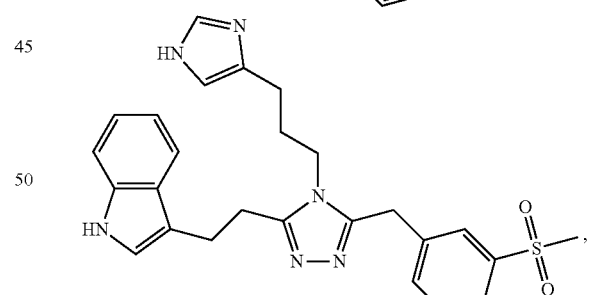
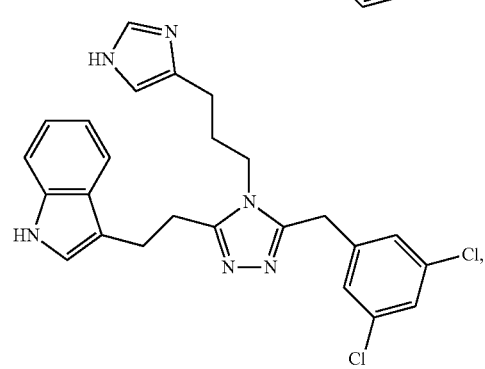
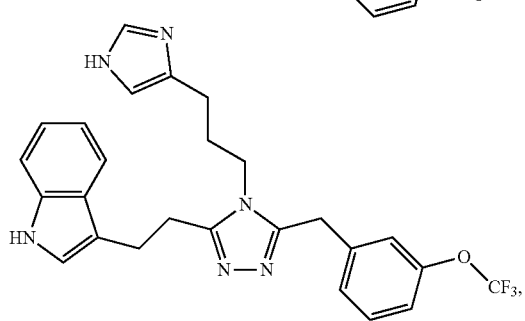

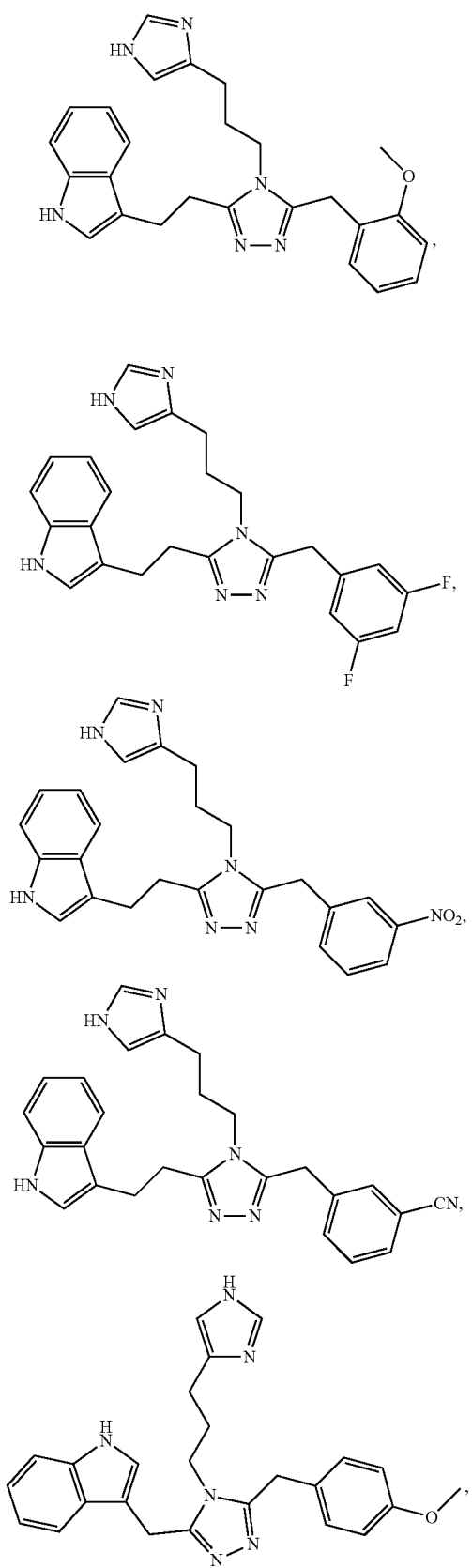
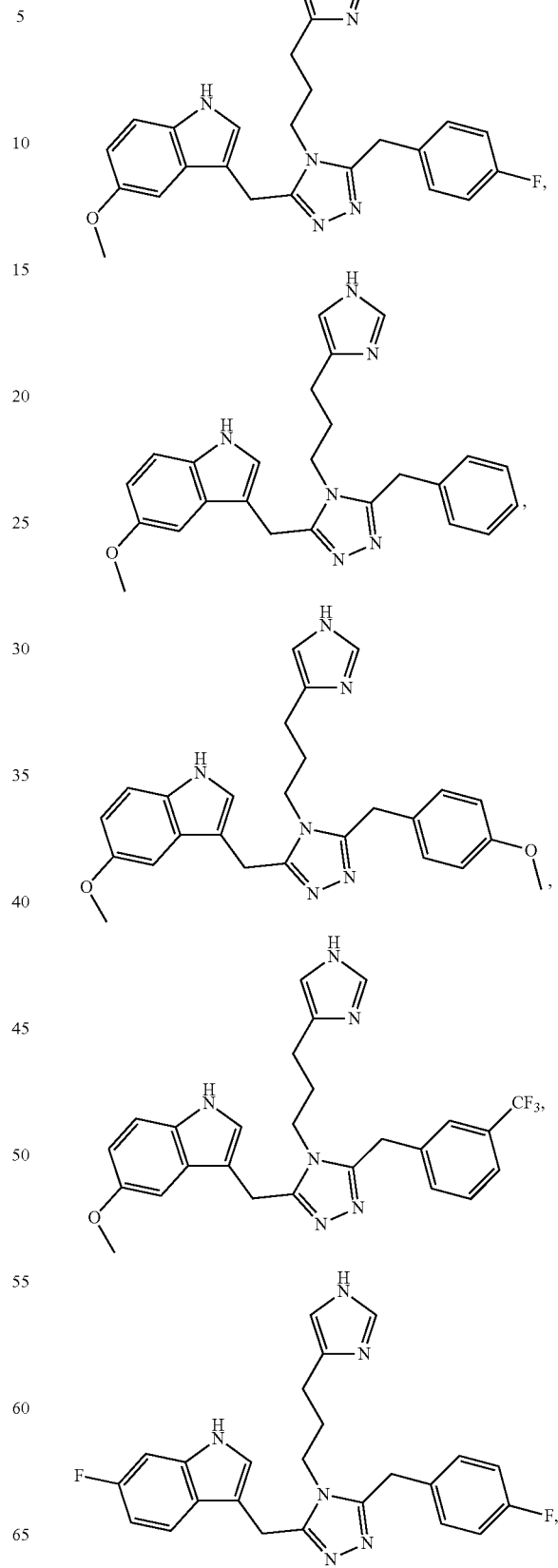

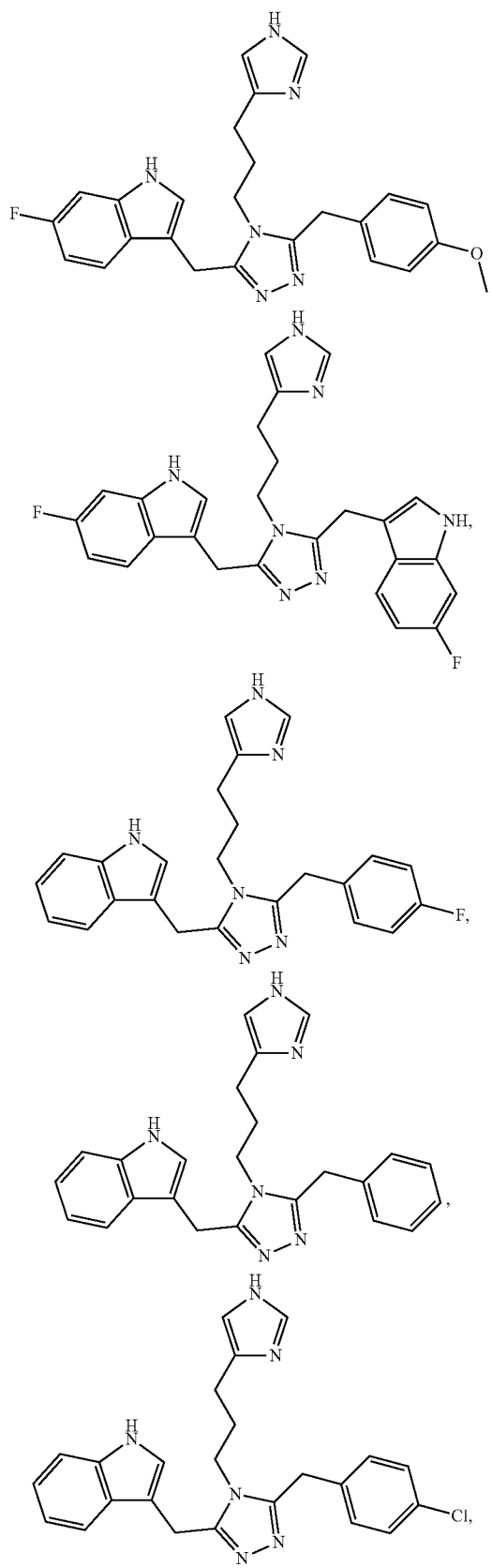
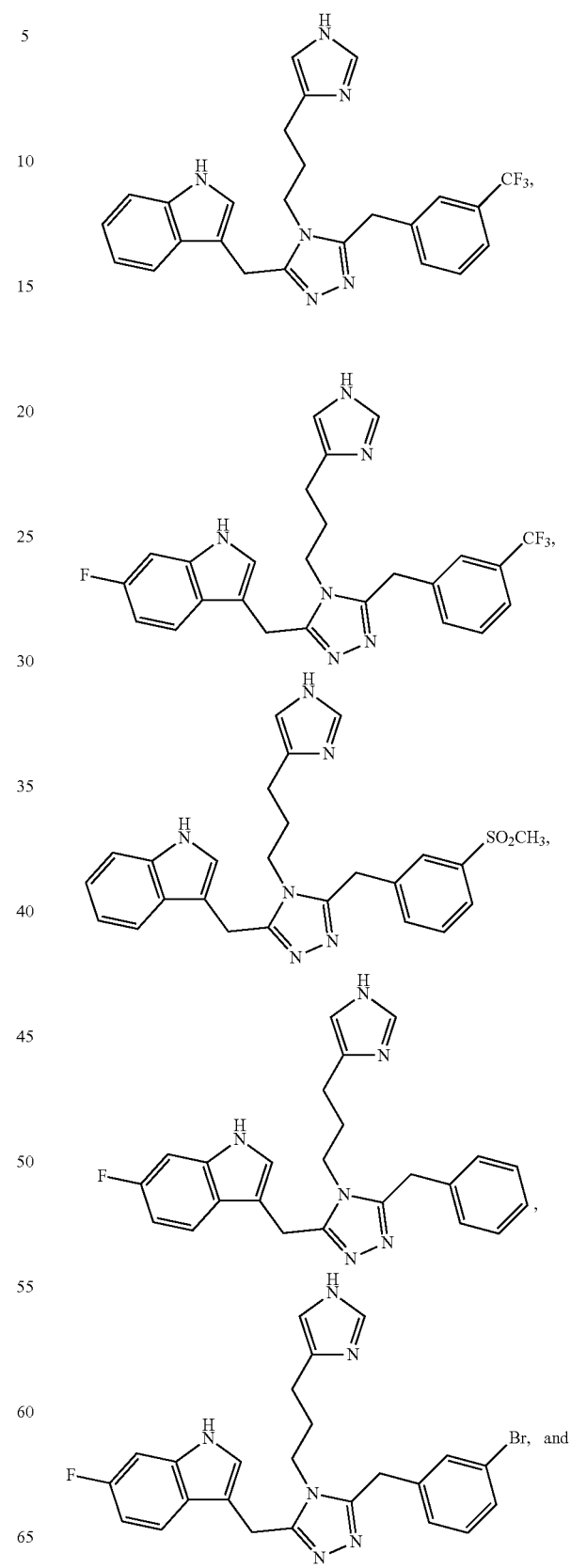

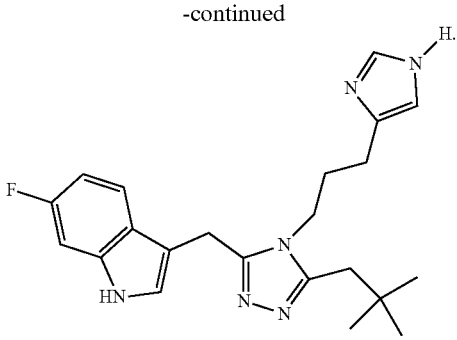

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{12}$ is fluoro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{11}$, $R^{12}$, $R^{13}$, and $R^{14}$ are hydrogen; and $R^{10}$ is chloro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; and $R^{10}$, $R^{11}$, $R^{12}$, $R^{13}$, and $R^{14}$ are hydrogen.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{11}$, $R^{13}$, and $R^{14}$ are hydrogen; and $R^{12}$ is chloro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is chloro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is 1-aminoethyl; $R^7$ is benzene; $R^{10}$, $R^{12}$, $R^{13}$, and $R^{14}$ are hydrogen; and $R^{11}$ is chloro.

In another aspect, a compound of the disclosure comprises Formula (I), wherein ⸝ are single bonds; A, and C are nitrogen; B is carbon; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{11}$, $R^{13}$, and $R^{14}$ are hydrogen; and $R^{12}$ is chloro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{11}$, $R^{13}$ and $R^{14}$ are hydrogen; and $R^{12}$ is methoxy.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is bromo.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is fluoro.

In another aspect, a compound of the disclosure comprises Formula (II), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is trifluoromethyl.

In another aspect, a compound of the disclosure comprises Formula (I), wherein ⸝ are single bonds; A, B, and C are nitrogen; $R^1$ is 1-methyl-3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is trifluoromethyl.

In another aspect, a compound of the disclosure comprises Formula (I, wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is methoxy.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, and $R^{14}$ are hydrogen; and $R^{11}$ and $R^{13}$ are chloro.

In another aspect, a compound of the disclosure comprises Formula (I), wherein ⸝ are single bonds; A, B, and C are nitrogen; $R^1$ is 1-methyl-3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{13}$, and $R^{14}$ are hydrogen; and $R^{11}$ and $R^{12}$ are chloro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{11}$, $R^{13}$, and $R^{14}$ are hydrogen; and $R^{12}$ is benzyl.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is oxomethylbenzene.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is sulfonylmethane.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is trifluoromethoxy.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{11}$, $R^{12}$, $R^{13}$, and $R^{14}$ are hydrogen; and $R^{10}$ is methoxy.

In another aspect, a compound of the disclosure comprises Formula (I), wherein ⸝ are single bonds; A, B, and C are nitrogen; R1 is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, R12, and $R^{14}$ are hydrogen; and R11 and $R^{13}$ are fluoro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is nitro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is ethyl; $R^7$ is benzene; $R^{10}$, $R^{12}$, $R^{13}$, and $R^{14}$ are hydrogen; and $R^{11}$ is cyano.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{12}$ is methoxy.

In another aspect, a compound of the disclosure comprises Formula (I), wherein ⸝ are single bonds; A, B, and C are nitrogen; $R^1$ is 5-methoxy-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{12}$ is fluoro.

In another aspect, a compound of the disclosure comprises Formula (I), wherein ⸝ are single bonds; A, B, and C are nitrogen; $R^1$ is 5-methoxy-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{12}$, $R^{13}$, and $R^{14}$ are hydrogen.

In another aspect, a compound of the disclosure comprises Formula (I), wherein ⸝ are single bonds; A, B, and C are nitrogen; $R^1$ is 5-methoxy-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{12}$ is methoxy.

In another aspect, a compound of the disclosure comprises Formula (I), wherein ⸝ are single bonds; A, B, and C are nitrogen; $R^1$ is 5-methoxy-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{11}$ is trifluoromethyl.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{12}$ is fluoro.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$ and $R^{14}$ are hydrogen; and $R^{12}$ is methoxy.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is 6-fluoro-3-indole.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$ and $R^{14}$ are hydrogen; and $R^{12}$ is fluoro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{12}$, $R^{13}$ and $R^{14}$ are hydrogen.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$ and $R^{14}$ are hydrogen; and $R^{12}$ is chloro.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{12}$, $R^{13}$, and $R^{14}$ are hydrogen; and $R^{11}$ is trifluoromethyl.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{13}$, and $R^{14}$ are hydrogen; and $R^{11}$ is trifluoromethyl.

In another aspect, a compound of the disclosure comprises Formula (I), wherein ⸝ are single bonds; A, B, and C are nitrogen; $R^1$ is 3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{12}$, $R^{13}$, and $R^{14}$ are hydrogen; and $R^{11}$ is sulfonylmethane.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{11}$, $R^{12}$, $R^{13}$, and $R^{14}$ are hydrogen.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is benzene; $R^{10}$, $R^{12}$, $R^{13}$, and $R^{14}$ are hydrogen; and $R^{11}$ is bromo.

In another aspect, a compound of the disclosure comprises Formula (I), wherein ⸝ are single bonds; A, B, and C are nitrogen; $R^1$ is 6-fluoro-3-indole; $R^2$ is propyl; $R^3$, $R^4$, and $R^5$ are hydrogen; $R^6$ and $R^8$ are hydrogen; $R^9$ is methyl; $R^7$ is tert-butyl.

II. Compounds of Formula (II)

Also provided herein are compounds comprising Formula (II)

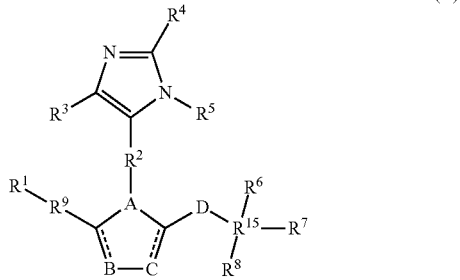

wherein

- ⟍ are independently a single bond or is absent;
- A, B, and C are independently C, N, O, or S;
- D is S, O, $NR^{16}$, P, sulfone, or sulfoxide;
- $R^1$ and $R^7$ are independently hydrogen, substituted or unsubstituted aryl, substituted or unsubstituted heteroaryl, substituted or unsubstituted $C_1$-$C_6$ alkyl, substituted or unsubstituted cycloalkyl or substituted or unsubstituted fused ring system;
- $R^2$ is substituted or unsubstituted $C_1$-$C_6$ alkyl;
- $R^3$, $R^4$, and $R^5$ are independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide.
- $R^6$ and $R^8$ are independently hydrogen, F, Cl, Br, I, substituted or unsubstituted $C_1$-$C_6$ alkyl, substituted or unsubstituted aryl, substituted or unsubstituted heteroaryl, or substituted or unsubstituted cycloalkyl;
- $R^9$ and R15 are independently substituted or unsubstituted $C_1$-$C_6$ alkyl, substituted or unsubstituted aryl, substituted or unsubstituted heteroaryl, or substituted or unsubstituted cycloalkyl; and
- $R^{16}$ is hydrogen, $C_1$-$C_6$ alkyl, aryl, or benzyl;

or a pharmaceutically acceptable salt thereof.

In one aspect, a compound of Formula (II) comprises any of the preceding compounds of Formula (II), wherein ⟍ are each a single bond and A, B, and C are N.

In another aspect, a compound of Formula (II) comprises any of the preceding compounds of Formula (II), wherein D is S.

In another aspect, a compound of Formula (II) comprises any of the preceding compounds of Formula (II), wherein $R^9$ is a bond.

In another aspect, a compound of Formula (II) comprises any of the preceding compounds of Formula (II), wherein $R^{15}$ is unsubstituted $C_1$-$C_3$ alkyl.

In another aspect, a compound of Formula (II) comprises any of the preceding compounds of Formula (II), wherein $R^{15}$ is unsubstituted $C_1$-$C_2$ alkyl.

In another aspect, a compound of Formula (II) comprises any of the preceding compounds of Formula (II), wherein $R^6$ and $R^8$ are independently hydrogen or substituted or unsubstituted $C_1$-$C_3$ alkyl.

In another aspect, a compound of Formula (II) comprises any of the preceding compounds of Formula (II), wherein $R^6$ and $R^8$ are hydrogen.

In another aspect, a compound of Formula (II) comprises any of the preceding compounds of Formula (II), wherein $R^1$ and $R^7$ are independently substituted or unsubstituted aryl or substituted or unsubstituted fused ring system.

In another aspect, a compound of Formula (II) comprises any of the preceding compounds of Formula (II), wherein $R^1$ is substituted or unsubstituted fused ring system.

In still another aspect, a compound of Formula (II) comprises any of the preceding compounds of Formula (II), wherein $R^1$ is substituted or unsubstituted indole, substituted or unsubstituted naphthalene, or substituted or unsubstituted quinolone.

In another aspect, a compound of Formula (II) comprises any of the preceding compounds of Formula (II), wherein $R^7$ is substituted or unsubstituted aryl or substituted or unsubstituted indole.

In another aspect, a compound of Formula (II) comprises any of the preceding compounds of Formula (II), wherein $R^7$ is

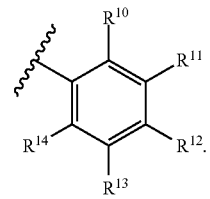

In another aspect, a compound of Formula (II) comprises any of the preceding compounds of Formula (II), wherein $R^{10}$, $R^{11}$, $R^{12}$, $R^{13}$, and $R^{14}$ is independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide.

In another aspect, a compound of Formula (II) comprises any of the preceding compounds of Formula (II), wherein $R^{10}$, $R^{11}$, $R^{12}$, $R^{13}$, and $R^{14}$ is independently hydrogen, F, Cl, Br, I, $CF_3$, $OCH_3$, $NO_2$, $OCH_2(C_6H_4)$, $C_6H_4$, $SO_2CH_3$, or $OCF_3$.

In another aspect, a compound of Formula (II) comprises any of the preceding compounds of Formula (II), wherein $R^2$ is substituted or unsubstituted $C_1$-$C_3$ alkyl.

In another aspect, a compound of Formula (II) comprises any of the preceding compounds of Formula (II), wherein $R^2$ is substituted or unsubstituted propyl.

In yet another aspect, a compound of Formula (II) comprises any of the preceding compounds of Formula (II), wherein $R^2$ is unsubstituted propyl.

In another aspect, a compound of Formula (II) comprises any of the preceding compounds of Formula (II), wherein $R^3$, $R^3$, and $R^4$ are independently hydrogen, F, Cl, Br, I, substituted or unsubstituted alkyl.

In another aspect, a compound of Formula (II) comprises any of the preceding compounds of Formula (II), wherein $R^3$, $R^3$, and $R^4$ are hydrogen.

In another aspect, a compound of Formula (II) comprises any of the preceding compounds of Formula (II), may be selected from the group consisting of.

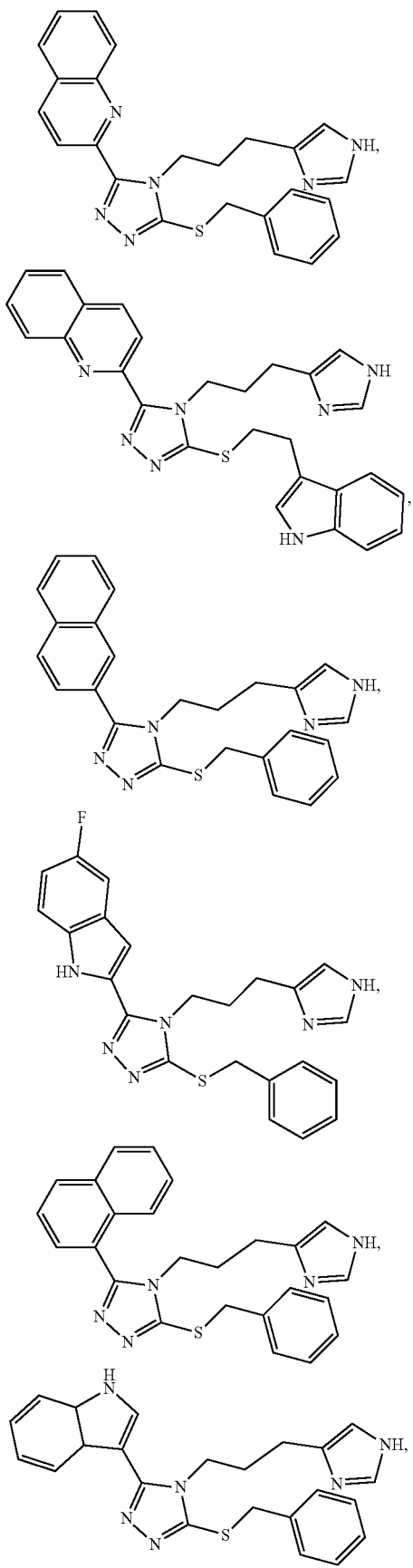

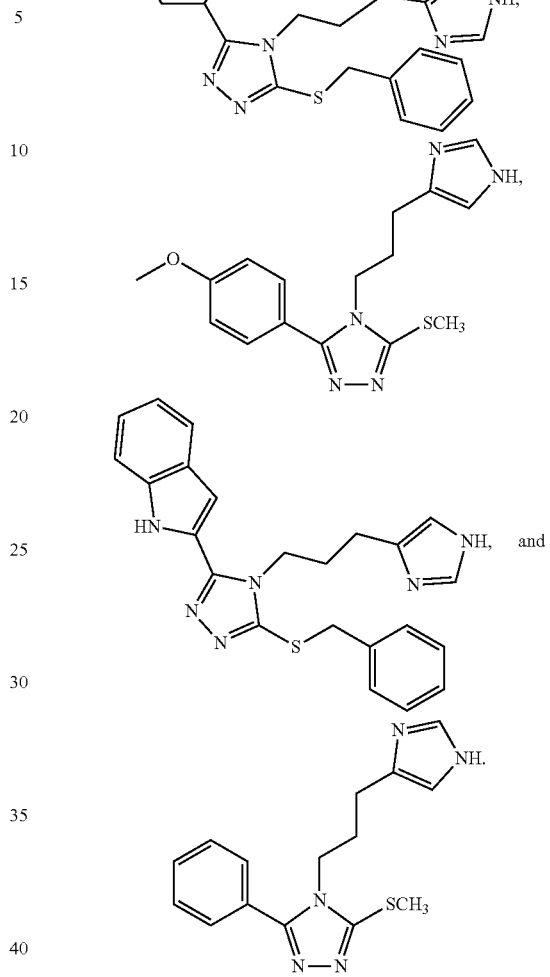

In another aspect, a compound of the disclosure comprises Formula (II), wherein ⟍ are single bonds; A, B, and C are nitrogen; D is sulfur; $R^1$ is 2-quinoline; $R^2$ is propyl; $R^3$, $R^4$, $R^5$, $R^6$ and $R^8$ are hydrogen; $R^7$ is 3-indole; $R^9$ is absent; $R^{15}$ is ethyl; and $R^{10}$, $R^{11}$, $R^{12}$, $R^{13}$, and $R^{14}$ are hydrogen.

In another aspect, a compound of the disclosure comprises Formula (II), wherein ⟍ are single bonds; A, B, and C are nitrogen; D is sulfur; $R^1$ is 2-naphthalene; $R^2$ is propyl; $R^3$, $R^4$, $R^5$, $R^6$ and $R^8$ are hydrogen; $R^7$ is benzene; $R^9$ is absent; $R^{15}$ is methyl; and $R^{10}$, $R^{11}$, $R^{12}$, $R^{13}$, and $R^{14}$ are hydrogen.

In another aspect, a compound of the disclosure comprises Formula (II), wherein ⟍ are single bonds; A, B, and C are nitrogen; D is sulfur; $R^1$ is 5-fluoro-3-indole; $R^2$ is propyl; $R^3$, $R^4$, $R^5$, $R^6$ and $R^8$ are hydrogen; $R^7$ is benzene; $R^9$ is absent; $R^{15}$ is methyl; and $R^{10}$, $R^{11}$, $R^{12}$, $R^{13}$, and $R^{14}$ are hydrogen.

In another aspect, a compound of the disclosure comprises Formula (II), wherein ⟍ are single bonds; A, B, and C are nitrogen; D is sulfur; $R^1$ is 1-naphthalene; $R^2$ is propyl; $R^3$, $R^4$, $R^5$, $R^6$ and $R^8$ are hydrogen; $R^7$ is benzene; $R^9$ is absent; $R^{15}$ is methyl; and $R^{10}$, $R^{11}$, $R^{12}$, $R^{13}$, and $R^{14}$ are hydrogen.

In another aspect, a compound of the disclosure comprises Formula (II), wherein ⸝ are single bonds; A, B, and C are nitrogen; D is sulfur; $R^1$ is 3-indole; $R^2$ is propyl; $R^3$, $R^4$, $R^5$, $R^6$ and $R^8$ are hydrogen; $R^7$ is benzene; $R^9$ is absent; $R^{15}$ is methyl; and $R^{10}$, $R^{11}$, $R^{12}$, $R^{13}$, and $R^{14}$ are hydrogen.

In another aspect, a compound of the disclosure comprises Formula (II), wherein ⸝ are single bonds; A, B, and C are nitrogen; D is sulfur; $R^1$ is aryl; $R^2$ is propyl; $R^3$, $R^4$, $R^5$, $R^6$ and $R^8$ are hydrogen; $R^7$ is benzene; $R^9$ is absent; $R^{15}$ is methyl; and $R^{10}$, $R^{11}$, $R^{12}$, $R^{13}$, and $R^{14}$ are hydrogen.

In another aspect, a compound of the disclosure comprises Formula (II), wherein ⸝ are single bonds; A, B, and C are nitrogen; D is sulfur; $R^1$ is 3-methyloxy-aryl; $R^2$ is propyl; $R^{15}$ is carbon; and $R^3$, $R^4$, $R^5$, $R^6$, $R^7$, and $R^8$ are hydrogen.

In another aspect, a compound of the disclosure comprises Formula (II), wherein ⸝ are single bonds; A, B, and C are nitrogen; D is sulfur; $R^1$ is 2-indole; $R^2$ is propyl; $R^3$, $R^4$, and $R^5$ are hydrogen; $R^7$ is benzene; $R^9$ is absent; $R^{15}$ is methyl; and $R^{10}$, $R^{11}$, $R^{12}$, $R^{13}$, and $R^{14}$ are hydrogen.

In another aspect, a compound of the disclosure comprises Formula (II), wherein ⸝ are single bonds; A, B, and C are nitrogen; D is sulfur; $R^1$ is benzene; $R^2$ is propyl; $R^{15}$ is carbon; and $R^3$, $R^4$, $R^5$, $R^6$, $R^7$, and $R^8$ are hydrogen.

In another aspect, a compound of Formula (II) comprises any of the preceding compounds of Formula (II), wherein $R^{12}$ is an unsubstituted $C_1$-$C_3$ alkyl.

In another aspect, a compound of Formula (II) comprises any of the preceding compounds of Formula (II), wherein $R^{15}$ is unsubstituted $C_1$-$C_6$ alkyl.

In another aspect, a compound of Formula (II) comprises any of the preceding compounds of Formula (II), wherein $R^{15}$ is unsubstituted $C_1$-$C_3$ alkyl.

In another aspect, a compound of Formula (II) comprises any of the preceding compounds of Formula (II), wherein $R^6$ and $R^8$ are independently hydrogen or substituted or unsubstituted $C_1$-$C_3$ alkyl.

In another aspect, a compound of Formula (II) comprises any of the preceding compounds of Formula (II), wherein $R^6$ and W are hydrogen.

In another aspect, a compound of Formula (II) comprises any of the preceding compounds of Formula (II), wherein $R^1$ and $R^7$ are independently substituted or unsubstituted aryl or substituted or unsubstituted fused ring system.

In another aspect, a compound of Formula (II) comprises any of the preceding compounds of Formula (II), wherein $R^1$ is substituted or unsubstituted fused ring system.

In still another aspect, a compound of Formula (II) comprises any of the preceding compounds of Formula (II), wherein $R^1$ is substituted or unsubstituted indole.

In another aspect, a compound of Formula (II) comprises any of the preceding compounds of Formula (II), wherein $R^7$ is substituted or unsubstituted aryl.

In still another aspect, a compound of Formula (II) comprises any of the preceding compounds of Formula (II), wherein $R^7$ is

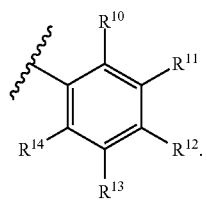

In another aspect, a compound of Formula (II) comprises any of the preceding compounds of Formula (II), wherein $R^{10}$, R, $R^{12}$, $R^{13}$, and $R^{14}$ is independently hydrogen, F, Cl, Br, I, substituted or unsubstituted alkyl, substituted or unsubstituted alkoxy, substituted or unsubstituted amine, sulfoxide, sulfone, thiosulfinate, thiosulfonate, thioamide, sulfimide, sulfoximide, sulfonediimine, or sulfur halide.

In another aspect, a compound of Formula (II) comprises any of the preceding compounds of Formula (II), wherein $R^{10}$, R, $R^{12}$, $R^{13}$, and $R^{14}$ is independently hydrogen, F, Cl, Br, I, $CF_3$, $OCH_3$, $NO_2$, $OCH_2(C_6H_4)$, $C_6H_4$, $SO_2CH_3$, or $OCF_3$.

In another aspect, a compound of Formula (II) comprises any of the preceding compounds of Formula (II), wherein $R^2$ is substituted or unsubstituted propyl.

In another aspect, a compound of Formula (II) comprises any of the preceding compounds of Formula (II), wherein $R^2$ is unsubstituted propyl.

In another aspect, a compound of Formula (II) comprises any of the preceding compounds of Formula (II), wherein $R^3$, $R^3$, and $R^4$ are independently hydrogen, F, Cl, Br, I, substituted or unsubstituted alkyl.

In another aspect, a compound of Formula (II) comprises any of the preceding compounds of Formula (II), wherein $R^3$, $R^3$, and $R^4$ are hydrogen.

In another aspect, a compound of Formula (II) comprises any of the preceding compounds of Formula (II), may be selected from the group consisting of:

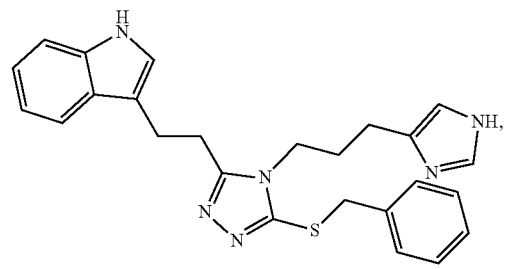

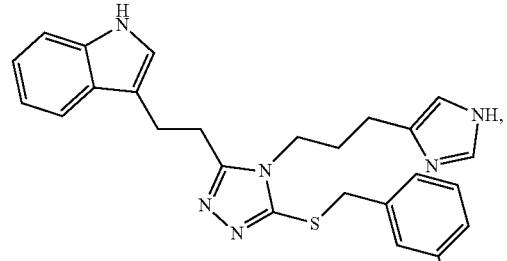

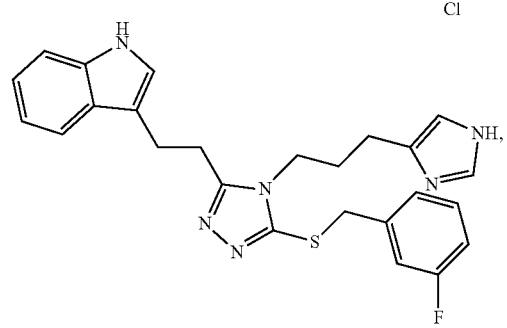

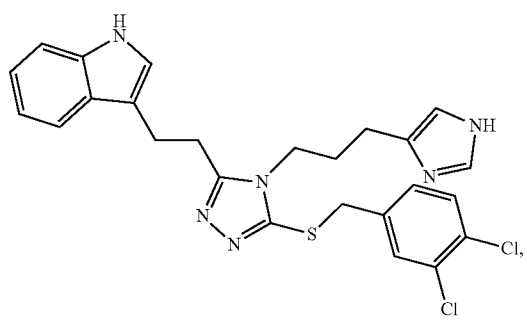
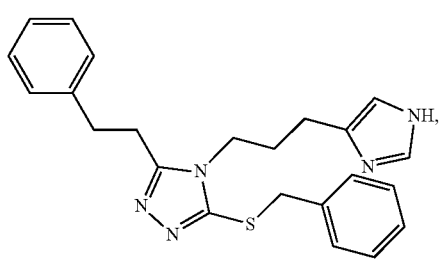
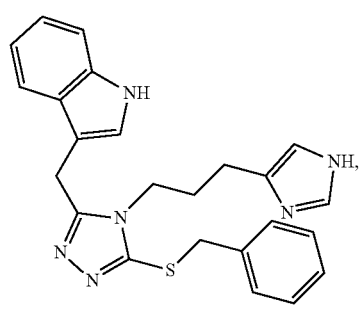
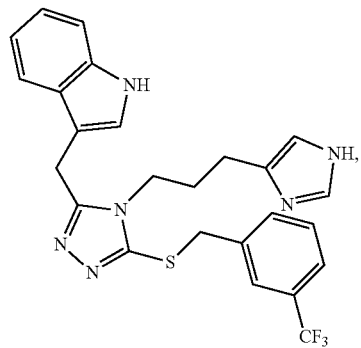
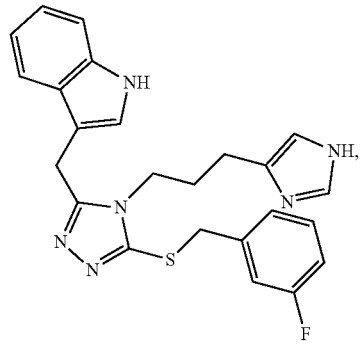
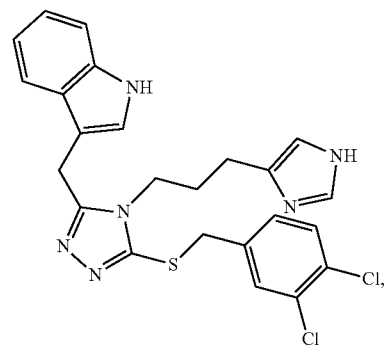
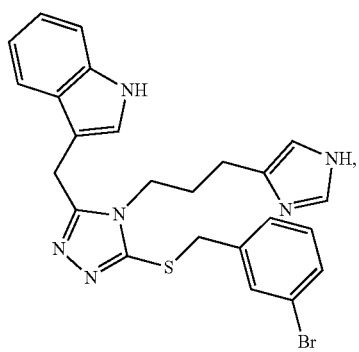
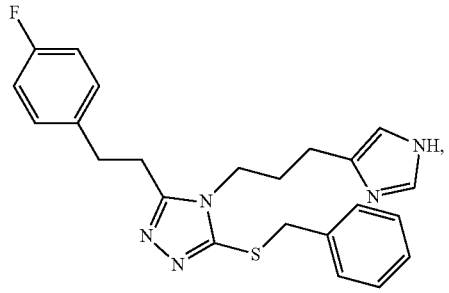
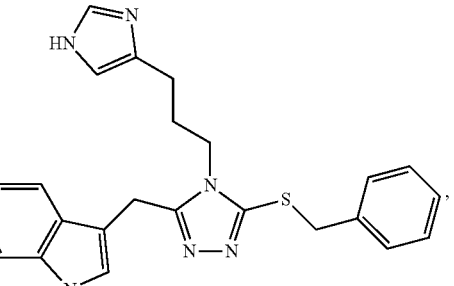
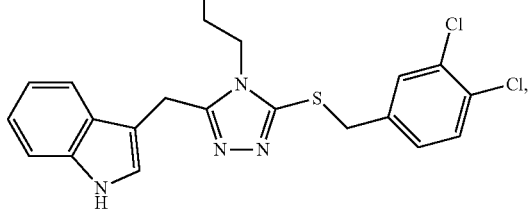

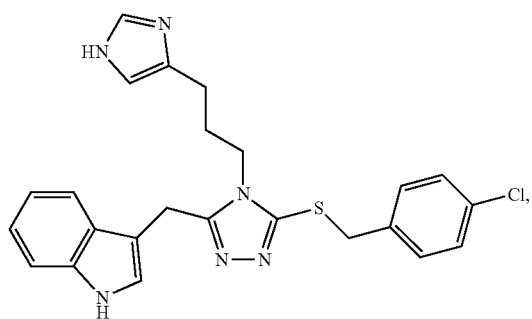
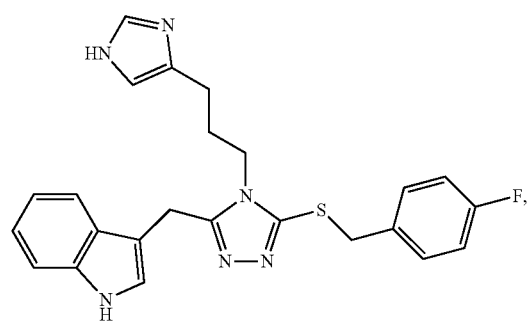
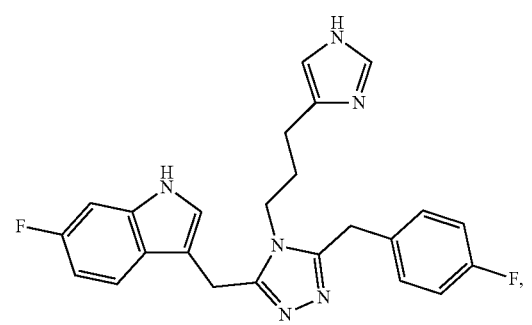
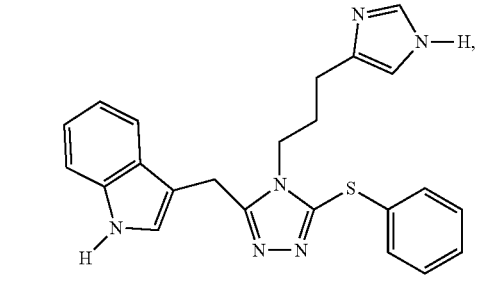
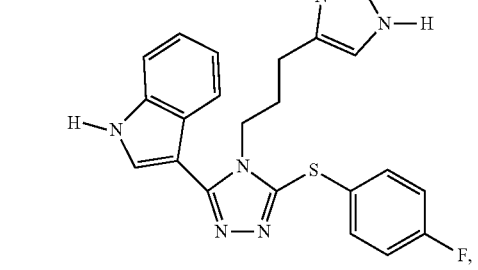
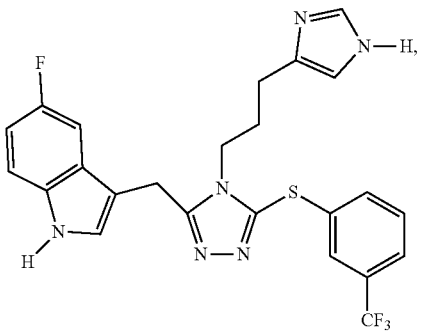
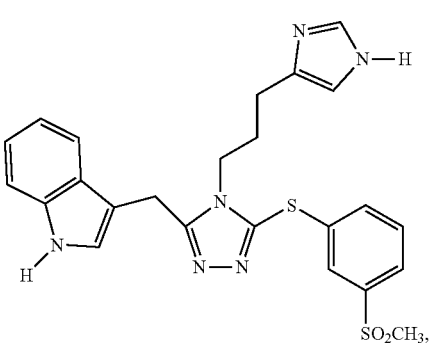
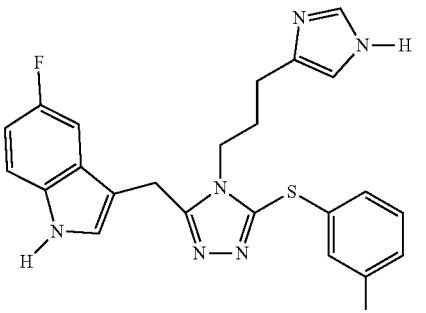
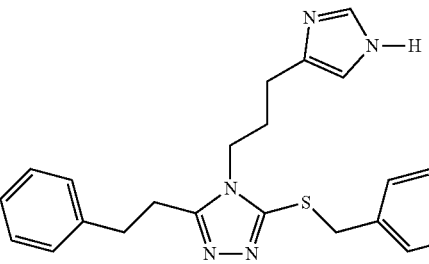
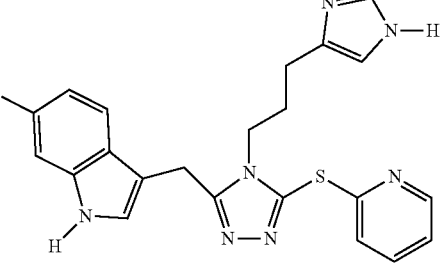

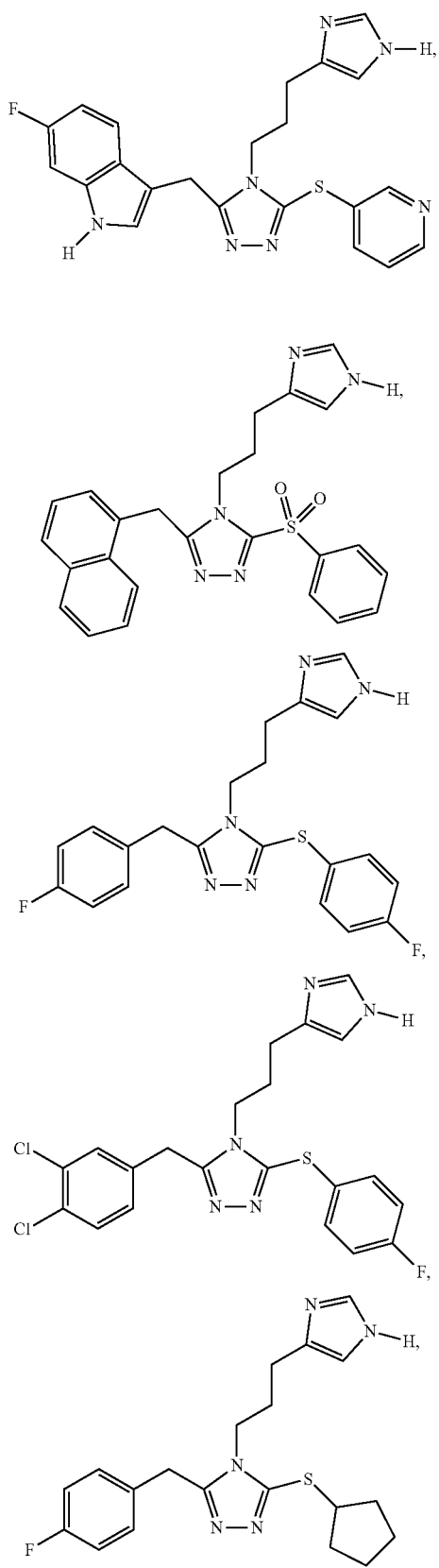
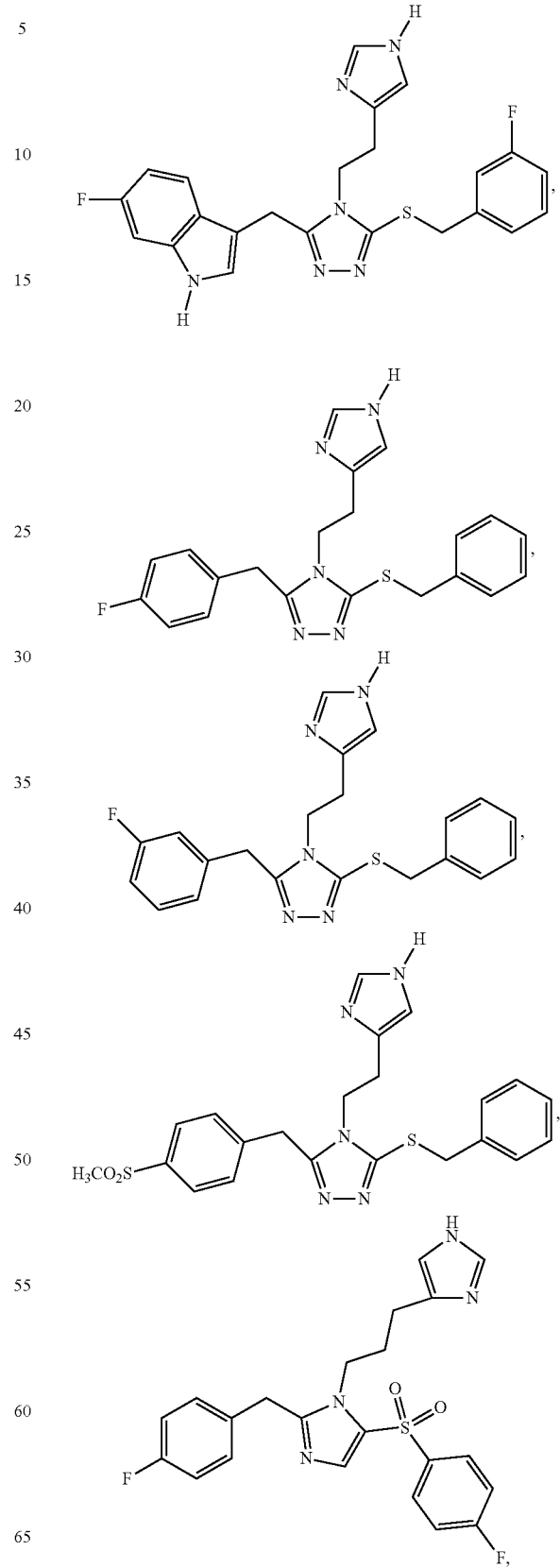

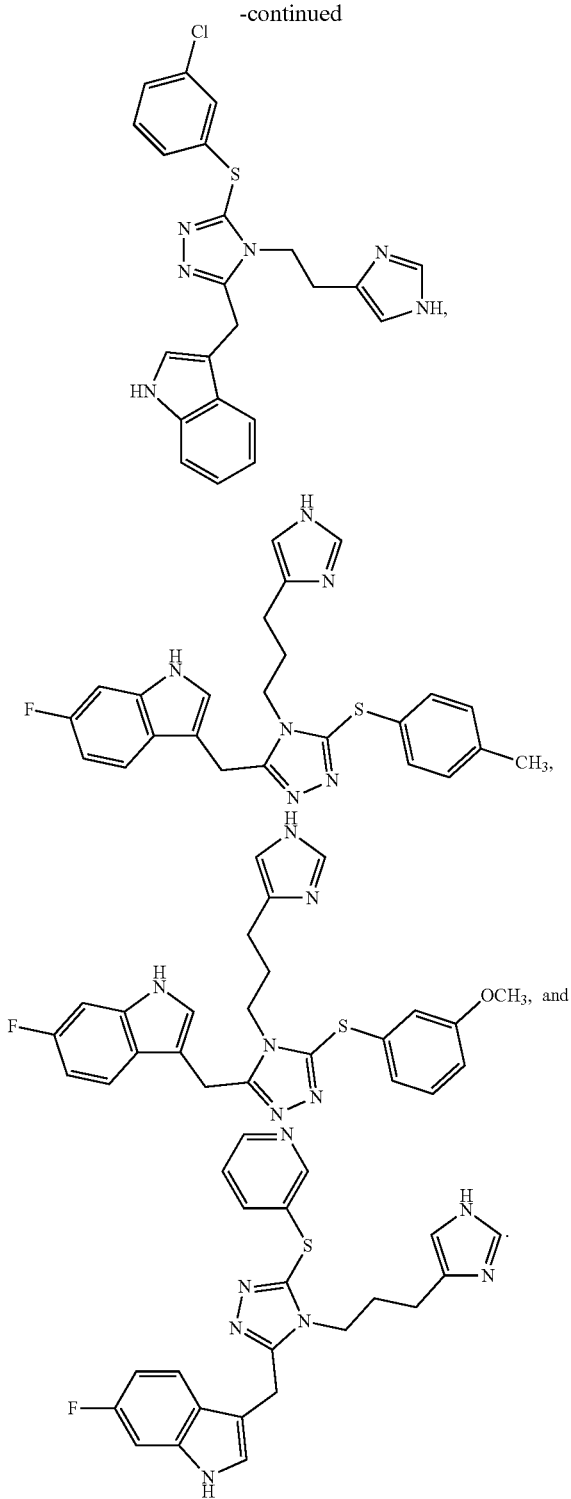

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is ethyl; $R^{15}$ is methyl; $R^7$ is benzene; and $R^{10}$, $R^{11}$, $R^{12}$, $R^{13}$, and $R^{14}$ are hydrogen.

In another aspect, a compound of the disclosure comprises Formula (II), use ⟍ wherein N are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is ethyl; $R^{15}$ is methyl; $R^7$ is benzene; $R^{10}$, $R^{11}$, $R^{12}$, and $R^{14}$ are hydrogen; and $R^{13}$ is chloro.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is ethyl; $R^{15}$ is methyl; $R^7$ is benzene; $R^{10}$, $R^{11}$, $R^{12}$, and $R^{14}$ are hydrogen; and $R^{13}$ is fluoro.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is ethyl; $R^{15}$ is methyl; $R^7$ is benzene; $R^{10}$, $R^{11}$, and $R^{14}$ are hydrogen; and $R^{12}$ and $R^{13}$ are chloro.

In another aspect, a compound of the disclosure comprises Formula (II), wherein ⟍ are single bonds; A, B, and C are nitrogen; D is sulfur; $R^1$ is benzene; $R^2$ is propyl; and $R^3$, $R^4$, and $R^5$ are hydrogen; $R^6$ and $R^8$ are hydrogen; $R^9$ is ethyl; $R^{15}$ is methyl; $R^7$ is benzene; and $R^{10}$, R, $R^{12}$, $R^{13}$, and $R^{14}$ are hydrogen.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; and $R^{10}$, R, $R^{12}$, $R^{13}$, and $R^{14}$ are hydrogen.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; $R^{10}$, $R^{11}$, $R^{12}$, and $R^{14}$ are hydrogen; and $R^{13}$ is trifluoromethyl.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; $R^{10}$, $R^{11}$, $R^{12}$, and $R^{14}$ are hydrogen; and $R^{13}$ is fluoro.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; $R^{10}$, $R^{11}$, and $R^{14}$ are hydrogen; and $R^{15}$ and $R^{13}$ chloro.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; $R^{10}$, $R^{11}$, $R^{12}$, and $R^{14}$ are hydrogen; and $R^{13}$ is bromo.

In another aspect, a compound of the disclosure comprises Formula (II), wherein ⟍ are single bonds; A, B, and C are nitrogen; D is sulfur; $R^1$ is 3-fluorobenzene; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; and $R^{10}$, $R^{11}$, $R^{12}$, $R^{13}$, and $R^{14}$ are hydrogen.

In another aspect, a compound of the disclosure comprises Formula (II), wherein ⟍ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; and $R^{10}$, $R^{11}$, $R^{12}$, $R^{13}$, and $R^{14}$ are hydrogen.

In another aspect, a compound of the disclosure comprises Formula (II), wherein ⸜ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; $R^{10}$, $R^{13}$, and $R^{14}$ are hydrogen; and $R^{11}$ and $R^{12}$ is chloro.

In another aspect, a compound of the disclosure comprises Formula (II), wherein ⸜ are single bonds; A, B, and C are nitrogen; D is sulfur; $R^1$ is 3-indole; $R^2$ is propyl; and $R^3$, $R^4$, and $R^5$ are hydrogen; $R^6$ and $R^8$ are hydrogen; $R^9$ is methyl; $R^{15}$ is methyl; $R^7$ is benzene; $R^{10}$, $R^{11}$, $R^{13}$, and $R^{14}$ are hydrogen; and $R^{12}$ is chloro.

In another aspect, a compound of the disclosure comprises Formula (II), wherein ⸜ are single bonds; A, B, and C are nitrogen; D is sulfur; $R^1$ is 3-indole; $R^2$ is propyl; and $R^3$, $R^4$, and $R^5$ are hydrogen; $R^6$ and Ware hydrogen; $R^9$ is methyl; $R^{15}$ is methyl; $R^7$ is benzene; $R^{10}$, $R^{11}$, $R^{13}$, and $R^{14}$ are hydrogen; and $R^{12}$ is fluoro.

In another aspect, a compound of the disclosure comprises Formula (II), wherein are single bonds; A, B, and C are nitrogen; D is sulfur; $R^1$ is 6-fluoro-3-indole; $R^2$ is propyl; and $R^3$, $R^4$, and $R^5$ are hydrogen; $R^6$, $R^7$, and Ware absent; $R^9$ is methyl; $R^{15}$ is methyl; $R^7$ is benzene; $R^{10}$, $R^{11}$, $R^{13}$, and $R^{14}$ are hydrogen; and $R^{12}$ is fluoro.

In another aspect, a compound of the disclosure comprises Formula (II), wherein ⸜ are single bonds; A, B, and C are nitrogen; D is sulfur; $R^1$ is 6-fluoro-3-indole; $R^2$ is propyl; and $R^3$, $R^4$, and $R^5$ are hydrogen; $R^6$, $R^7$, and Ware absent; $R^9$ is methyl; $R^{15}$ is benzene; $R^{10}$, $R^{11}$, $R^{13}$, and $R^{14}$ are hydrogen; and $R^{12}$ is methyl.

In another aspect, a compound of the disclosure comprises Formula (II), wherein ⸜ are single bonds; A, B, and C are nitrogen; D is sulfur; $R^1$ is 6-fluoro-3-indole; $R^2$ is propyl; and $R^3$, $R^4$, and $R^5$ are hydrogen; $R^6$, $R^7$, and Ware absent; $R^9$ is methyl; $R^{15}$ is benzene; $R^{10}$, $R^{12}$, $R^{13}$, and $R^{14}$ are hydrogen; and $R^{11}$ is methoxy.

In another aspect, a compound of the disclosure comprises Formula (II), wherein ⸜ are single bonds; A, B, and C are nitrogen; D is sulfur; $R^1$ is 6-fluoro-3-indole; $R^2$ is propyl; and $R^3$, $R^4$, and $R^5$ are hydrogen; $R^6$, $R^7$, and $R^8$ are absent; $R^9$ is methyl; $R^{15}$ is 5-pyridinyl.

It will be understood that depending upon the selection of certain substituents, certain compounds within the scope of general Formula (I) may be more readily synthesizable than other compounds also within the scope within Formula (I). Similarly, certain compounds within the scope of general Formula (II) are more readily synthesizable than other compounds also within the scope of general Formula (II). Art-recognized principles and routine methods can be used for identifying the most readily synthesized compounds within the scope of the disclosure.

In another aspect, the present disclosure provides processes of manufacture of the novel compounds as disclosed herein, and of any prodrug forms thereof.

In another aspect, the present disclosure provides a pharmaceutically acceptable salt, hydrate or solvate of any of the compounds disclosed herein, which are encompassed by general Formula (I) or Formula (II). Pharmaceutically acceptable salts include for example salts of inorganic or organic acids as well known in the art. Any compound of general Formula (I) or Formula (II), or a pharmaceutically acceptable salt, hydrate, solvate or prodrug of any thereof, is optionally combined with one or more pharmaceutically acceptable carriers or excipients to provide a pharmaceutical composition.

In another aspect, the present disclosure provides methods of using the 3,4,5-trisubstituted-1,2,4-triazoles and 3,4,5-trisubstituted-3-thio-1,2,4-triazole analogues disclosed herein as somatostatin receptor subtype-4 (SSTR4) agonists for use in the prevention and/or treatment of diseases or disorders related to SSTR4, e.g., disorders caused or influenced by activation of SSTR4. Such disorders include but are not limited to various forms of pain, including chronic, acute, visceral and neuropathic pain; and inflammation and inflammation-related disorders. Thus, any of the novel compounds disclosed herein can be used as a medicament for the treatment of pain, inflammation or inflammation-related disorders. Inflammation-related disorders include disorders of the cardiovascular, respiratory, gastrointestinal, nervous and skeletal systems which involve inflammation. Such disorders include, for example, atherosclerosis; thrombosis; diseases of the lungs and airways such as asthma, bronchitis, chronic obstructive lung disease (COPD) and emphysema; diseases of the gastrointestinal system including pancreatitis, Crohn's disease, irritable bowel syndrome, and ulcerative colitis; diabetes-associated disorders such as diabetic nephropathy, neuropathy, retinopathy, and vasculopathy; disorders of the eye including conjunctivitis, blepharitis, iritis, uveitis and glaucoma; disorders of skeletal joints and connective tissue including arthritis and back pain; diseases and disorders of the central nervous system including epilepsy, dementia, Alzheimer's disease, learning disorders, neurodegenerative diseases such as Parkinson's Disease, multiple sclerosis, and amyotrophic lateral sclerosis, and psychiatric disorders such as anxiety and depression; morbid obesity; and cancer including benign and malignant tumors.

Any of the compounds of Formula (I) or Formula (II) are useful for the prevention and/or treatment of pain or inflammation, such as pain or inflammation associated with any one of the diseases or disorders disclosed herein. According to the present disclosure, a method of treatment for pain or inflammation comprises administering a therapeutically effective amount of a compound of Formula (I) or Formula (II) to a subject in need thereof. The subject is a mammal, for example, a human. A therapeutically effective amount of the compound of Formula (I) or Formula (II) will vary with the compound, the subject, the degree and severity of the disorder being treated, and the route of administration, and can be readily determined according to guidance generally available to those of skill in the art, using routine methods of optimization as needed. Usually an effective amount is a range of about 0.01 milligrams (mg) to about 100 mg/kilogram (kg) of body weight of the subject, which may be contained in a single dose or in doses formulated for administration multiple (e.g., 2, 3 or 4) times per day. The therapeutically effective amount of the compound may be contained together with a pharmaceutically acceptable carrier or excipient in a pharmaceutical composition as described herein.

Definitions

When introducing elements of the different aspects as described herein, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

"Alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_{1-20}$ alkyl), 1 to 10 carbon atoms ($C_{1-10}$ alkyl), 1 to 8 carbon atoms ($C_{1-8}$ alkyl), 1 to 6 carbon atoms ($C_{1-4}$ alkyl), or 1 to 4 carbon atoms ($C_{1-4}$ alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

"Alkenyl" as used herein alone or as part of a group refers to monovalent hydrocarbon radicals having a straight or branched hydrocarbon chains having one or more double bonds and containing from 2 to about 18 carbon atoms, from 2 to about 8 carbon atoms, or from 2 to about 5 carbon atoms. Examples of suitable alkenyl radicals include ethenyl, propenyl, alkyl, 1,4-butadienyl and the like.

"Alkynyl" as used herein alone or as part of a group refers to monovalent hydrocarbon radicals having a straight or branched hydrocarbon chains having one or more triple bonds and containing from 2 to about 10 carbon atoms, or from 2 to about 5 carbon atoms. Examples of alkynyl radicals include ethynyl, propynyl, (propargyl), butynyl and the like.

"Aryl" as used herein, alone or as part of a group, includes an organic radical derived from an aromatic hydrocarbon by removal of one hydrogen, and includes monocyclic and polycyclic radicals, such as phenyl, biphenyl, naphthyl.

"Alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy and the like.

"Cycloalkyl" as used herein, alone or in combination, means a saturated or partially saturated monocyclic, bicyclic or tricyclic alkyl radical wherein each cyclic moiety contains from 3 to 8 carbon atoms, or from 3 to 6 carbon atoms. Examples of such cycloalkyl radicals include cyclopropyl, cyclobutyl, cyclopentyl, cyclohexyl and the like.

"Cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups. "Unsubstituted" means that the carbon chain or ring contains no other substituents other than carbon and hydrogen.

"Hydrocarbon group" means a chain of 1 to 25 carbon atoms, 1 to 12 carbon atoms, 1 to 10 carbon atoms, or 1 to 8 carbon atoms. Hydrocarbon groups may have a linear or branched chain structure. Suitably the hydrocarbon groups have one branch.

"Carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, 4 to 7 carbon atoms, or 5 to 6 carbon atoms in the ring. Bicyclic carbocyclic groups contain 8 to 12 carbon atoms, or 9 to 10 carbon atoms in the rings.

"Heteroatom" means an atom other than carbon e.g., in the ring of a heterocyclic group or the chain of a heterogeneous group. Heteroatoms may be selected from the group consisting of sulfur, phosphorous, nitrogen, and oxygen atoms. Groups containing more than one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), 4 to 7, or 5 to 6 in the ring. Bicyclic heterocyclic groups contain 8 to 18 member atoms, 9 or 10 in the rings.

"Isomer," "isomeric form," "stereochemically isomeric forms," or "stereoisomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E- or Z-configuration. All stereochemically isomeric forms of said compound both in pure form or in admixture with each other are intended to be embraced within the scope of the present disclosure.

EXAMPLES

The following examples are included to demonstrate various aspects of the present disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific examples which are disclosed and still obtain a like or similar result without departing from the spirit and scope of the disclosure.

The compounds of the present disclosure may be prepared in a number of ways well known to one skilled in the art of organic synthesis. More specifically, the novel compounds of this disclosure may be prepared using the reactions and techniques described herein. In the description of the synthetic methods described below, it is to be understood that all proposed reaction conditions, including choice of solvent, reaction atmosphere, reaction temperature, duration of the experiment and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used. Unless otherwise stated, the starting materials for the examples contained herein are either commercially available or are readily prepared by standard methods from known materials. The compounds of Formula (I) or (II) may be synthesized through standard organic chemistry methodology and purification known to those trained in the art of organic synthesis by using commercially available starting materials and reagents.

All reactions were performed under a positive pressure of dry argon unless otherwise indicated. Analytical thin layer chromatography (TLC) was performed on ANALTECH 0.15 mm silica gel 60-GF254 plates. Visualization was accomplished with exposure to UV light, exposure to Iodine or by dipping in an ethanolic phosphomolybdic acid solution followed by heating. Solvents for extraction were HPLC or ACS grade. Flash chromatography was performed with DYNAMIC ADSORBENTS silica gel 60A (32-63μ, 230-400 mesh) with the indicated solvent system. NMR spectra were collected on a JEOL ECS-400 NMR spectrometer. $^1$H NMR spectra were reported in ppm from tetramethylsilane (TMS) on the δ scale. Data are reported as follows: chemical shift, multiplicity (s=singlet, d=doublet, t=triplet, q=quartet, quint=quintet, etc.; m=multiplet, complex multiplets used where overlapping multiplets are not resolved, b=broadened, obs=obscured, ABq=AB quartet, "apparent" used (e.g. apparent t) when spin systems are distorted due to non-first order effects), coupling constants (Hz), and assignments or relative integration where appropriate. $^{13}$C NMR spectra were reported in ppm from the central deuterated solvent peak (multiplicities indicated when determined). Grouped shifts are provided where an ambiguity has not been resolved. LCMS were run on a WATERS ALLIANCE—SQ 3100 system using a Thermo Scientific HYPERSIL GOLD (C18, 4.6×150 mm, 5-Micron) column and acetonitrile-water (0.05% trifluoroacetic acid) gradients.

The following abbreviations are used herein: ACN=acetonitrile; $CH_2Cl_2$=dichloromethane; DCC=N,N-Dicyclohexylcarbodiimide; DIAD=diisopropyl azodicarboxylate; DMF=dimethylformamide; DMSO=dimethylsulfoxide; EDC=N'-ethylcarbodiimide hydrochloride; HCl=hydrochloric acid; HOBt·$H_2O$=1-hydroxybenzotriazole hydrate; IRMS=high resolution mass spectroscopy; Hz=hertz; LCMS=liquid chromatography mass spectroscopy; $LiAlH_4$=lithium aluminum hydride; MeOH=methanol; $Na_2SO_4$=sodium sulfate; TEA=triethylamine; TFA=trifluoroacetic acid; THF=tetrahydrofuran; Trt-Cl=trityl chloride; Pd/C=palladium on carbon; $PPh_3$=triphenylphosphine; ppm=parts per million; and $SiO_2$=silicon dioxide.

Example 1: Synthesis of 3,4,5-Trisubstituted-1,2,4-Triazoles

Synthesis of (E)-methyl 3-(1H-imidazol-4-yl)acrylate hydrochloride (2)

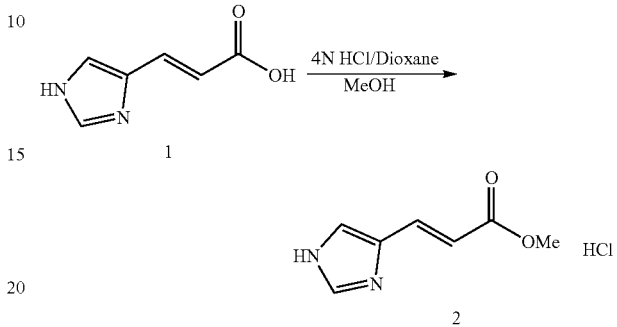

Urocanic acid 1 (25.0 g, 181 mmol) was suspended in MeOH (700 mL) and treated with 4N HCl/Dioxane (118 mL). The resulting mixture was stirred overnight at room temperature. Concentration of the reaction afforded 34.0 g (100% yield) of compound 2 as a white solid: $^1$H NMR (400 MHz, DMSO-$d_6$) δ 9.17 (s, 1H), 8.01 (s, 1H), 7.54 (d, J=16.0 Hz, 1H), 6.81 (d J=16.0 Hz, 1H), 3.69 (s, 3H). LCMS (5-95% acetonitrile in 0.05% TFA over 10 minutes) retention time=4.77 minutes, ESI m/z=153, [M+H]+.

Synthesis of methyl 3-(1H-imidazol-4-yl)propanoate hydrochloride (3)

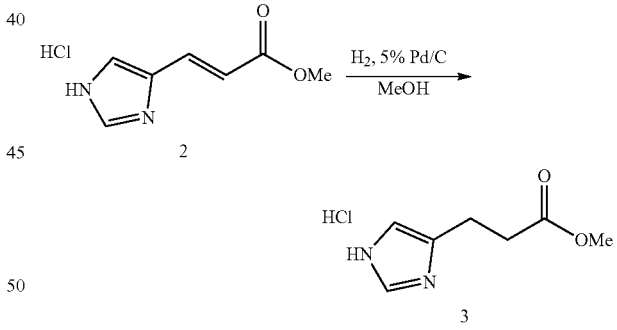

(E)-Methyl 3-(1H-imidazol-4-yl)acrylate hydrochloride (2) (29.4 g, 156 mmol) was dissolved in MeOH (700 mL) in an argon filled glovebox. To this solution was added 5% Pd/C (4 g). The mixture was brought out of the glovebox and fitted with a balloon of $H_2$ gas. The mixture was stirred for 48 hours at room temperature. During this time the balloon was periodically refilled with $H_2$. When the reaction was complete (as judged by LCMS analysis), the mixture was purged with argon and filtered through a pad of CELITE. Concentration of the filtrate afforded 28.9 g (98% yield) of compound 3 as a white solid: $^1$H NMR (400 MHz, DMSO-$d_6$) δ 8.94 (s, 1H), 7.37 (s, 1H), 3.57 (s, 3H), 2.87 (t, J=7.30 Hz, 2H), 2.71 (t, J=7.30 Hz, 2H). $^{13}$C (100 MHz, DMSO-$d_6$) δ 172.58 (s), 133.92 (d), 132.55 (s), 116.13 (d), 52.08 (q), 32.42 (t), 20.01 (t). LCMS (5-95% acetonitrile in 0.05% TFA over 10 minutes) retention time=3.67 minutes, ESI m/z=155, [M+H]$^+$.

Synthesis of methyl 3-(1-trityl-1H-imidazol-4-yl)propanoate (4)

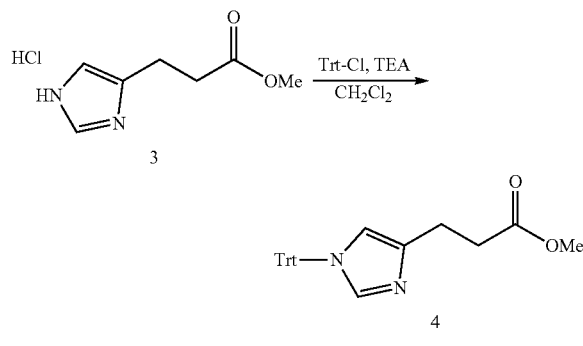

Methyl 3-(1H-imidazol-4-yl)propanoate hydrochloride (3) (15.0 g, 78.7 mmol) was dissolved in CH$_2$Cl$_2$ (400 mL) and treated with trimethylamine (23.0 mL, 165 mmol). To this stirred mixture was added a solution of triphenylmethyl chloride (21.9 g, 78.7 mmol) in CH$_2$Cl$_2$ (200 mL) dropwise. After stirring for 16 hours at room temperature, the mixture was transferred to a separatory funnel and washed with water (2×250 mL). The organic layer was dried (Na$_2$SO$_4$), filtered and concentrated. The residue was recrystallized from methanol-water to afford 24.1 g (77% yield) of compound 4 as a white solid: $^1$H NMR (400 MHz, CHCl$_3$) δ 7.30-7.34 (complex multiplets, 10H), 7.08-7.13 (m, 5H), 6.53 (s, 1H), 3.60 (s, 3H), 2.86 (t, J=7.80 Hz, 2H), 2.64 (t, J=7.30 Hz, 2H). $^{13}$C NMR (100 MHz, CHCl$_3$) δ 173.70 (s), 142.51 (s), 139.97 (d), 138.46 (s), 129.86 (d), 128.08 (d), 118.18 (d), 75.61 (s), 51.61 (q), 33.97 (t), 23.93 (t). LCMS (50-95% acetonitrile in 0.05% TFA over 10 minutes) retention time=3.78 minutes, ESI m/z=397, [M+H]$^+$.

Synthesis of 3-(1-trityl-1H-imidazol-4-yl)propan-1-ol (5)

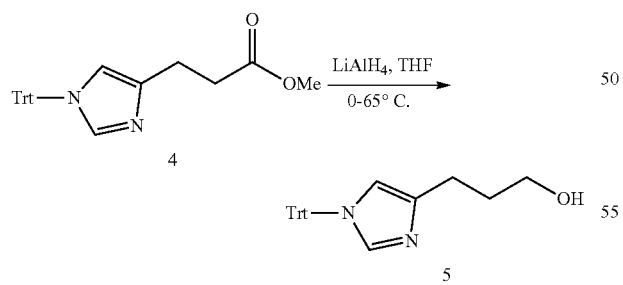

To a solution of methyl 3-(1-trityl-1H-imidazol-4-Apropanoate (4) (56.6 g, 143 mmol) in THF (300 mL) cooled in an ice-salt bath, was added LiAlH$_4$ (100 mL of a 2.4 M solution in THF, 240 mmol) drop-wise at a rate which maintained the temperature under 5° C. The reaction was stirred at 0-5° C. for 10 minutes post-addition, allowed to warm to room temperature (~1 hour) and heated to reflux for 1 hour. The mixture was then cooled to 0-5° C. and carefully quenched by the drop-wise addition of 0.5 N NaOH (20 mL). The mixture was then filtered and the solids washed with CH$_2$Cl$_2$. The filtrate was concentrated to afford 41.2 g (78% yield) of compound 5 as a white solid: $^1$H NMR (400 MHz, CHCl$_3$) δ 7.37 (d, J=1.40 Hz, 1H), 7.31-7.34 (m, 10H), 7.09-7.14 (m, 5H), 6.54 (s, 1H), 3.72 (t, J=6.00 Hz, 2H), 2.68 (t, J=6.90 Hz, 2H), 1.85 (quint., J=6.8 Hz, 2H). $^{13}$C NMR (100 MHz, CHCl$_3$) δ 142.92 (s), 141.57 (d), 138.10 (s), 129.72 (d), 128.69 (d), 128.46 (d), 117.85 (d), 74.84 (s), 60.79 (t), 32.75 (t), 24.96 (t). LCMS (50-95% acetonitrile in 0.05% TFA over 10 minutes) retention time=2.97 minutes, ESI m/z=369, [M+H]$^+$.

Synthesis of 2-(3-(1-trityl-1H-imidazol-4-yl)pro-pypisoindoline-1,3-dione (6)

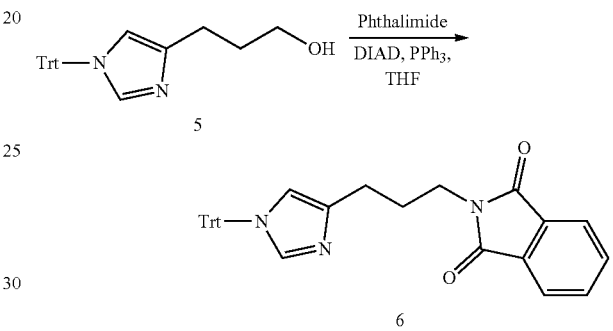

To a solution of 3-(1-trityl-1H-imidazol-4-Apropan-1-ol (5) (11.0 g, 29.9 mmol) in THF (200 mL) was added phthalimide (6.51 g, 44.2 mmol) and triphenylphosphine (11.7 g, 44.6 mmol). The resulting mixture was cooled to 0-5° C. and treated with a solution of diisopropylazodicarboxylate (12.6 mL, 63.8 mmol) in THF (50 mL) dropwise over 2.5 hours. The reaction was allowed to stir for 16 hours and warm to room temperature. The solid product was filtered and washed with cold THF (100 mL). The solid was triturated with hot ACN (~500 mL) and filtered to afford 13.1 g (88% yield) of compound 6 as a fine white powder: $^1$H NMR (400 MHz, CHCl$_3$) δ 7.80 (ddd, J=8.20, 5.00, 1.40 Hz, 2H), 7.68 (ddd, J=8.20, 5.00, 1.40 Hz, 2H), 7.36 (d, J=0.90 Hz, 1H), 7.29-7.33 (m, 10H), 7.09-7.14 (m, 5H), 6.57 (s, 1H), 3.71 (t, J=6.90 Hz, 2HH), 2.60 (t, J=7.40 Hz, 2H), 1.99 (quint., J=7.30 Hz, 2H). LCMS (50-95% acetonitrile in 0.05% TFA over 10 minutes) retention time=5.35 minutes, ESI m/z=498, [M+H]$^+$.

Synthesis of 3-(1-Trityl-1H-imidazol-4-yl)propan-1-amine (7)

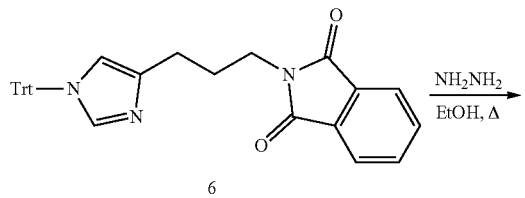

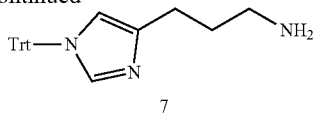

7

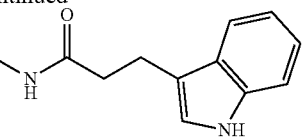

9

A suspension of 2-(3-(1-trityl-1H-imidazol-4yl)propyl)isoindoline-1,3-dione (6) (10.2 g, 20.6 mmol) in ethanol (500 mL) was treated with hydrazine hydrate (8.00 mL of 98%, 162 mmol) and heated to reflux for 5 hours. The reaction mixture was allowed to cool and stir over night. The mixture was filtered to remove the precipitated phthalhydrazide and triturated with $CH_2Cl_2$ (400 mL) for 5 hours. Filtration to remove the remaining phthalhydrazide and concentration of the filtrate afforded 7.66 g (100% yield) of pure amine 7 as an off white foam: $^1$H NMR (400 MHz, CHCl$_3$) δ 7.29-7.32 (m, 10H), 7.09-7.13 (m, 6H), 6.51 (s, 1H), 2.73 (t, J=6.90 Hz, 2H), 2.57 (t, J=7.80 Hz, 2H), 2.41 (bs, 2H), 1.77 (quint., J=6.90 Hz, 2H). $^{13}$C NMR (100 MHz, CHCl$_3$) δ 142.60 (s), 141.23 (d), 138.37 (s), 129.86 (d), 128.08 (d), 117.92 (s), 75.17 (s), 41.67 (t), 32.77 (t), 25.88 (t). LCMS (25-95% acetonitrile in 0.05% TFA over 10 minutes) retention time=5.75 minutes, ESI m/z=368, [M+H]$^+$.

Synthesis of 3-(1H-indol-3-3/1)-N-(3-(1-trityl-1H-imidazol-4-Apropyl) propanamide (9)

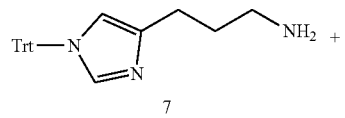

7

To a solution of 3-(1H-indol-3-yl)propanoic acid (8) (5.66 g, 29.9 mmol) in DMF (80 mL) was added EDC·HCl (8.60 g, 44.9 mmol) and HOBt·H$_2$O (5.70 g, 37.2 mmol). The resulting mixture was stirred at room temperature for 45 minutes. A solution of the amine 7 (11.0 g, 29.9 mmol) in DMF (80 mL) and TEA (6.00 mL, 43.0 mmol) was added and the reaction was stirred for 16 hours at room temperature. The mixture was poured into water (500 mL) in a large beaker and stirred for 30 minutes at room temperature. The solid was collected by filtration. Recrystallization from ACN afforded 11.8 g (73% yield) of pure amide 9: $^1$H NMR (400 MHz, DMSO-d$_6$) δ 10.70 (bs, 1H), 7.78 (t, J=5.50 Hz, 1H), 7.46 (d, J=7.80 Hz, 1H), 7.31-7.38 (complex multiplets, 9H), 7.25 (d, J=7.80 Hz, 1H), 7.20 (s, 1H), 7.02-7.05 (m, 7H), 6.99 (t, J=8.20 Hz, 1H), 6.56 (s, 1H), 2.99 (q, J=5.9 Hz, 2H), 2.85 (t, J=7.70 Hz, 2H), 2.34-2.38 (m, 4H), 1.58 (quint., J=7.40 Hz, 2H). $^{13}$C NMR (100 MHz, DMSO-d$_6$) A 172.20 (s), 142.90 (s), 141.17 (d), 138.14 (s), 136.71 (s), 129.72 (d), 128.71 (d), 128.47 (d), 127.54 (s), 122.57 (d), 121.36 (d), 118.87 (d), 118.60 (d), 118.11 (d), 114.3 (s), 111.78 (d), 74.85 (s), 38.58 (t), 36.89 (t), 29.37 (t), 25.79 (t), 21.61 (t). LCMS (50-95% acetonitrile in 0.05% TFA over 10 minutes) retention time=4.87 minutes, ESI m/z=539, [M+H]$^+$.

Synthesis of 3-(1H-indol-3-yl)-N-(3-(1-trityl-1H-imidazol-4-yl)propyl) propanethioamide (10)

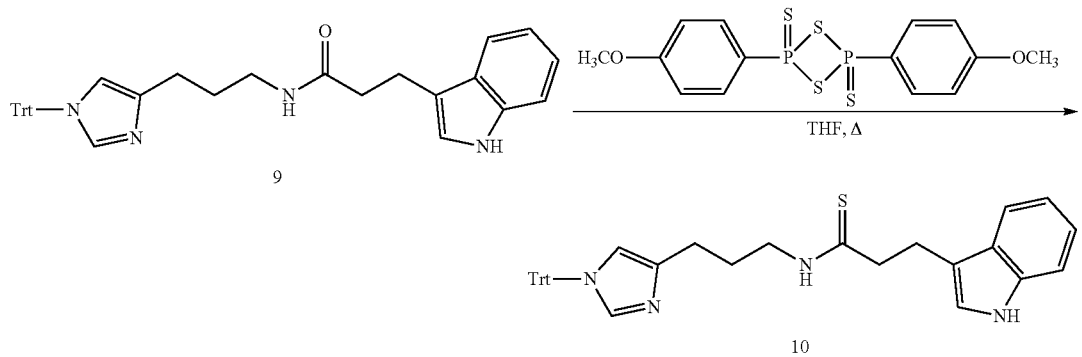

10

A mixture of 3-(1H-indol-3-yl)-N-(3-(1-trityl-1H-imidazol-4-yl)propyl)propanamide (9) (6.46 g, 12.0 mmol) and Lawesson's reagent (3.15 g, 7.80 mmol) in THF (100 mL) was heated to 65° C. for 4 hours. The reaction was cooled and concentrated. The residue was purified by flash column chromatography (SiO$_2$, 10/1 CH$_2$Cl$_2$/MeOH) to afford 3.34 g (50% yield) of thioamide 10 as a tan foam: $^1$H NMR (400 MHz, DMSO-d$_6$) contains a small amount of inseparable imidothioic phosphonate intermediate adduct of the starting amide with Lawesson's reagent (ESI m/z=741, [M+H]$^+$); desired thioamide component: δ 10.73 (bs, 1H), 9.96 (t, J=5.10 Hz, 1H), 7.50 (d, J=7.80 Hz, 1H), 7.34-7.40 (com- -continued

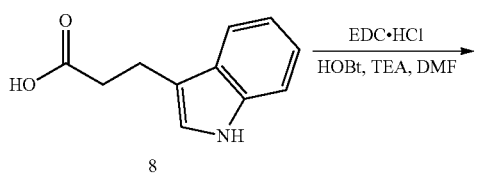

8 plex multiplets, 10H), 7.26 (d, J=7.80 Hz, 1H), 7.05-7.09 (m, 6H), 6.99 (t, J=7.70 Hz, 1H), 6.90 (t, J=7.70 Hz, 1H), 3.43 (apparent q, J=6.00 Hz, 2H), 3.02 (apparent t, J=7.80 Hz, 2H), 2.82 (apparent t, J=7.75 Hz, 2H), 2.42 (t, J=6.80 Hz, 2H), 1.76 (quint, J=7.30 Hz, 2H). $^{13}$C NMR (100 MHz, DMSO-d$_6$) δ 203.79 (s), 142.45 (s), 137.93 (s), 136.70 (d), 129.74 (d), 128.83 (d), 128.63 (d), 127.54 (s), 122.75 (d), 121.41 (d), 118.91 (d), 118.64 (d), 113.86 (s), 111.83 (s), 75.53 (s), 46.51 (t), 45.22 (t), 27.15 (t), 25.67 (t), 25.02 (t). LCMS (50-95% acetonitrile in 0.05% TFA over 10 minutes) retention time=5.85 minutes, ESI m/z=555, [M+H]$^+$ Synthesis of 3-(1-methyl-1H-indol-3-yl)propanoic acid (12)

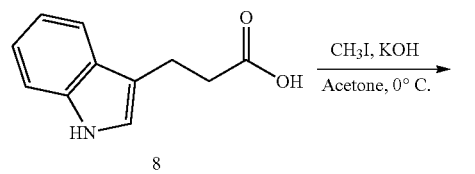

8

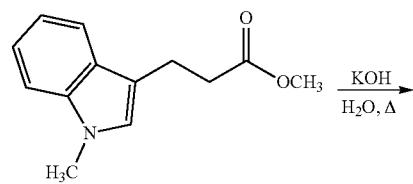

11

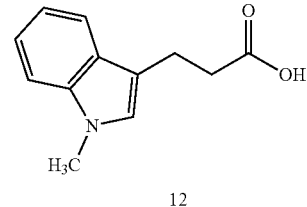

12

To a solution of 3-(1H-indol-3-yl)propanoic acid (8) (3.00 g, 15.9 mmol) in acetone (70 mL) was added methyl iodide (5.00 mL, 80.3 mmol) and KOH (5.30 g, 94.4 mmol) at 0° C. The reaction was stirred for 4 hours and the solvent was evaporated. The residue was dissolved in H$_2$O (100 mL) and treated with KOH (4.50 g, 80.2 mmol). The resulting mixture was refluxed for 2 hours, cooled to 0° C., and acidified to pH ~1 with 6N HCl. The product was isolated by filtration and washed with heptane (~100 mL) to afford 3.20 g (99% yield) of compound 12 as a yellow solid: $^1$H NMR (400 MHz, DMSO-d$_6$) δ 12.06 (bs, 1H), 7.48 (d, J=7.80 Hz, 1H), 7.33 (d, J=8.20 Hz, 1H), 7.09 (t, J=8.20 Hz, 1H), 7.05 (s, 1H), 6.96 (t, J=7.80 Hz, 1H), 3.68 (s, 3H), 2.87 (t, J=7.80 Hz, 2H), 2.53 (t, J=7.40 Hz, 2H). $^{13}$C NMR (100 MHz, DMSO-d$_6$) δ 174.68, 137.13, 127.75, 127.23, 121.59, 118.85, 113.26, 110.06, 35.11, 32.75, 20.66. LCMS (50-95% acetonitrile in 0.05% TFA over 10 minutes) retention time=3.50 minutes, ESI m/z=204, [M+H]$^+$.

Synthesis of 3-(1-methyl-1H-indol-3-yl)-N-(3-(1-trityl-1H-imidazol-4-yl)propyl)-propanamide 13)

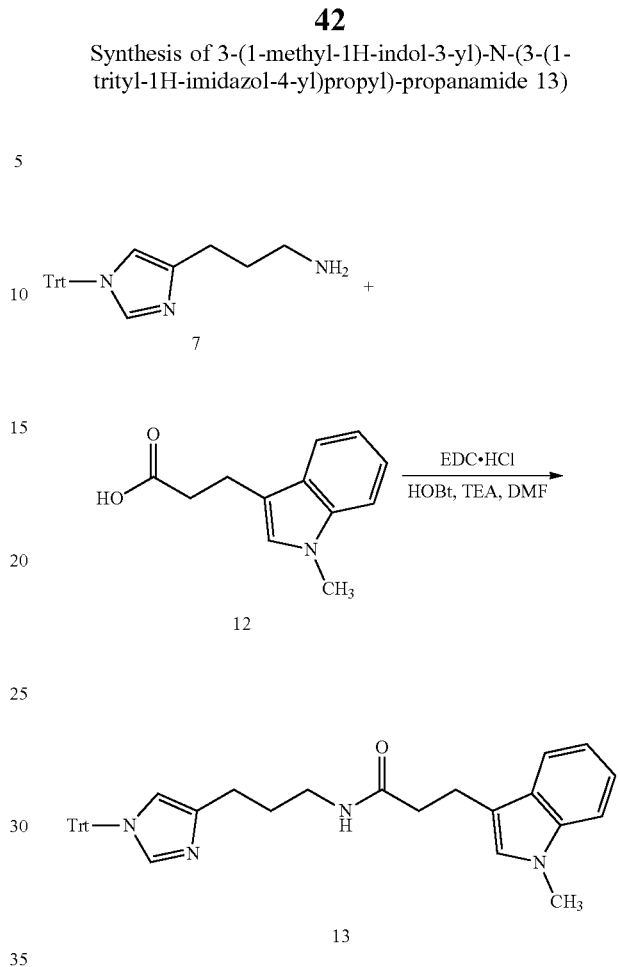

To a solution of 3-(1-methyl-1H-indol-3-yl)propanoic acid (12) (503 mg, 2.47 mmol) in DMF (30 mL) was added EDC·HCl (592 mg, 3.09 mmol) and HOBt·H$_2$O (476 mg, 3.09 mmol). The resulting mixture was stirred at room temperature for 45 minutes. A solution of the amine 7 (908 mg, 2.47 mmol) in DMF (20 mL) and TEA (700 µL, 5.00 mmol) was added and the reaction was stirred for 16 hours at room temperature. The DMF was evaporated and the residue was partitioned with CH$_2$Cl$_2$ (150 mL) and water (150 mL). The layers were separated and the organic solution was washed with saturated NaHCO$_3$ (150 mL) and brine (150 mL). The organic layer was then dried (Na$_2$SO$_4$), filtered and concentrated to afford 650 mg (48% yield) of compound 13 as a tan solid: $^1$H NMR (400 MHz, CDCl$_3$) δ 7.54 (d, J=7.80 Hz, 1H), 7.30-7.34 (complex multiplets, 10H), 7.28 (d, J=4.50 Hz, 1H), 7.22-7.25 (m, 1H), 7.17 (dt, J=6.80, 0.90 Hz, 1H), 7.08-7.11 (m, 5H), 7.02 (dt, J=6.90, 0.90 Hz, 1H), 6.83 (s, 1H), 6.47 (s, 1H), 6.25 (bt, J=4.60 Hz, 1H), 3.66 (t, 3H), 3.22 (apparent q, J~6.00 Hz, 2H), 3.07 (t, J=7.30 Hz, 2H), 2.51 (t, J=7.80 Hz, 2H), 2.44 (t, J=7.30 Hz, 2H), 1.72 (quint, J=6.80 Hz, 2H). $^{13}$C NMR (100 MHz, CDCl$_3$) δ 172.85, 142.40, 140.61, 138.17, 137.05, 129.81, 128.15, 128.01, 126.57, 121.57, 118.93, 118.76, 118.25, 113.72, 109.24, 75.36, 39.11, 37.75, 32.63, 28.55, 25.46, 21.45. LCMS (50-95% acetonitrile in 0.05% TFA over 10 minutes) retention time=6.40 minutes, ESI m/z=553, [M+H]$^+$.

Synthesis of 3-(1-methyl-1H-indol-3-0-N-(3-(1-trityl-1H-imidazol-4-yl)propyl)propanethioamide 14)

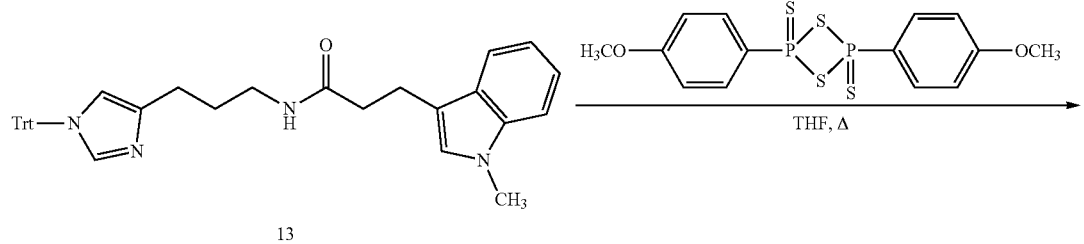

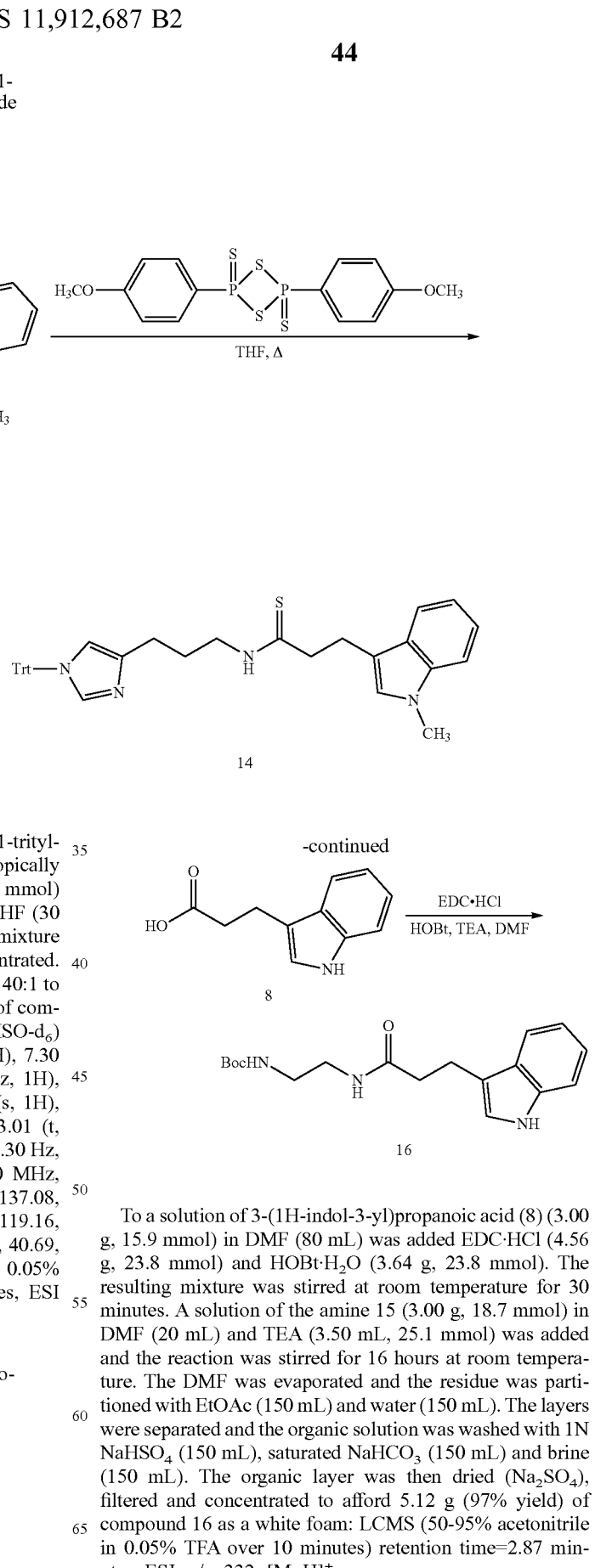

A solution of 3-(1-methyl-1H-indol-3-yl)-N-(3-(1-trityl-1H-imidazol-4-yl)propyl)-propanamide (13) (azeotropically dried by coevaporation with toluene, 620 mg, 1.12 mmol) and Lawesson's reagent (295 mg, 0.73 mmol) in THF (30 mL) was heated to 65° C. for 4 hours. The resulting mixture was allowed to cool to room temperature and concentrated. Purification by flash column chromatography (SiO$_2$, 40:1 to 20:1 CH$_2$Cl$_2$/MeOH) afforded 470 mg (78% yield) of compound 14 as a yellow foam: $^1$H NMR (400 MHz, DMSO-d$_6$) δ 9.92 (bt, J~5.00 Hz, 1H), 7.51 (d, J=8.20 Hz, 1H), 7.30 7.39 (complex multiplets, 10H), 7.27 (t, J=8.20 Hz, 1H), 7.02-7.06 (m, 7H), 6.93 (t, J=7.30 Hz, 1H), 6.60 (s, 1H), 3.62 (s, 3H), 3.42 (apparent q, J~6.20 Hz, 2H), 3.01 (t, J=7.40 Hz, 2H), 2.79 (t, J=7.30 Hz, 2H), 2.36 (t, J=7.30 Hz, 2H), 1.73 (quint, J=7.30 Hz, 2H). $^{13}$C NMR (100 MHz, DMSO-d$_6$) δ 203.59, 142.71, 140.29, 138.09, 137.08, 129.73, 128.77, 128.53, 127.85, 127.25, 121.53, 119.16, 118.73, 118.39, 113.15, 109.98, 75.13, 46.56, 45.33, 40.69, 32.70, 27.27, 25.45. LCMS (50-95% acetonitrile in 0.05% TFA over 10 minutes) retention time=6.40 minutes, ESI m/z=569, [M+H]$^+$.

Synthesis of tert-butyl (2-(3-(1H-indol-3-yl)propanamido)ethyl) carbamate (16)

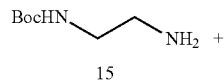

To a solution of 3-(1H-indol-3-yl)propanoic acid (8) (3.00 g, 15.9 mmol) in DMF (80 mL) was added EDC·HCl (4.56 g, 23.8 mmol) and HOBt·H$_2$O (3.64 g, 23.8 mmol). The resulting mixture was stirred at room temperature for 30 minutes. A solution of the amine 15 (3.00 g, 18.7 mmol) in DMF (20 mL) and TEA (3.50 mL, 25.1 mmol) was added and the reaction was stirred for 16 hours at room temperature. The DMF was evaporated and the residue was partitioned with EtOAc (150 mL) and water (150 mL). The layers were separated and the organic solution was washed with 1N NaHSO$_4$ (150 mL), saturated NaHCO$_3$ (150 mL) and brine (150 mL). The organic layer was then dried (Na$_2$SO$_4$), filtered and concentrated to afford 5.12 g (97% yield) of compound 16 as a white foam: LCMS (50-95% acetonitrile in 0.05% TFA over 10 minutes) retention time=2.87 minutes, ESI m/z=332, [M+H]$^+$.

Synthesis of tert-butyl (2-(3-(1H-indol-3-yl)
Drobanethioamido)ethyl) carbamate (17)

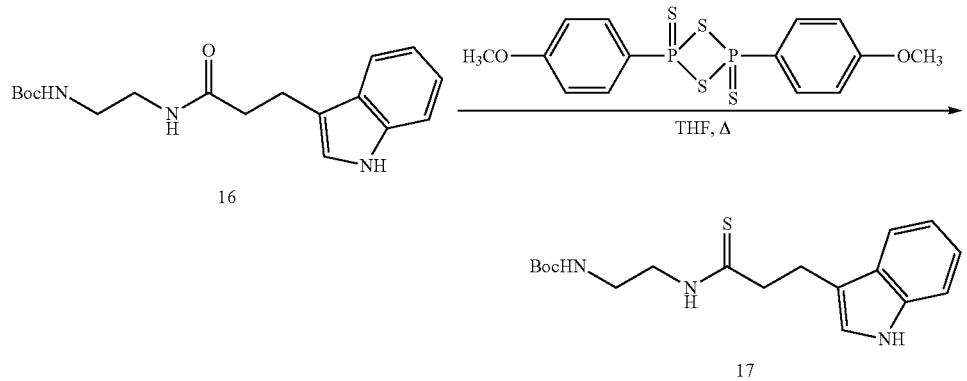

16

17

A solution of tert-butyl (2-(3-(1H-indol-3-yl)propanamido)ethyl)carbamate (16) (azeotropically dried by coevaporation with toluene, 4.74 g, 14.3 mmol) and Lawesson's reagent (3.18 g, 7.86 mmol) in THF (50 mL) was heated to 65° C. for 4 hours. The resulting mixture was allowed to cool to room temperature and concentrated. Purification by flash column chromatography (SiO$_2$, 3:1 hexanes/EtOAc to 1:1) afforded 3.86 g (78% yield) of compound 17 as an orange foam: LCMS (50-95% acetonitrile in 0.05% TFA over 10 minutes) retention time=5.45 minutes, ESI m/z=348, [M+H]$^+$.

Synthesis of tert-butyl (4-(3-(1H-indol-3-yl)propanamido)butyl) carbamate (19)

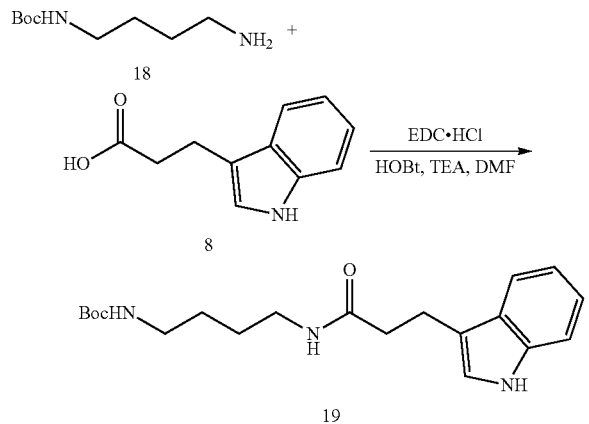

19

To a solution of 3-(1H-indol-3-yl)propanoic acid (8) (1.00 g, 5.29 mmol) in DMF (40 mL) was added EDC·HCl (1.52 g, 7.93 mmol) and HOBt·H$_2$O (1.21 g, 7.93 mmol). The resulting mixture was stirred at room temperature for 30 minutes. A solution of the amine 18 (1.10 g, 5.82 mmol) in DMF (10 mL) and TEA (1.50 mL, 10.8 mmol) was added and the reaction was stirred for 16 hours at room temperature. The DMF was evaporated and the residue was partitioned with EtOAc (150 mL) and water (150 mL). The layers were separated and the organic solution was washed with 1N NaHSO$_4$ (150 mL), saturated NaHCO$_3$ (150 mL) and brine (150 mL). The organic layer was then dried (Na$_2$SO$_4$), filtered and concentrated to afford 1.90 g (100% yield) of compound 19 as a white foam: $^1$H NMR (400 MHz, CDCl$_3$) δ 8.59 (bs, 1H0, 7.59 (d, J=7.80 Hz, 1H), 7.36 (d, J=8.20 Hz, 1H), 7.17 (t, J=7.30 Hz, 1H), 7.09 (t, J=7.20 Hz, 1H), 6.99 (d, J=1.40 Hz, 1H), 5.47 (bs, 1H), 4.59 (bs, 1H), 3.09-3.13 (m, 4H), 2.97-3.02 (m, 2H), 2.54 (t, J=6.90 Hz, 2H), 1.45 9s, 9H), 1.17-1.31 (complex multiplets, 4H). $^{13}$C NMR (100 MHz, CDCl$_3$) δ 173.05, 156.39, 136.51, 127.09, 122.33, 121.98, 118.71, 114.53, 111.47, 79.51, 40.30, 39.12, 37.60, 28.57, 27.69, 26.79, 21.68. LCMS (40-95% acetonitrile in 0.05% TFA over 10 minutes) retention time=3.83 minutes, ESI m/z=360, [M+H]$^+$.

Synthesis of tert-butyl (4-(3-(1H-indol-3-yl)propanethioamido)butyl) carbamate (20)

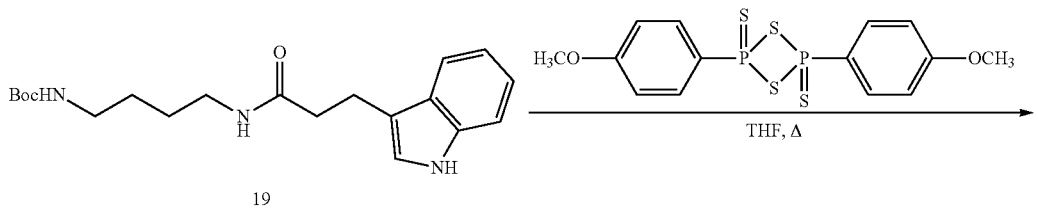

19

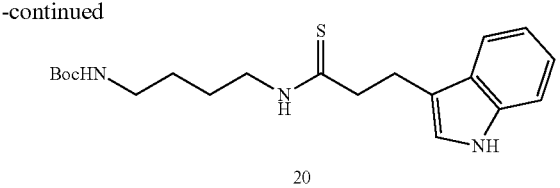

A solution of tert-butyl (4-(3-(1H-indol-3-yl)propanamido)butyl)carbamate (19) (azeotropically dried by coevaporation with toluene, 654 mg, 1.82 mmol) and Lawesson's reagent (404 mg, 1.00 mmol) in THF (50 mL) was heated to 65° C. for 1 hour. The resulting mixture was allowed to cool to room temperature and concentrated. Purification by flash column chromatography (SiO$_2$, 1:1 hexanes/EtOAc) afforded 471 mg (69% yield) of compound 20 as a yellow foam: $^1$H NMR (400 MHz, CDCl$_3$) δ 8.58 (bs, 1H), 7.61 (d, J=7.80 Hz, 1H), 7.39 (d, J=8.30 Hz, 1H), 7.32 (bs, 1H), 7.18 (dt, J=7.10, 0.90 Hz, 1H), 7.10 (dt, J=7.80, 0.90 Hz, 1H), 7.01 (s, 1H), 4.56 (bs, 1H), 3.46 (apparent q, J=5.95 Hz, 2H), 3.25 (t, J=6.90 Hz, 2H), 3.02 (t, J=6.90 Hz, 2H), 2.95 (bt, J~6.40 Hz, 1H), 1.46 (s, 9H), 1.27-1.34 (m, 2H), 1.10-1.18 (m, 2H). LCMS (40-95% acetonitrile in 0.05% TFA over 10 minutes) retention time=5.78 minutes, ESI m/z=376, [M+H]$^+$.

Synthesis of tert-butyl (5-(3-(1H-indol-3-yl)propanamido)pentyl) carbamate (22)

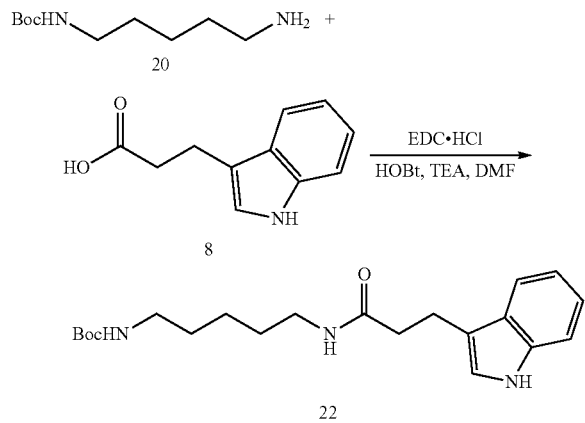

To a solution of 3-(1H-indol-3-yl)propanoic acid (8) (1.00 g, 5.29 mmol in DMF (30 mL) was added EDC·HCl (1.52 g, 7.93 mmol) and HOBt·H$_2$O (1.21 g, 7.93 mmol). The resulting mixture was stirred at room temperature for 30 minutes. A solution of the amine 21 (1.18 g, 5.82 mmol) in DMF (10 mL) and TEA (2.00 mL, 14.3 mmol) was added and the reaction was stirred for 16 hours at room temperature. The DMF was evaporated and the residue was partitioned with EtOAc (150 mL) and water (150 mL). The layers were separated and the organic solution was washed with 1N NaHSO$_4$ (150 mL), saturated NaHCO$_3$ (150 mL) and brine (150 mL). The organic layer was then dried (Na$_2$SO$_4$), filtered and concentrated to afford 1.99 g (100% yield) of compound 22 as a tan foam: $^1$H NMR (400 MHz, CDCl$_3$) δ 9.06 (bs, 1H), 7.58 (d, J=7.80 Hz, 1H), 7.38 (d, J=7.80 Hz, 1H), 7.17 (dt, J=6.90, 1.00 Hz, 1H), 7.09 (dt, J=7.80, 0.90 Hz, 1H), 7.00 (d, J=2.30 Hz, 1H), 5.34 (bs, 1H), 4.62 (bs, 1H), 3.07-3.13 (m, 4H), 3.02 (apparent q, J~6.75 Hz, 2H), 2.54 (t, J=7.30 Hz, 2H), 1.46 (s, 9H), 1.33 (quint, J=7.30 Hz, 2H), 1.20-1.26 (m, 2H), 0.93-1.01 (m, 2H). $^{13}$C NMR (100 MHz, CDCl$_3$) δ 173.05, 156.49, 136.67, 127.02, 122.42, 121.86, 119.17, 118.60, 114.21, 111.57, 79.57, 40.50, 39.16, 37.59, 30.05, 29.15, 28.55, 23.70, 21.72. LCMS (40-95% acetonitrile in 0.05% TFA over 10 minutes) retention time=4.12 minutes, ESI m/z=374, [M+H]$^+$.

Synthesis of tert-butyl (5-(3-(1H-indol-3-yl)propanethioamido)pentyl) carbamate (23)

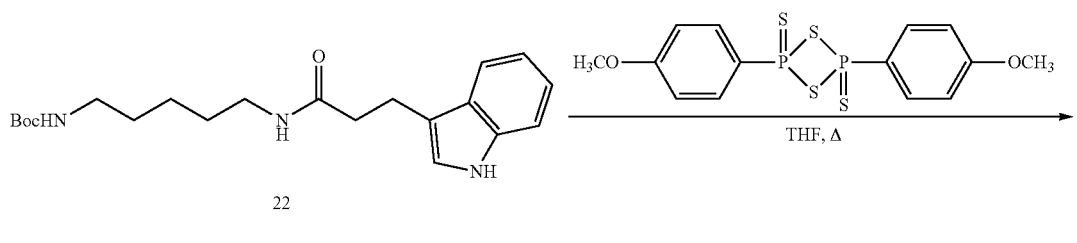

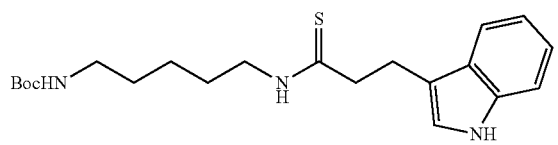

A solution of tert-butyl (5-(3-(1H-indol-3-yl)propanamido)pentyl) carbamate (22) (azeotropically dried by coevaporation with toluene, 1.99 g, 5.33 mmol) and Lawesson's reagent (1.19 g, 2.93 mmol) in THF (50 mL) was heated to 65° C. for 1 hour. The resulting mixture was allowed to cool to room temperature and concentrated. Purification by flash column chromatography (SiO$_2$, 1:1 hexanes/EtOAc) afforded 1.20 g (58% yield) of compound 23 as a yellow foam: LCMS (40-95% acetonitrile in 0.05% TFA over 10 minutes) retention time=6.17 minutes, ESI m/z=390, [M+H]$^+$.

Synthesis of (R)-tert-butyl (3-(1H-indol-3-yl)-1-oxo-1-((3-(1-trityl-1H-imidazol-4-yl)propyl)-amino)propan-2-yl)carbamate (25)

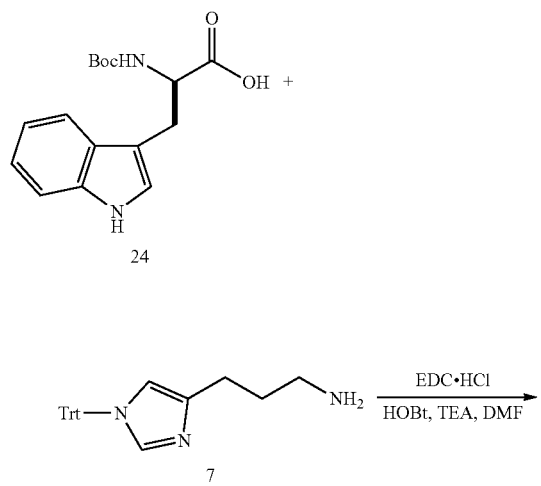

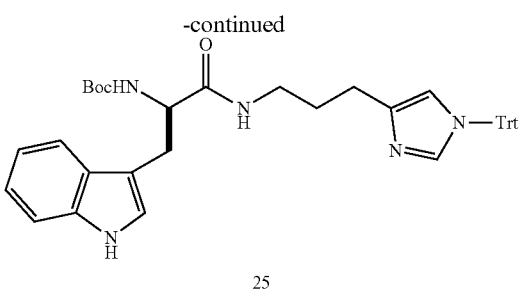

To a solution of N-Boc-D-Tryptophan (597 mg, 1.96 mmol, purchased from Chem-Impex International, Cat. #01387) (24) in DMF (50 mL) was added EDC·HCl (470 mg, 2.45 mmol) and HOBt·H$_2$O (375 mg, 2.45 mmol). The resulting mixture was stirred at room temperature for 30 minutes. A solution of the amine 7 (721 mg, 1.96 mmol) in DMF (30 mL) and TEA (400 μL, 2.87 mmol) was added and the reaction was stirred for 16 hours at room temperature. The DMF was evaporated and the residue was partitioned with EtOAc (75 mL) and water (75 mL). The layers were separated and the organic solution was washed with 1N NaHSO$_4$ (75 mL), saturated NaHCO$_3$ (75 mL) and brine (75 mL). The organic layer was then dried (Na$_2$SO$_4$), filtered and concentrated to afford 1.02 g (80% yield) of compound 25 as a tan solid: $^1$H NMR (400 MHz DMSO-d$_6$) δ 10.75 (bs, 1H), 7.84 (t, J=6.00 Hz, 1H), 7.71 (d, J=8.30 Hz, 1H), 7.32-7.39 (complex m, 10H), 7.27-7.27 (m, 2H), 7.20 (d, J=0.90 Hz, 1H), 7.03-7.06 (m, 3H), 6.97 (t, J=7.30 Hz, 1H), 6.89 (t, J=6.80 Hz, 1H), 6.69 (d, J=8.20 Hz, 1H), 6.54 (s, 1H), 4.08 (dt, J=8.70, 5.00 Hz, 1H), 2.95-3.02 (m, 3H), 2.80-2.86 (m, 1H), 2.33 (t, J=7.30 Hz, 2H), 1.56 (quint, J=7.30 Hz, 2H). LCMS (50-95% acetonitrile in 0.05% TFA over 10 minutes) retention time=5.88 minutes, ESI m/z=654, [M+H]$^+$.

Synthesis of (R)-tert-butyl (3-(1H-indol-3-yl)-1-thioxo-1-((3-(1-trityl-1H-imidazol-4-yl)propyl)amino)propan-2-yl)carbamate (26)

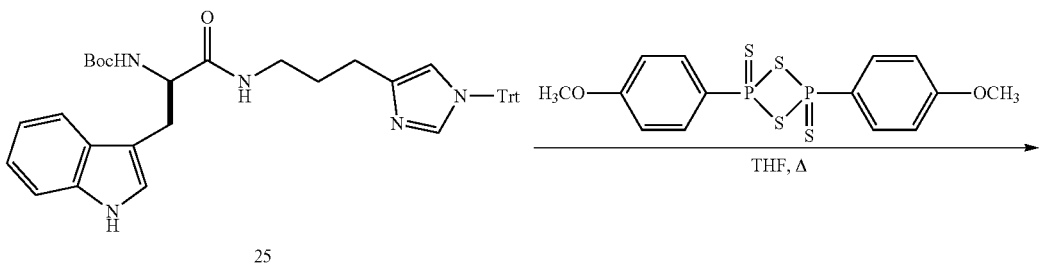

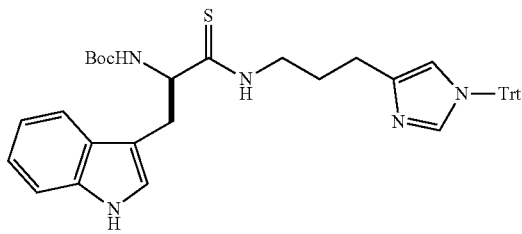

A solution of (R)-tert-butyl (3-(1H-indol-3-yl)-1-oxo-1-((3-(1-trityl-1H-imidazol-4-yl)propyl)-amino)propan-2-yl)carbamate (25) (azeotropically dried by coevaporation with toluene, 450 mg, 0.69 mmol) and Lawesson's reagent (240 mg, 0.59 mmol) in THF (40 mL) was heated to 65° C. for 4 hours. The resulting mixture was allowed to cool to room temperature and concentrated. Purification by flash column chromatography (SiO$_2$, 1:1 hexanes/EtOAc) afforded 289 mg (58% yield) of compound 26 as an orange-brown foam: LCMS (50-95% acetonitrile in 0.05% TFA over 10 minutes) retention time=6.81 minutes, ESI m/z=670, [M+H]$^+$.

General Procedure 1A: Boc-Protected Hydrazides

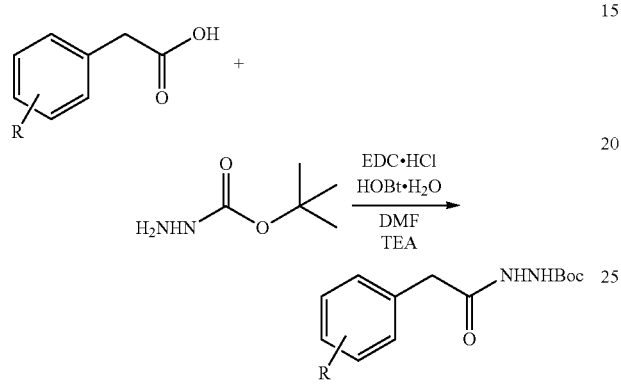

A mixture of the carboxylic acid (1.00 mmol), EDC·HCl (1.25 equiv.), HOBt·H$_2$O (1.25 equiv.) in DMF (50 mL) was stirred at room temperature for 30 minutes. The resulting mixture was treated with tert-butyl hydrazinecarboxylate (1.25 equiv.) and TEA (5 mL) and stirred for 16 hours. The solvent was evaporated and the residue was partitioned between EtOAc (150 mL) and 1N Na$_2$SO$_4$ (150 mL). The layers were separated and organic layer was washed with H$_2$O (150 mL), saturated NaHCO$_3$ (150 mL) and brine (150 mL). The organic layer was dried (anhydrous Na$_2$SO$_4$), filtered, and concentrated.

Synthesis of tert-Butyl 2-(2-(4-chloroDhenynacetyl) hydrazine carboxylate (28a)

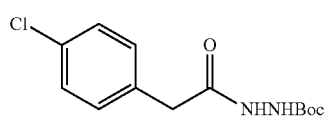

Prepared according to the General Procedure 1A from 2-(4-chlorophenyl)acetic acid (27a) (3.00 g, 17.6 mmol) and tert-butyl hydrazinecarboxylate (2.91 g, 22.0 mmol) to afford 4.91 g (98% yield) of compound 28a as a white solid: $^1$H NMR (400 MHz, DMSO-d$_6$) δ 9.79 (bs, 1H), 8.75 (bs, 1H), 7.33 (d, J=8.70 Hz, 2H), 7.25 (d, J=8.70 Hz, 2H), 3.30 (s, 2H), 1.34 (s, 9H). LCMS (50-95% acetonitrile in 0.05% TFA over 10 minutes) retention time=3.65 minutes, ESI m/z=285, [M+H]$^+$.

Synthesis of tert-Butyl 2-(2-(3-chloroDhenynacetyl) hydrazine carboxylate (28b)

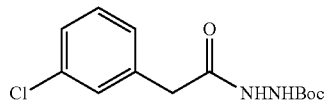

Prepared according to the General Procedure 1A from 2-(3-chlorophenyl)acetic acid (27b) (3.17 g, 18.6 mmol) and tert-butyl hydrazinecarboxylate (3.07 g, 23.3 mmol) to afford 5.25 g (99% yield) of compound 28b as a white solid: $^1$H NMR (400 MHz, CDCl$_3$) δ 7.81 (bs, 1H), 7.24 (m, 2H), 7.17-7.19 (m, 1H), 6.64 (bs, 1H), 3.55 (s, 2H), 1.43 (s, 9H). $^{13}$C NMR (100 MHz, CDCl$_3$) δ 169.71 (s), 155.60 (s) 135.75 (s), 134.72 (s), 130.23 (d), 129.55 (d), 127.77 (d), 127.63 (d), 82.21 (s), 40.84 (t), 28.20 (q). LCMS (50-95% acetonitrile in 0.05% TFA over 10 minutes) retention time=3.73 minutes, ESI m/z=285, [M+H]$^+$, m/z=569 [2M+H]$^+$.

Synthesis of tert-Butyl 2-(2-(2-chlorophenyl)acetyl) hydrazine carboxylate (28c)

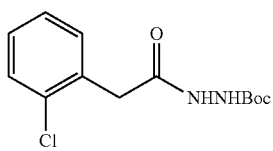

Prepared according to the General Procedure 1A from 2-(2-chlorophenyl)acetic acid (27c) (3.01 g, 17.6 mmol) and tert-butyl hydrazinecarboxylate (2.91 g, 22.1 mmol) to afford 2.30 g (46% yield) of compound 28c as a white solid: $^1$H NMR (400 MHz, DMSO-d$_6$) δ 9.78 (bs, 1H), 8.77 (bs, 1H), 7.36-7.39 (m, 2H), 7.22-7.27 (m, 2H), 3.53 (s, 2H), 1.35 (s, 9H). $^{13}$C NMR (100 MHz, DMSO-d$_6$) δ 169.17 (s), 155.74 (s), 134 (s), 132.31 (d), 129.49 (d), 129.05 (d), 127.53 (d), 127.45 (s), 79.60 (s), 38.03 (t), 28.57 (q). LCMS (50-95% acetonitrile in 0.05% TFA over 10 minutes) retention time=3.30 minutes, ESI m/z=285, [M+H]$^+$, m/z=569 [2M+H]$^+$.

Synthesis of tert-Butyl 2-(2-(4-methoxyphenyl)acetyl) hydrazine carboxylate (28d)

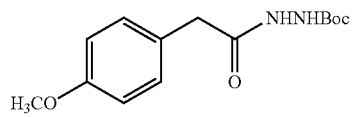

Prepared according to the General Procedure 1A from 2-(4-methoxyphenyl)acetic acid (27d) (3.00 g, 18.0 mmol) and tert-butyl hydrazinecarboxylate (2.98 g, 22.5 mmol) to afford 4.97 g (98% yield) of compound 28d as white solid: $^1$H NMR (400 MHz, DMSO-d$_6$) δ 9.70 (bs, 1H), 8.70 (bs, 1H), 7.14 (d, J=8.70 Hz, 2H), 6.82 (d, J=8.70 Hz, 2H), 3.68 (s, 3H), 3.29 (s, 2H), 1.35 (s, 9H). $^{13}$C NMR (100 MHz, DMSO-d$_6$) δ 171.07, 158.89, 155.76, 130.51, 126.00, 114.34, 81.83, 55.03, 40.39, 28.21. LCMS (40-95% acetonitrile in 0.05% TFA over 10 minutes) retention time=3.88 minutes, ESI m/z=281, [M+H]$^+$, m/z=561 [2M+H]$^+$.

Synthesis of tert-Butyl
2-(2-(3-methoxyphenyl)acetyl) hydrazine
carboxylate (28e)

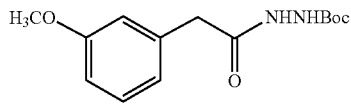

Prepared according to the General Procedure 1A from 2-(3-methoxyphenyl)acetic acid (27e) (2.43 g, 14.6 mmol) and tert-butyl hydrazine carboxylate (2.41 g, 18.3 mmol) to afford 4.16 g (100% yield) of compound 28e as white solid: $^1$H NMR (400 MHz, CDCl$_3$) δ 7.40 (bs, 1H), 7.25 (t, J=8.3 Hz, 1H), 6.81-6.87 (m, 3H), 6.51 (bs, 1H), 3.79 (s, 3H), 3.58 (s, 2H), 1.43 (s, 9H). $^{13}$C NMR (100 MHz, CDCl$_3$) δ 170.24 (s), 160.06 (s), 155.39 (s), 135.10 (s), 130.17 (d), 121.74 (d), 115.00 (d), 113.28 (d), 82.00 (s), 55.33 (q), 41.71 (t), 28.19 (q). LCMS (40-95% acetonitrile in 0.05% TFA over 10 minutes) retention time=4.13 minutes, ESI m/z=281, [M+H]$^+$, m/z=561 [2M+H]$^+$.

Synthesis of tert-Butyl
2-(2-(2-methoxyphenyl)acetyl)hydrazine
carboxylate (28f)

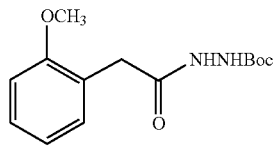

Prepared according to the General Procedure 1A from 2-(2-methoxyphenyl)acetic acid (27f) (3.00 g, 18.0 mmol) and tert-butyl hydrazinecarboxylate (2.98 g, 22.5 mmol) to afford 4.62 g (91% yield) of compound 28f as white solid: $^1$H NMR (400 MHz, CDCl$_3$) rotational isomers observed, δ 7.52 (bd, J 2.80 Hz, 1H), 7.24-7.29 (m, 2H), 6.93 (dt, J=7.70, 1.30 Hz, 1H), 6.90 (d, J=8.20 Hz, 1H). $^{13}$C NMR (100 MHz, CDCl$_3$) rotational isomers observed, δ 170.53, 157.09, 155.30, 131.35, 129.14, 122.50, 121.27, 110.86, 81.74, 55.69, 36.74, 28.16. LCMS (50-95% acetonitrile in 0.05% TFA over 10 minutes) retention time=3.07 minutes, ESI m/z=281, [M+H]$^+$, m/z=561 [2M+H]$^+$.

Synthesis of tert-Butyl
2-(2-(3-fluorophenyl)acetyl)hydrazine carboxylate
(28g)

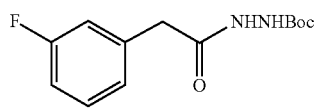

Prepared according to the General Procedure 1A from 2-(3-fluorophenyl)acetic acid (27 g) (3.07 g, 19.9 mmol) and tert-butyl hydrazinecarboxylate (3.29 g, 24.9 mmol) to afford 5.14 g (96% yield) of compound 28g as a white solid: $^1$H NMR (400 MHz, DMSO-d$_6$) δ 9.81 (bs, 1H), 8.77 (bs, 1H), 7.31 (apparent q, JH,F~6.90, JH,H~6.90 Hz, 1H), 7.01-7.08 (m, 3H), 3.41 (s, 2H), 1.35 (s, 9H). LCMS (50-95% acetonitrile in 0.05% TFA over 10 minutes) retention time=2.98 minutes, ESI m/z=269, [M+H]$^+$, m/z=537 [2M+H]$^+$.

Synthesis of tert-Butyl
2-(2-(3-bromophenyl)acetyl)hydrazine carboxylate
(28h)

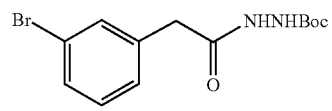

Prepared according to the General Procedure 1A from 2-(3-bromophenyl)acetic acid (27h) (5.00 g, 23.2 mmol) and tert-butyl hydrazinecarboxylate (3.84 g, 29.0 mmol) to afford 7.14 g (97% yield) of compound 28h as a white solid: $^1$H NMR (400 MHz, CDCl$_3$) δ 7.71 (bs, 1H), 7.45 (bs, 1H), 7.40 (d, J=6.00 Hz, 1H), 7.17-7.23 (m, 2H), 6.60 (bs, 1H), 3.55 (s, 2H), 1.44 (s, 9H). $^{13}$C NMR (100 MHz, CDCl$_3$) δ 169.68, 155.56, 136.00, 132.43, 130.73, 130.54, 128.10, 122.95, 82.23, 40.83, 28.21. LCMS (50-95% acetonitrile in 0.05% TFA over 10 minutes) retention time=3.97 minutes, ESI m/z=329, [M+H]$^+$, m/z=657 [2M+H]$^+$.

Synthesis of tert-Butyl 2-(2-(3-(trifluoromethyl)
phenylacetyl) hydrazine carboxylate (28i)

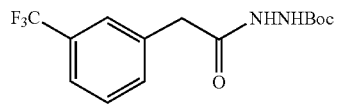

Prepared according to the General Procedure 1A from 2-(3-bromophenyl)acetic acid (27i) (3.00 g, 14.7 mmol) and tert-butyl hydrazinecarboxylate (1.94 g, 14.7 mmol) to afford 4.52 g (97% yield) of compound 28i as a white solid: $^1$H NMR (400 MHz, CDCl$_3$) δ 8.01 (bs, 1H), 7.49-7.54 (m, 3H), 7.41-7.45 (m, 1H), 3.61 (s, 2H), 1.43 (s, 9H). $^{13}$C NMR (100 MHz, CDCl$_3$) δ 169.64, 155.65, 134.81, 132.82, 131.18 (q, J$_{C,F}$=32.6 Hz), 129.39, 126.15 (q, J$_{C,F}$=3.80 Hz), 124.38 (q, J$_{C,F}$=3.90 Hz), 124.00 (q, J$_{C,F}$=272.2 Hz), 82.30, 40.78, 28.16. LCMS (50-95% acetonitrile in 0.05% TFA over 10 minutes) retention time=4.43 minutes, ESI m/z=319, [M+H]⁺, m/z=637 [2M+H]⁺.

Synthesis of tert-Butyl 2-(2-(3,5-difluorophenynacetyl)hydrazine carboxylate (28j)

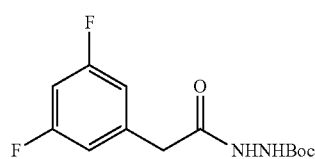

Prepared according to the General Procedure 1A from 2-(3,5-difluorophenyl)acetic acid (27j) (3.00 g, 17.4 mmol) and tert-butyl hydrazinecarboxylate (2.88 g, 21.8 mmol) to afford 3.05 g (61% yield) of compound 28j as a white solid: LCMS (50-95% acetonitrile in 0.05% TFA over 10 minutes) retention time=3.45 minutes, ESI m/z=287, [M+H]⁺, m/z=573 [2M+H]⁺.

Synthesis of tert-Butyl 2-(2-(3,5-difluorophenypacetyphydrazine carboxylate (28k)

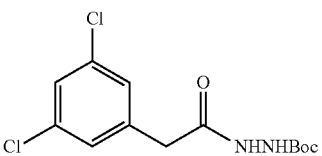

Prepared according to the General Procedure 1A from 2-(3,5-dichlorophenyl)acetic acid (27k) (5.06 g, 24.7 mmol) and tert-butyl hydrazinecarboxylate (3.26 g, 24.7 mmol) to afford 6.81 g (86% yield) of compound 28k as a white solid: LCMS (50-95% acetonitrile in 0.05% TFA over 10 minutes) retention time=4.90 minutes, ESI m/z=319, [M+H]⁺; m/z=639, [2M+H]⁺.

Synthesis of tert-Butyl 2-(2-(3,4-dichlorophenylacetyl)hydrazine carboxylate (28l)

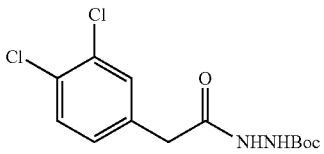

Prepared according to the General Procedure 1A from 2-(3,4-dichlorophenyl)acetic acid (27l) (2.43 g, 11.9 mmol) and tert-butyl hydrazinecarboxylate (1.97 g, 14.9 mmol) to afford 3.61 g (95% yield) of compound 28l as a white solid: ¹H NMR (400 MHz, CDCl₃) δ 7.95 (bs, 1H), 7.39 (d, J=2.30 Hz, 1H), 7.38 (d, J=8.30 Hz, 1H), 7.14 (dd, J=8.30, 2.30 Hz, 1H), 6.67 (bs, 1H), 3.51 (s, 2H), 1.44 (s, 9H). LCMS (40-95% acetonitrile in 0.05% TFA over 10 minutes) retention time=2.10 minutes, ESI m/z=319, [M+H]⁺.

Synthesis of tert-Butyl 2-(2-(1-1,11-biphenyl-4-ynacetyl)hydrazine carboxylate (AH.2.182)

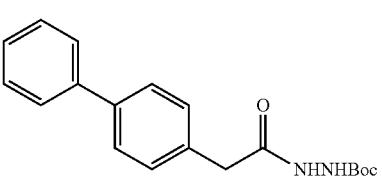

Prepared according to the General Procedure 1A from 2-([1,1'-biphenyl]-4-yl)acetic acid (27m) (3.00 g, 14.1 mmol) and tert-butyl hydrazinecarboxylate (3.39 g, 17.7 mmol) to afford 3.96 g (86% yield) of compound 28m as a white solid: ¹H NMR (400 MHz, DMSO-d₆) δ 9.80 (bs, 1H), 8.72 (bs, 1H), 7.55-7.62 (m, 4H), 7.41 (t, J=7.30 Hz, 2H), 7.31-7.34 (m, 3H), 3.42 (s, 2H), 1.35 (s, 9H). ¹³C NMR (100 MHz, DMSO-d₆) δ 170.16, 155.79, 140.49, 138.95, 135.44, 130.16, 129.44, 127.83, 127.08, 127.05, 79.62, 28.57. LCMS (50-95% acetonitrile in 0.05% TFA over 10 minutes) retention time=5.23 minutes, ESI m/z=327, [M+H]⁺, 653 [2M+H]+.

General Procedure 1B: Synthesis of Hydrazide Free Bases

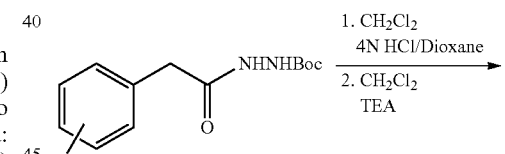

To the Boc-hydrazide (1.00 mmol) in CH₂Cl₂ was added 4N HCl/Dioxane (10 mL) and the reaction was stirred at room temperature. After 1.5 hours a white precipitate was formed. The precipitated HCl salt was filtered and washed with CH₂Cl₂ and dried under high vacuum. The salt (1.00 mmol) was suspended in CH₂Cl₂ (75 mL) or dissolved in methanol (or methanol/water) and treated with TEA (6 mL). The resulting mixture was stirred at room temperature for 30 minutes, transferred to a separatory funnel and partitioned with additional CH₂Cl₂ (75 mL) and water (150 mL). The layers were separated and the organic solution was dried (anhydrous Na₂SO₄), filtered, and concentrated. This compound was used in the next step without further purification.

Synthesis of 2-(4-Chlorophenyl)acetic hydrazide (29a)

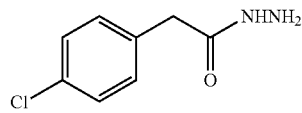

Prepared according to the General Procedure 1B from tert-Butyl 2-(2-(4-chlorophenyl)acetyl)hydrazinecarboxylate (28a) (4.90 g, 17.2 mmol) to afford 3.18 g (84% yield) of the intermediate HCI salt as a white solid. The HCI salt was then converted to 860 mg (32% yield) of freebase 29a (27% for two steps), isolated as a white solid: LCMS (50-95% acetonitrile in 0.05% TFA over 10 minutes) retention time=2.08 minutes, ESI m/z=185, [M+H]$^+$.

Synthesis of 2-(3-Chlorophenyl)acetic hydrazide (29b)

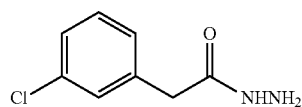

Prepared according to the General Procedure 1B from tert-butyl 2-(2-(3-chlorophenyl)acetyl)hydrazinecarboxylate (28b) (5.00 g, 17.6 mmol) to afford 3.02 g (78% yield) of the intermediate HCI salt as a white solid. The HCI salt was then converted to 1.73 g (69% yield) of freebase 29b (54% for two steps), isolated as a white solid: $^1$H NMR (400 MHz, DMSO-d$_6$) δ 9.20 (bs, 1H), 7.23 7.30 (complex m, 3H), 1.15-7.18 (complex m, 1H), 4.20 (bs, 2H), 3.32 (s, 2H). $^{13}$C NMR (100 MHz, CDCl$_3$) δ 171.00 (s), 135.92 (s), 134.83 (s), 130.30 (d), 129.52 (d), 127.82 (d), 127.60 (d), 41.4 (t). LCMS (50-95% acetonitrile in 0.05% TFA over 10 minutes) retention time=1.95 minutes, ESI m/z=185, [M+H]$^+$; m/z=369, [2M+H]$^+$; m/z=391, [2M+Na].

Synthesis of 2-(2-Chlorophenyl)acetic hydrazide (29c)

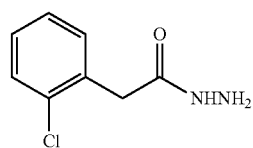

Prepared according to the General Procedure 1B from tert-butyl 2-(2-(2-chlorophenyl)acetyl)hydrazinecarboxylate (28c) (2.10 g, 7.37 mmol) to afford 1.63 g (100% yield) of the intermediate HCI salt as a white solid. The HCI salt (1.23 g, 5.56 mmol) was then converted to 830 mg (81° A yield) of freebase 29c (81° A for two steps), isolated as a white solid: $^1$H NMR (400 MHz, DMSO-d$_6$) δ 9.17 (bs, 1H), 7.31-7.38 (complex m, 2H), 7.20-7.26 (complex m, 2H), 4.20 (bs, 2H), 3.47 (s, 2H). $^{13}$C NMR (100 MHz, DMSO-d$_6$) δ 168.95 (s), 134.54 (s), 133.94 (s), 132.32 (d), 129.50 (d), 128.90 (d), 127.51 (d), 38.34 (t). LCMS (50-95% acetonitrile in 0.05% TFA over 10 minutes) retention time=2.08 minutes, ESI m/z=185, [M+H]$^+$; m/z=369, [2M+H]+; m/z=391, [2M+Na]$^+$.

Synthesis of 2-(4-Methoxyphenyl)acetic hydrazide (29d)

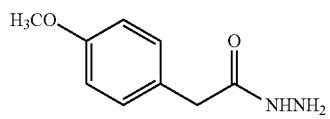

Prepared according to the General Procedure 1B from tert-butyl 2-(2-(4-methoxyphenyl)acetyl)hydrazinecarboxylate (28d) (4.67 g, 16.7 mmol) to afford 2.78 g (77% yield) of the intermediate HCI salt as a white solid. The HCI salt (2.68 g, 12.4 mmol) was then converted to 1.18 g (53% yield) of freebase 29d (41% for two steps), isolated as a white solid: $^1$H NMR (400 MHz, DMSO-d$_6$) δ 9.12 (bs, 2H), 7.12 (d, J=6.40 Hz, 2H), 6.81 (d, J=6.90 Hz, 2H), 4.15 (bs, 2H), 3.67 (s, 3H), 3.22 (s, 2H).

Synthesis of 2-(3-Methoxyphenyl)acetic hydrazide (29e)

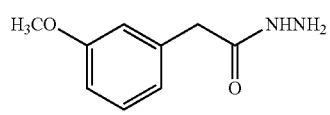

Prepared according to the General Procedure 1B from tert-butyl 2-(2-(3-methoxyphenyl)acetyl)hydrazinecarboxylate (28e) (4.09 g, 14.6 mmol) to afford 3.10 g (98% yield) of the intermediate HCI salt as a white solid. The HCI salt (2.50 g, 11.5 mmol) was then converted to 1.10 g (53% yield) of freebase 29e (52% for two steps), isolated as a white solid: $^1$H NMR (400 MHz, DMSO-d$_6$) δ 9.15 (bs, 1H), 7.15 (t, J=7.8 Hz, 1H), 6.79 (s, 1H), 6.74-6.77 (complex m, 2H), 4.17 (bs, 2H), 3.68 (s, 3H), 3.26 (s, 2H). $^{13}$C NMR (100 MHz, DMSO-d$_6$) δ 169.93 (s), 159.63 (s), 138.23 (s), 129.69 (d), 121.71 (d), 115.20 (d), 112.27 (d), 55.45 (q), 41.03 (t). LCMS (50-95% acetonitrile in 0.05% TFA over 10 minutes) retention time=1.85 minutes, ESI m/z=181, [M+H]$^+$; m/z=361, [2M+H]+.

Synthesis of 2-(2-Methoxyphenyl)acetic hydrazide (29f)

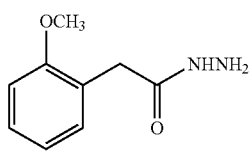

Prepared according to the General Procedure 1B from tert-butyl 2-(2-(2-methoxyphenyl)acetyl)hydrazinecarboxylate (28f) (4.61 g, 16.4 mmol) to afford 3.08 g (86% yield) of the intermediate HCl salt as a white solid. The HCl salt (3.08 g, 14.2 mmol) was then converted to 1.88 g (73% yield) of freebase 29f (63% for two steps), isolated as a white solid: $^1$H NMR (400 MHz, DMSO-$d_6$) δ 8.98 (bs, 1H), 7.16 (dt, J=7.80, 1.90 Hz, 1H), 7.11 (d, J=7.30 Hz, 1H), 6.90 (d, J=7.80 Hz, 1H), 6.82 (t, J=7.30 Hz, 1H), 4.15 (bs, 1H), 3.70 (s, 3H), 3.28 (s, 2H). $^{13}$C NMR (100 MHz, DMSO-$d_6$) δ 170.13 (s), 157.59 (s), 130.98 (d), 128.33 (d), 124.73 (s), 120.57 (d), 111.10 (d), 55.86 (q), 35.02 (t). LCMS (50-95% acetonitrile in 0.05% TFA over 10 minutes) retention time=1.85 minutes, ESI m/z=181, [M+H]$^+$; m/z=361, [2M+H]$^+$.

Synthesis of 2-(3-Fluorophenyl)acetic hydrazide (29 g)

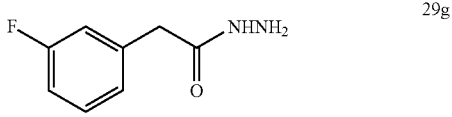 [SMILES: NNC(=O)Cc1cccc(F)c1]

Prepared according to the General Procedure 1B from tert-butyl 2-(2-(3-fluorophenyl)acetyl)hydrazinecarboxylate (28 g) (5.06 g, 18.9 mmol) to afford 2.59 g (67% yield) of the intermediate HCl salt as a white solid. The HCl salt (2.47 g, 12.1 mmol) was then converted to 882 mg (43% yield) of freebase 29 g (29% for two steps), isolated as a white solid: $^1$H NMR (400 MHz, DMSO-$d_6$) δ 8.98 (bs, 1H), 7.29 (dt, J=6.90, 6.00 Hz, 1H), 6.99-7.05 (complex m, 3H), 4.20 (s, 2H). $^{13}$C NMR (100 MHz, DMSO-$d_6$) δ 169.55 (s), 162.52 (d, $J_{C,F}$=243 Hz), 139.55 (d, $J_{C,F}$=7.60 Hz), 130.57 (d, $J_{C,F}$=8.60 Hz), 125.64 (d, $J_{C,F}$=2.90 Hz), 116.19 (d, $J_{C,F}$=22.1 Hz), 113.72 (d, $J_{C,F}$=20.2 Hz), 40.55 (d, $J_{C,F}$=1.90 Hz). LCMS (50-95% acetonitrile in 0.05% TFA over 10 minutes) retention time=1.90 minutes, ESI m/z=169, [M+H]$^+$.

Synthesis of 2-(3-Bromophenyl)acetic hydrazide (29h)

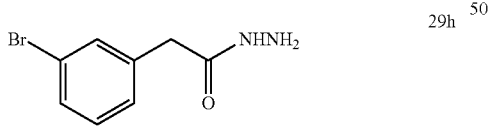

Prepared according to the General Procedure 1B tert-butyl 2-(2-(3-bromophenyl)acetyl)hydrazinecarboxylate (X28h) (7.41 g, 22.5 mmol) to afford 4.00 g (67% yield) of the intermediate HCl salt as a white solid. The HCl salt (4.00 g, 15.1 mmol) was then converted to 2.73 g (79% yield) of freebase 29h (53% for two steps), isolated as a white solid: $^1$H NMR (400 MHz, DMSO-$d_6$) δ 9.22 (bs, 1H), 7.43-7.44 (m, 1H), 7.37-7.40 (complex m, 1H), 7.20-7.23 (complex m, 2H), 4.26 (bs, 2H).). $^{13}$C NMR (100 MHz, CDCl$_3$) δ 171.01 (s), 136.28 (s), 132.40 (d), 130.71 (d), 130.55 (d), 128.07 (d), 122.99 (s), 41.32 (t). LCMS (50-95% acetonitrile in 0.05% TFA over 10 minutes) retention time=1.98 minutes, ESI m/z=229, [M+H]+; 270, [M+H+ACN]+; 459, [2M+H]+.

Synthesis of 2-(3-(Trifluoromethyl)phenyl)acetic hydrazide (29i)

Prepared according to the General Procedure 1B from tert-butyl 2-(2-(3-(trifluoromethyl)phenyl)acetyl)hydrazinecarboxylate (28i) (4.20 g, 13.2 mmol) to afford 3.26 g (97% yield) of the intermediate HCl salt as a white solid. The HCl salt (3.26 g, 12.8 mmol) was then converted to 2.14 g (77% yield) of freebase 29i (75% for two steps), isolated as a white solid: $^1$H NMR (400 MHz, CD$_3$OD) δ 7.59 (bs, 1H), 7.45-7.54 (m, 3H), 3.53 (s, 2H). $^{13}$C NMR (100 MHz, CD$_3$OD) δ 170.92, 136.72, 132.61, 130.42 (q, $J_{C,F}$=32.6 Hz), 128.95, 125.42 (q, $J_{C,F}$=3.80 Hz), 124.30 (q, $J_{C,F}$=271 Hz), 123.37 (q, $J_{C,F}$=3.90 Hz), 39.93. LCMS (50-95% acetonitrile in 0.05% TFA over 10 minutes) retention time=2.00 minutes, ESI m/z=219, [M+H]$^+$; 437 [2M+1−1]$^+$.

Synthesis of 2-(3,5-Difluorophenyl)acetic hydrazide (29j)

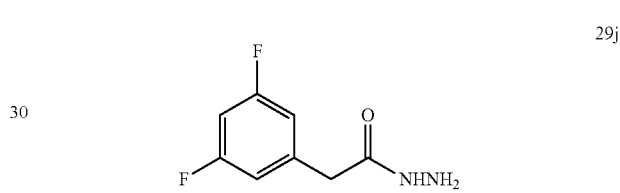

Prepared according to the General Procedure 1B from tert-butyl 2-(2-(3,5-difluorophenyl)acetyl)hydrazinecarboxylate (28j) (3.05 g, 10.7 mmol) to afford 2.02 g (85% yield) of the intermediate HCl salt as a white solid. The HCl salt (1.91 g, 8.58 mmol) was then converted to 740 mg (46% yield) of freebase 29j (39% for two steps), isolated as a white solid: $^1$H NMR (400 MHz, DMSO-$d_6$) δ 9.21 (bs, 1H), 7.05 (tt, J=9.20, 2.30 Hz, 1H), 6.91-6.96 (m, 2H), 4.21 (bs, 1H), 3.36 (s, 2H). $^{13}$C NMR (100 MHz, CDCl$_3$) δ 170.39 (s), 163.64 (dd, $J_{C,F}$=249, 13.4 Hz), 137.63 (t, $J_{C,F}$=8.60 Hz), 112.39 (dd, $J_{C,F}$=25.9, 7.70 Hz), 103.13 (t, $J_{C,F}$=24.9 Hz), 41.29 (t, CH$_2$). LCMS (50-95% acetonitrile in 0.05% TFA over 10 minutes) retention time=1.98 minutes, ESI m/z=229, [M+H]$^+$; 270, [M+H+ACN]$^+$; 459 [2M+H]$^+$.

Synthesis of 2-(3,5-Dichlorophenyl)acetic hydrazide (29k)

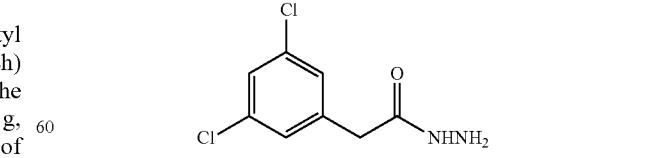

Prepared according to the General Procedure 1B from tert-butyl 2-(2-(3,5-dichlorophenyl)acetyl)hydrazinecarboxylate (28k) (6.00 g, 18.8 mmol) to afford 4.34 g (90% yield) of the intermediate HCl salt as a white solid. The HCl salt (4.34 g, 17.0 mmol) was then converted to 2.65 g (71% yield) of freebase 29k (64% for two steps), isolated as a white solid: ¹H NMR (400 MHz, DMSO-d₆) δ 9.18 (bs, 1H), 7.42 (t, J=1.90 Hz, 1H), 7.27 (d, J=1.90 Hz, 2H), 4.20 (bs, 2H), 3.35 (s, 2H). ¹³C NMR (100 MHz, CDCl₃) δ 170.21, 137.21, 135.44, 127.86, 127.83, 40.93. LCMS (50-95% acetonitrile in 0.05% TFA over 10 minutes) retention time=2.10 minutes, ESI m/z=219, [M+H]⁺.

Synthesis of 2-(3,4-Dichlorophenyl)acetic hydrazide (29l)

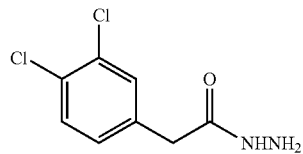

29l

Prepared according to the General Procedure 1B from tert-butyl 2-(2-(3,4-dichlorophenyl)acetyl)hydrazinecarboxylate (28l) (3.00 g, 9.40 mmol) to afford 2.40 g (100% yield) of the intermediate HCl salt as a white solid. The HCl salt (549 mg, 2.15 mmol) was then converted to 473 mg (100% yield) of freebase 29l (100% for two steps), isolated as a white solid: LCMS (40-95% acetonitrile in 0.05% TFA over 10 minutes) retention time=2.38 minutes, ESI m/z=219, [M+H]⁺.

Synthesis of 2-(1-1,1¹-Biphenyl-4-ypacetic hydrazide (29m)

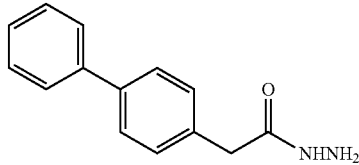

29m

Prepared according to the General Procedure 1B from tert-butyl 2-(2-([1,1'-biphenyl]-4-yl)acetyl)hydrazinecarboxylate (AH.2.182) (3.83 g, 11.7 mmol) to afford 2.75 g (89% yield) of the intermediate HCl salt as a white solid. The HCl salt (2.75 g, 10.5 mmol) was then converted to 1.84 g (77% yield) of freebase 29m (69% for two steps), isolated as a white solid: ¹H NMR (400 MHz, DMSO-d₆) δ 9.21 (bs, 1H), 7.53-7.61 (m, 4H), 7.41 (t, J=7.30 Hz, 2H), 7.29-7.32 (m, 3H), 4.19 (bs, 2H), 3.35 (s, 2H). ¹³C NMR (100 MHz, DMSO-d₆) δ 170.03, 140.53, 138.86, 136.07, 130.05, 129.44, 127.81, 127.08, 127.04, 40.68. LCMS (15-95% acetonitrile in 0.05% TFA over 10 minutes) retention time=6.25 minutes, ESI m/z=227, [M+H]⁺; 453, [2M+H].

Synthesis of 2-phenylacetic hydrazide (29n)

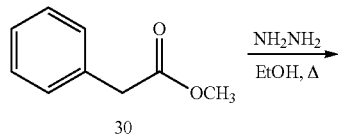

30

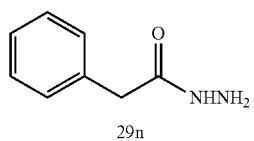

29n

To a solution of methyl phenylacetate (30) (1.00 g, 6.66 mmol) in ethanol (50 mL) was added hydrazine hydrate (66.6 mmol). The resulting mixture was heated to reflux for 4 hours. The reaction was cooled and partitioned with water (200 mL) and EtOAc (200 mL). The EtOAc solution was washed again with water (2×200 mL), dried (Na₂SO₄), filtered and concentrated to afford 370 mg (37% yield) of compound 29n as a viscous oil: ¹H NMR (400 MHz, DMSO-d₆) δ 9.18 (bs, 1H), 7.15-7.27 (m, 5H), 4.17 (bs, 2H), 3.30 (s, 2H). ¹³C NMR (100 MHz, DMSO-d₆) δ 170.07, 136.81, 129.47, 128.70, 126.88, 40.99. LCMS (15-95% acetonitrile in 0.05% TFA over 10 minutes) retention time=3.43 minutes, ESI m/z=151, [M+H]⁺.

General Procedure 1C: Synthesis of Triazoles

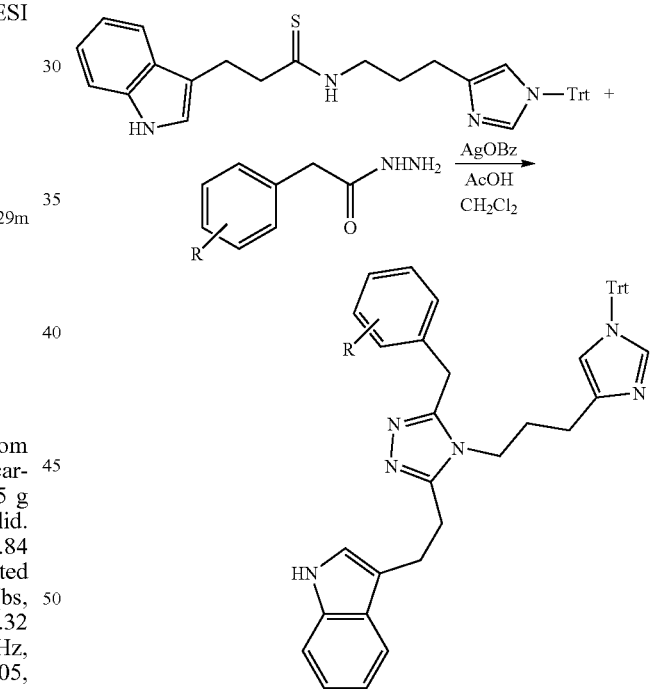

A mixture of thioamide (1 mmol) and hydrazide (1.2 mmol) was dissolved in CH₂Cl₂ (30 mL) and treated with silver benzoate (2 mmol) followed immediately with acetic acid (3 mmol). The black solution was stirred at room temperature overnight. The solution was concentrated and the residue was dissolved in 1:1 MeOH/CH₂Cl₂ and treated with 1N HCl (2 mmol). The mixture was stirred for 5 minutes, treated with diisopropylethylamine (~10 mmol) and concentrated. The residue was suspended in MeOH (50 mL), filtered through CELITE (1 inch pad) and concentrated. The final residue was purified by flash chromatography.

Synthesis of 3-(2-(5-(4-Chlorobenzyl)-4-(3-(1-trityl-H-imidazol-4-yl)propyl)-4H-1,2,4-triazol-3-yl)ethyl)-1H-indole (31)

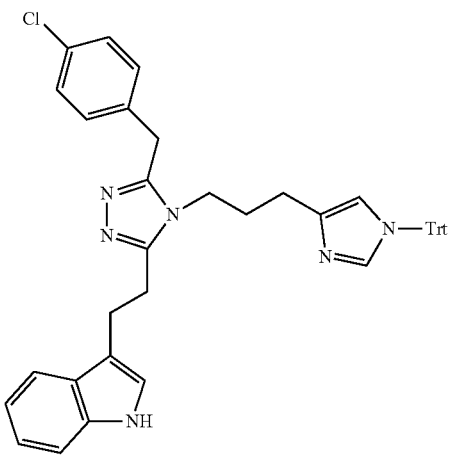

31a

Prepared according to the General Procedure 1C from 3-(1H-indol-3-yl)-N-(3-(1-trityl-1H-imidazol-4-yl)propyl)propanethioamide (10) (475 mg, 0.86 mmol) and 2-(4-chlorophenyl)acetic hydrazide (29a) (190 mg, 1.03 mmol). Purification by flash chromatography (SiO$_2$, 20:1 CH$_2$Cl$_2$/methanol) afforded 360 mg (61% yield) of compound 31a as a white solid: LCMS (50-95% acetonitrile in 0.05% TFA over 10 minutes) retention time=4.35 minutes, ESI m/z=687, [M+H]$^+$.

Synthesis of 3-(2-(5-(3-Chlorobenzyl)-4-(3-(1-trityl-1H-imidazol-4-yl)propyl)-4H-1,2,4-triazol-3-yl)ethyl)-1H-indole (31b)

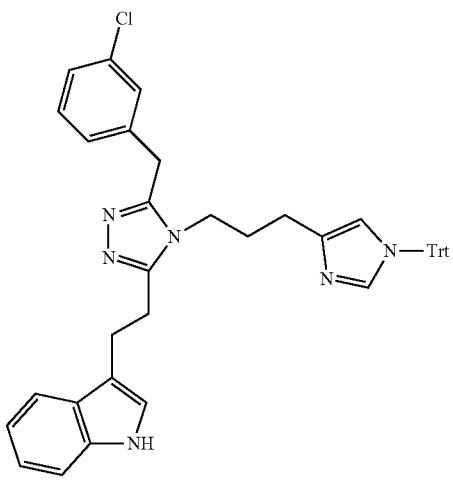

31b

Prepared according to the General Procedure 1C from 3-(1H-indol-3-yl)-N-(3-(1-trityl-1H-imidazol-4-yl)propyl)propanethioamide (10) (200 mg, 0.36 mmol) and 2-(3-chlorophenyl)acetic hydrazide (80.0 mg, 0.45 mmol). Purification by flash chromatography (SiO$_2$, 20:1 CH$_2$Cl$_2$/methanol) afforded 147 mg (60% yield) of compound 31b as a white solid: H NMR (400 MHz, DMSO-d$_6$) δ 10.83 (bs, 1H), 8.73 (bs, 1H), 7.44 (d, J=8.20 Hz, 1H), 7.37-7.42 (m, 10H), 7.21-7.33 (complex multiplets, 4H), 7.05-7.15 (complex multiplets, 8H), 7.01 (t, J=8.20 Hz, 1H), 6.90 (t, J=8.20 Hz, 1H), 4.20 (s, 2H), 3.89 (distorted triplet, J=7.30 Hz, 2H), 3.07-3.16 (m, 4H), 2.53 (distorted t, J=7.30 Hz, 2H), 1.63 (quint, J=7.40 Hz, 2H). $^{13}$C NMR (100 MHz, DMSO-d$_6$) δ 155.21 (s), 153.37 (s), 140.85 (s), 138.27 (s), 137.71 (s), 133.69 (s), 131.03 (d), 129.68 (d), 129.21 (d), 128.14 (d), 127.59 (d), 127.31 (s), 123.42 (d), 121.57 (d), 119.97 (s), 118.89 (d), 118.65 (d), 113.07 (d), 111.99 (d), 77.85 (s), 43.04 (t), 29.90 (t), 28.15 (t), 25.66 (t), 22.39 (t), 21.88 (t). LCMS (50-95% acetonitrile in 0.05% TFA over 10 minutes) retention time=4.38 minutes, ESI m/z=687, [M+H]$^+$.

Synthesis of 3-(2-(5-(2-Chlorobenzyl)-4-(3-(1-trityl-1H-imidazol-4-yl)propyl)-4H-1,2,4-triazol-3-yl)ethyl)-1H-indole (31c)

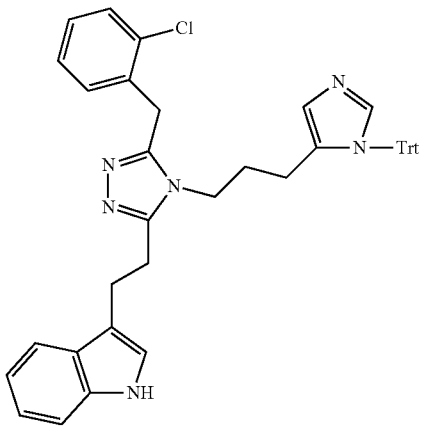

31c

Prepared according to the General Procedure 1C from 3-(1H-indol-3-yl)-N-(3-(1-trityl-1H-imidazol-4-yl)propyl)propanethioamide (10) (500 mg, 0.90 mmol) and 2-(2-chlorophenyl)acetic hydrazide (199 mg, 1.08 mmol). Purification by flash chromatography (SiO$_2$, 20:1 CH$_2$Cl$_2$/methanol) afforded 286 mg (46% yield) of compound 31c as a white solid: LCMS (50-95% acetonitrile in 0.05% TFA over 10 minutes) retention time=3.90 minutes, ESI m/z=687, [M+H]$^+$.

Synthesis of 3-(2-(5-(4-Methoxybenzyl)-4-(3-(1-trityl-1H-imidazol-5-yl)propyl)-4H-1,2,4-triazol-3-yl)-ethyl)-1H-indole (31d)

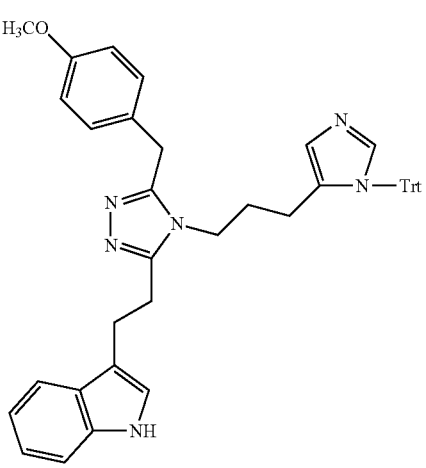

31d

Prepared according to the General Procedure 1C from 3-(1H-indol-3-yl)-N-(3-(1-trityl-1H-imidazol-4-yl)propyl) propanethioamide (10) (540 mg, 0.97 mmol) and 2-(4-methoxy-phenyl)acetic hydrazide (209 mg, 1.16 mmol). Purification by flash chromatography (SiO$_2$, 30:1 to 20:1 CH$_2$Cl$_2$/methanol) afforded 250 mg (38% yield) of compound 31d as a white solid: $^1$H NMR (400 MHz, DMSO-d$_6$) δ 10.74 (bs, 1H), 6.73-7.91 (complex multiplets, 25H), 6.51 (s), 3.93 (s, 2H), 3.63 (apparent t, J=7.40 Hz, 2H), 3.61 (s, 3H), 3.05 (apparent t, J=7.40 Hz, 2H), 2.89 (apparent t, J=6.90 Hz, 2H), 2.29 (t, J=6.90 Hz, 2H), 1.54 (quint, J=7.30 Hz, 2H). $^{13}$C NMR (100 MHz, DMSO-d$_6$) δ 158.44 (s), 154.46 (s), 153.21 (s), 142.82 (s), 140.16, 138.30, 136.67, 130.51, 129.90, 129.66 (d), 128.95, 128.69 (d), 128.46, 127.43, 123.08, 121.40, 118.72, 118.19, 114.38, 114.14, 113.87, 111.84, 74.88 (s), 55.49 (q), 42.43 (t), 29.92 (t), 29.55 (t), 25.88 (t), 25.05 (t), 23.22 (t). LCMS (25-95% acetonitrile in 0.05% TFA over 10 minutes) retention time=6.75 minutes, ESI m/z=683, [M+H]$^+$.

Synthesis of 3-(2-(5-(3-Methoxybenzyl)-4-(3-(1-trityl-1H-imidazol-4-yl)propyl)-4H-1,2,4-triazol-3-yl)ethyl))-1H-indole (31e)

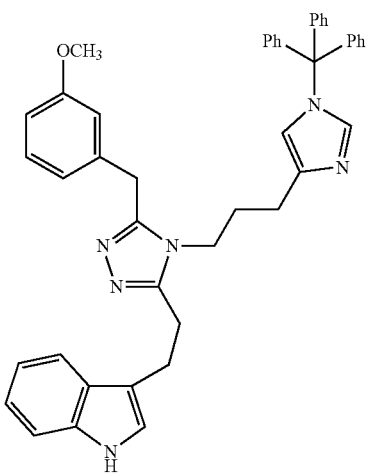

31e

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(3-methoxyphenyl)acetic hydrazide (195 mg, 1.08 mmol). Purification by flash chromatography (SiO$_2$, 20:1 to 10:1 CH$_2$Cl$_2$/methanol) afforded 190 mg (31% yield) of compound 31e as a white solid: $^1$H NMR (400 MHz, CDCl$_3$) δ 7.99 (bs, 1H), 7.49 (d, J=7.80 Hz, 1H), 7.27-7.34 (complex multiplets, 10H), 7.21 (d, J=8.30 Hz, 1H), 6.99-7.11 (complex multiplets, 9H), 6.86 (d, J=2.30 Hz, 1H), 6.65-6.68 (m, 3H), 6.36 (s, 1H), 4.05 (s, 2H), 3.32 (apparent t, J=7.80 Hz, 2H), 3.26 (t, J=7.80 Hz, 2H), 2.97 (t, J=7.80 Hz, 2H), 2.25 (t, J=7.30 Hz, 2H), 1.51 (quint, J=7.80 Hz, 2H). $^{13}$C NMR (100 MHz, CDCl$_3$) δ 159.91 (s), 155.16 (s), 152.17 (s), 142.41 (s), 138.49, 137.61, 136.22, 129.79, 129.77, 128.20, 128.17, 122.08, 122.00, 120.92, 119.50, 118.62, 118.14, 114.77, 114.16, 112.52, 111.24, 75.33 (s), 55.35 (q), 42.72 (t), 31.70 (t), 29.42 (t), 26.20 (t), 25.20 (t), 23.68 (t). LCMS (25-95% acetonitrile in 0.05% TFA over 10 minutes) retention time=6.78 minutes, ESI m/z=683, [M+H]$^+$.

Synthesis of 3-(2-(5-(2-Methoxybenzyl)-4-(3-(1-trityl-1H-imidazol-4-yl)propyl)-4H-1,2,4-triazol-3-yl)ethyl)-1H-indole (31f)

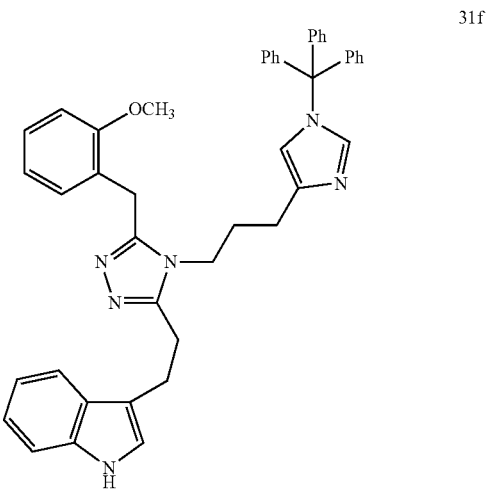 [SMILES: COc1ccccc1Cc1nnc(CCc2c[nH]c3ccccc23)n1CCCc1cn(C(c2ccccc2)(c2ccccc2)c2ccccc2)cn1]

31f

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(2-methoxyphenyl)acetic hydrazide (195 mg, 1.08 mmol). Purification by flash chromatography (SiO$_2$, 30:1 to 20:1 CH$_2$Cl$_2$/methanol) afforded 203 mg (33% yield) of compound 31f as a white solid: LCMS (50-95% acetonitrile in 0.05% TFA over 10 minutes) retention time=3.70 minutes, ESI m/z=683, [M+H]$^+$.

Synthesis of 3-(2-(5-(3-Fluorobenzyl)-4-(3-(1-trityl-1H-imidazol-5-0propyl)-4H-1,2,4-triazol-3-yl)-ethyl)-1H-indole (31q)

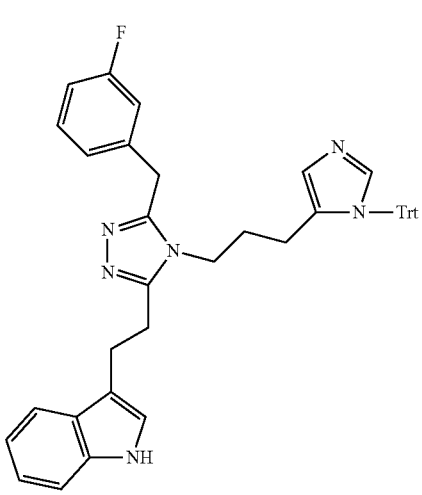

31g

Prepared according to the General Procedure 1C from 3-(1H-indol-3-yl)-N-(3-(1-trityl-1H-imidazol-4-yl)propyl) propanethioamide (10) (514 mg, 0.93 mmol) and 2-(3-fluorophenyl)acetic hydrazide (188 mg, 1.11 mmol). Purification by flash chromatography (SiO$_2$, 20:1 CH$_2$Cl$_2$/methanol) afforded 300 mg (49% yield) of compound 31g as a white solid: $^1$H NMR (400 MHz, DMSO-d$_6$) contains minor inseparable aromatic impurity related to the previous use of Lawesson's reagent, hydrogen-bonded forms observed, major form: δ 10.74 (bs, 1H), 9.20 (bs, 0.5H), 7.90 (d, J=6.40 Hz, 1H), 7.58 (t, J=6.40 Hz, 0.5H), 6.90-7.46 (complex multiplets, 23H), 6.84 (t, J=7.70 Hz, 1H), 6.48 (s, 1H), 4.05 (s, 2H), 3.69 (apparent t, J=8.20 Hz, 2H), 3.06 (apparent t, J=7.55 Hz, 2H), 2.91 (apparent, t, J=7.55 Hz, 2H), 2.30 (apparent t, J=6.90 Hz, 1H), 1.52 (quint., J=7.30 Hz, 2H). LCMS (25-95% acetonitrile in 0.05% TFA over 10 minutes) retention time=6.82 minutes, ESI m/z=671, [M+H]$^+$.

Synthesis of 3-(2-(5-(3-Bromobenzyl)-4-(3-(1-trityl-1H-imidazol-5-yl)propyl)-4H-1,2,4-triazol-3y) ethyl)-1H-indole (31h)

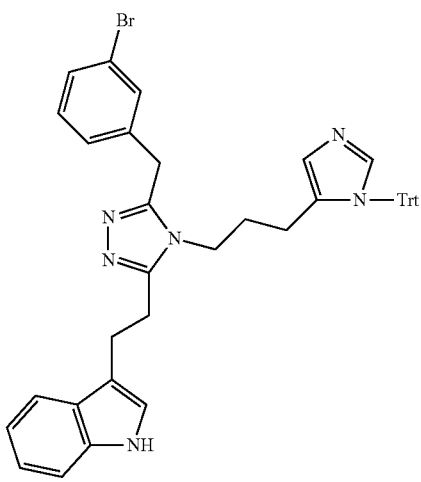

Prepared according to the General Procedure 1C from 3-(1H-indol-3-yl)-N-(3-(1-trityl-1H-imidazol-4-yl)propyl) propanethioamid (10) (748 mg, 1.40 mmol) and 2-(3-bromophenyl)acetic hydrazide (371 mg, 1.62 mmol). Purification by flash chromatography (SiO$_2$, 20:1 CH$_2$Cl$_2$/methanol) afforded 492 mg (48% yield) of compound 31h as a white solid: $^1$H NMR (400 MHz, DMSO-d$_6$) contains minor inseparable aromatic impurity related to the previous use of Lawesson's reagent, hydrogen-bonded forms observed, major form: δ 10.75 (bs, 1H), 7.90 (d, J=6.80 Hz, 1H), 6.98-7.47 (complex multiplets, 23H), 6.84 (t, J=8.00 Hz, 1H), 6.49 (s, 1H), 4.03 (s, 2H), 3.70 (apparent t, J=8.20 Hz, 2H), 3.05-3.07 (m, 2H), 2.89-2.933 (m, 2H), 2.28-2.32 (m, 2H), 1.51 (quint., J=7.30 Hz, 2H). LCMS (50-95% acetonitrile in 0.05% TFA over 10 minutes) retention time=4.30 minutes, ESI m/z=731, [M+H]$^+$.

Synthesis of 3-(2-(5-(3-(Tri fluoromethyl)benzyl)-4-(3-(1-trityl-1H-imidazol-4-Apropyl)-4H-1,2,4-triazol-3-yl)ethyl)-1H-indole (31i)

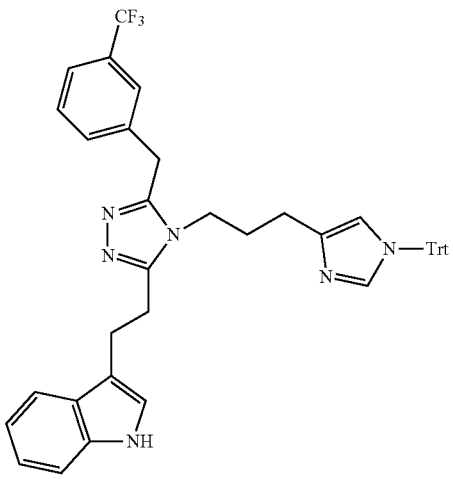

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(3,5-difluorophenyl)acetic hydrazide (236 mg, 1.08 mmol). Purification by flash chromatography (SiO$_2$, 40:1 CH$_2$Cl$_2$/methanol to 20:1) afforded 279 mg (36% yield) of compound 31i as a white solid: LCMS (50-95% acetonitrile in 0.05% TFA over 10 minutes) retention time=4.90 minutes, ESI m/z=721, [M+H]$^+$.

Synthesis of 3-(2-(5-(3,5-Di fluorobenzyl)-4-(3-(1-trityl-H-imidazol-5-yl)propyl)-4H-1,2,4-triazol-3-yl)ethyl)-1H-indole (3i)

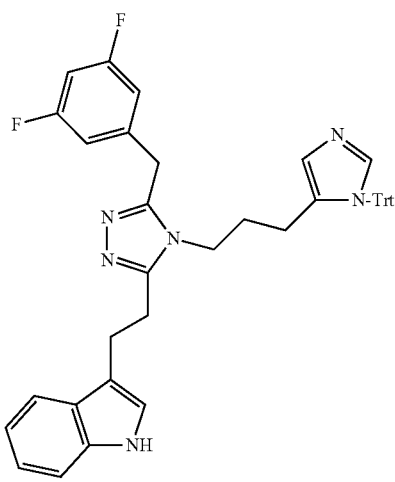

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(3,5-difluorophenyl)acetic hydrazide (206 mg, 1.10 mmol). Purification by flash chromatography (SiO$_2$, 20:1 CH$_2$Cl$_2$/methanol) afforded 300 mg (47% yield) of compound 31j as a white solid: $^1$H NMR (400 MHz, DMSO-d$_6$) conformational forms present; major form: δ 10.74 (bs, 1H), 7.89-7.91 (m, 1H), 7.40 (d, J=8.20 Hz, 1H), 7.29-7.33 (complex multiplets, 9H), 7.26 (d, J=7.80 Hz, 1H), 7.19 (d, J=1.30 Hz, 1H), 7.08 (d, J=2.30 Hz, 1H), 6.07-7.01 (complex multiplets, 8H), 6.86-6.89 (m, 1H), 6.83 (t, J=6.80 Hz, 1H), 6.51 (s, 1H), 4.07 (s, 2H), 3.72 (apparent t, J=6.30 Hz, 2H), 3.06 (apparent t, J=6.90 Hz, 2H), 2.92 (apparent t, J=6.40 Hz, 2H), 2.33 (t, J=6.90 Hz, 2H), 1.58 (quint, J=7.80 Hz, 2H). $^{13}$C NMR (100 MHz, DMSO-d$_6$) δ 162.79 (dd, J$_{C,F}$=246, 13.4 Hz), 154.70 (s), 152.14 (s), 142.81 (s), 141.82 (t, J$_{C,F}$=9.50 Hz), 140.15, 138.30, 136.68, 129.77, 129.65 (d), 129.06, 128.69 (d), 128.45, 127.43, 123.08, 121.40, 118.71, 118.68, 118.13, 113.88, 112.35 (dd, J$_{C,F}$=18.2, 6.70 Hz), 111.85, 102.70 (t, J$_{C,F}$=24.9 Hz), 74.87 (s), 42.51 (t), 30.17 (t), 29.67 (t), 25.91 (t), 24.99 (t), 23.17 (t). LCMS (50-95% acetonitrile in 0.05% TFA over 10 minutes) retention time=4.13 minutes, ESI m/z=689, [M+H]$^+$.

Synthesis of 3-(2-(5-(3,5-Dichlorobenzyl)-4-(3-(1-trityl-1H-imidazol-4-yl)propyl)-4H-1,2,4-triazol-3-yl)ethyl)-1H-indole (31k)

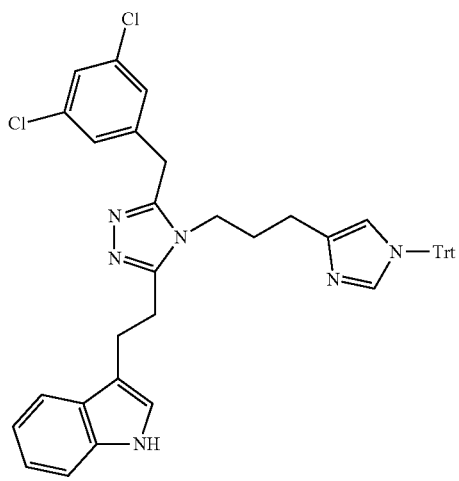

31k

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(3,5-difluorophenyl)acetic hydrazide (237 mg, 1.08 mmol). Purification by flash chromatography (SiO$_2$, 20:1 CH$_2$Cl$_2$/methanol) afforded 378 mg (58% yield) of compound 31k as a white solid: LCMS (50-95% acetonitrile in 0.05% TFA over 10 minutes) retention time=5.25 minutes, ESI m/z=721, [M+H]$^+$.

Synthesis of 3-(2-(5-(1-1,11-Biphenyl]-4-ylmethyl)-4-(3-(1-trityl-H-imidazol-4-Apropyl)-4H-1,2,4-triazol-3-yl)ethyl))-1H-indole (31m)

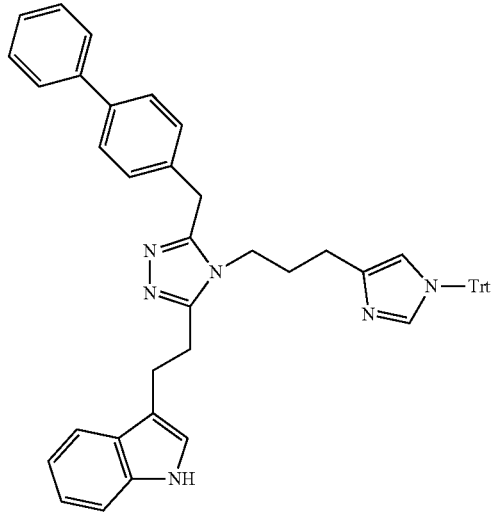

31m

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-([1,1'-biphenyl]-4-yl)acetic hydrazide (244 mg, 1.08 mmol). Purification by flash chromatography (SiO$_2$, 20:1 CH$_2$Cl$_2$/methanol) and recrystallization of the product from ACN afforded 235 mg (36% yield) of compound 31m as a white solid: $^1$H NMR (400 MHz, DMSO-d$_6$) δ 10.71 (bs, 1H), 7.54 (d, J=7.40 Hz, 2H), 7.48 (d, J=8.20 Hz, 2H), 7.35-7.43 (m, 3H), 7.25-7.31 (complex m, 11H), 7.16-7.19 (complex m, 3H), 7.07 (d, J=2.30 Hz, 1H), 6.96-6.98 (m, 7H), 6.85 (t, J=7.30 Hz, 1H), 6.50 (s, 1H), 4.05 (s, 2H), 3.68 (apparent t, J=8.20 Hz, 2H), 3.07 (apparent t, J~7.55 Hz, 2H), 2.92 (apparent t, J~7.80 Hz, 2H), 2.32 (t, J=6.90 Hz, 2H), 1.61 (quint, J=7.80 Hz, 2H). $^{13}$C NMR (100 MHz, DMSO-d$_6$) δ 154.54, 152.84, 142.81, 140.34, 140.18, 139.05, 138.31, 136.72, 136.47, 130.11, 129.65, 129.48, 129.39, 128.65, 128.42, 127.85, 127.47, 127.28, 127.06, 123.10, 121.39, 118.73, 118.69, 118.20, 113.90, 111.85, 74.90, 42.53, 30.40, 29.60, 25.95, 25.06, 23.28. LCMS (50-95% acetonitrile in 0.05% TFA over 10 minutes) retention time=5.40 minutes, ESI m/z=729, [M+H]$^+$.

Synthesis of 3-(2-(5-Benzyl-4-(3-(1-trityl-1H-imidazol-4-yl)propyl)-4H-1,2,4-triazol-3-yl)ethyl))-1H-indole 31n)

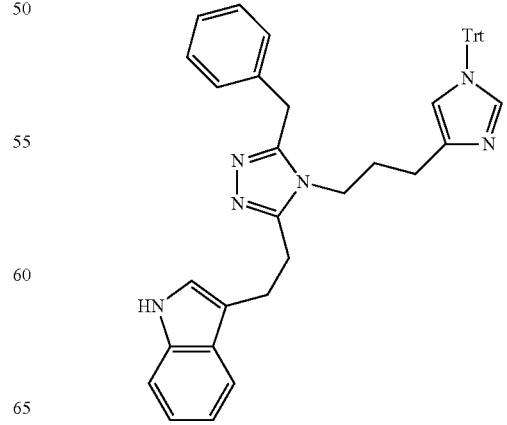

31n

Prepared according to the General Procedure 1C from 3-(1H-indol-3-yl)-N-(3-(1-trityl-1H-imidazol-4-yl)propyl)propanethioamide (10) (580 mg, 1.04 mmol) and 2-phenylacetic hydrazide (187 mg, 1.24 mmol). Purification by flash chromatography (SiO₂, 20:1 CH₂Cl₂/methanol) afforded 310 mg (46% yield) of compound 31n as a white solid: $^1$H NMR (400 MHz, DMSO-d$_6$) δ 10.74 (bs, 1H), 9.18 (bs, 1H), 7.90 (d, J=6.90 Hz, 1H), 6.98-7.55 (complex multiplets, 24H), 6.84 (t, J=6.80 Hz, 1H), 6.45 (s, 1H), 4.01 (s, 2H), 3.65 (apparent t, J=8.30 Hz, 2H), 3.06 (apparent t, J=8.20 Hz, 2H), 2.90 (apparent t, J=7.80 Hz, 2H), 2.27 (t, J=7.30 Hz, 2H), 1.47 (quint., J=7.40 Hz, 2H). $^{13}$C NMR (100 MHz, DMSO-d$_6$) δ 154.54 (s), 152.95 (s), 142.83 (s), 140.17, 138.26, 137.28, 136.81, 136.69, 133.35, 129.79, 129.68 (d), 129.47, 129.09, 128.98, 128.90, 128.70 (d), 128.48, 127.45, 127.08, 126.88, 123.10, 121.41, 118.74, 118.71, 118.16, 113.90, 111.86, 74.88 (s), 42.51 (t), 40.99 (t), 30.77 (t), 29.58 (t), 25.91 (t), 25.09 (t), 23.22 (t). LCMS (50-95% acetonitrile in 0.05% TFA over 10 minutes) retention time=3.97 minutes, ESI m/z=653, [M+H]⁺.

Synthesis of (R)-tert-butyl (1-(5-(3-chlorobenzyl)-4-(3-(1-trityl-1H-imidazol-4-yl)propyl)-4H-1,2,4-triazol-3-0-2-(1H-indol-3-yl)ethyl)carbamate (33)

33

Prepared according to the General Procedure 1C from (R)-tert-butyl (3-(1H-indol-3-0-1-thioxo-1-((3-(1-trityl-1H-imidazol-4-Apropyl)amino)propan-2-yl)carbamate (26) (289 mg, 0.43 mmol) and 2-(3-chlorophenyl)acetic hydrazide (95.6 mg, 0.52 mmol). Purification by flash chromatography (SiO₂, 20:1 CH₂Cl₂/methanol) afforded 80 mg (23% yield) of compound 33 as a tan foam: LCMS (50-95% acetonitrile in 0.05% TFA over 10 minutes) retention time=5.90 minutes, ESI m/z=802, [M+H]⁺.

Synthesis of 3-(2-(5-(3,4-Dichlorobenzyl)-4-(3-(1-trityl-1H-imidazol-4-yl)propyl)-4H-1,2,4-triazol-3-yl)ethyl)-1-methyl-1H-indole (35)

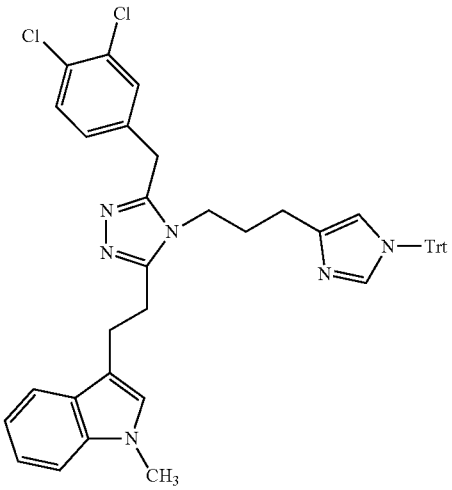

35

Prepared according to the General Procedure 1C from 3-(1-methyl-1H-indol-3-yl)-N-(3-(1-trityl-1H-imidazol-4-yl)propyl)propanethioamide (14) (440 mg, 0.77 mmol) and 2-(3,4-Dichlorophenyl)acetic hydrazide (29l) (203 mg, 0.93 mmol). Purification by flash chromatography (SiO₂, 40:1 CH₂Cl₂/methanol to 20:1) and recrystallization of the product from ACN afforded 390 mg (67% yield) of compound 35 as a white solid: LCMS (50-95% acetonitrile in 0.05% TFA over 10 minutes) retention time=5.62 minutes, ESI m/z=735, [M+H]⁺.

Synthesis of 1-Methyl-3-(2-(5-(3-(trifluoromethyl)benzyl)-4-(3-(1-trityl-1H-imidazol-4-yl)propyl)-4H-1,2,4-triazol-3-yl)ethyl)-1H-indole (37)

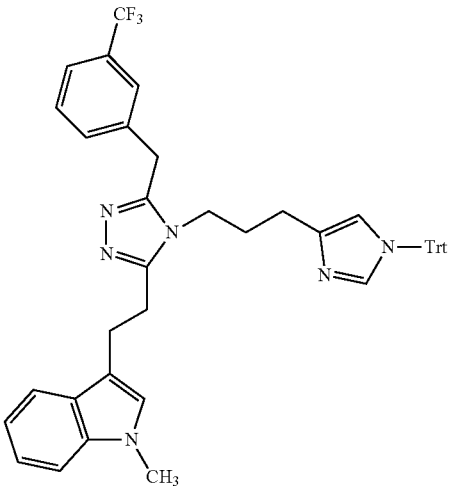

37

Prepared according to the General Procedure 1C from 3-(1-methyl-1H-indol-3-yl)-N-(3-(1-trityl-1H-imidazol-4-yl)propyl)propanethioamide (14) (720 mg, 1.26 mmol) and 2-(3-(trifluoromethyl)phenyl)acetic hydrazide (29i) (331 mg, 1.52 mmol). Purification by flash chromatography (SiO$_2$, 40:1 CH$_2$Cl$_2$/methanol to 20:1) afforded 463 mg (50% yield) of compound 37 as a white solid: LCMS (50-95% acetonitrile in 0.05% TFA over 10 minutes) retention time=5.47 minutes, ESI m/z=735, [M+H]$^+$.

General Procedure 1D: Trityl Deprotection

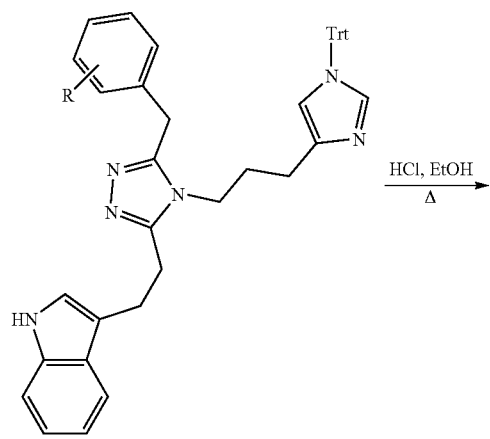

A mixture of the trityl-protected compound (1 mmol) in ethanol (50 mL) was added 2N HCl (25 mL) and the mixture was heated to 70° C. for 2-4 hours. The reaction was cooled, transferred to a separatory funnel, and diluted with water (50 mL). The solution was washed with CH$_2$Cl$_2$ (3×50 mL). The resulting aqueous solution was made basic with 2N NaOH (checked with pH paper) and extracted with CH$_2$Cl$_2$ (3×50 mL). The combined extracts were dried (Na$_2$SO$_4$), filtered and concentrated. The residue was purified by recrystallization, flash chromatography, or used as is.

Synthesis of 342444341H-Imidazol-4-yl)propyl)-5-(4-chlorobenzyl)-4H-1,2,4-triazol-3-yl)ethyl)-1H-indole (BN-VI-62)

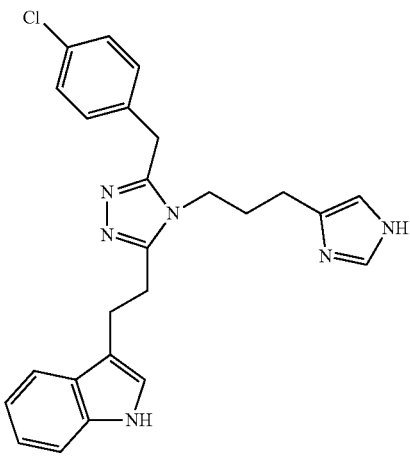

Prepared according to the General Procedure 1D from 3-(2-(5-(2-chlorobenzyl)-4-(3-(1-trityl-1H-imidazol-4-yl)propyl)-4H-1,2,4-triazol-3-yl)ethyl)-1H-indole (31a) (257 mg, 0.37 mmol) to afford 114 mg (69% yield) of BN-VI-62 as a white solid: LCMS (25-95% acetonitrile in 0.05% TFA over 10 minutes) retention time=5.43 minutes, ESI m/z=445, [M+H]$^+$.

Synthesis of 3-(2-(4-(3-(1H-Imidazol-4-yl)propyl)-5-(3-chlorobenzyl)-4H-1,2,4-triazol-3-yl)ethyl)-1H-indole (BN-VI-56)

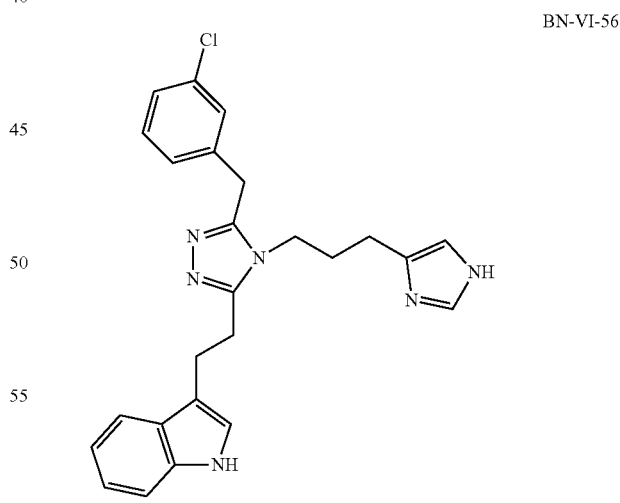

Prepared according to the General Procedure 1D from 3-(2-(5-(3-chlorobenzyl)-4-(3-(1-trityl-1H-imidazol-4-yl)propyl)-4H-1,2,4-triazol-3-ypethyl)-1H-indole (31b) (48.0 mg, 0.07 mmol) to afford 27.0 mg (87% yield) of BN-VI-56 as a white solid: LCMS (25-95% acetonitrile in 0.05% TFA over 10 minutes) retention time=5.38 minutes, ESI m/z=445, [M+H]$^+$.

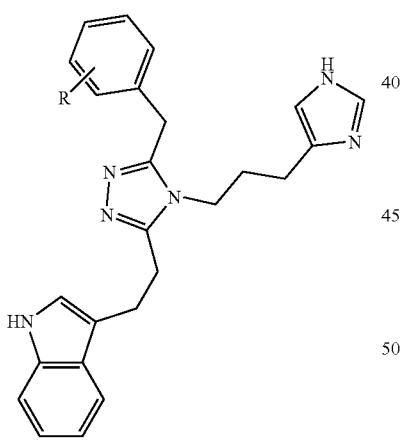

Synthesis of 3-(2-(4-(3-(1H-Imidazol-4-yl)propyl)-5-(2-chlorobenzyl)-4H-1,2,4-triazol-3-yl)ethyl)-1H-indole (MM-I-17)

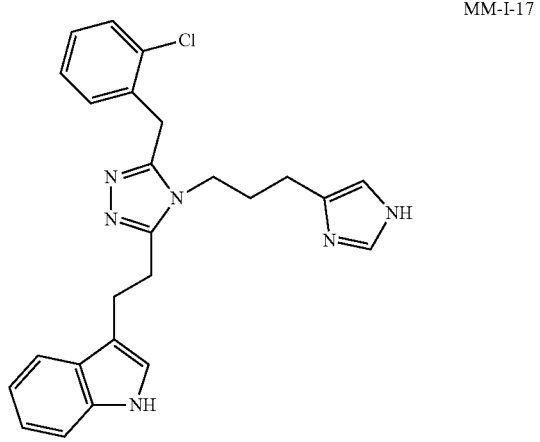 [SMILES: Clc1ccccc1Cc1nnc(CCc2c[nH]c3ccccc23)n1CCCc1c[nH]cn1]

MM-I-17

Prepared according to the General Procedure 1D from 3-(2-(5-(2-chlorobenzyl)-4-(3-(1-trityl-1H-imidazol-4-yl)propyl)-4H-1,2,4-triazol-3-ypethyl)-1H-indole (31c) (234 mg, 0.34 mmol). Recrystallization from ACN afforded 76.0 mg (50% yield) of MM-I-17 (Example 3) as a white solid: $^1$H NMR (400 MHz, DMSO-$d_6$) imidazole tautomers observed: δ 11.77 and 11.70 (two overlapping bs, 1H overall), 10.78 (bs, 1H), 7.41-7.44 (m, 3H), 7.29 (d, J=8.20 Hz, 1H), 7.22-7.27 (m, 2H), 7.06-7.10 (complex multiplet, 2H), 7.02 (t, J=7.30 Hz, 1H), 6.92 (t, J=7.30 Hz, 1H), 6.71 and 6.51 (two broadened singlets, 1H overall), 4.08 (s, 2H), 3.68-3.78 (m, 2H), 3.05-3.08 (m, 2H), 2.94-2.98 (m, 2H), 2.36 (t, J=6.90 Hz, 2H), 1.71 (quint, J=7.30 Hz, 2H). LCMS (15-95% acetonitrile in 0.05% TFA over 10 minutes) retention time=5.98 minutes, ESI m/z=445, [M+H]$^+$.

Synthesis of 3-(2-(4-(3-(1H-Imidazol-4-0propyl)-5-(4-methoxybenzyl)-4H-1,2,4-triazol-3-yl)ethyl)-1H-indole (SM-I-29)

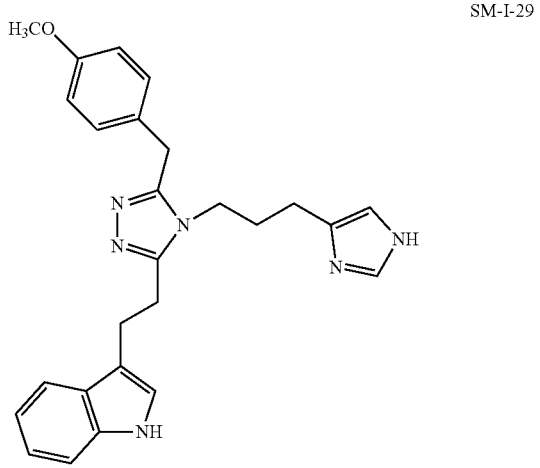 [SMILES: COc1ccc(Cc2nnc(CCc3c[nH]c4ccccc34)n2CCCc2c[nH]cn2)cc1]

SM-I-29

Prepared according the General Procedure 1D rom 3-(2-(5-(4-methoxybenzyl)-4-(3-(1-trityl-1H-imidazol-4-yl)propyl)-4H-1,2,4-triazol-3-yl)ethyl)-1H-indole (31d) (210 mg, 0.30 mmol) to afford 110 mg (83% yield) of SM-I-29 as a white solid: $^1$H NMR (400 MHz, DMSO-$d_6$) imidazole tautomers observed: δ 11.73 (bs, 1H), 10.77 (bs, 1H), 7.49 and 7.45 (2 bs, 1H overall), 7.42 (d, J=7.40 Hz, 1H), 7.11-7.34 (complex multiplets, 5H), 7.09 (d, J=2.30 Hz, 1H), 7.02 (dt, J=6.60, 0.90 Hz, 1H), 6.97 (d, J=8.30 Hz, 2H), 6.92 (t, J=6.90 Hz, 1H), 6.78-6.81 (m, 2H), 6.69 and 6.50 (2 bs, 1H overall), 3.93 (s, 2H), 3.66 (s, 3H), 3.60-3.66 (m, 2H), 3.06 (apparent t, J=8.20 Hz, 2H), 2.91 (apparent t, J=6.90 Hz, 2H), 2.29-2.38 (m, 2H), 1.53-1.62 (m, 2H). $^{13}$C NMR (100 MHz, DMSO-$d_6$) imidazole tautomers observed: δ 158.48 (s), 154.53 (s), 153.24 (s), 148.29, 144.63, 139.80, 136.68, 135.20, 130.43, 129.91, 128.93, 128.65, 128.41, 128.29, 128.06, 127.45, 127.17, 123.11, 121.43, 118.80, 118.71, 114.45, 114.2, 113.90, 112.55, 111.86, 55.54 (q), 42.49 (t), 42.34 (t), 29.99 (t), 29.90 (t), 29.52 (t), 25.88 (t), 25.00 (t), 23.26 (t), 23.18 (t). LCMS (5-95% acetonitrile in 0.05% TFA over 10 minutes) retention time=6.30 minutes, ESI m/z=441, [M+H]$^+$.

Synthesis of 3-(2-(4-(3-(1H-Imidazol-4-yl)propyl)-5-(3-methoxybenzyl)-4H-1,2,4-triazol-3-Methyl)-1H-indole (BN-VI-61)

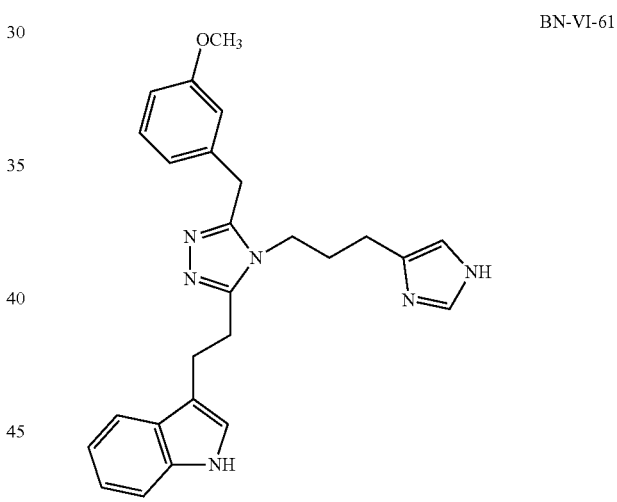

BN-VI-61

Prepared according to the General Procedure 1D rom 3-(2-(5-(3-methoxybenzyl)-4-(3-(1-trityl-1H-imidazol-4-yl)propyl)-4H-1,2,4-triazol-3-ypethyl)-1H-indole (31e) (177 mg, 0.26 mmol) to afford 96 mg (84% yield) of BN-VI-61 as a white solid: $^1$H NMR (400 MHz, DMSO-$d_6$) δ 11.80 (bs, 1H), 10.78 (bs, 1H), 7.49 (s, 1H), 7.43 (d, J=7.80 Hz, 1H), 7.29 (d, J=7.80 Hz, 1H), 7.15 (t, J=7.80 Hz, 1H), 7.10 (d, J=1.80 Hz, 1H), 7.02 (t, J=7.40 Hz, 1H), 6.92 (t, J=7.40 Hz, 1H), 6.72-6.76 (m, 2H), 6.62-6.68 (m, 2H), 3.99 (s, 2H), 3.69 (apparent t, J=7.40 Hz, 2H), 3.07 (apparent t, J=6.90 Hz, 2H), 2.92 (apparent t, J=6.90 Hz, 2H), 2.34 (t, J=6.80 Hz, 2H), 1.59 (quint, J=7.80 Hz, 2H). $^{13}$C NMR (100 MHz, DMSO-$d_6$) δ 159.88 (s), 154.57 (s), 152.91 (s), 138.74, 136.71, 135.19, 130.13, 127.47, 123.10, 121.45, 121.11, 118.81, 118.73, 114.69, 113.94, 112.55, 111.88, 55.50 (q), 42.50 (t), 30.79 (t), 29.74 (t), 25.91 (t), 23.19 (t). LCMS (25-95% acetonitrile in 0.05% TFA over 10 minutes) retention time=4.02 minutes, ESI m/z=441, [M+H]$^+$.

Synthesis of 3-(2-(4-(3-(1H-Imidazol-4-yl)propyl)-5-(2-methoxybenzyl)-4H-1,2,4-triazol-3-yl)ethyl)-1H-indole (MM-I-21)

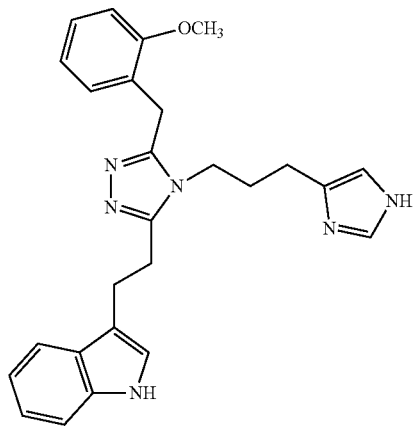

MM-I-21

Prepared according to the General Procedure 1D from 3-(2-(5-(2-methoxybenzyl)-4-(3-(1-trityl-1H-imidazol-4-yl)propyl)-4H-1,2,4-triazol-3-ypethyl)-1H-indole (31f) (102 mg, 0.15 mmol) to afford 21 mg (74% yield) of MM-I-21 as a white solid: $^1$H NMR (400 MHz, DMSO-$d_6$) imidazole tautomers observed: δ 11.75 and 11.69 (two overlapping bs, 1H overall), 10.77 (bs, 1H), 7.41-7.44 (m, 2H), 7.29 (d, J=8.30 Hz, 1H), 7.18 (broadened dt, J=6.40, 1.80 Hz, 1H), 7.09 (d, J=1.80 Hz, 1H), 7.02 (dt, J=6.90, 0.9 Hz, 1H), 6.90-6.95 (m, 2H), 6.80-6.88 (m, 3H), 6.69 and 6.50 (two bs, 1H overall), 3.92 and 3.91 (two overlapping s, 2H overall), 3.73 and 3.72 (two overlapping s, 3H overall), 3.64-3.73 (m, 2H), 3.04-3.09 (m, 2H), 2.91-2.95 (m, 2H), 2.38 and 2.33 (two t, J=7.80 and 6.90 Hz, respectively, 2H overall), 1.61-1.70 (m, 2H). LCMS (15-95% acetonitrile in 0.05% TFA over 10 minutes) retention time=5.95 minutes, ESI m/z=441, [M+H]$^+$.

Synthesis of 3-(2-(4-(3-(1H-Imidazol-4-yl)propyl)-5-(3-fluorobenzyl)-4H-1,2,4-triazol-3-yl)ethyl)-1H-indole (SM-I-38)

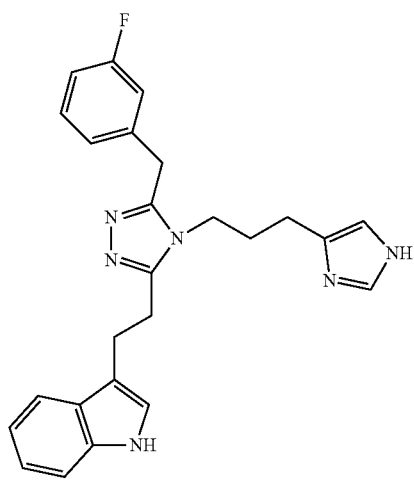

SM-I-38

Prepared according to the General Procedure 1D from 3-(2-(5-(3-fluorobenzyl)-4-(3-(1-trityl-1H-imidazol-4-yl)propyl)-4H-1,2,4-triazol-3-yl)ethyl)-1H-indole (31 g) (290 mg, 0.43 mmol) to afford 120 mg (65% yield) of SM-I-38 as a white solid: $^1$H NMR (400 MHz, DMSO-$d_6$) imidazole tautomers observed: δ 11.75 and 9.21 (two bs, 1H overall), 10.78 (bs, 1H), 7.47 (s, 1H), 7.42 (d, J=7.70 Hz, 1H), 7.29 (apparent q, J=7.80 Hz, 2H), 7.10 (bs, 1H), 6.97-7.05 (m, 3H), 6.89-6.95 (m, 2H), 6.65 (bs, 1H), 4.05 (s, 2H), 3.70 (apparent t, J=7.80 Hz, 2H), 3.07 (apparent t, J=7.55 Hz, 2H), 2.93 (apparent t, J=7.55 Hz, 2H), 2.35 (t, J=6.90 Hz, 2H), 1.61 (quint, J=7.30 Hz, 2H). $^{13}$C NMR (100 MHz, DMSO-$d_6$) imidazole tautomers observed: δ 162.68 (d, $J_{C,F}$=243 Hz), 162.68 (d, $J_{C,F}$=243 Hz), (s), 154.68 (s), 152.56 (s), 140.07 (d, $J_{C,F}$=7.60 Hz), 139.54 (d, $J_{C,F}$=7.60 Hz), 136.60, 135.21, 130.99 (d, $J_{C,F}$=8.70 Hz), 130.55 (d, $J_{C,F}$=8.70 Hz), 127.45, 125.63, 125.09, 123.11, 121.44, 118.79, 118.70, 116.18 (d, $J_{C,F}$=22.1 Hz), 115.82 (d, $J_{C,F}$=21.1 Hz), 114.12, 113.91, 113.71 (d, $J_{C,F}$=21.1 Hz), 111.87, 42.27 (t), 31.22 (t), 30.35 (t), 29.81 (t), 25.92 (t), 23.2 (t). LCMS (40-95% acetonitrile in 0.05% TFA over 10 minutes) retention time=1.88 minutes, ESI m/z=429, [M+H]$^+$.

Synthesis of 3-(2-(4-(3-(1H-Imidazol-4-yl)propyl)-5-(3-bromobenzyl)-4H-1,2,4-triazol-3-yl)ethyl)-1H-indole (SM-I-50)

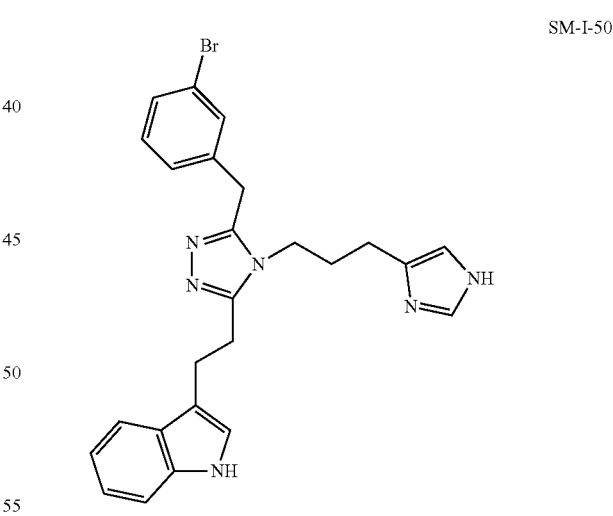

SM-I-50

Prepared according to the General Procedure 1D from 3-(2-(5-(3-(bromobenzyl)-4-(3-(1-trityl-1H-imidazol-4-yl)propyl)-4H-1,2,4-triazol-3-yl)ethyl)-1H-indole (31h) (270 mg, 0.37 mmol) to afford 100 mg (55% yield) of SM-I-50 as a white solid: $^1$H NMR (400 MHz, DMSO-$d_6$) major tautomer δ 11.75 (bs, 1H), 10.77 (bs, 1H), 7.48 (s, 1H), 7.42 (d, J=8.30 Hz, 1H), 7.38-7.40 (m, 2H), 7.15 7.34 (complex multiplets, 5H), 7.08-7.11 (m, 2H), 7.02 (t, J=6.90 Hz, 1H), 6.91 (t, J=7.30 Hz, 1H), 6.66 (bs), 4.04 (s, 2H), 3.71 (apparent t, J=7.70 Hz, 2H), 3.07 (apparent t, J=7.55 Hz, 2H), 2.93 (apparent t, J=7.55 Hz, 2H), 2.36 (t, J=7.30 Hz, 2H), 1.62 (quint, J=7.80 Hz, 2H). $^{13}$C NMR (100 MHz, DMSO-d$_6$) major tautomer δ 154.67 (s), 152.57 (s), 140.02, 136.69, 135.20, 131.81, 131.16, 130.08, 128.40, 128.29, 128.17, 128.06, 127.45, 123.11, 122.24, 121.44, 118.80, 118.70, 113.90, 111.87, 42.48 (t), 30.18 (t), 29.94 (t), 25.91 (t), 23.20 (t). LCMS (5-95% acetonitrile in 0.05% TFA over 10 minutes) retention time=6.47 minutes, ESI m/z=489, [M+H]$^+$.

Synthesis of 3-(2-(4-(3-(1H-Imidazol-4-yl)propyl)-5-(3-(trifluoromethyl) benzyl)-4H-1,2,4-triazol-3-yl)ethyl)-1H-indole (BN-VI-97)

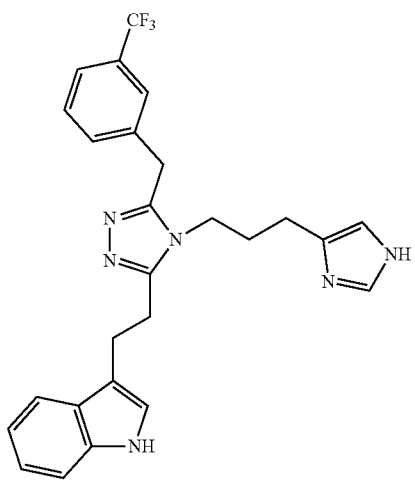

BN-VI-97

Prepared according to the General Procedure 1D from 3-(2-(5-(3-(trifluoromethyl)benzyl)-4-(3-(1-trityl-1H-imidazol-4-yl)propyl)-4H-1,2,4-triazol-3-yl)ethyl)-1H-indole (31i) (268 mg, 0.37 mmol) to afford 121 mg (68% yield) of BN-VI-97 as a white solid: $^1$H NMR (400 MHz, DMSO-d$_6$, 80° C.) imidazole tautomers observed δ 11.54 and 9.06 (2 bs, 1H overall), 10.56 (bs, 1H), 7.58 (s, 1H), 7.48-7.55 (m, 3H), 7.41-7.44 (m, 2H), 7.30 (d, J=8.20 Hz, 1H), 7.07 (s, 1H), 7.02 (t, J=6.80 Hz, 1H), 6.92 (t, J=7.80 Hz, 1H), 6.66 (bs, 1H), 4.14 (s, 2H), 3.71-3.79 (m, 2H), 3.10 (apparent t, J=6.80 Hz, 2H), 2.96 (apparent t, J=7.30 Hz, 2H), 2.36-2.41 (m, 2H), 1.69 (b quint, J~6.50 Hz, 2H). $^{13}$C NMR (100 MHz, DMSO-d$_6$, 80° C.) imidazole tautomers observed δ 156.06, 152.63, 136.92, 136.67, 134.83, 131.88, 130.72 (q, J$_{C,F}$=32.6 Hz), 129.46, 126.97, 124.91 (q, J$_{C,F}$=3.80 Hz), 124.14 (q, J$_{C,F}$=271 Hz), 123.68 (q, J$_{C,F}$=3.80 Hz), 122.13, 121.10, 118.46, 117.62, 112.91, 111, 42.08, 29.93, 28.79, 25.81, 23.66. LCMS (5-95% acetonitrile in 0.05% TFA over 10 minutes) retention time=6.58 minutes, ESI m/z=479, [M+H]$^+$.

Synthesis of 3-(2-(4-(3-(1H-Imidazol-4-yl)propyl)-5-(3,5-di fluorobenzyl)-4H-1,2,4-triazol-3-yl)ethyl)-1H-indole (SM-I-55)

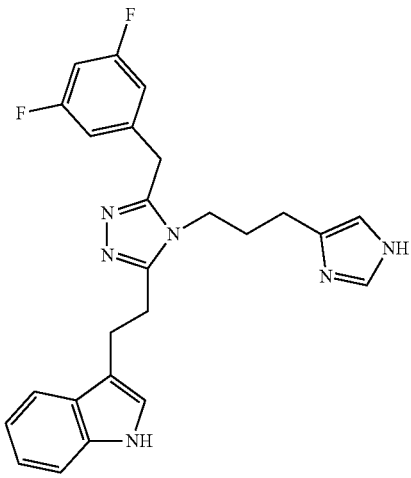

SM-I-55

Prepared according to the General Procedure 1D from 3-(2-(5-(3,5-difluorobenzyl)-4-(3-(1-trityl-1H-imidazol-4-yl)propyl)-4H-1,2,4-triazol-3-yl)ethyl)-1H-indole (31j) (250 mg, 363 mmol) to afford 130 mg (80% yield) of SM-I-55 as a white solid. A small fraction was recrystallized from ACN to afford pure material: $^1$H NMR (400 MHz, DMSO-d$_6$) imidazole tautomers observed δ 11.74 (bs, 1H), 10.77 (bs, 1H), 7.48 (bs, 1H), 7.41 (d, J=7.70 Hz, 1H), 7.28 (d, J=8.30 Hz, 1H), 7.05-7.11 (m, 2H), 7.01 (t, J=7.40 Hz, 1H), 6.86-6.92 (m, 3H), 6.72 and 6.51 (two bs, 1H overall), 4.07 (s, 2H), 3.66-3.76 (m, 2H), 3.05-3.08 (m, 2H), 2.92-2.95 (m, 2H), 2.33-2.37 (m, 2H), 1.59-1.68 (m, 2H). LCMS (5-95% acetonitrile in 0.05% TFA over 10 minutes) retention time=6.40 minutes, ESI m/z=447, [M+H]$^+$.

Synthesis of 3-(2-(4-(3-(1H-Imidazol-4-yl)propyl)-5-(3,5-dichlorobenzyl)-4H-1,2,4-triazol-3-yl)ethyl)-1H-indole (BN-VI-89)

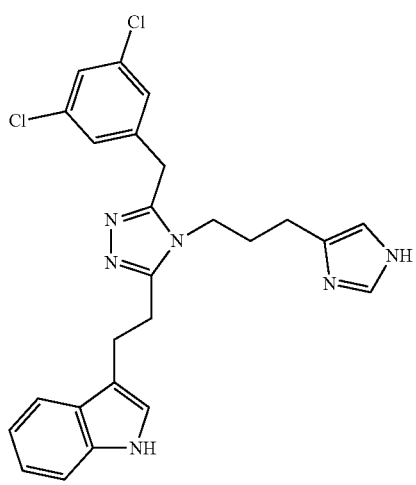

BN-VI-89

Prepared according to the General Procedure 1D from 3-(2-(5-(3,5-dichlorobenzyl)-4-(3-(1-trityl-1H-imidazol-4-yl)propyl)-4H-1,2,4-triazol-3-yl)ethyl)-1H-indole (31k) (328 mg, 0.45 mmol) to afford 179 mg (83% yield) of BN-VI-89 as an off white solid: $^1$H NMR (400 MHz, DMSO-$d_6$) imidazole tautomers observed δ 11.73 and 9.19 (2 bs, 1H overall), 10.74 (bs, 1H), 7.40-7.47 (m, 3H), 7.25-7.30 (m, 3H), 7.10 (s, 1H), 7.02 (t, J=6.90 Hz, 1H), 6.91 (t, J=6.90 Hz, 1H), 6.72 and 6.58 (2 bs, 1H overall), 4.07 (s, 2H), 3.73-3.79 (bm, 2H), 3.08 (apparent t, J=7.40 Hz, 2H), 2.94 (apparent t, J=7.40 Hz, 2H), 2.35-2.42 (bm, 2H), 1.67 (bquint, J=6.80 Hz, 2H). LCMS (25-95% acetonitrile in 0.05% TFA over 10 minutes) retention time=5.82 minutes, ESI m/z=479, [M+H]$^+$.

Synthesis of 3-(2-(4-(3-(1H-Imidazol-4-yl)propyl)-5-(1,1'-biphenyl-4-ylmethyl)-4H-1,2,4-triazol-3-yl)ethyl)-1H-indole (MM-I-26)

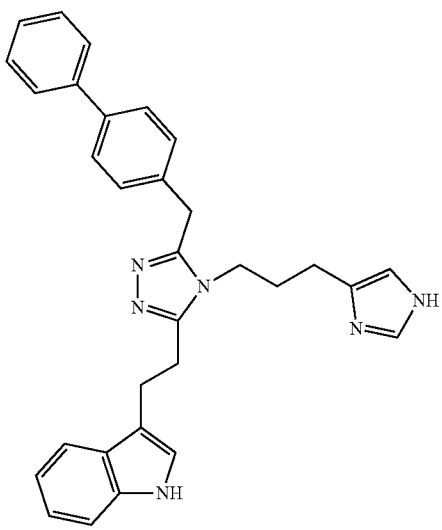

MM-I-26

Prepared according to the General Procedure 1D from 3-(2-(5-([1,1'-biphenyl]-4-ylmethyl)-4-(3-(1-trityl-1H-imidazol-4-yl)propyl)-4H-1,2,4-triazol-3-yl)ethyl)-1H-indole (31k) (204 mg, 0.28 mmol) to afford 36 mg (26% yield) of MM-I-26 as a white solid: $^1$H NMR (400 MHz, CD$_3$OD) δ 7.51-7.54 (complex m, 3H), 7.47 (d, J=7.30 Hz, 2H), 7.39 (t, J=7.40 Hz, 2H), 7.28-7.32 (m, 2H), 7.26 (d, J=7.80 Hz, 1H), 7.01-7.06 (m, 1H), 7.00 (d, J=8.30 Hz, 2H), 6.92 (dt, J=7.80 Hz, 1H), 6.89 (s, 1H), 6.53 (bs, 1H), 4.03 (s, 2H), 3.31 (apparent t, J=7.30 Hz, 2H), 3.81 (apparent t, J=6.90 Hz, 2H), 3.01 (apparent t, J=6.90 Hz, 2H), 2.25 (t, J=7.30 Hz, 2H), 1.38 (apparent quint, J~7.80 Hz, 2H). $^{13}$C NMR (100 MHz, CD$_3$OD) δ 156.03, 153.15, 140.44, 140.06, 136.67, 135.99 (broadened), 134.73, 134.38, 129.21, 128.53, 128.46, 127.13, 127.09, 126.55, 122.19, 121.10, 118.50, 117.68, 115.68, 112.90, 111.00, 42.19, 30.05, 28.68, 25.77, 23.68, 23.13. LCMS (15-95% acetonitrile in 0.05% TFA over 10 minutes) retention time=6.30 minutes, ESI m/z=487, [M+H]$^+$.

Synthesis of 342444341H-Imidazol-4-yl)propyl)-5-benzyl-4H-1,2,4-triazol-3-ypethyl)-1H-indole (S M-I-26)

SM-I-26

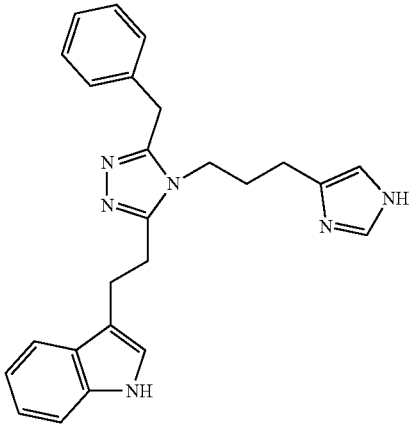

Prepared according to the General Procedure 1D from 3-(2-(5-benzyl-4-(3-(1-trityl-1H-imidazol-4-yl)propyl)-4H-1,2,4-triazol-3-yl)ethyl)-1H-indole (31n) (250 mg, 0.38 mmol). Recrystallization from ACN afforded 46.0 mg (30% yield) of SM-I-26 as a white solid: H NMR (400 MHz, DMSO-$d_6$) imidazole tautomers observed: δ 11.74 and 9.18 (2 bs, 1H overall), 10.77 (bs, 1H), 7.47 (s, 1H), 7.42 (d, J=8.20 Hz, 1H), 7.15-7.30 (complex m, 5H), 7.06-7.10 (m, 3H), 7.02 (t, J=7.30 Hz, 1H), 6.91 (t, J=7.40 Hz, 1H), 6.67 and 6.53 (2 bs, 1H overall), 4.01 (s, 2H), 3.62-3.69 (bm, 2H), 3.06 (apparent t, J~7.55 Hz, 2H), 2.92 (apparent t, J~7.80 Hz, 2H), 2.30-2.35 (bm, 2H), 1.53-1.64 (bm, 2H). $^{13}$C NMR (100 MHz, DMSO-$d_6$) imidazole tautomers observed: δ 154.58, 152.95, 137.18, 136.68, 135.19, 129.46, 129.05, 128.91, 128.69, 127.45, 127.13, 126.87, 123.11, 121.43, 118.80, 118.71, 113.90, 111.87, 42.45, 30.81, 29.78 (broadened), 25.90, 24.86 (broadened), 23.22. LCMS (15-95% acetonitrile in 0.05% TFA over 10 minutes) retention time=5.88 minutes, ESI m/z=411, [M+H]$^+$.

Synthesis of (R)-1-(4-(3-(1H-Imidazol-4-yl)propyl)-5-(3-chlorobenzyl)-4H-1,2,4-triazol-3-Vl)-2-(1H-indol-3-yl)ethanamine (BN-VI-87)

BN-VI-87

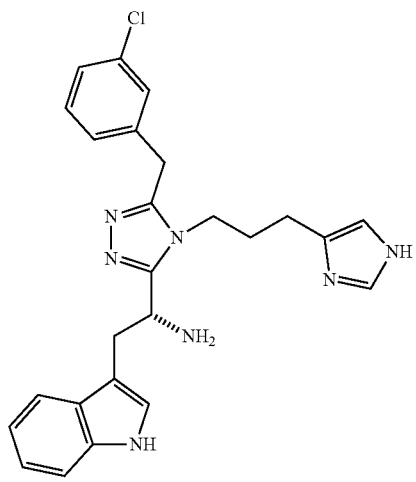

Prepared according to the General Procedure 1D from (R)-tert-butyl (1-(5-(3-chlorobenzyl)-4-(3-(1-trityl-1H-imidazol-4-yl)propyl)-4H-1,2,4-triazol-3-yl)-2-(1H-indol-3-yl)ethyl)carbamate (33) (80.0 mg, 0.10 mmol) to afford 32 mg (72% yield) of BN-VI-87 as a tan foam: LCMS (25-95% acetonitrile in 0.05% TFA over 10 minutes) retention time=3.00 minutes, ESI m/z=460, [M+H]$^+$.

Synthesis of 3-(2-(4-(3-(1H-Imidazol-4-yl)propyl)-5-(3,4-dichlorobenzyl)-4H-1,2,4-triazol-3-yl)ethyl)-1-methyl-1H-indole (SM-I-60)

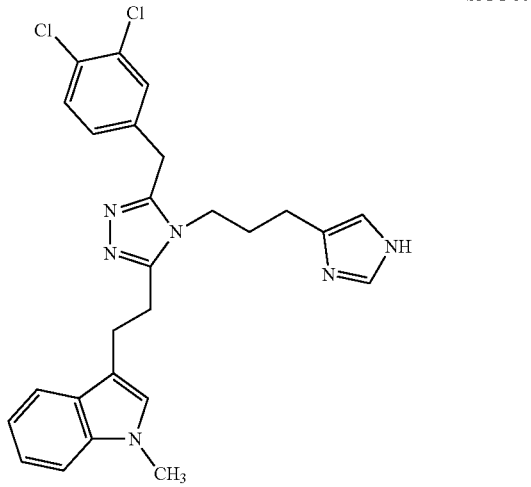

SM-I-60

Prepared according to the General Procedure 1D from 3-(2-(5-(3,4-dichlorobenzyl)-4-(3-(1-trityl-1H-imidazol-4-yl)propyl)-4H-1,2,4-triazol-3-yl)ethyl)-1-methyl-1H-indole (35) (320 mg, 0.44 mmol) to afford 120 mg (56% yield) of SM-I-60 as a white foam: $^1$H NMR (400 MHz, DMSO-d$_6$) imidazole tautomers observed δ 11.75 and 9.20 (2 bs, 1H overall), 7.52 (d, J=8.20 Hz, 1H), 7.47-7.49 (bm, 1H), 7.45 (d, J=1.80 Hz, 1H), 7.41 (d, J=7.80 Hz, 1H), 7.32 (d, J=8.20 Hz, 1H), 7.05-7.12 (complex m, 3H), 6.94 (t, J=7.40 Hz, 1H), 6.66 (bs, 1H), 4.05 (s, 2H), 3.65-3.72 (m, 2H), 3.66 (s, 3H), 3.05 (apparent t, J~7.55 Hz, 2H), 2.91 (apparent t, J~7.55 Hz, 2H), 2.36 (t, J=7.30 Hz, 2H), 1.61 (quint, J=7.30 Hz, 2H). LCMS (15-95% acetonitrile in 0.05% TFA over 10 minutes) retention time=6.45 minutes, ESI m/z=493, [M+H]$^+$.

Synthesis of 3-(2-(4-(3-(1H-imidazol-4-0propyl)-5-(3-(tri fluoromethyl)benzyl)-4H-1,2,4-triazol-3-yl)ethyl)-1-methyl-1H-indole (SM-I-76)

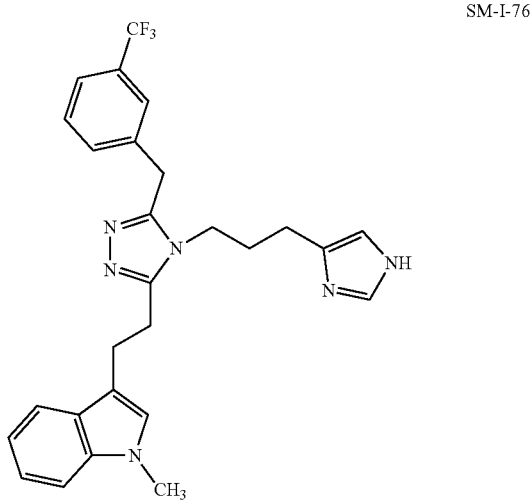 [SMILES: Cn1cc(CCc2nnc(Cc3cccc(C(F)(F)F)c3)n2CCCc2c[nH]cn2)c2ccccc21]

SM-I-76

Prepared according to General Procedure 1D from 1-methyl-3-(2-(5-(3-(trifluoromethyl)benzyl)-4-(3-(1-trityl-1H-imidazol-4-yl)propyl)-4H-1,2,4-triazol-3yl)ethyl)-1H-indole (37) (0.620 g, 0.843 mmol) to afford 0.220 g (77% yield) of compound SM-I-76 as a yellow solid: $^1$H NMR (400 MHz, CD$_3$OD) δ 7.53-7.51 (m, 2H), 7.46-7.42 (m, 2H), 7.28 (d, J=8.00 Hz, 1H), 7.24-7.22 (m, 2H), 7.10 (dt, J=7.00, 0.84 Hz, 1H), 6.93 (dt, J=7.23, 0.78 Hz, 1H), 6.77 (s, 1H), 6.55 (bs, 1H), 4.09 (s, 2H), 3.60 (s, 3H), 3.35-3.31 (m, 2H), 3.15 (t, J=7.15 Hz, 2H), 3.00 (t, J=6.79 Hz, 2H), 2.26 (t, J=7.07 Hz, 2H), 1.41 (quint., J=7.18 Hz, 2H). $^{13}$C NMR (100 MHz, CD$_3$OD) δ 155.98, 152.66, 137.13, 136.96, 134.85, 131.97, 130.74 (q, $J_{C,F}$=32.2 Hz), 129.48, 127.48, 126.56, 124.92 (q, $J_{C,F}$=3.76 Hz), 124.14 (q, $J_{C,F}$=271.3 Hz), 123.71 (q, $J_{C,F}$=3.73 Hz), 121.24, 118.53, 117.96, 112.42, 108.93, 42.13, 31.25, 29.94, 28.75, 25.87, 23.47, 23.15. LCMS (25-95% acetonitrile in 0.05% TFA over 10 minutes) retention time=5.98 minutes, ESI m/z=493, [M+H]$^+$.

Synthesis of 3-((4-(3-(1H-imidazol-4-yl)propyl)-5-benzyl-4H-1,2,4-triazol-3-yl)methyl)-1H-indole (SK-I-25)

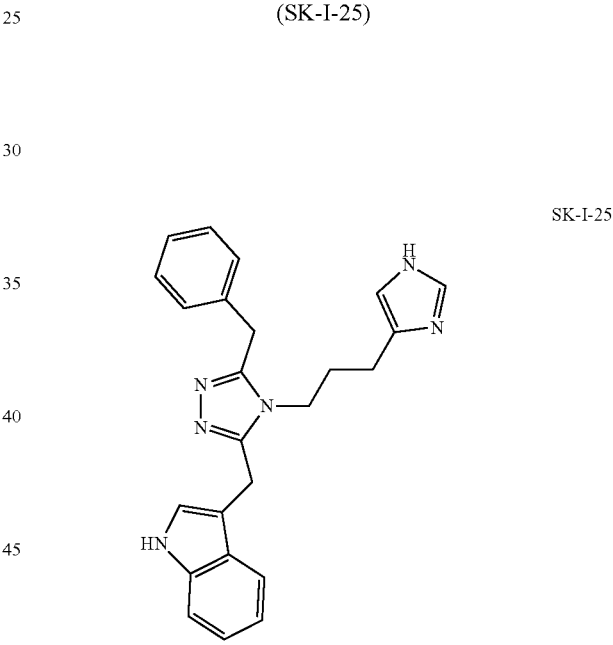

SK-I-25

Prepared according to General Procedure 1D from 3-((5-benzyl-4-(3-(1-trityl-1H-imidazol-4-yl)propyl)-4H-1,2,4-triazol-3-yl)methyl)-1H-indole (237 mg, 0.37 mmol) to afford 113 mg (77% yield) of compound SK-I-25 as a white solid: $^1$H NMR (400 MHz, CD$_3$OD) δ 7.53 (s, 1H), 7.35 (d, J=7.92 Hz, 1H), 7.30 (d, J=8.21 Hz, 1H), 7.23-7.14 (complex m, 3H), 7.06 (dt, J=7.11, 0.66 Hz, 1H), 7.02 (d, J=6.89, 2H), 6.94 (apparent t, J=6.83 Hz, 2H), 6.51 (s, 1H), 4.25 (s, 2H), 4.06 (s, 2H), 3.59 (apparent t, J=8.33 Hz, 2H), 2.24 (t, J=7.07 Hz, 2H), 1.35 (quint., J=7.21 Hz, 2H). $^{13}$C NMR (100 MHz, CD$_3$OD) δ 154.82, 154.21, 136.84, 135.41, 134.66, 128.59, 128.01, 126.89, 126.66, 122.96, 121.51, 118.83, 117.88, 111.16, 107.93, 42.75, 30.37, 28.88, 23.18, 21.55. LCMS (50-95% acetonitrile in 0.05% TFA over 10 minutes) retention time=1.75 minutes, ESI m/z=397, [M+H]$^+$.

Synthesis of 3-((4-(3-(1H-imidazol-4-yl)propyl)-5-(4-fluorobenzyl)-4H-1,2,4-triazol-3-yl)methyl)-1H-indole (SK-I-16)

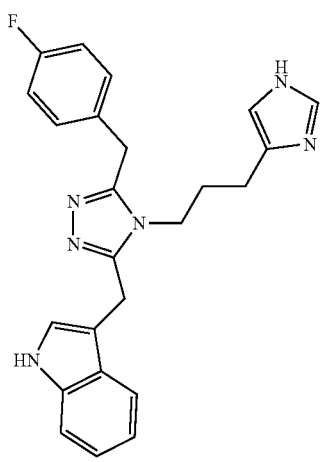

SK-I-16

Prepared according to General Procedure 1D from 3-((5-(4-fluorobenzyl)-4-(3-(1-trityl-1H-imidazol-4-yl)propyl)-4H-1,2,4-triazol-3-yl)methyl)-1H-indole (150 mg, 0.23 mmol) to afford 86 mg (91% yield) of compound SK-I-16 as a white solid: $^1$H NMR (400 MHz, CD$_3$OD) δ 7.53 (s, 1H), 7.34 (d, J=8.02 Hz, 1H), 7.30 (d, J=8.23 Hz, 1H), 7.28-7.25 (m, 1H), 4.26 (s, 2H), 4.04 (s, 2H), 3.63-3.59 (m, 2H), 2.27 (t, J=7.07 Hz, 2H), 1.39 (t, J=7.10 Hz, 2H). LCMS (50-95% acetonitrile in 0.05% TFA over 10 minutes) retention time=1.78 minutes, ESI m/z=415, [M+H]$^+$ Synthesis of 3-((4-(3-(1H-imidazol-4-yl)propyl)-5-(4-chlorobenzyl)-4H-1,2,4-triazol-3-yl)methyl)-1H-indole (SK-I-22)

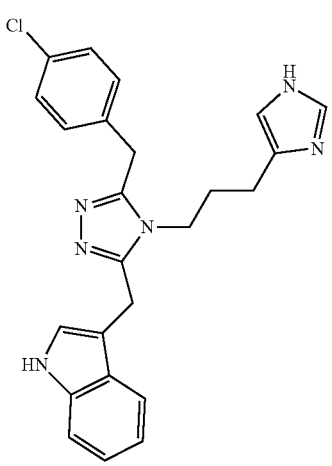

SK-I-22

Prepared according to General Procedure 1D from 3-((5-(4-chlorobenzyl)-4-(3-(1-trityl-1H-imidazol-4-yl)propyl)-4H-1,2,4-triazol-3-yl)methyl)-1H-indole (220 mg, 0.33 mmol) to afford 115 mg (83% yield) of compound SK-I-22 as a white solid: $^1$H NMR (400 MHz, CD$_3$OD) δ 7.54 (s, 1H), 7.34 (d, J=7.91 Hz, 1H), 7.30 (d, J=8.07 Hz, 1H), 7.26-7.20 (m, 4H), 7.07 (dt, J=8.01, 0.97 Hz, 1H), 7.01 (d, J=8.43 Hz, 2H), 6.96-6.92 (m, 2H), 4.26 (s, 2H), 4.04 (s, 2H), 3.63-3.59 (m, 2H), 2.26 (t, J=7.10 Hz, 2H), 1.38 (t, J=7.02 Hz, 2H). LCMS (50-95% acetonitrile in 0.05% TFA over 10 minutes) retention time=1.82 minutes, ESI m/z=431, [M+H]$^+$.

Synthesis of 3-((4-(3-(1H-imidazol-4-yl)propyl)-5-(3-(trifluoromethyl)benzyl)-4H-1,2,4-triazol-3-yl)methyl)-1H-indole (MM-I-66)

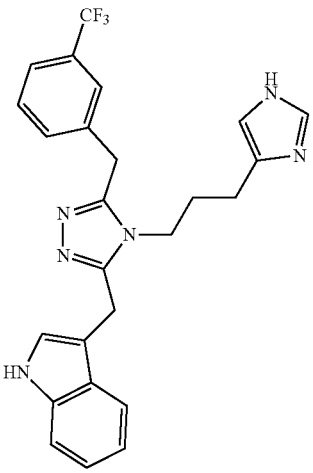

MI-I-66

Prepared according to General Procedure 1D from 3-((5-(3-(trifluoromethyl)benzyl)-4-(3-(1-trityl-1H-imidazol-4-yl)propyl)-4H-1,2,4-triazol-3-yl)methyl)-1H-indole (242 mg, 0.34 mmol) to afford 120 mg (75% yield) of compound MM-I-66 as a white solid: $^1$H NMR (400 MHz, CD$_3$OD) δ 7.53-7.49 (m, 2H), 7.45-7.41 (m, 2H), 7.32 (m, 3H), 7.06 (dt, J=8.05, 0.79 Hz, 1H), 6.95 (s, 1H), 6.93 (t, J=7.30 Hz, 1H), 6.53 (bs, 1H), 4.27 (s, 2H), 4.16 (s, 2H), 3.68-3.64 (m, 2H), 2.27 (t, J=7.10 Hz, 2H), 1.40 (quint., J=7.20 Hz, 2H). $^{13}$C NMR (100 MHz, CD$_3$OD) δ 154.93, 153.61, 136.97, 136.85, 134.73, 132.60, 131.99, 130.78 (q, $J_{C,F}$=31.9 Hz), 129.40, 128.95, 126.65, 124.80 (q, $J_{C,F}$=3.58 Hz), 124.1 (q, $J_{C,F}$=271.3 Hz), 123.71 (q, $J_{C,F}$=3.69 Hz), 122.96, 121.51, 118.86, 117.82, 111.17, 107.88, 42.78, 29.93, 28.76, 23.22, 21.58. LCMS (50-95% acetonitrile in 0.05% TFA over 10 minutes) retention time=2.05 minutes, ESI m/z=465, [M+H]$^+$.

Synthesis of 3-((4-(3-(1H-imidazol-4-yl)propyl)-5-(3-(trifluoromethyl)benzyl)-4H-1,2,4-triazol-3-yl)methyl)-6-fluoro-JH-indole (MM-I-87)

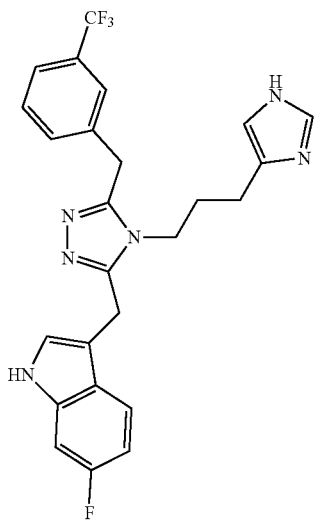

MM-I-87

Prepared according to General Procedure 1D from 6-fluoro-3-((5-(3-(trifluoromethyl)benzyl)-4-(3-(1-trityl-1H-imidazol-4-yl)propyl)-4H-1,2,4-triazol-3-yl)methyl)-1H-indole (125 mg, 0.17 mmol) to afford 60 mg (72% yield) of compound MM-I-87 as a white solid: $^1$H NMR (400 MHz, CD$_3$OD) δ 7.54 (s, 1H), 7.51 (d, J=7.79 Hz, 1H), 7.44 (t, J=7.61 Hz, 1H), 7.42 (s, 1H), 7.34-7.28 (m, 2H), 6.99 (dd, J=9.98, 2.22 Hz, 1H), 6.95 (s, 1H), 6.72 (dt, J=9.63, 2.32 Hz, 1H), 6.57 (bs, 1H), 4.25 (s, 2H), 4.17 (s, 2H), 3.70-3.66 (m, 2H), 2.31 (t, J=7.08 Hz, 2H), 1.42 (quint., J=7.12 Hz, 2H). $^{13}$C NMR (100 MHz, CD$_3$OD) δ (d, $J_{C,F}$=235.96 Hz), 154.71, 153.67, 136.95, 136.80 (d, $J_{C,F}$=12.54 Hz), 134.77, 132.60, 132.02, 130.78 (q, $J_{C,F}$=32.24 Hz), 129.42, 128.95, 124.80 (q, $J_{C,F}$=3.70 Hz), 124.10 (q, $J_{C,F}$=271.45 Hz), 123.71 (q, $J_{C,F}$=3.68 Hz), 123.50 (d, $J_{C,F}$=2.84 Hz), 123.37, 122.74, 118.86, 118.76, 108.20, 107.34 (d $J_{C,F}$=24.93 Hz), 97.06 (d, $J_{C,F}$=26.00 Hz), 42.75, 29.92, 29.4228.78, 21.51. LCMS (50-95% acetonitrile in 0.05% TFA over 10 minutes) retention time=2.07 minutes, ESI m/z=483, [M+H]$^+$.

Synthesis of 3-((4-(3-(1H-imidazol-4-yl)propyl)-5-(3-(methylsulfonyl)benzyl)-4H-1,2,4-triazol-3-yl)methyl)-1H-indole (MM-I-72)

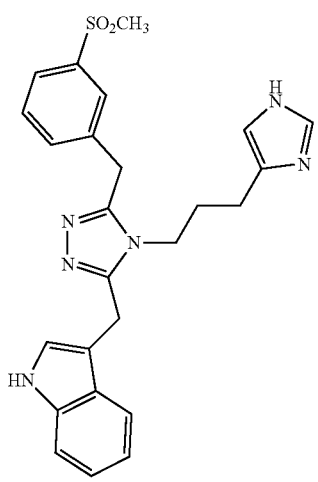

MM-I-72

Prepared according to General Procedure 1D from 3-((5-(3-(methylsulfonyl)benzyl)-4-(3-(1-trityl-1H-imidazol-4-yl)propyl)-4H-1,2,4-triazol-3-yl)methyl)-1H-indole (65 mg, 0.09 mmol) to afford 37 mg (86% yield) of compound MM-1-72 as a white solid: $^1$H NMR (400 MHz, CD$_3$OD) δ 7.79 (d, J=7.79 Hz, 1H), 7.71 (s, 1H), 7.54 (bs, 1H), 7.51 (t, J=7.75 Hz, 1H), 7.42 (d, J=7.73 Hz, 1H), 7.36 (d, J=7.91 Hz, 1H), 7.30 (d, J=8.23 Hz, 1H), 7.06 (dt, J=8.08, 0.84 Hz, 1H), 6.97 (s, 1H), 6.95 (dt, J=8.03, 0.77 Hz, 1H), 6.55 (bs, 1H), 4.28 (s, 2H), 4.19 (s, 2H), 3.69-3.65 (m, 2H), 2.98 (s, 3H), 2.29 (t, J=7.07 Hz, 2H), 1.41 (t, J=6.95 Hz, 2H). $^{13}$C NMR (100 MHz, CD$_3$OD) δ 154.97, 153.51, 141.35, 137.51, 136.85, 134.81, 133.64, 129.75, 126.91, 126.67, 125.92, 123.02, 121.52, 118.91, 117.85, 111.19, 107.89, 42.89, 42, 80, 29.93, 28.84, 23.34, 21.59. LCMS (50-95% acetonitrile in 0.05% TFA over 10 minutes) retention time=1.72 minutes, ESI m/z=475, [M+H]$^+$.

Synthesis of 3-(2-(4-(3-(1H-imidazol-4-yl)propyl)-5-(3-(methylsulfonyl)benzyl)-4H-1,2,4-triazol-3-yl)ethyl)-1H-indole (SM-I-92)

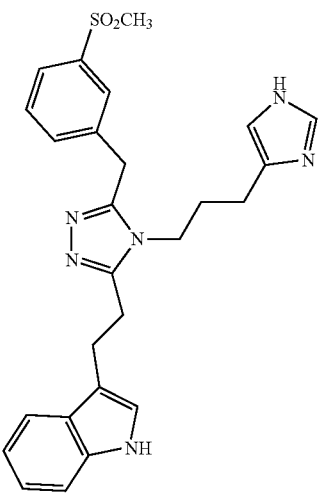

SM-I-92

Prepared according to General Procedure 1D from 3-(2-(5-(3-(methylsulfonyl)benzyl)-4-(3-(1-trityl-1H-imidazol-4-yl)propyl)-4H-1,2,4-triazol-3-yl)ethyl)-1H-indole (80 mg, 0.11 mmol) to afford 39 mg (73% yield) of compound SM-I-92 as a white solid: $^1$H NMR (400 MHz, CD$_3$OD) δ 7.81 (d, J=7.80 Hz, 1H), 7.70 (s, 1H), 7.54-7.50 (m, 2H), 7.30-7.25 (m, 4H), 7.04 (t, J=7.31 Hz, 1H), 6.92 (t, J=7.69 Hz, 1H), 6.88 (s, 1H), 6.57 (s, 1H), 4.10 (s, 2H), 3.31-3.26 (obscured m, 2H), 3.17 (t, J=7.00 Hz, 2H), 3.08-3.01 (m, 1H), 3.05 (s, 3H), 2.26 (t, J=7.04 Hz, 2H), 1.44 (quint., J=7.26 Hz, 2H). $^{13}$C NMR (100 MHz, CD$_3$OD) δ 156.13, 152.45, 141.30, 137.47, 136.64, 134.90, 133.53, 129.80, 126.98, 126.91, 125.88, 122.20, 121.13, 118.51, 117.62, 112.85, 111.02, 42.90, 42.08, 29.94, 28.81, 25.77, 23.72, 23.15. LCMS (50-95% acetonitrile in 0.05% TFA over 10 minutes) retention time=1.73 minutes, ESI m/z=489, [M+H]$^+$

Synthesis of 3-((4-(3-(1H-imidazol-4-yl)propyl)-5-benzyl-4H-1,2,4-triazol-3-yl)methyl)-6-fluoro-1H-indole (MM-I-89)

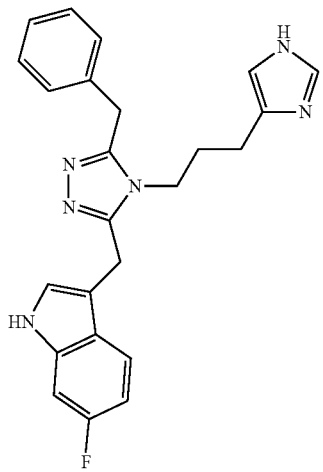

MM-I-89

Prepared according to General Procedure 1D from 3-((5-benzyl-4-(3-(1-trityl-1H-imidazol-4-yl)propyl)-4H-1,2,4-triazol-3-yl)methyl)-6-fluoro-1H-indole (180 mg, 0.27 mmol) to afford 89 mg (78% yield) of compound MM-I-89 as a white solid: $^1$H NMR (400 MHz, CD$_3$OD) δ 7.55 (bs, 1H), 7.31-7.15 (complex m, 5H), 7.03 (d, J=6.95 Hz, 2H), 7.99 (dd, J=9.89, 2.32 Hz, 1H), 6.93 (s, 1H), 6.73 (dt, J=9.69, 2.31 Hz, 1H), 6.55 (bs, 1H), 4.23 (s, 2H), 4.07 (s, 2H), 3.63-3.59 (m, 2H), 2.28 (t, J=7.04 Hz, 2H), 1.38 (quint., J=7.09 Hz, 1H). LCMS (50-95% acetonitrile in 0.05% TFA over 10 minutes) retention time=1.78 minutes, ESI m/z=415, [M+H]$^+$.

Synthesis of 3-((4-(3-(1H-imidazol-4-yl)propyl)-5-(3-bromobenzyl)-4H-1,2,4-triazol-3-yl)methyl)-6-fluoro-1H-indole (MM-I-83)

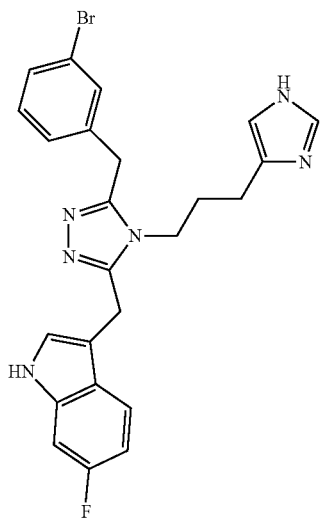

MM-I-83

Prepared according to General Procedure 1D from 3-((5-benzyl-4-(3-(1-trityl-1H-imidazol-4-yl)propyl)-4H-1,2,4-triazol-3-yl)methyl)-6-fluoro-1H-indole (180 mg, 0.24 mmol) to afford 94 mg (78% yield) of compound MM-I-83 as a white solid: $^1$H NMR (400 MHz, CD$_3$OD) δ 7.56 (bs, 1H), 7.35 (d, J=8.85 Hz, 1H), 7.29 (dd, J=8.72, 5.27 Hz, 1H), 7.25 (m, 1H), 7.15 (t, J=7.84 Hz, 1H), 7.03-6.09 (m, 2H), 6.95 (s, 1H), 6.74 (dt, J=9.59, 2.30 Hz, 1H), 6.59 (bs, 1H), 4.24 (s, 2H), 4.06 (s, 2H), 3.66-3.62 (m, 2H), 2.31 (t, J=7.04 Hz, 2H), 1.38 (quint., J=7.13 Hz, 1H). $^{13}$C NMR (100 MHz, CD$_3$OD) δ 159.95 (d, J$_{C,F}$=235.84 Hz), 154.70, 153.71, 138.04, 136.82 (d, J$_{C,F}$=12.54 Hz), 134.80, 131.71, 131.07, 130.34, 130.08, 126.97, 123.53 (d, J$_{C,F}$=2.91 Hz), 123.38, 122.44, 118.87, 118.77, 108.20, 107.39 (d, J$_{C,F}$=24.81 Hz), 97.06 (d, J$_{C,F}$=25.93 Hz), 42.75, 29.80, 28.79, 23.37, 21.52. LCMS (15-95% acetonitrile in 0.05% TFA over 10 minutes) retention time=6.18 minutes, ESI m/z=493, 495 [M+H]$^+$.

Synthesis of tert-butyl 2-(2-(3-(trifluoromethoxy)phenyl)acetyl)hydrazine carboxylate (28n)

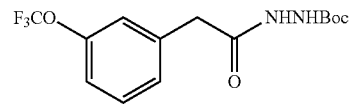

28n

Prepared according to General Procedure 1A from 2-(2-trifluoromethoxyphenyl)acetic acid (27n) (3.00 g, 18.05 mmol) and tert-butyl hydrazinecarboxylate (2.98 g, 22.6 mmol) to afford 4.62 g (91% yield) of compound 28n as yellow solid: $^1$H NMR (400 MHz, CDCl$_3$) δ 7.71 (bd, J=2.62 Hz, 1H), 7.29-7.24 (m, 3H), 6.95-6.89 (m, 2H), 6.43 (bs, 1H), 3.86 (s, 3H), 3.60 (s, 2H), 1.41 (bs, 9H). $^{13}$C NMR (100 MHz, CDCl$_3$) δ 170.53, 157.09, 155.30, 131.35, 129.14, 122.50, 121.27, 110.86, 81.74, 55.69, 36.74, 28.16. LCMS (50-95% acetonitrile in 0.05% TFA over 10 minutes) retention time=3.07 min, ESI m/z=281, [M+H]$^+$.

Synthesis of tert-butyl 2-(2-(3-nitrophenyl)acetyl)hydrazinecarboxylate (28o)

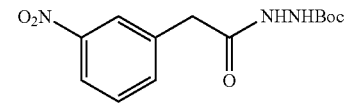

28o

Prepared according to General Procedure 1A from 2-(3-nitrophenyl)acetic acid (27o) (3.00 g, 16.6 mmol) and tert-butyl hydrazinecarboxylate (2.74 g, 20.7 mmol) to afford 2.32 g (47% yield) of compound 28o as yellow solid: $^1$H NMR (400 MHz, CD$_3$OD) δ 8.18-8.23 (m, 1H), 8.07-8.14 (m, 1H), 7.71 (d, J=7.84 Hz, 1H), 7.54 (t, J=7.93 Hz, 1H), 3.66 (bs, 2H), 1.44 (s, 9H). $^{13}$C NMR (100 MHz, CD$_3$OD) δ 171.04, 156.39, 148.35, 137.09, 135.46, 129.30, 123.89, 121.61, 80.58, 39.34, 27.16. LCMS (50-95% acetonitrile in 0.05% TFA over 10 minutes) retention time=3.00 min, ESI m/z=196, [M-Boc]$^+$.

Synthesis of tert-butyl 2-(2-(3-(benzyloxy)phenyl)acetyl)hydrazinecarboxylate (28p)

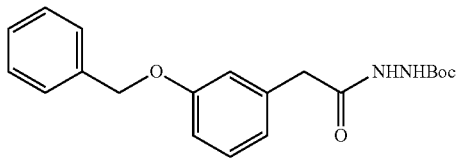

Prepared according to General Procedure 1A from 2-(3-(benzyloxy)phenyl)acetic acid (27p) (3.00 g, 12.4 mmol) and tert-butyl hydrazinecarboxylate (2.05 g, 15.5 mmol) to afford 4.06 g (92% yield) of compound 28p as yellow solid: $^1$H NMR (400 MHz, CD$_3$OD) δ 7.44-7.36 (m, 2H), 7.35-7.25 (complex m, 3H), 7.18 (t, J=7.93 Hz, 1H), 6.99 (bs, 1H), 6.90-6.80 (m, 2H), 5.04 (s, 2H), 3.48 (bs, 2H), 1.44 (bs, 9H). $^{13}$C NMR (100 MHz, CD$_3$OD) δ 172.15, 159.05, 156.39 137.40, 136.31, 129.17, 128.13, 127.50, 127.26, 121.46, 115.34, 113.22, 80.47, 69.56, 40.20, 27.19. LCMS (50-95% acetonitrile in 0.05% TFA over 10 minutes) retention time=5.32 min, ESI m/z=357, [M+H]$^+$.

Synthesis of tert-butyl 2-(2-(3-cyanophenyl)acetyl)hydrazinecarboxylate (28q)

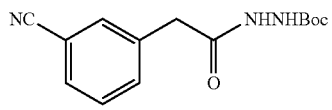

Prepared according to General Procedure 1A from 2-(3-cyanophenyl)acetic acid (27q) (4.95 g, 30.7 mmol) and tert-butyl hydrazinecarboxylate (5.07 g, 38.4 mmol) to afford 4.42 g (52% yield) of compound 28q as yellow solid: $^1$H NMR (400 MHz, DMSO-d$_6$) δ 9.83 (bs, 1H), 8.77 (bs, 1H), 7.69-7.67 (m, 1H), 7.67 (s, 1H), 7.57 (d, J=7.62 Hz, 1H), 7.49 (t, J=7.94 Hz, 1H), 3.48 (bs, 2H), 1.35 (bs, 9H). $^{13}$C NMR (100 MHz, DMSO-d$_6$) δ 169.53, 155.76, 137.80, 134.69, 133.11, 130.94, 130.03, 119.29, 111.68, 79.72, 28.55. LCMS (25-95% acetonitrile in 0.05% TFA over 10 minutes) retention time=5.70 min, ESI m/z=276, [M+H]$^+$.

Synthesis of tert-butyl 2-(2-(4-fluorophenynacetyl)hydrazinecarboxylate (28r)

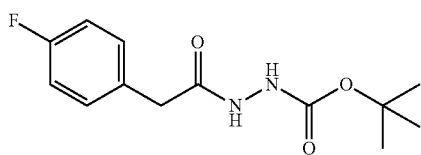

Prepared according to General Procedure 1A from 2-(4-fluorophenyl)acetic acid (2.00 g, 12.9 mmol) and tert-butyl hydrazinecarboxylate (2.13 g, 16.1 mmol) to afford 3.34 g of compound 28r (97% yield) as a white solid. $^1$H NMR (400 MHz, DMSO-d$_6$) δ 9.74 (s, 1H), 8.71 (s, 1H), 7.26 (dd, $^3J_{HF}$=8.20, J$_{HH}$=5.50 Hz, 2H), 7.08 (apparent t, $^3J_{HF}$=9.10, J$_{HH}$=9.10 Hz, 2H), 3.36 (s, 2H), 1.35 (s, 9H). $^{13}$C NMR (100 MHz, DMSO-d$_6$) δ 170.08, 161.61 (d, $^1J_{CF}$=241 Hz), 155.78, 132.34 (d, $^4J_{CF}$=2.80 Hz), 131.4 (d, $^3J_{CF}$=7.60 Hz), 115.4 (d, $^2J_{CF}$ 21.1 Hz), 79.62, 28.56. LCMS (50-95% acetonitrile in 0.05% TFA over 10 minutes) retention time=3.08 minutes, ESI m/z=269, [M+H]$^+$.

Synthesis of 2-(3-(trifluoromethoxy)phenyl)acetic hydrazide (29n)

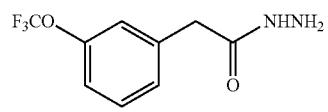

Prepared according to the General Procedure 1B from tert-butyl 2-(2-(3-(trifluoromethoxy)phenyl)acetyl)hydrazinecarboxylate (28n) (3.76 g, 11.2 mmol) to afford 2.54 g (83% yield) of the intermediate HCl salt as a white solid. The HCl salt (2.54 g, 9.37 mmol) was then converted to 1.88 g (71% yield) of freebase 29n (69% for two steps), isolated as a white solid: $^1$H NMR (400 MHz, CDCl$_3$) δ 7.36 (t, J=5.86 Hz, 1H), 7.19 (bd, J=7.73 Hz, 1H), 7.16-7.11 (m, 2H), 5.54 (s, 2H). $^{13}$C NMR (100 MHz, CDCl$_3$) δ 170.86, 149.62, 136.22, 130.37, 127.77, 121.93, 120.47 (q, J$_{C,F}$=257.48 Hz), 119.96, 41.39. LCMS (15-95% acetonitrile in 0.05% TFA over 10 minutes) retention time=6.17 minutes, ESI m/z=235, [M+H]$^+$; 276, [M+H+ACN]$^+$.

Synthesis of 2-(3-nitrophenyl)acetic hydrazide (29o)

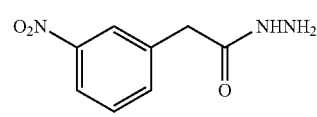

Prepared according to the General Procedure 1B from tert-butyl 2-(2-(3-nitrophenyl)acetyl)hydrazinecarboxylate (28o) (2.27 g, 7.69 mmol) to afford 1.66 g (93% yield) of the intermediate HCl salt as a white solid. The HCl salt (1.66 g, 7.17 mmol) was then converted to 1.31 g (94% yield) of freebase 29o (87% for two steps), isolated as a light yellow solid: $^1$H NMR (400 MHz, CD$_3$OD) δ 8.19-8.17 (m, 1H), 8.12-8.10 (m, 1H), 7.68 (d, J=7.10 Hz, 1H), 7.54 (t, J=8.01 Hz, 1H), 3.59 (s, 2H). $^{13}$C NMR (100 MHz, CD$_3$OD) δ 170.57, 148.35, 137.60, 135.24, 129.33, 123.59, 121.56, 39.65. LCMS (50-95% acetonitrile in 0.05% TFA over 10 minutes) retention time=2.05 minutes, ESI m/z=196, [M+H]$^+$; 237, [M+H+ACN]$^+$.

Synthesis of 2-(3-(benzyloxy)phenyl)acetic hydrazide (29p)

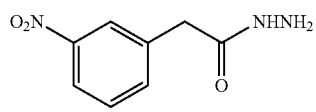

Prepared according to the General Procedure 1B from tert-butyl 2-(2-(3-(benzyloxy)phenyl)acetyl)hydrazinecarboxylate (28p) (4.02 g, 11.3 mmol) to afford 2.65 g (81% yield) of the intermediate HCl salt as a white solid. The HCl salt (2.65 g, 9.07 mmol) was then converted to 2.00 g (86% yield) of freebase 29p (70% for two steps), isolated as a white solid: $^1$H NMR (400 MHz, CD$_3$OD) δ 7.42-7.25 (complex m, 5H), 7.18 (t, J=8.00 Hz, 1H), 6.93 (apparent t, J=1.90 Hz, 1H), 6.85 (dd, J=8.10, 2.06 Hz, 2H), 5.04 (s, 2H), 3.40 (s, 2H). $^{13}$C NMR (100 MHz, CD$_3$OD) δ 171.69, 159.05, 137.37, 136.73, 129.21, 128.14, 127.51, 127.25, 121.27, 115.37, 113, 69.54, 40.45. LCMS (25-95% acetonitrile in 0.05% TFA over 10 minutes) retention time=5.43 minutes (broad), ESI m/z=257, [M+H]$^+$; 535, [2M+Na]$^+$.

Synthesis of 2-(3-cyanophenyl)acetic hydrazide (29 g)

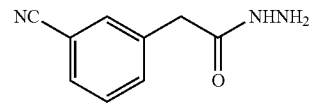

Prepared according to the General Procedure 1B from tert-butyl 2-(2-(3-cyanophenyl)acetyl)hydrazinecarboxylate (28q) (4.32 g, 15.7 mmol) to afford 2.60 g (79% yield) of the intermediate HCl salt as a white solid. The HCl salt (2.60 g, 12.3 mmol) was then converted to 1.41 g (75% yield) of freebase 29q (59% for two steps), isolated as a white solid: $^1$H NMR (400 MHz, DMSO-d$_6$) δ 9.23 (bs, 1H), 7.68-7.65 (m, 2H), 7.57-7.54 (m, 1H), 7.47 (t, J=7.79 Hz, 1H), 4.21 (bs, 2H), 3.39 (s, 2H). $^{13}$C NMR (100 MHz, DMSO-d$_6$) δ 169.29, 138.41, 134.59, 132.98, 130.82, 129.98, 119.32, 111.64, benzyl carbon obscured by DMSO-d$_6$ solvent peaks. LCMS (25-95% acetonitrile in 0.05% TFA over 10 minutes) retention time=2.07 minutes, ESI m/z=176, [M+H]$^+$.

Synthesis of 2-(4-fluorophenyl)acetic hydrazide (29r)

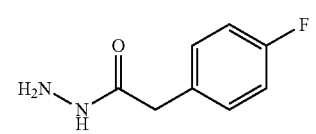

Produced according to General Procedure B from tert-butyl 2-(2-(4-fluorophenyl)acetyl)hydrazinecarboxylate 28r (3.23 g, 12.0 mmol) to afford 2.18 g of the intermediate HCl salt (89% yield) as a white solid. The HCl salt was converted to freebase afford 1.57 g of compound 29r (90% yield) (78% yield over two steps) as a white solid. $^1$H NMR (400 MHz, DMSO-d$_6$) δ 9.15 (s, 1H), 7.24 (dd, $^4$J$_{HF}$=8.80, J$_{HH}$=5.50 Hz, 2H), 7.07 (apparent t, $^3$J$_{HF}$=8.70, J$_{HH}$=8.70 Hz, 2H), 4.17 (s, 2H). $^{13}$C NMR (100 MHz, DMSO-d$_6$) δ 169.95, 161.54 (d, $^1$J$_{CF}$=243 Hz), 132.96, 131.25 (d, $^3$J$_{CF}$=7.60 Hz), 115.39 (d, 2J$_{CF}$=21.1 Hz), 40.73 (partially obscured by DMSO solvent peak). LCMS (50-95% acetonitrile in 0.05% TFA over 10 minutes) retention time=1.85 minutes, ESI m/z=169, [M+H]$^+$.

Synthesis of 3-(2-(5-(3-(trifluoromethoxy)benzyl)-4-(3-(1-trityl-1H-imidazol-4-yl) propyl)-4H-1,2,4-triazol-3-yl)ethyl)-1H-indole (31o)

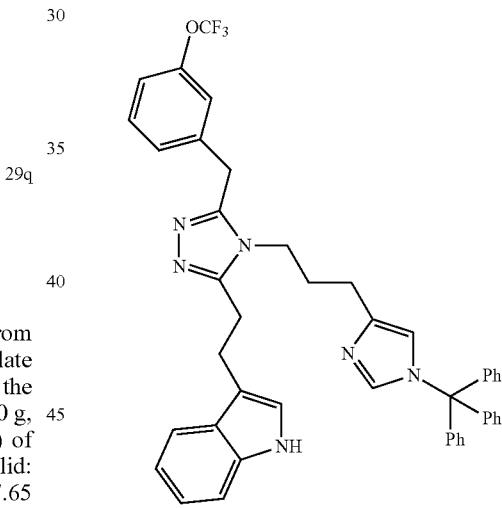

Prepared according to the General Procedure 1C from 3-(1H-indol-3-yl)-N-(3-(1-trityl-1H-imidazol-4-yl)propyl) propanethioamide (10) (325 mg, 0.59 mmol) and 2-(3-(trifluoromethoxy)phenyl)acetic hydrazide (29n) (165.8 mg, 0.71 mmol). Purification by flash chromatography (SiO$_2$, 30:1 CH$_2$Cl$_2$/methanol) afforded 203 mg (47% yield) of compound 31o as a tan solid: $^1$H NMR (400 MHz, CD$_3$OD) δ 7.98 (dd, J=8.51, 1.45 Hz, 1H), 7.41 (t, J=7.85 Hz, 1H), 7.33-7.30 (m, 9H), 7.28 (t, J=7.85 Hz, 1H), 7.18 (d, J=8.16 Hz, 1H), 7.05-7.02 (m, 8H), 6.98-6.93 (m, 2H), 6.89 (s, 1H), 6.84 (t, J=7.65 Hz, 1H), 6.44 (bs, 1H), 4.07 (s, 2H), 3.38-3.34 (m, 2H), 3.17 (t, J=7.03 Hz, 2H), 3.00 (t, J=7.06 Hz, 2H), 2.19 (t, J=7.09 Hz, 1H), 1.36-1.32 (m, 4H). $^{13}$C NMR (100 MHz, CD$_3$OD) δ 155.97, 152.63, 149.38, 142.24, 138.98, 138.28, 138.14, 136.67, 130.29, 129.44, 129.26, 127.99, 127.92, 126.97, 126.90, 122.13, 121.10, 120.88, 120.46 (q, $J_{C,F}$=255.77 Hz), 119.41, 118.45, 117.71, 112.95, 111.05, 75.42, 42.26, 29.85, 28.63, 25.79, 24.13, 23.57. LCMS (50-95% acetonitrile in 0.05% TFA over 10 minutes) retention time=5.25 minutes, ESI m/z=737, [M+H]+.

Synthesis of 3-(2-(5-(3-nitrobenzyl)-4-(3-(1-trityl-1H-imidazol-4-yl)propyl)-4H-1,2,4-triazol-3-yl)ethyl))-1H-indole (31p)

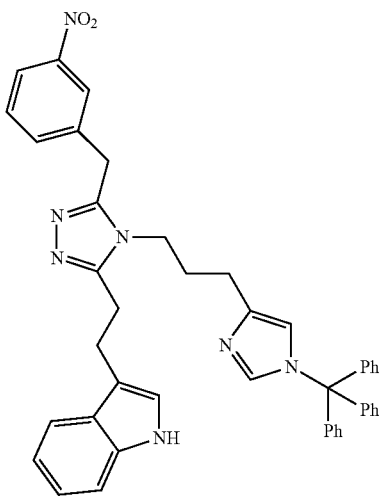

31p

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(3-nitrophenyl)acetic hydrazide (29o) (211 mg, 1.08 mmol). Purification by flash chromatography (SiO$_2$, 40:1 CH$_2$Cl$_2$/methanol to 10/1) afforded 328 mg (52% yield) of compound 31p as a tan solid: $^1$H NMR (400 MHz, CD$_3$OD) δ 8.02-7.97 (m, 1H), 8.00 (s, 1H), 7.47-7.42 (m, 1H), 7.40-7.35 (m, 1H), 7.34-7.28 (m, 11H), 7.15 (d, J=8.20 Hz, 1H), 7.05-7.01 (m, 6H), 6.92 (t, J=7.63 Hz, 1H), 6.89 (s, 1H), 6.83 (t, J=7.70 Hz, 1H), 6.43 (s, 1H), 4.13 (s, 2H), 3.35-3.31 (m, 2H), 3.17 (t, J=7.14 Hz, 2H), 3.02 (t, J=6.92 Hz, 2H), 2.21 (t, J=7.01 Hz, 2H), 1.38 (quint., J=7.17 Hz, 2H). $^{13}$C NMR (100 MHz, CD$_3$OD) & 156.06, 152.36, 148.46, 142.23, 138.90, 138.20, 137.86, 136.65, 134.45, 132.34, 129.79, 129.44, 129.31, 128.00, 127.93, 126.99, 123.10, 122.20, 121.88, 121.10, 118.46, 117.68, 112.91, 111.07, 75.42, 42.23, 29.74, 28.61, 25.79, 24.08, 23.68. LCMS (50-95% acetonitrile in 0.05% TFA over 10 minutes) retention time=3.87 minutes, ESI m/z=698, [M+H]+.

Synthesis of 3-(2-(5-(3-(benzyloxy)benzyl)-4-(3-(1-trityl-1H-imidazol-4-yl)propyl)-4H-1,2,4-triazol-3-yl)ethyl)-1H-indole (31q)

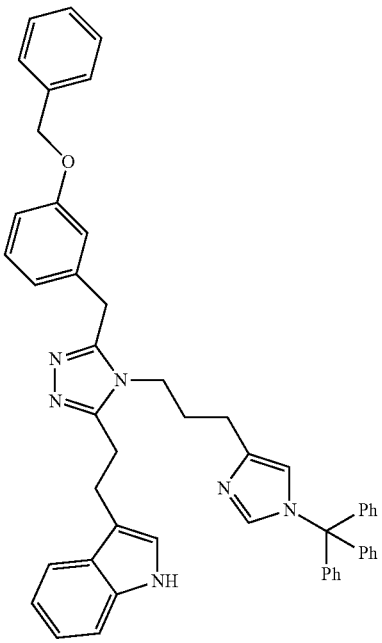

31o

Prepared according to the General Procedure 1C from 3-(1H-indol-3-yl)-N-(3-(1-trityl-1H-imidazol-4-yl)propyl) propanethioamide (10) (500 mg, 0.90 mmol) and 2-(3-(benzyloxy)phenyl)acetic hydrazide (29p) (277 mg, 1.08 mmol). Purification by flash chromatography (SiO$_2$, 30:1 CH$_2$Cl$_2$/methanol to 20/1) afforded 335 mg (49% yield) of compound 31q as a white foam: $^1$H NMR (400 MHz, CD$_3$OD) δ 7.35-7.26 (m, 11H), 7.25-7.23 (m, 4H), 7.18 (d, J=8.12 Hz, 1H), 7.13-7.10 (m, 1H), 7.04-7.00 (m, 7H), 6.95 (t, J=7.01 Hz, 1H), 6.89 (s, 1H), 6.88 (t, J=7.31 Hz, 1H), 6.68-6.64 (m, 2H), 6.55 (d, J=7.61 Hz, 1H), 6.36 (s, 1H), 5.65 (s, 2H), 4.90 (s, 2H), 3.98 (bs, 2H), 3.16 (t, J=7.24 Hz, 2H), 2.97 (t, J=7.15 Hz, 2H), 2.10 (t, J=7.23 Hz, 2H), 1.15 (quint., J=7.45 Hz, 2H). $^{13}$C NMR (100 MHz, CD$_3$OD) δ 159.08, 155.83, 153.17, 142.24, 139.07, 138.05, 137.09, 137.01, 136.67, 129.70, 129.47, 128.18, 127.99, 127.94, 127.49, 127.18, 126.99, 122.12, 121.10, 120.43, 118.46, 118.41, 117.71, 114.52, 113.66, 112.98, 111.04, 75.41, 69.40, 42.33, 30.35, 28.45, 25.76, 24.29, 23.52. LCMS (50-95% acetonitrile in 0.05% TFA over 10 minutes) retention time=5.50 minutes, ESI m/z=759, [M+H]+.

Synthesis of 3-((5-(2-(1H-indol-3-yl)ethyl)-4-(3-(1-trityl-1H-imidazol-4-yl)propyl)-4H-1,2,4-triazol-3-yl)methyl)benzonitrile (31r)

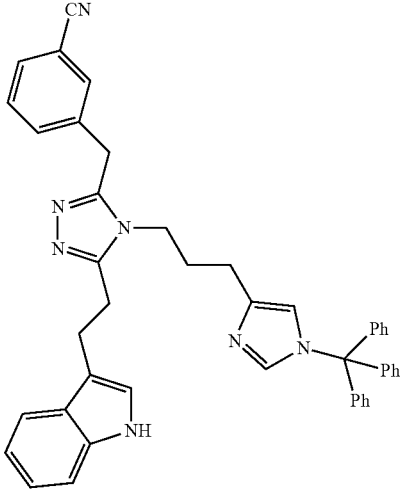

31r

Prepared according to the General Procedure 1C from 3-(1H-indol-3-yl)-N-(3-(1-trityl-1H-imidazol-4-yl)propyl)propanethioamide (10) (500 mg, 0.90 mmol) and 2-(3-cyanophenyl)acetic hydrazide (29q) (189 mg, 1.08 mmol). Purification by flash chromatography (SiO$_2$, 40:1 CH$_2$Cl$_2$/methanol to 20/1) afforded 330 mg (54% yield) of compound 31r as a white foam: $^1$H NMR (400 MHz, DMSO-d$_6$) δ 10.75 (bs, 1H), 7.90 (dd, J=8.34, 1.46 Hz, 1H), 7.64 (s, 1H), 7.60 (dt, J=7.23, 1.65 Hz, 1H), 7.48-7.45 (m, 1H), 7.43 (d, J=7.50 Hz, 1H), 7.39 (d, J=7.32 Hz, 1H), 7.35-7.29 (m, 9H), 7.26 (d, J=8.15 Hz, 1H), 7.20 (d, J=0.93 Hz, 1H), 7.08 (d, J=2.19 Hz, 1H), 7.01-6.95 (m, 6H), 6.83 (t, J=7.26 Hz, 1H), 6.50 (s, 1H), 4.08 (s, 2H), 3.71 (apparent t, J=7.89 Hz, 2H), 3.05 (apparent t, J=7.09 Hz, 2H), 2.92 (dd, J=8.63, 6.70 Hz, 2H), 2.32 (t, J=7.02 Hz, 2H), 1.56 (quint., J=7.52 Hz, 2H). $^{13}$C NMR (100 MHz, DMSO-d$_6$) δ 154.70, 152.34, 142.81, 140.13, 138.96, 138.31, 136.68, 134.20, 133.39, 132.73, 130.99, 130.18, 129.78, 129.65, 129.10, 128.70, 128.46, 127.43, 123.10, 121.41, 119.20, 118.72, 118.67, 118.10, 113.85, 111.85, 74.85, 42.49, 30.10, 29.64, 25.90, 25.00, 23.20. LCMS (50-95% acetonitrile in 0.05% TFA over 10 minutes) retention time=3.58 minutes, ESI m/z=678, [M+H]$^+$.

Synthesis of 3-(2-(4-(3-(1H-imidazol-4-yl)propyl)-5-(3-(trifluoromethoxy)benzyl)-4H-1,2,4-triazol-3-yl)ethyl)-1H-indole (MM-I-36)

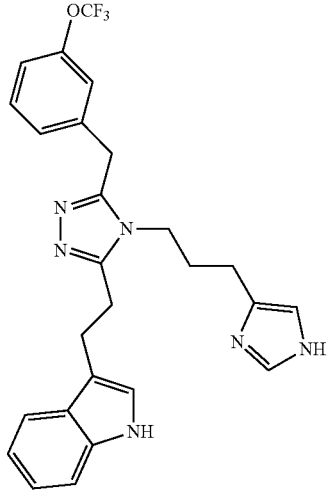

MM-I-36

Prepared according to the General Procedure 1D from 3-(2-(5-(3-(trifluoromethoxy)benzyl)-4-(3-(1-trityl-1H-imidazol-4-yl)propyl)-4H-1,2,4-triazol-3-ypethyl)-1H-indole (31o) (172 mg, 0.23 mmol) to afford 82 mg (71% yield) of MM-I-36 as a white solid: $^1$H NMR (400 MHz, CD$_3$OD) δ 7.52 (s, 1H), 7.34 (t, J=7.97 Hz, 1H), 7.27 (t, J=7.74 Hz, 2H), 7.10 (bd, J=8.24 Hz, 1H), 7.03 (t, J=7.85 Hz, 1H), 7.02 (bd, J=1.54 Hz, 1H), 6.92 (d, J=7.65 Hz, 2H), 6.89-6.87 (m, 1H), 6.57 (s, 1H), 4.04 (s, 2H), 3.34-3.30 (m, obscured by NMR solvent, 2H), 3.16 (t, J=7.13 Hz, 2H), 3.01 (t, J=7.14 Hz, 2H), 2.26 (t, J=7.03 Hz, 2H), 1.43 (quint., J=7.12 Hz, 2H). $^{13}$C NMR (100 MHz, CD$_3$OD) δ 156.07, 152.61, 149.39, 138.16, 136.67, 134.81, 130.30, 126.97, 126.86, 122.13, 121.10, 120.83, 120.51 (q, J$_{C,F}$=255.66 Hz), 119.36, 118.47, 117.62, 112.91, 111.00, 42.10, 29.85, 28.77, 25.81, 23.65, 23.12. LCMS (15-95% acetonitrile in 0.05% TFA over 10 minutes) retention time=2.15 minutes, ESI m/z=495, [M+H]$^+$, 989 [2M+H]$^+$.

Synthesis of 3-(2-(4-(3-1H-Imidazol-4-yl)propyl)-5-(3-nitrobenzyl)-4H-1,2,4-triazol-3-yl)ethyl))-1H-indole (MM-I-43)

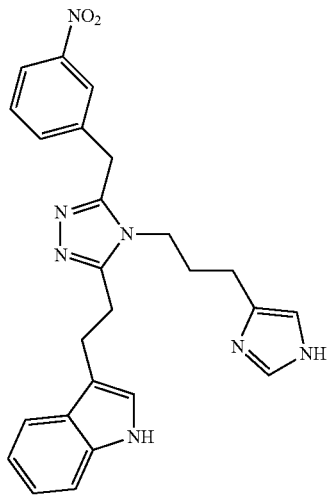

MM-I-43

Prepared according to General Procedure 1D from 3-(2-(5-(3-nitrobenzyl)-4-(3-(1-trityl-1H-imidazol-4-yl)propyl)-4H-1,2,4-triazol-3-yl)ethyl)-1H-indole (31p) (0.148 g, 0.212 mmol) to afford 0.085 g (88% yield) of MM-I-43 as a white solid: $^1$H NMR (400 MHz, CD$_3$OD) imidazole tautomers observed: δ 8.05-8.12 (m, 1H), 7.97 (bs, 1H), 7.44-7.55 (m, 2H), 7.21-7.37 (m, 4H), 6.98-7.05 (m, 1H), 6.85-6.95 (m, 2H), 6.57 (bs, 1H), 4.10 (s, 2H), 3.31 (obs s, 1H), 3.17 (apparent t, J=6.9, 2H), 3.03 (apparent t, J=8.08, 2H), 2.28 (apparent t, J=7.1, 2H), 1.46 (quint., J=7.71, 2H). $^{13}$C NMR (100 MHz, CD$_3$OD) imidazole tautomers observed: δ 156.14, 152.36, 148.50, 137.75, 136.66, 134.88, 134.42, 129.80, 126.98, 123.04, 122.19, 121.80, 121.09, 118.47, 117.59, 112.89, 111.00, 42.07, 32.42, 29.75, 28.80, 25.84, 23.74. LCMS (50-95% acetonitrile in 0.05% TFA over 10 minutes) retention time=3.87 min, ESI m/z=699, [M+H]$^+$.

Synthesis of 3-(2-(4-(3-(1H-imidazol-4-yl)propyl)-5-(3-(benzyloxy)benzyl)-4H-1,2,4-triazol-3-yl)-ethyl)-1H-indole (MM-I-53)

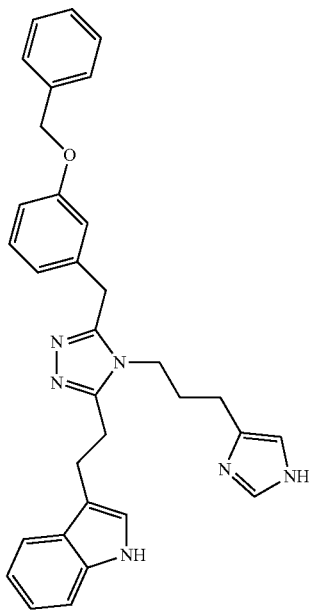

MM-I-53

Prepared according to general procedure 1D from 3-(2-(5-(3-(benzyloxy)benzyl)-4-(3-(1-trityl-1H-imidazol-4-yl)propyl)-4H-1,2,4-triazol-3-yl)ethyl)-1H-indole (31q) (148 mg, 0.21 mmol) to afford 85.0 mg (88% yield) of MM-I-53 as a white solid: $^1$H NMR (400 MHz, CD$_3$OD), significant broadening observed at room temperature: δ 7.52 (bs, 1H), 7.34-7.22 (m, 5H), 7.14 (t, J=7.90 Hz, 1H), 7.03 (t, J=7.28 Hz, 1H), 6.92 (t, J=7.45 Hz, 1H), 6.87 (s, 1H), 6.82 (dd, J=8.13, 1.31 Hz, 1H), 6.67 (s, 1H), 6.54 (d, J=7.41 Hz, 1H), 4.99 (s, 2H), 3.96 (s, 2H), 3.29-3.25 (m, obscured by NMR solvent, 2H), 3.16 (bt, J=6.87 Hz, 2H), 2.98 (bt, J=6.67 Hz, 2H), 2.22-2.15 (bm, 2H), 1.34-1.25 (bm, 2H). $^{13}$C NMR (100 MHz, CD$_3$OD): δ 159.15, 137.19, 136.88, 136.67, 129.71, 128.18, 127.52, 127.22, 126.98, 122.11, 121.10, 120.47, 118.48, 117.64, 114.58, 113.52, 112.93, 111.00, 69.45, 42.23, 30.37, 28.63, 25.80, 23.57, 23.25 (broad). LCMS (50-95% acetonitrile in 0.05% TFA over 10 minutes) retention time=2.20 min, ESI m/z=517, [M+H]$^+$.

Synthesis of 3-((4-(3-(1H-imidazol-4-yl)propyl)-5-(2-(1H-indol-3-yl)ethyl)-4H-1,2,4-triazol-3-yl)methyl)benzonitrile (MM-I-63)

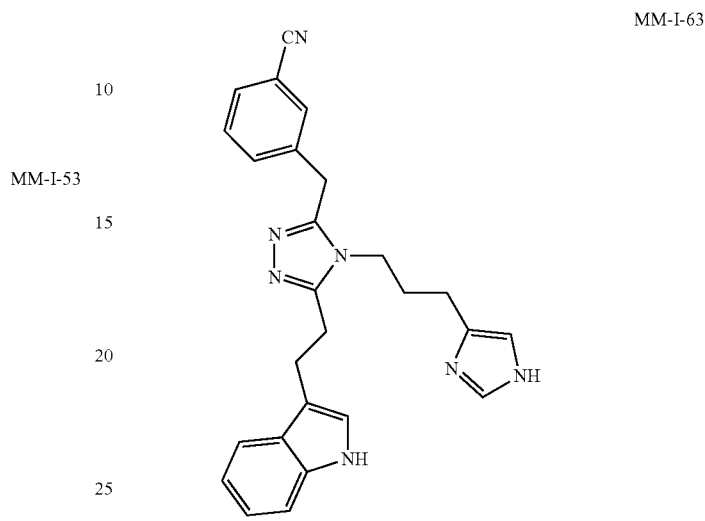

MM-I-63

Prepared according to general procedure 1D from 3-((5-(2-(1H-indol-3-yl) ethyl)-4-(3-(1-trityl-1H-imidazol-4-yl) propyl)-4H-1,2,4-triazol-3-yl) methyl)benzonitrile (31r) (292 mg, 0.43 mmol) to afford 135 mg (72% yield) of MM-I-63 as a white solid: $^1$H NMR (400 MHz, DMSO-d$_6$): δ 11.74 (bs, 1H), 10.77 (s, 1H), 7.68 (dt, J=6.91, 1.58 Hz, 1H), 7.64 (s, 1H), 7.50-7.44 (m, 3H), 7.40 (d, J=7.85 Hz, 1H), 7.28 (d, J=8.11 Hz, 1H), 7.11 (d, J=2.17 Hz, 1H), 7.01 (dt, J=7.01, 0.76 Hz, 1H), 6.91 (t, J=7.26 Hz, 1H), 6.70 (bs, 1H), 4.10 (bs, 2H), 3.72 (bt, J=6.70 Hz, 2H), 3.07 (dd, J=8.50, 5.42 Hz, 2H), 2.93 (dd, J=8.66, 5.49 Hz, 2H), 2.36 (bt, J=6.23 Hz, 2H), 1.63 (quint., J=7.29 Hz, 2H). $^{13}$C NMR (100 MHz, DMSO-d$_6$): δ 154.74, 152.36, 138.92, 136.68, 135.22, 134.20, 132.71, 131.08, 130.25, 127.45, 123.13, 121.44, 119.25, 118.80, 118.69, 113.88, 111.88, 42.49, 30.18, 29.87 (2 broadened carbons), 25.92, 23.22. LCMS (50-95% acetonitrile in 0.05% TFA over 10 minutes) retention time=1.70 min, ESI m/z=436, [M+H]$^+$.

Synthesis of 2-(5-methoxy-1H-indol-3yl)-N-(3-(1-trityl-1H-imidazol-4-yl)propyl)-acetamide (B)

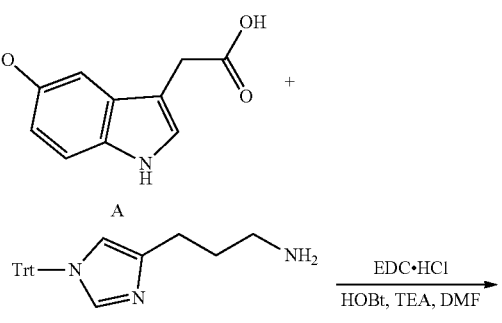

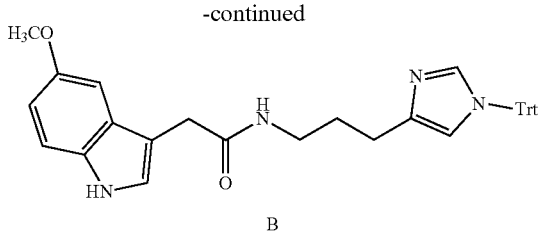

B

To a solution of 2-(5-methoxy-1H-indol-3-yl)acetic acid (A) (2.00 g, 4.87 mmol) in DMF (40 mL) was added EDC·HCl (1.40 g, 7.31 mmol) and HOBt·H$_2$O (933 mg, 6.09 mmol). The resulting mixture was stirred at RT for 45 min and treated with compound 7 (1.79 g, 4.87 mmol). The "pH" of the solution was adjusted ~9 by the addition of TEA (~1.35 mL) and the reaction was stirred at RT for 16 hours. After this time water (200 mL) was added and the resulting precipitate was collected by filtration and dried by azeotropic distillation with toluene to afford 2.38 g (88% yield) of compound B as a white solid: $^1$H NMR (400 MHz, DMSO-d$_6$): δ 10.64 (bs, 1H), 7.85 (t, J=5.50 Hz, 1H), 7.38-7.30 (m, 9H), 7.18 (s, 1H), 7.15 (d, J=8.70 Hz, 1H), 7.07-6.98 (m, 8H), 6.63 (dd, J=8.60, 2.80 Hz, 1H), 6.52 (s, 1H), 3.63 (s, 3H), 3.38 (s, 2H), 3.00 (q J=6.00 Hz, 2H), 2.36 (t, J=7.30 Hz, 2H), 1.59 (quint. J=7.30 Hz, 2H). $^{13}$C NMR (100 MHz, DMSO-d$_6$): δ 171.01, 153.46, 142.90, 141.17, 138.14, 131.75, 129.71, 128.70, 128.45, 128.00, 124.91, 118.02, 112.44, 111.59, 109.29, 100.96, 74.83, 55.75, 38.76, 33.42, 29.53, 25.83. LCMS (50-95% acetonitrile in 0.05% TFA over 10 minutes) retention time=3.87 min, ESI m/z=555, [M+H]$^+$.

Synthesis of 2-(5-methoxy-1H-indol-3-yl)-N-(3-(1-trityl-1H-imidazol-4-yl)propylethane-thioamide C)

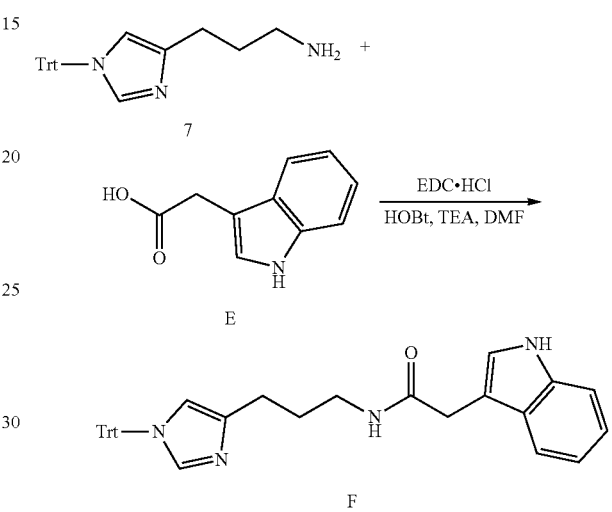

A solution of 2-(5-methoxy-1H-indol-3-yl)-N-(3-(1-trityl-1H-imidazol-4-yl)propyl)acetamide (B) (azeotropically dried by coevaporation with toluene, 2.00 g, 3.61 mmol) and Lawesson's reagent (946 mg, 2.34 mmol) in THF (35 mL) was heated to 70° C. for 3 hours. The resulting mixture was allowed to cool to room temperature and concentrated. Purification by flash column chromatography (SiO$_2$, 40:1 to 20:1 CH$_2$Cl$_2$/MeOH) afforded 1.82 g (88% yield) of compound C as a yellow foam: $^1$H NMR (400 MHz, DMSO-d$_6$) δ 10.69 (bs, 1H), 9.94 (bt, J~5.0 Hz, 1H), 7.38-7.30 (m, 9H), 7.15 (d, J=9.10 Hz, 1H), 7.13 (d, J=2.30 Hz, 1H), 7.07-7.03 (m, 8H), 6.64 (d, J=2.30 Hz, 1H), 6.61 (bs, 1H), 3.91 (s, 2H), 3.63 (s, 3H), 3.44 (q, J=6.80 Hz, 2H), 2.40 (t, J=7.40 Hz, 2H), 1.76 (quint., J=7.30 Hz, 2H). $^{13}$C NMR (100 MHz, DMSO-d$_6$): δ 202.13, 153.50, 142.65, 138.07, 131.71, 129.71, 128.76, 128.53, 127.76, 125.20, 118.39, 112.50, 111.57, 110.33, 101.15, 75.19, 55.78, 45.49, 42.94, 27.43, 25.44. LCMS (50-95% acetonitrile in 0.05% TFA over 10 minutes) retention time=5.32 min, ESI m/z=571, [M+H]$^+$.

Synthesis of 2-(1H-indol-3-yl)-N-(3-(1-trityl-H-imidazol-4-yl)propyl)acetamide (F)

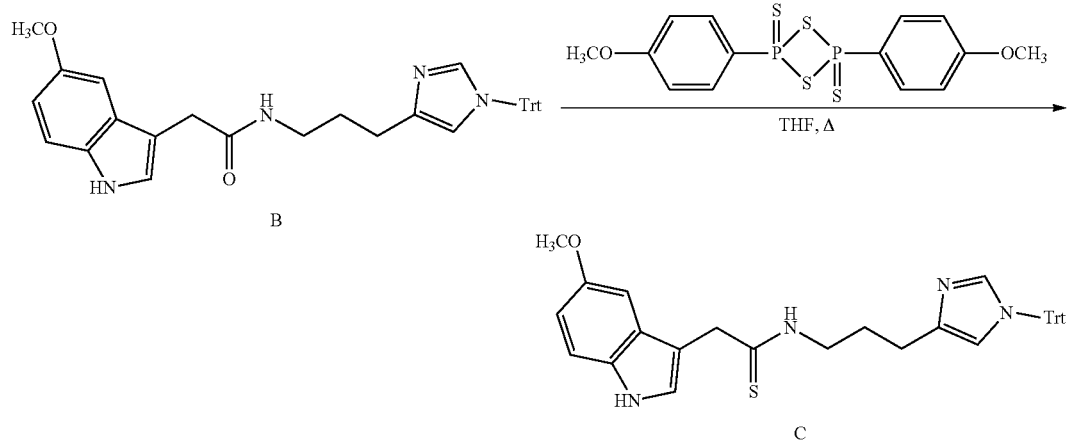

To a solution of 2-(1H-indol-3-yl)acetic acid (E) (816 mg, 4.66 mmol) in DMF (50 mL) was added EDC·HCl (1.34 g, 6.99 mmol) and HOBt·H$_2$O (892 mg, 5.83 mmol). The resulting mixture was stirred at room temperature for 45 min. A solution of the amine 7 (1.71 g, 4.66 mmol) in DMF (50 mL) and TEA (1.70 mL) were added and the reaction was stirred for 16 hours at room temperature. The mixture was poured into water (150 mL) in a large beaker and stirred for 30 minutes at room temperature. The solid was collected by filtration. Trituration of the solid with hot ACN and filtration afforded 1.10 g (45% yield) of pure amide F: $^1$H NMR (400 MHz, DMSO-d$_6$) δ 10.80 (bs, 1H), 7.84 (t, J=5.38 Hz, 1H), 7.47 (d, J=7.88 Hz, 1H), 7.38-7.38 (m, 8H), 7.27 (d, J=8.13 Hz, 2H), 7.18 (d, =1.03 Hz, 1H), 7.11 (d, J=2.03 Hz, 1H), 7.04-7.02 (m, 6H), 6.97 (t, J=7.23 Hz, 1H), 6.84 (t, J=7.21 Hz, 1H), 6.52 (s, 1H), 3.42 (s, 2H), 2.98 (apparent q, J=6.59 Hz, 2H), 2.34 (t, J=7.42 Hz, 2H), 1.59 (quint., J=7.06 Hz, 2H). LCMS (50-95% acetonitrile in 0.05% TFA over 10 minutes) retention time=4.33 min, ESI m/z=525, [M+H]$^+$.

Synthesis of 2-(1H-indol-3-yl)-N-(3-(1-trityl-1H-imidazol-4-yl)propyl)ethanethioamide (G)

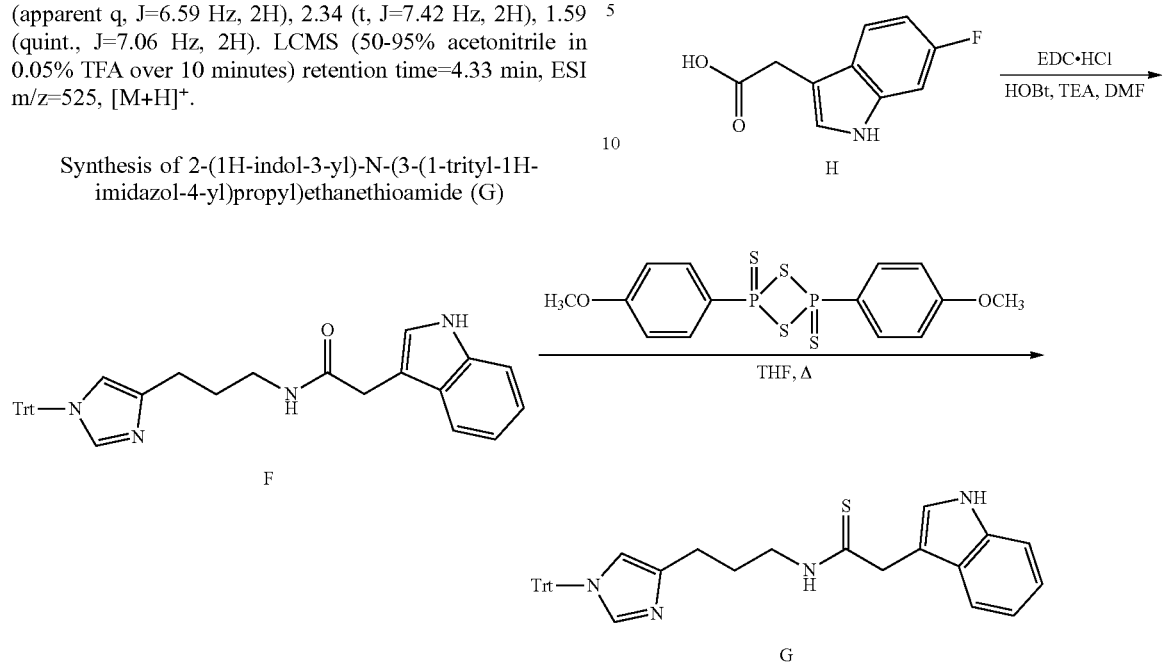

A mixture of 3-(1H-indol-3-yl)-N-(3-(1-trityl-1H-imidazol-4-yl)propyl) propanamide (F) (1.01 g, 1.90 mmol; previously dried by 3 azeotropic coevaporations with toluene, 30 mL each) and Lawesson's reagent (499.5 mg, 1.24 mmol) in THF (45 mL) was heated to 65° C. for 3.5 hours. After this time, the reaction was cooled and concentrated. The residue was purified by flash column chromatography (SiO2, 30/1 CH$_2$Cl$_2$/MeOH) to afford 314 mg (31% yield) of thioamide G as a tan foam: $^1$H NMR (400 MHz, DMSO-d$_6$) δ 10.84 (bs, 1H), 9.90 (t, J=5.03 Hz, 1H), 7.53 (d, J=7.80 Hz, 1H), 7.38-7.28 (m, 10H), 7.26 (d, J=7.99 Hz, 1H), 7.16 (d, J=2.31 Hz, 1H), 7.05-7.02 (m, 6H), 6.97 (dt, J=7.02, 0.58 Hz, 1H), 6.84 (dt, J=7.89, 0.80 Hz, 1H), 6.57 (bs, 1H), 3.95 (s, 2H), 3.45-3.39 (m, 2H), 2.38 (t, J=7.33 Hz, 2H), 1.75 (quint., J=7.31, 2H). $^{13}$C NMR (100 MHz, DMSO-d$_6$) δ 202.11, 142.75, 140.40, 138.10, 136.59, 129.72, 128.74, 128.50, 127.45, 124.53, 121.43, 119.27, 118.82, 118.32, 111.86, 110.61, 75.04, 45.50, 42.84, 27.40, 25.57. LCMS (50-95% acetonitrile in 0.05% TFA over 10 minutes) retention time=5.42 min, ESI m/z=541, [M+H]$^+$.

Synthesis of 2-(6-fluoro-1H-indol-3-yl)-N-(3-(1-trityl-H-imidazol-4-yl)propyl) acetamide (I)

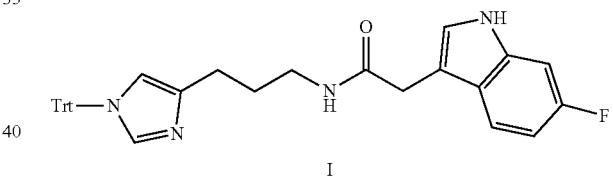

-continued

[structure H with EDC·HCl, HOBt, TEA, DMF]

[structure I]

To a solution of 2-(6-fluoro-1H-indol-3-yl)acetic acid (H) (1.00 g, 5.18 mmol) in DMF (50 mL) was added EDC·HCl (1.50 g, 7.77 mmol) and HOBt·H$_2$O (1.19 g, 7.77 mmol). The resulting mixture was stirred at room temperature for 1 h. A solution of the amine 7 (1.90 g, 5.18 mmol) and TEA (2.80 mL) were added and the reaction was stirred for 16 hours at room temperature. The mixture was partitioned with EtOAc (120 mL) and 1N NaHSO$_4$ (100 mL). The layers were separated and the EtOAc solution was washed with water (150 mL), sat. NaHCO$_3$ (150 mL) and brine (150 mL). The EtOAc layer was dried (Na$_2$SO$_4$), filtered and concentrated. Trituration of the solid with hot ACN and filtration afforded 1.58 g (56% yield) of pure amide I. $^1$H NMR (400 MHz, DMSO-d$_6$) δ 10.88 (bs, 1H), 7.89 (t, J=5.48 Hz, 1H), 7.45 (dd, J=8.69, 5.53 Hz, 1H), 7.37-7.23 (complex m, 9H), 7.19 (d, J=1.20 Hz, 1H), 7.11 (d, J=2.36 Hz, 1H), 7.06-7.01 (m, 7H), 6.73 (ddd, J=11.04, 9.73, 2.33 Hz, 1H), 6.53 (bs, 1H), 3.40 (s, 2H), 2.98 (apparent q, J=6.71 Hz, 2H), 2.35 (t, J=7.44 Hz, 2H), 1.58 (quint., J=7.19 Hz, 2H). LCMS (50-95% acetonitrile in 0.05% TFA over 10 minutes) retention time=4.38 min, ESI m/z=543, [M+H]$^+$.

Synthesis of 2-(6-fluoro-1H-indol-3-yl)-N-(3-(1-trityl-1H-imidazol-4 yl)propyl)ethane-thioamide (J)

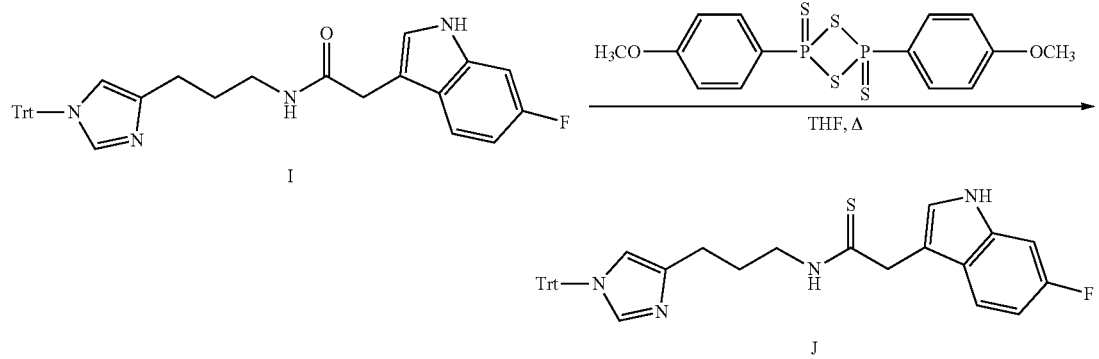

A mixture of 2-(6-fluoro-1H-indol-3-yl)-N-(3-(1-trityl-1H-imidazol-4-yl)propyl)-acetamide (I) (1.58 g, 2.91 mmol; previously dried by 3 azeotropic coevaporations with toluene, 30 mL each) and Lawesson's reagent (789 mg, 1.95 mmol) in THE (75 mL) was heated to 65° C. for 2.5 hours. After this time, the reaction was cooled and concentrated. The residue was purified by flash column chromatography (SiO$_2$, 40/1 CH$_2$Cl$_2$/MeOH to 20/1) to afford 1.18 g (73% yield) of thioamide J as a tan foam: $^1$H NMR (400 MHz, DMSO-d$_6$) δ 10.88 (bs, 1H), 9.90 (t, J=4.95 Hz, 1H), 7.52 (dd, J=8.70, 5.53 Hz, 1H), 7.39-7.31 (complex m, 9H), 7.16 (d, J=2.30 Hz, 1H), 7.08-7.03 (m, J=7H), 6.73 73 (ddd, J=11.05, 8.80, 2.32 Hz, 1H), 3.93 (s, 2H), 3.42 (apparent q, J=6.65 Hz, 2H), 2.42 (t, J=7.43 Hz, 2H), 1.76 (quint., J=7.36 Hz, 2H). $^{13}$C NMR (100 MHz, DMSO-d$_6$) δ 201.98, 159.30 (d, $J_{C,F}$=234.1 Hz), 142.56, 139.73, 137.99, 136.44 (d, $J_{C,F}$=12.7 Hz), 129.72, 128.78, 128.57, 125.11, 124.36, 120.30 (d, $J_{C,F}$=10.3 Hz), 118.53, 110.95, 107.29 (d, $J_{C,F}$=24.3 Hz), 97.80 (d, $J_{C,F}$=25.7 Hz), 75.40, 45.44, 42.72, 27.26, 25.22. LCMS (50-95% acetonitrile in 0.05% TFA over 10 minutes) retention time=5.83 min, ESI m/z=559, [M+H]$^+$.

Synthesis of 3,3-dimethyl-N-(3-(1-trityl-1H-imidazol-4-yl)Propyl)butanamide (L)

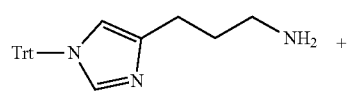

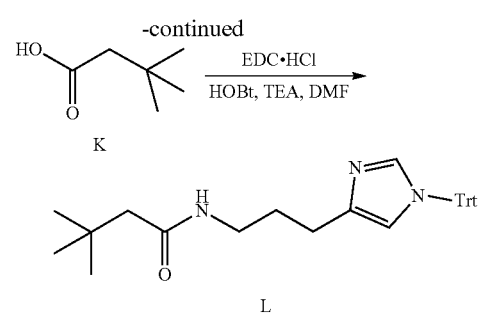

To a solution of 3,3-dimethylbutanoic acid K (1.00 g, 8.61 mmol) in DMF (50 Ml) was added EDC·HCl (2.48 g, 12.9 mmol) and HOBt·H$_2$O (1.65 g, 10.8 mmol) and the resulting mixture was stirred for 30 minutes at room temperature. After this time, a solution of amine 7 (3.00 g, 8.61 mmol), and TEA (1.74 g, 2.40 mL, 17.2 mmol) in DMF (20 mL) was added and the reaction was stirred for 16 hours thereafter. Workup as described in the previous examples afforded 3.10 g of compound L (77% yield) as a white: $^1$H NMR (400 MHz, DMSO-d$_6$) δ 7.65 (t, J=5.10 Hz, 1H), 7.35 (m, 9H), 7.20 (apparent d, J=1.40 Hz, 1H), 7.04 (dd, J=8.90, J=2.60 Hz, 6H), 6.56 (apparent d, J=1.40 Hz, 1H), 2.96 (q, J=6.90 Hz, 2H), 2.37 (t, J=7.40 Hz, 2H), 1.87 (s, 2H), 1.58 (quint., J=7.30 Hz, 2H), 0.88 (s, 9H). $^{13}$C NMR (100 MHz, DMSO-d$_6$) δ 171.07, 142.90, 141.15, 138.17, 129.71, 128.70, 128.46, 118.09, 74.84, 49.38, 38.37, 30.88, 30.21, 29.45, 25.81. LCMS (50-95% acetonitrile in 0.05% TFA over 10 minutes) retention time=4.93 minutes, ESI m/z=466, [M+H]$^+$

Synthesis of 3,3-dimethyl-N-(3-(1-trityl-1H-imidazol-4-yl)propyl)butanethioamide (M)

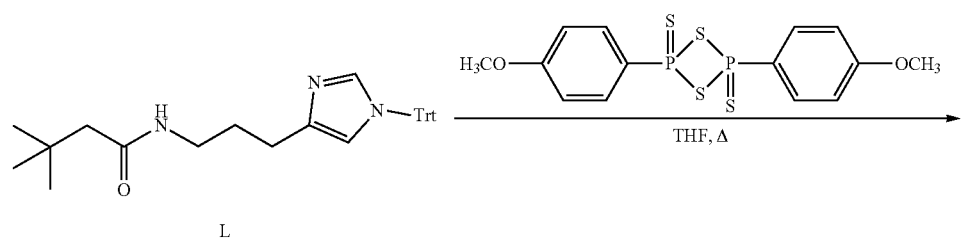

-continued

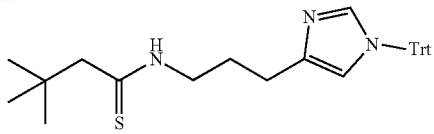

M

Produced following General Procedure D from amide L (2.95 g, 6.34 mmol) and Lawesson's reagent (1.67 g, 4.12 mmol), which afforded ~5.5 g crude material as a brown oil after 7 hours of reflux (reaction determined to be mostly complete by LCMS). The crude was purified by flash chromatography (SiO$_2$, 80:1 CH$_2$Cl$_2$:MeOH to 40:1) which afforded 1.32 g of M as a tan foam (43% purified yield): LCMS (50-95% acetonitrile in 0.05% TFA over 10 minutes) retention time=6.13 minutes, ESI m/z=482, [M+H]$^+$.

Synthesis of 3-((5-(4-methoxybenzyl)-4-(3-(1-trityl-1H-imidazol-4-yl)propyl)-4H-1,2,4-triazol-3-yl)methyl)-1H-indole (70)

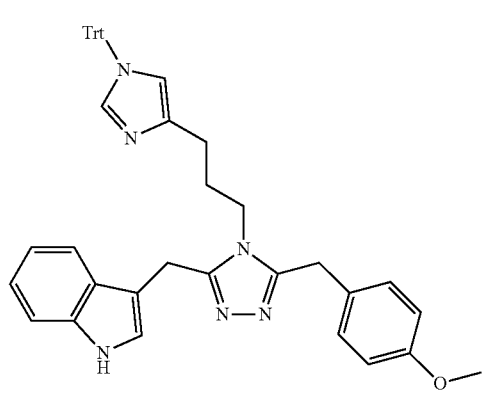

70

Prepared according to the General Procedure 1C from 2-(1H-indol-3-yl)-N-(3-(1-trityl-1H-imidazol-4-yl)propyl)ethanethioamide G (500 mg, 0.93 mmol), 2-(4-methoxyphenyl)acetic hydrazide (208 mg, 1.16 mmol), silver benzoate (424 mg, 1.85 mmol), and acetic acid (167 mg, 159 μL, 2.78 mmol), which formed ~1.4 g of crude material. The crude was purified by flash chromatography (SiO$_2$, 40:1 CH$_2$Cl$_2$:MeOH to 30:1, to 20:1) afforded 97 mg (16% yield) of compound 70 as a white solid: LCMS (50-95% acetonitrile in 0.05% TFA over 10 minutes) retention time=3.63 minutes, ESI m/z=669, [M+H]$^+$.

Synthesis of 3-((4-(3-(1H-imidazol-4-yl)propyl)-5-(4-methoxybenzyl)-4H-1,2,4-triazol-3-yl)methyl)-1H-indole (SK-I-23)

SK-I-23

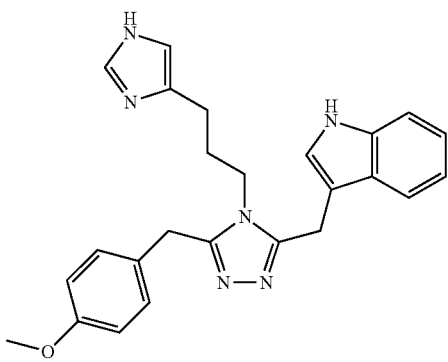

Prepared according to general procedure 1D from 3-((5-(4-methoxybenzyl)-4-(3-(1-trityl-1H-imidazol-4-yl)propyl)-4H-1,2,4-triazol-3-yl)methyl)-1H-indole 70 (97 mg, 0.15 mmol) and afforded 48 mg (77% yield) of compound SK-I-23 as a tan solid: LCMS (50-95% acetonitrile in 0.05% TFA over 10 minutes) retention time=1.72 minutes, ESI m/z=427, [M+H]$^+$.

Synthesis of 3-((5-(4-fluorobenzyl)-4-(3-(1-trityl-1H-imidazol-4-yl)propyl)-4H-1,2,4-triazol-3-yl)methyl)-5-methoxy-1H-indole (72)

72

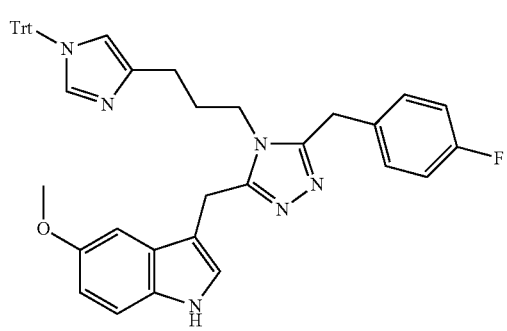

Prepared according to General Procedure 1C from thioamide C (300 mg, 0.53 mmol), 2-(4-fluorophenyl)acetic hydrazide (111 mg, 0.66 mmol), silver benzoate (243 mg, 1.06 mmol), and acetic acid (95 mg, 90.9 μL, 1.59 mmol), which afforded 735 mg of crude material. The crude was purified by flash chromatography (SiO$_2$, 40:1 CH$_2$Cl$_2$:

MeOH to 20:1) to afford 159 mg (43% yield) of compound 72: $^1$H NMR (400 MHz, DMSO-d$_6$) δ 10.70 (bs, 1H), 7.90 (d, J=8.20 Hz, 1H), 7.46 (t, J=8.10 Hz, 1H), 7.36-7.29 (m, 9H), 7.21 (bs, 1H), 7.14-7.10 (m, 3H), 7.06 (d, J=1.80 Hz, 1H), 7.00-6.98 (m, 6H), 6.91 (d, J=2.30 Hz, 1H), 6.62 (dd, J=8.30, 2.30 Hz, 1H), 6.45 (bs, 1H), 4.08 (s, 2H), 3.97 (s, 2H), 3.68 (apparent t, J=7.80 Hz, 2H), 2.24 (t, J=7.60 Hz, 2H), 1.41 (quint., J=7.50 Hz, 2 h). $^{13}$C NMR (100 MHz, DMSO-d$_6$) δ 161.47 (d, $^1J_{CF}$=242 Hz), 160.26, 153.80, 153.47, 153.19, 142.82, 140.17, 138.25, 133.39, 133.31 (d, 4$J_{CF}$=2.90 Hz), 131.85, 130.83 (3$J_{CF}$=8.70 Hz), 129.78, 139.66, 129.10, 128.69, 128.46, 127.63, 124.63, 118.11, 115.64 (d, $^2J_{CF}$=22.0 Hz), 112.57, 111.66, 109.02, 100.93, 74.87, 55.73, 42.70, 29.84, 29.44, 25.06, 21.87. LCMS (50-95% acetonitrile in 0.05% TFA over 10 minutes) retention time=3.77 minutes, ESI m/z=687, [M+H]$^+$.

Synthesis of 3-((4-(3-(1H-imidazol-4-yl)propyl)-5-(4-fluorobenzyl)-4H-1,2,4-triazol-3-yl)methyl)-5-methoxy-JH-indole (SK-I-55)

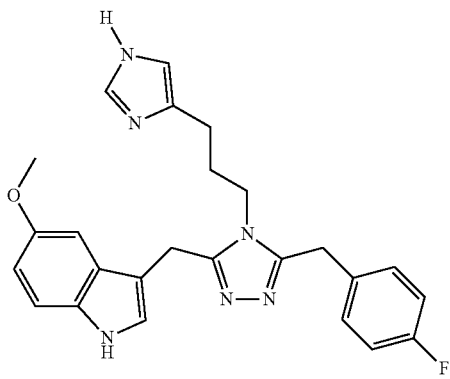

SK-I-55

Prepared according to General Procedure 1D from 3-((5-(4-fluorobenzyl)-4-(3-(1-trityl-1H-imidazol-4-yl)propyl)-4H-1,2,4-triazol-3-yl)methyl)-5-methoxy-1H-indole 72 (144 mg, 0.21 mmol) and afforded 66 mg (71% yield) of compound SK-I-55 as a tan residue. $^1$H NMR (400 MHz, MeOH-d$_4$) δ 7.55 (s, 1H), 7.19 (d, J=8.70 Hz, 1H), 7.05-7.02 (m, 2H), 7.97-7.92 (m, 3H), 6.83 (d, J=2.40 Hz, 1H), 6.72 (dd, J=8.70, 2.30 Hz, 1H), 6.55 (s, 1H), 4.24 (s, 2H), 4.04 (s, 2H), 3.70 (s, 3H), 3.63-3.58 (m, 2H), 2.28 (t, J=6.80 Hz, 2H), 1.38 (quint., J=6.80 Hz, 2H). $^{13}$C NMR (100 MHz, MeOH-d$_4$) δ 162.01 (d, 1 $J_{CF}$=244 Hz), 154.87, 154.16, 153.92, 134.71, 131.99, 131.38 (d, $^4J_{CF}$=2.90 Hz), 129.84 (d, $^3J_{CF}$=8.60 Hz), 126.97, 123.61, 115.22 (d, $^2J_{CF}$=22.1 Hz), 111.89, 107.52, 99.54, 54.78, 42.75, 29.51, 28.69, 23.33 (broad), 21.72. LCMS (50-95% acetonitrile in 0.05% TFA over 10 minutes) retention time=5.92 minutes, ESI m/z=445, [M+H]$^+$.

Synthesis of 3-((5-benzyl-4-(3-(1-trityl-1H-imidazol-4-yl)propyl)-4H-1,2,4-triazol-3-yl)methyl)-5-methoxy-1H-indole (74)

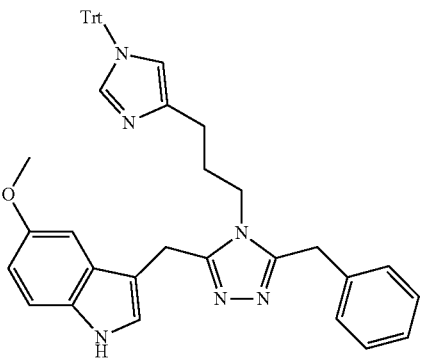

74

Prepared according to General Procedure 1C from thioamide C (300 mg, 0.53 mmol), phenylacetic hydrazide (29n) (99 mg, 0.66 mmol), silver benzoate (243 mg, 1.06 mmol), and acetic acid (95 mg, 90.9 µL, 1.59 mmol), affording 738 mg of crude material. The crude was purified by flash chromatography (SiO$_2$, 40:1 CH$_2$Cl$_2$:MeOH to 20:1) to afford 118 mg (33% yield) of compound 74. $^1$H NMR (400 MHz, DMSO-d$_6$) δ 10.69 (bs 1H), 7.90 (d, J=7.40 Hz, 1H), 7.46 (t, J=7.80 Hz, 1H), 7.36-7.32 (m, 9H), 7.20 (s, 1H), 7.14-7.03 (complex m, 7H), 7.00-6.97 (m, 6H), 6.90 (d, J=2.30 Hz, 1H), 6.62 (dd, J=8.70, 2.30 Hz, 1H), 6.39 (s, 1H), 4.08 (s, 2H), 3.98 (s, 2H), 3.68-3.64 (m, 2H), 2.22 (apparent t, J=6.90 Hz, 2H), 1.36 (apparent quint., J~7.00 Hz, 2H). $^{13}$C NMR (100 MHz, DMSO-d$_6$) δ 153.79, 153.47, 153.24, 142.81, 140.17, 138.17, 137.19, 133.39, 131.85, 129.78, 129.67, 129.09, 128.91, 128.87, 128.70, 128.47, 127.63, 127.01, 124.62, 118.10, 112.57, 111.68, 109.02, 100.90, 74.88, 55.73, 42.73, 30.71, 29.40, 25.11, 21.89. LCMS (50-95% acetonitrile in 0.05% TFA over 10 minutes) retention time=3.43 minutes, ESI m/z=669, [M+H]$^+$.

Synthesis of 3-((4-(3-(1H-imidazol-4-yl)propyl)-5-benzyl-4H-1,2,4-triazol-3-yl)methyl)-5-methoxy-1H-indole (SK-I-53)

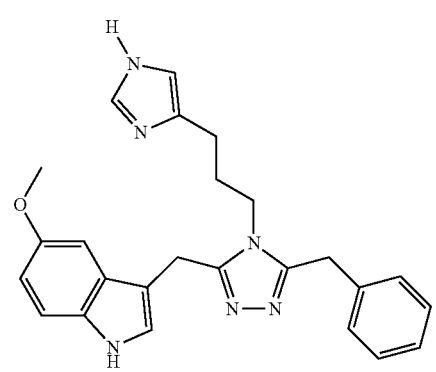

SK-I-53

Synthesized according to General Procedure 1D from 3-((5-benzyl-4-(3-(1-trityl-1H-imidazol-4-yl)propyl)-4H-1,2,4-triazol-3-yl)methyl)-5-methoxy-1H-indole 74 (118 mg, 0.18 mmol) to afford 64 mg (85% yield) of compound SK-I-53 as a tan solid. $^1$H NMR (400 MHz, MeOH-$d_4$) δ 7.54 (s, 1H), 7.23-7.14 (complex m, 4H), 7.02 (d, J=6.80 Hz, 2H), 6.92 (s, 1H), 6.84 (d, J=2.20 Hz, 1H), 6.72 (dd, J=8.70 Hz, 2.70 Hz, 1H), 6.52 (s, 1H), 4.23 (s, 2H), 4.06 (s, 2H), 3.70 (s, 3H), 3.61-3.57 (m, 2H), 2.25 (t, J=6.80 Hz, 2H), 1.35 (quint., J=7.80 Hz, 2H). $^{13}$C NMR (100 MHz, MeOH-$d_4$) δ 154.82, 154.27, 153.92, 135.43, 134.67, 131.98, 128.58, 127.99, 126.89, 123.58, 111.91, 107.54, 99.51, 54.77, 42.77, 30.04, 28.61, 23.24 (broad), 21.73. LCMS (50-95% acetonitrile in 0.05% TFA over 10 minutes) retention time=5.80 minutes, ESI m/z=427, [M+H]$^+$.

Synthesis of 5-methoxy-3-((5-(4-fluorobenzyl)-4-(3-(1-trityl-1H-imidazol-4-yl)propyl)-4H-1,2,4-triazol-3-yl)methyl)-1H-indole (76)

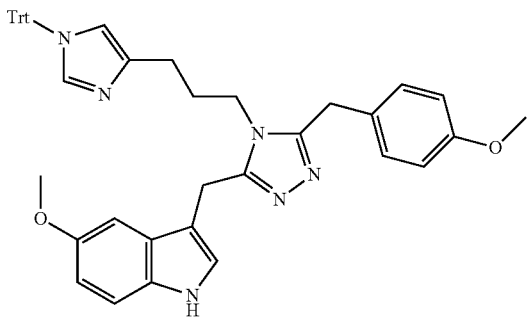

76

Created according to General Procedure 1C from thioamide C (311 mg, 0.54 mmol), 2-(4-methoxyphenyl)acetic hydrazide (29d) (123 mg, 0.68 mmol), silver benzoate (247 mg, 1.08 mmol), and acetic acid (97 mg, 93 μL, 1.62 mmol), which afforded 760 mg of crude material. The crude was purified by flash chromatography (SiO2, 40:1 CH$_2$Cl$_2$/MeOH to 20:1) to afford 132 mg (39% yield) of compound 76. $^1$H NMR (400 MHz, DMSO-$d_6$) δ 10.7 (s, 1H), 7.90 (d, J=6.80 Hz, 1H), 7.45 (t, J=7.80 Hz, 1H), 7.33 (m, 9H), 7.21 (s, 1H), 7.11 (d, J=8.70 Hz, 1H), 7.04 (apparent d, J=1.80 Hz, 1H), 6.99 (m, 6H), 6.90 (apparent d, J=2.30 Hz, 1H), 6.70 (d, J=8.70 Hz, 2H), 6.62 (dd, J=8.70, J=2.30 Hz, 1H) 6.46 (s, 1H), 4.06 (s, 2H), 3.90 (s, 2H), 3.64 (partially obs. t, J=7.30 Hz, 2H), 3.59 (s, 3H), 3.59 (s, 3H), 2.23 (t, J=6.80 Hz, 2H), 1.41 (quint., J=6.80 Hz, 2H). LCMS (50-95% acetonitrile in 0.05% TFA over 10 minutes) retention time=3.38 minutes, ESI m/z=699, [M+H]$^+$.

Synthesis of 3-((4-(3-(1H-imidazol-4-yl)propyl)-5-(4-methoxybenzyl)-4H-1,2,4-triazol-3-yl)methyl)-5-methoxy-1H-indole (SK-I-56)

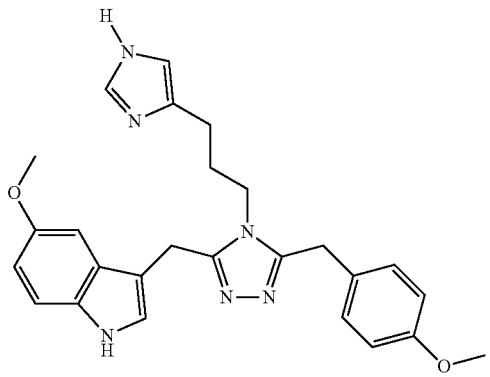

SK-I-56

Prepared according to General Procedure 1D from 5-methoxy-3-((5-(4-methoxybenzyl)-4-(3-(1-trityl-1H-imidazol-4-yl)propyl)-4H-1,2,4-triazol-3-yl)methyl)-1H-indole (76) (112 mg, 0.16 mmol) and afforded 67 mg (92% yield) of compound SK-I-56 as a light tan solid. $^1$H NMR (400 MHz, MeOH-$d_4$) δ 7.54 (s, 1H), 7.18 (d, J=8.70 Hz, 1H), 6.94-6.90 (m, 3H), 6.83 (d, J=2.70 Hz, 1H), 6.77-6.74 (m, 2H), 6.72 (dd, J=8.70, 2.70 Hz, 1H), 6.53 (bs, 1H), 4.23 (s, 2H), 3.99 (s, 2H), 3.70 (s, 3H), 3.69 (s, 3H), 3.61-3.56 (m, 2H), 2.25 (t, J=7.40 Hz, 2H), 1.33 (quint., J=7.70 Hz, 2H). $^{13}$C NMR (100 MHz, MeOH-$d_4$) δ 158.97, 154.78, 154.59, 153.92, 134.64, 131.99, 129.03, 127.12, 126.97, 123.58, 113.93, 111.89, 107.57, 99.54, 54.78, 54.31, 42.77, 29.56, 28.58, 23.59 (broad), 21.71. LCMS (50-95% acetonitrile in 0.05% TFA over 10 minutes) retention time=1.75 minutes, ESI m/z=457, [M+H]$^+$.

Synthesis of 5-methoxy-3-((5-(3-(tri fluoromethyl) benzyl)-4-(3-(1-trityl-1H-imidazol-4-yl)propyl)-4H-1,2,4-triazol-3-yl)methyl)-1H-indole (78)

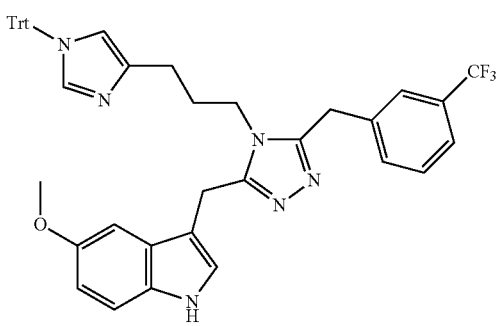

78

Prepared according to General Procedure 1C from thioamide C (360 mg, 0.63 mmol), 3-(trifluoromethyl)phenylacetic hydrazide (29i) (172 mg, 0.79 mmol), silver benzoate (286 mg, 1.26 mmol), and acetic acid (113 mg, 108 μL, 1.89 mmol), to afford 932 mg of crude material. The crude was purified by flash chromatography (SiO$_2$, 20:1 CH$_2$Cl$_2$/MeOH to 10:1) afforded 209 mg (45% yield) of compound 78. $^1$H NMR (400 MHz, DMSO-$d_6$) δ 10.7 (s, 1H), 7.90 (d, J=8.20 Hz, 1H), 7.60-7.38 (complex m, 3H), 7.32 (m, 9H), 7.19 (s, 1H), 7.11 (d, J=8.70 Hz, 1H), 7.06 (s, 1H), 6.99 (m, 6H), 6.91 (apparent d, J=1.80 Hz, 1H), 6.62 (dd, J=8.70, J=2.30 Hz, 1H) 6.43 (s, 1H), 4.10 (s, 2H), 4.09 (s, 2H), 3.75 (t, J=7.30 Hz, 2H), 3.59 (s, 3H), 2.25 (t, J=6.90 Hz, 2H), 1.42 (J=7.70 Hz, 2H). LCMS (50-95% acetonitrile in 0.05% TFA over 10 minutes) retention time=7.98 minutes, ESI m/z=737, [M+H]$^+$.

Synthesis of 3-((4-(3-(1H-imidazol-4-yl)propyl)-5-(3-(trifluoromethyl)benzyl)-4H-1,2,4-triazol-3yl)methyl)-5-methoxy-1H-indole (SK-I-57)

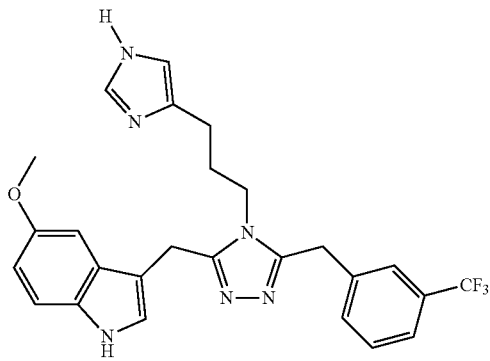

Prepared according to General Procedure 1D from 5-methoxy-3-((5-(3-(trifluoromethyl)benzyl)-4-(3-(1-trityl-1H-imidazol-4-yl)propyl)-4H-1,2,4-triazol-3-yl)-methyl)-1H-indole (78) (209 mg, 0.28 mmol) to afford 105 mg (76% yield) of compound SK-I-57 as a tan solid. $^1$H NMR (400 MHz, MeOH-d$_4$) δ 7.59 7.41 (complex overlapping m, 5H), 7.31 (d, J=7.80 Hz, 1H), 7.18 (d, J=8.70 Hz, 1H), 6.93 (s, 1H), 6.85 (d, J=2.30 Hz, 1H), 6.72 (dd, J=8.70, 2.30 Hz, 1H), 6.54 (bs, 1H), 4.25 (s, 2H), 4.16 (s, 2H), 3.70 (s, 3H), 3.69-3.66 (m, 2H), 2.28 (t, J=7.30 Hz, 2H), 1.39 (quint., J=7.50 Hz, 2H). LCMS (50-95% acetonitrile in 0.05% TFA over 10 minutes) retention time=1.85 minutes, ESI m/z=495, [M+H]$^+$.

Synthesis of 6-fluoro-3-((5-(4-fluorobenzyl)-4-(3-(1-trityl-1H-imidazol-4-yl)propyl)-4H-1,2,4-triazol-3-yl)methyl)-1H-indole (80)

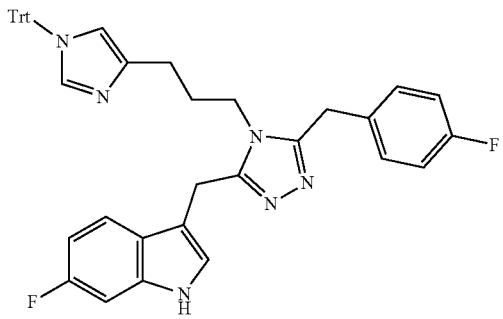

Synthesized following General Procedure 1C from thioamide J (547 mg, 0.98 mmol), 2-(4-fluorophenyl)acetic hydrazide (206 mg, 1.22 mmol), silver benzoate (449 mg, 1.96 mmol), and acetic acid (177 mg, 168 µL, 2.94 mmol), which afforded 1.37 mg of crude material. The crude was purified by flash chromatography (SiO$_2$, 40:1 CH$_2$Cl$_2$/MeOH to 20:1) afforded 327 mg (49% yield) of compound 80. LCMS (50-95% acetonitrile in 0.05% TFA over 10 minutes) retention time=4.42 minutes, ESI m/z=675, [M+H]$^+$.

Synthesis of 3-((4-(3-(1H-imidazol-4-yl)propyl)-5-(4-fluorobenzyl)-4H-1,2,4-triazol-3-yl)methyl)-6-fluoro-1H-indole (SK-I-91)

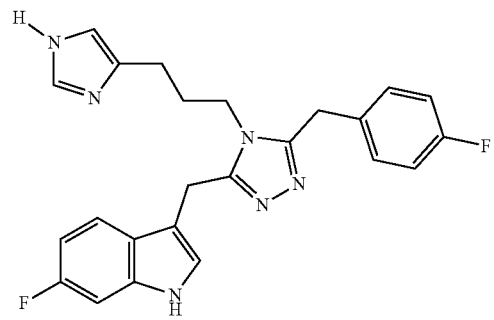

Prepared according to General Procedure 1D from 6-fluoro-34(5-(4-fluorobenzyl)-4-(3-(1-trityl-1H-imidazol-4-yl)propyl)-4H-1,2,4-triazol-3-yl)methyl)-1H-indole (80) (136 mg, 0.20 mmol) and afforded 51 mg (59% yield) of compound SK-I-91 as a tan solid. $^1$H NMR (400 MHz, DMSO-d$_6$) δ 11.75 (bs, 1H), 10.95 (s, 1H), 7.51 (s, 1H), 7.38 (dd, J=8.70, 5.5 Hz, 1H), 7.26-7.21 (m, 1H), 7.14-7.02 (complex overlapping m, 7H), 6.77 (dt, J=8.70, 2.30 Hz, 1H), 6.67 (bs, 1H), 4.09 (s, 2H), 3.97 (s, 2H), 3.71-3.65 (m, 2H), 2.32-2.26 (m, 2H), 1.49-1.40 (m, 2H). LCMS (50-95% acetonitrile in 0.05% TFA over 10 minutes) retention time=1.83 minutes, ESI m/z=433, [M+H]$^+$.

Synthesis of 6-fluoro-345-(4-methoxybenzyl)-4-(3-(1-trityl-1H-imidazol-4-yl)propyl)-4H-1,2,4-triazol-3-yl)methyl)-1H-indole (82)

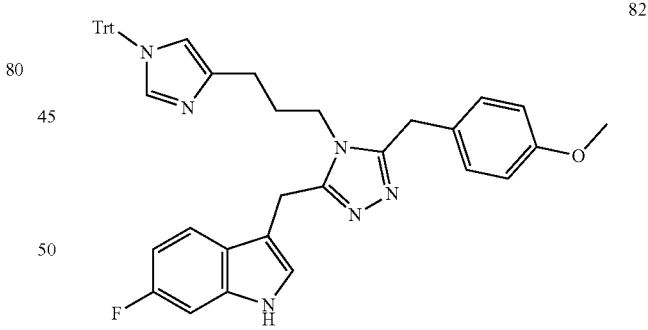

Prepared according to General Procedure 1C from thioamide C (300 mg, 0.54 mmol), 2-(4-methoxyphenyl)acetic hydrazide (29d) (121 mg, 0.67 mmol), silver benzoate (247 mg, 1.08 mmol), and acetic acid (97 mg, 93 µL, 1.62 mmol), which formed 737 mg of crude material. The crude was purified by flash chromatography (SiO$_2$, 40:1 CH$_2$Cl$_2$/MeOH to 20:1) afforded 234 mg (63% yield) of compound 82. $^1$H NMR (400 MHz, DMSO-d$_6$) δ 10.92 (bs, 1H), 7.91-7.89 (m, 2H), 7.45 (t, J=7.80 Hz, 2H), 7.39-7.30 (complex overlapping m, 8H), 7.22 (d, J=1.40 Hz, 1H), 7.11 (d, J=2.30 Hz, 1H), 7.01-6.97 (m, 6H), 6.73-6.68 (m, 3H), 6.47 (bs, 1H), 4.08 (s, 2H), 3.90 (s, 2H), 3.59 (s, 3H), 3.67-3.63 (m, 2H), 2.25 (t, J=7.30 Hz, 2H), 1.41 (apparent quint., J~7.30 Hz, 2H). LCMS (50-95% acetonitrile in 0.05% TFA over 10 minutes) retention time=3.43 minutes, ESI m/z=687, [M+H]⁺.

Synthesis of 3-((4-(3-(1H-imidazol-4-yl)propyl)-5-(4-methocybenzyl)-4H-1,2,4-triazol-3-yl)methyl)-6-fluoro-JH-indole (SK-I-105)

SK-I-105

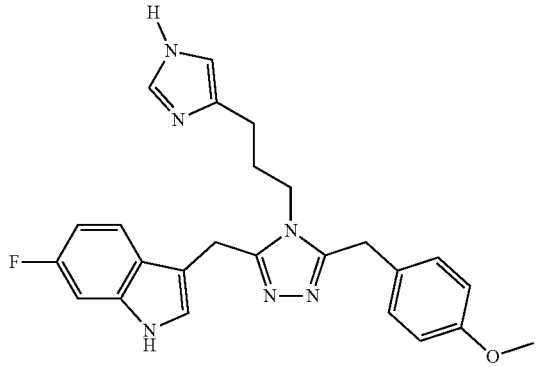

Synthesized according to General Procedure 1D from 6-fluoro-3-((5-(4-methoxybenzyl)-4-(3-(1-trityl-1H-imidazol-4-yl)propyl)-4H-1,2,4-triazol-3-yl)methyl)-1H-indole (82) (224 mg, 0.33 mmol) and afforded 111 mg (76% yield) of compound SK-1-105 as a tan solid. ¹H NMR (400 MHz, DMSO-d₆) δ 11.75 (bs, 1H), 10.95 (bs, 1H), 7.51 (s, 1H), 7.38 (dd, J=8.20, 5.90 Hz, 1H), 7.06-7.03 (m, 2H), 6.97 (d, J=8.20 Hz, 2H), 6.79-6.74 (m, 3H), 6.66 (s, 1H), 4.08 (s, 2H), 3.90 (s, 2H), 3.64 (s, 3H), 3.62-3.56 (bm, 2H), 2.32-2.24 (bm, 2H), 1.48-1.38 (bm, 2H). ¹³C NMR (100 MHz, DMSO-d₆) δ 159.40 (d, 1 $J_{CF}$=234 Hz), 158.47, 153.63, 153.53, 136.61 (d, $J_{CF}$=13.4 Hz), 135.18, 130.42, 129.93, 128.79, 124.57 (d, $J_{CF}$=2.80 Hz), 124.16, 120.15 (d, $J_{CF}$=9.60 Hz), 114.41, 114.11, 109.59, 107.52 (d, $J_{CF}$=24.9 Hz), 98.88 (d, $J_{CF}$=25.8 Hz), 55.51, 42.61, 29.96, 29.59, 24.94 (broad), 21.84. LCMS (50-95% acetonitrile in 0.05% TFA over 10 minutes) retention time=1.78 minutes, ESI m/z=445, [M+H]⁺.

Synthesis of 6-fluoro-34(5-neopentyl-4-(3-(1-trityl-1H-imidazol-4-0propyl)-4H-1,2,4-triazol-3-yl)methyl)-1H-indole (84)

84

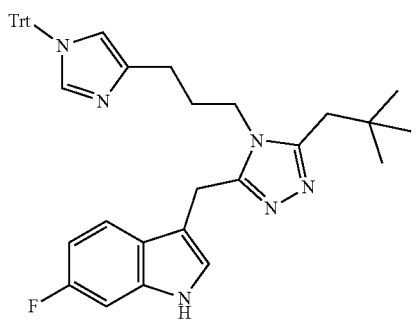

(Prepared from the hydrazide hydrochloride; modification of General Method 1C) To a solution of thioamide M (300 mg, 0.62 mmol) and hydrazide (3m) (189 mg, 0.78 mmol), in CH₂Cl₂ (40 mL) was added silver benzoate (284 mg, 1.24 mmol) followed immediately with acetic acid (112 mg, 106 μL, 1.86 mmol). The black solution (Ag₂S formation) was stirred at room temperature for 16 hrs. LCMS determined minimal reaction progress was made; TEA (78 mg, 108 μL, 0.78 mmol) was added and the reaction was stirred at room temperature for 18 hrs. LCMS showed further reaction progress was made; silver benzoate (284 mg, 1.24 mmol) and acetic acid (112 mg, 106 μL, 1.86 mmol) were added to the reaction, which was allowed to stir at room, temperature for an additional 72 hours. The solution was concentrated and the residue was dissolved in 1:1 MeOH/CH₂Cl₂ and treated with 1N HCl (1.24 mmol, 1.24 mL). The mixture was stirred for 5 min, treated with diisopropylethylamine (~10 mmol, ~5 mL) and concentrated. The residue was suspended in MeOH (120 mL), filtered through celite (1 inch pad) and concentrated to afford 1.11 g of crude material. The crude residue was purified by flash chromatography (SiO₂, 40:1 CH₂Cl₂/MeOH to 20:1) to afford 200 mg (51% yield) of compound 84. This compound was not pure but was taken on "as is." LCMS (50-95% acetonitrile in 0.05% TFA over 10 minutes) retention time=4.62 minutes, ESI m/z=637, [M+H]⁺.

Synthesis of 3-((4-(3-(1H-imidazol-4-yl)propyl)-5-neopentyl-4H-1,2,4-triazol-3-yl)methyl)-6-fluoro-1H-indole (SK-I-119)

SK-I-119

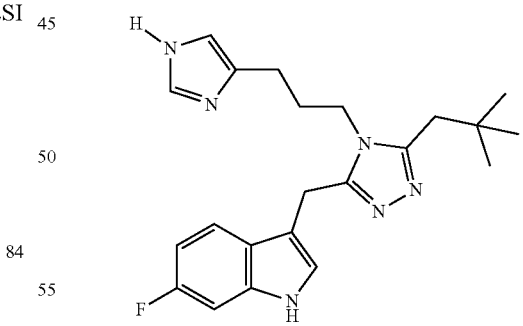

Prepared according to General Procedure 1D from 6-fluoro-34(5-neopentyl-4-(3-(1-trityl-1H-imidazol-4-yl)propyl)-4H-1,2,4-triazol-3-yl)methyl)-1H-indole (84) (186 mg, 0.29 mmol) and afforded 112 mg (97% yield) of compound SK-I-119 as a pale yellow solid. LCMS (50-95% acetonitrile in 0.05% TFA over 10 minutes) retention time=1.80 minutes, ESI m/z=395, [M+H]⁺.

Synthesis of 3,3'4(4-(3-(1-trityl-1H-imidazol-4-yl)
propyl)-4H-1,2,4-triazol-3,5-diyl)bis(methylene))bis
(6-fluoro-1H-indole) (86)

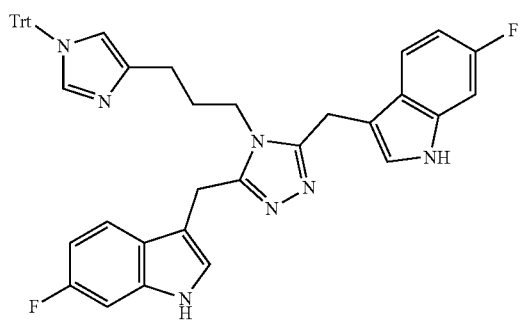

86

(Prepared from the hydrazide hydrochloride; modification of General Method 1C) To a solution of of thioamide J (300 mg, 0.54 mmol) and hydrazide hydrochloride (3m) (164 mg, 0.68 mmol), in CH$_2$Cl$_2$ (40 mL) was added silver benzoate (247 mg, 1.08 mmol) followed immediately with acetic acid (97 mg, 93 µL, 1.62 mmol). The black solution (Ag$_2$S formation) was stirred at room temperature for 16 hours. LCMS determined minimal reaction progress was made; TEA (68 mg, 94 µL, 0.68 mmol) was added and the reaction was stirred at room temperature for 18 hours. LCMS showed further reaction progress was made; silver benzoate (247 mg, 1.08 mmol) and acetic acid (97 mg, 93 µL, 1.62 mmol) were added to the reaction, which was allowed to stir at room temperature for an additional 72 hours. The solution was concentrated and the residue was dissolved in 1:1 MeOH:CH$_2$Cl$_2$ and treated with 1N HCl (1.08 mmol, 1.08 mL). The mixture was stirred for 5 min, treated with diisopropylethylamine (~10 mmol, ~5 mL) and concentrated. The residue was suspended in MeOH (120 mL), filtered through celite (1 inch pad) and concentrated to afford 1.18 g of crude material. The crude residue was purified by flash chromatography (SiO$_2$, 40:1 CH$_2$Cl$_2$/MeOH to 20:1, to 10:1) afforded 68 mg (18% yield) of compound 86. LCMS (50-95% acetonitrile in 0.05% TFA over 10 minutes) retention time=4.32 minutes, ESI m/z=714, [M+H]$^+$.

Synthesis of 3,3-((4-(3-(1H-imidazol-4-yl)propyl)-
4H-1,2,4-triazol-3,5-diyl)bis(methylene))bis(6-
fluoro-1H-indole) (SK-I-124)

Prepared following General Procedure 1D from 3,3'((4-(3-(1-trityl-1H-imidazol-4-yl)propyl)-4H-1,2,4-triazol-3,5-diyl)bis(methylene))bis(6-fluoro-1H-indole) (86) (68 mg, 0.095 mmol) and afforded 33 mg (73% yield) of compound SK-I-124 as a tan solid. $^1$H NMR (400 MHz, DMSO-d$_6$) δ 11.71 (bs, 1H), 10.90 (bs, 1H), 7.48 (s, 1H), 7.36-7.32 (m, 2H), 7.04-7.01 (m, 4H), 6.74-6.69 (m, 2H), 6.64 (s, 1H), 4.07 (s, 4H), 3.69 (apparent t, J~7.30 Hz, 2H), 2.30-2.24 (m, 2H), 1.53-1.44 (m, 2H). LCMS (50-95% acetonitrile in 0.05% TFA over 10 minutes) retention time=1.97 minutes, ESI m/z=472, [M+H]$^+$.

Example 2: Synthesis of
3,4,5-Trisubstituted-3-Thio-1,2,4-Triazoles

Synthesis of 3-1-1-(Triphenylmethyl)-1H-imidazol-
4-yl] propyl Isothiocyanate (1)

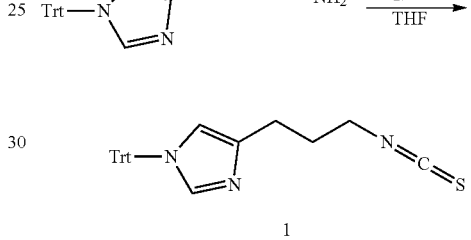

1

A mixture of N,N-Dicyclohexylcarbodiimide (1.10 g, 5.3 mmol) and CS$_2$ (3.36 mL, 53 mmol) in THF (16 mL) was treated with a solution of commercially available N-boc-1, 4-diaminobutane (1.0 g, 5.3 mmol) in THF (32 mL). The reaction mixture was stirred overnight under nitrogen. Removal of the solvent under reduce pressure afforded a white solid. The solid was triturated with Et$_2$O (150 mL) and the dicyclohexylthiourea was filtered. The filtrate was evaporated to afford a yellow solid. The residue was used in the next step without further purification.

Synthesis of tert-butyl (4-isothiocyanatobutyl)
carbamate (2)

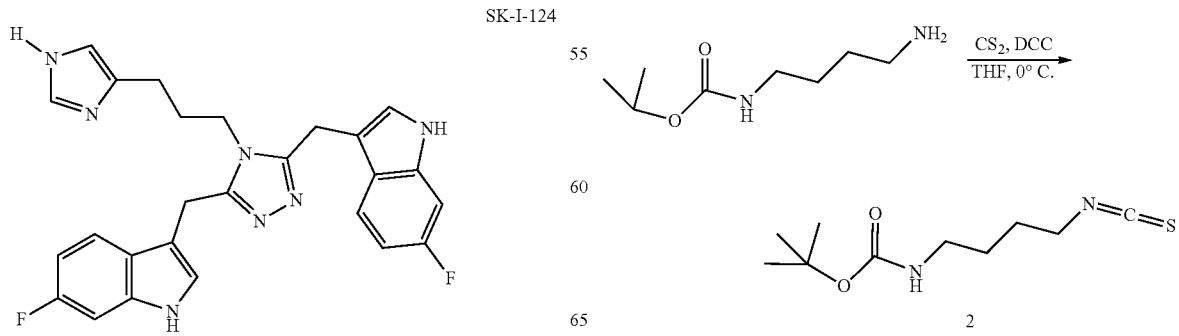

A mixture of DCC (3.37 g, 16.3 mmol) and CS2 (13.3 g, 174 mmol) in THF (50 mL) was treated with a solution of 3-(1-Trityl-1H-imidazol-4-yl)propan-1-amine (6.0 g, 16.3 mmol) in THF (100 mL). The reaction mixture was stirred overnight under nitrogen. Removal of the solvent under reduced pressure afforded a white solid. The solid was triturated with Et₂O (300 mL) and the dicyclohexylthiourea was filtered. The filtrate was evaporated to afford an oil. Flash chromatography on silica gel using EtOAc/hexanes (2:8) gave the desired compound 2 (4.8 g, 72%) as a yellow solid.

General Procedure 2A: General Condensation Reactions

The isothiocyanate (1-2) (1 eq.) was added to the desired hydrazide (3a-3l) (1 eq.) in anhydrous THF (minimum for solubilization) and the reaction was stirred at room temperature under N₂ for 18 to 24 hours. The corresponding hydrazinecarbothioamides (14a-l) were obtained after evaporation of the solvent and appropriate purification.

General Procedure 2B: General Cyclization Reactions

The hydrazinecarbothioamide (14a-l) (1 eq.) was dissolved in EtOH (5 mL/mmol), and NaOH 1 M (1.5 eq.) is added. The mixture is heated 85° C. for 3 to 4 hours. At the end of the reaction, water was added. The aqueous layer was washed with DCM, acidified to pH 2 with conc. HCl 1M, and extracted twice with DCM. After evaporation, the 3-thiol-1,2,4-triazole (15a-k) was purified by precipitation, recrystallization, flash chromatography, or used without further purification.

General Procedure 2C: Genera/Alkylation of the thiol Reactions

To a mixture of a benzyl bromide derivative (1 eq.) and a cyclized derivative (15a-k) (1 eq.) in DCM (8 mL/mmol) was added triethylamine (1 eq.). The reaction mixture was stirred 5 to 12 hours, and the solvent was evaporated and the residue was partitioned between EtOAc (150 mL) and brine (150 mL). The layers were separated, and the organic layer was dried (anhydrous MgSO₄), filtered, and concentrated. The reaction mixture was evaporated and purified by chromatography on silica column (gradient DCM to EtOAc or DCM to DCM/MeOH (9:1).

General Procedure 2D: General N-Boc Deprotection Reactions

To a mixture of the N-Boc-protected compound (1 eq.) in DCM (5.5 m L/mmol) was added 6N HCl in iPrOH (5.5 mL/mmol) and the mixture was stirred at room temperature overnight. The reaction was co-evaporated three times with absolute EtOH. The desired deprotected compound was obtained after purification (recrystallization, or used without further purification).

General Procedure 2E: General Trityl Deprotection Reactions

A mixture of the trityl-protected compound (1 mmol) in DCM (26.5 m L/mmol) was added 1N HCl (10.6 mL/mmol) and the mixture was stirred at room temperature overnight. The reaction was co-evaporated three times with absolute ethanol, and the desired unprotected compound was obtained after purification (recrystallization, or used without further purification).

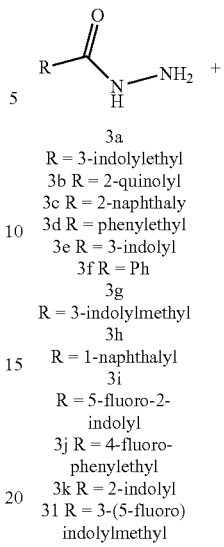

3a
R = 3-indolylethyl
3b R = 2-quinolyl
3c R = 2-naphthaly
3d R = phenylethyl
3e R = 3-indolyl
3f R = Ph
3g
R = 3-indolylmethyl
3h
R = 1-naphthalyl
3i
R = 5-fluoro-2-indolyl
3j R = 4-fluoro-phenylethyl
3k R = 2-indolyl
3l R = 3-(5-fluoro)indolylmethyl

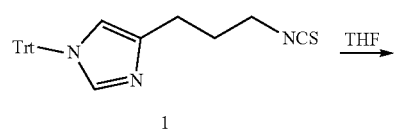

1

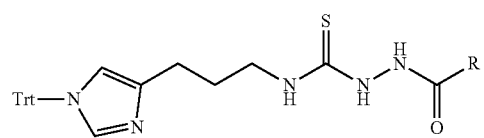

14a R = 3-indolylethyl
14b R = 2-quinolyl
14c R = 2-naphthaly
14d R = phenylethyl
14e R = 3-indolyl
14f R = Ph
14g R = 3-indolylmethyl
14h R = 1-naphthalyl
14i R = 5-fluoro-2-indolyl
14j R = 4-fluoro-2-phenylethyl
14k R = 2-indolyl
14 I R = 3-(5-fluoro)indolylmethyl Synthesis of 2-(3-(1H-indol-3-yl)propanoyl)-N-(3-(1-trityl-1H-imidazol-4-yl)propyl)hydrazinecarbothioamide (4a)

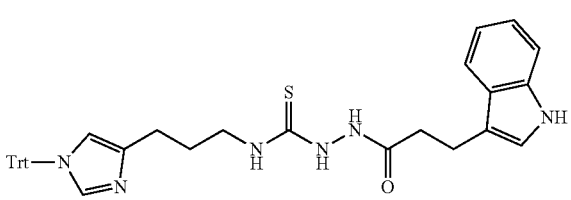

Prepared according to the General Procedure 2A from compound 1 (2.09 g, 5.1 mmol) and hydrazine 3a (942 mg, 4.6 mmol) to afford 2.41 g (77%) of compound 14a as a yellow foam: $^1$H NMR (400 MHz, DMSO-d$_6$) δ 10.82 (s, 1H), 9.71 (s, 1H), 9.13 (s, 1H), 7.76 (m, 1H), 7.51 (d, J=7.6 Hz, 1H), 7.40-7.31 (m, 11H), 7.25 (d, J=1.4 Hz, 1H), 7.10-7.02 (m, 8H), 6.96 (t, J=7.8 Hz, 1H), 3.33 (m, 2H, under H$_2$O peak), 2.94 (m, 2H), 2.46 (m, 2H under DMSO), 2.43 (m, 2H), 1.68 (m, 2H). $^{13}$C NMR (100 MHz, DMSO-d$_6$) δ 171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39. LCMS (50-95% acetonitrile in 0.05% TFA over 10 minutes) retention time=3.28 minutes, ESI m/z=613.36 [M+H]$^+$.

Synthesis of 2-(quinoline-2-carbonyl)-N-(3-(1-trityl-1H-imidazol-4-yl)propyl) hydrazinecarbothioamide (4b)

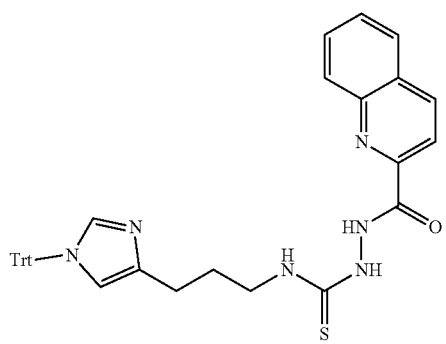

Prepared according to the General Procedure 2A from compound 3b (415 mg, 2.2 mmol) and 1 (1.00 g, 2.4 mmol) to afford 873 mg (66%) of compound 10b as a white solid: $^1$H NMR (400 MHz, DMSO-d$_6$) δ 10.73 (s, 1H), 9.38 (s, 1H), 8.55 (d, J=8.7 Hz, 1H), 8.29 (s, 1H), 8.11-8.07 (m, 3H), 7.89 (t, J=6.9 Hz, 1H), 7.75 (t, J=6.9 Hz, 1H), 7.40-7.33 (m, 9H), 7.13 (s, 1H), 7.08-7.03 (m, 6H), 6.61 (s, 1H), 3.47 (m, 2H), 2.45 (t, J=7.3 Hz, 2H), 1.75 (m, 2H). $^{13}$C NMR (100 MHz, DMSO-d$_6$) δ 181.25, 149.54, 145.91, 142.33, 140.68, 137.62, 137.54, 130.56, 129.26, 129.16, 128.84, 128.25, 128.17, 127.91, 119.00, 117.39, 74.30, 43.58, 28.26, 25.24.

Synthesis of 2-(2-naphthoyl)-N-(3-(1-trityl-1H-imidazol-4-yl)propyl) hydrazine carbothioamide (14c)

Prepared according to the General Procedure 2A from compound 3c (413 mg, 2.2 mmol) and 1 (1.00 g, 2.4 mmol) to afford 1.26 g (95%) of compound 14c as a white solid: $^1$H NMR (400 MHz, DMSO-d$_6$) δ 10.49 (bs, 1H), 9.32 (bs, 1H), 8.52 (s, 1H), 8.33 (bs, 1H), 8.00-7.95 (m, 5H), 7.60 (m, 2H), 7.35 (m, 10H), 7.04 (m, 7H), 6.61 (s, 1H), 3.46 (m, 2H), 2.45 (m, 2H), 1.74 (m, 2H). $^{13}$C NMR (100 MHz, DMSO-d$_6$) δ 165.97, 142.34, 140.67, 137.59, 134.33, 131.97, 129.92, 129.18, 128.92, 128.37, 128.19, 127.92, 127.77, 127.68, 126.84, 124.41, 117.45, 74.34, 43.51, 28.35, 25.23.

Synthesis of 2-(3-phenylpropanoyl)-N-(3-(1-trityl-1H-imidazol-4-yl)propyphydrazinecarbothioamide (14d)

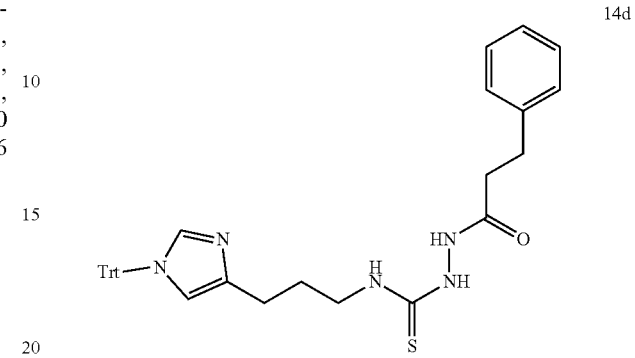

Prepared according to the General Procedure 2A from compound 3d (417 mg, 2.5 mmol) and 1 (1.04 g, 2.5 mmol) to afford 558 mg (38%) of compound 14d as a white solid: $^1$H NMR (400 MHz, DMSO-d$_6$) δ 9.68 (s, 1H), 9.12 (s, 1H), 7.82 (m, 1H), 7.41-7.33 (m, 9H), 7.27-7.23 (m, 3H), 7.19-7.14 (m, 3H), 7.08 (m, 6H), 6.63 (s, 1H), 3.41 (m, 2H), 2.80 (m, 2H), 2.41 (m, 2H), 1.72 (m, 2H). $^{13}$C NMR (100 MHz, DMSO-d$_6$) δ 171.17, 142.38, 141.08, 140.65, 137.64, 129.23, 128.37, 128.22, 127.97, 125.99, 117.54, 74.39, 43.31, 34.90, 30.35, 28.40, 25.15.

Synthesis of 2-(1H-indole-3-carbonyl)-N-(3-(1-trityl-1H-imidazol-4-yl)propyl) hydrazine carbothioamide (14e)

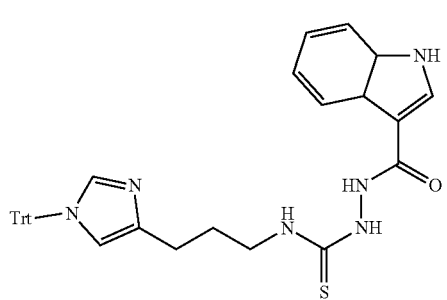

Prepared according to the General Procedure 2A from compound 3e (396 mg, 2.3 mmol) and 1 (1.02 g, 2.5 mmol) to afford 1.11 g (85% yield) of compound 14e as a white solid: $^1$H NMR (400 MHz, DMSO-d$_6$) δ 11.66 (s, 1H), 9.76 (s, 1H), 9.17 (s, 1H), 8.15-8.08 (m, 2H), 7.45 (d, J=8.3 Hz, 1H), 7.40-7.33 (m, 9H), 7.18-7.06 (m, 10H), 6.62 (s, 1H), 3.47 (m, 2H), 2.42 (m, 2H), 1.75 (m, 2H). $^{13}$C NMR (100 MHz, DMSO-d$_6$) δ 164.36, 142.38, 140.73, 137.61, 135.94, 129.22, 128.91, 128.20, 127.94, 126.35, 122.12, 120.95, 120.72, 117.45, 111.92, 108.03, 74.36, 67.05, 43.43, 28.48, 25.29, 25.16.

Synthesis of 2-benzoyl-N-(3-(1-trityl-1H-imidazol-4-yl)propyl) hydrazine carbothioamide (14f)

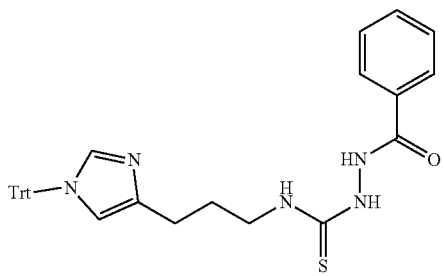

14f

Prepared according to the General Procedure 2A from phenylhydrazide (3f) (305 mg, 2.24 mmol) and 1 (1.009 g, 2.46 mmol) to afford 913 mg (75% yield) of compound 14f as a white solid: $^1$H NMR (400 MHz, DMSO-d$_6$) δ 10.34 (s, 1H), 9.27 (s, 1H), 8.26 (s, 1H), 7.91 (d, J=6.8 Hz, 2H), 7.56 (d, J=7.3 Hz, 1H), 7.47-7.34 (m, 13H), 7.16 (s, 1H), 7.08-7.06 (m, 7H), 6.62 (s, 7H), 3.48-3.44 (m, 2H), 2.45 (d, J=7.3 Hz, 2H), 1.74 (m, 2H). $^{13}$C NMR (100 MHz, DMSO-d$_6$) δ 165.90, 142.36, 140.67, 137.61, 132.48, 131.82, 129.22, 128.22, 127.96, 127.80, 117.45, 74.37, 43.54, 28.34, 25.24.

Synthesis of 2-(2-(1H-indol-3-yl)acetyl)-N-(3-(1-trityl-H-imidazol-4-yl)propyl)hydrazine carbothioamide (14 g)

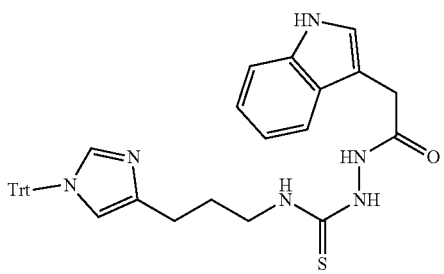

14g

Prepared according to the General Procedure 2A from compound 3g (424 mg, 2.24 mmol) and 1 (1.009 g, 2.48 mmol) to afford 1.002 g (75% yield) of compound 14g as a white solid: $^1$H NMR (400 MHz, DMSO-d$_6$) δ 10.90 (s, 1H), 9.87 (s, 1H), 9.18 (s, 1H), 7.95 (s, 1H), 7.55 (d, J=8.2 Hz, 1H), 7.42-7.21 (m, 12H), 7.11-7.02 (m, 7H), 6.96 (m, 1H), 6.65 (s, 1H), 3.56 (s, 2H), 3.44 (m, 2H), 2.45 (t, J=7.3 Hz, 2H), 1.72 (m, 2H). $^{13}$C NMR (100 MHz, DMSO-d$_6$) δ 142.40, 140.66, 137.69, 136.06, 129.26, 128.24, 127.99, 127.23, 123.97, 121.00, 118.78, 118.34, 117.56, 111.31, 108.01, 74.42, 43.42, 30.66, 28.36, 25.22.

Synthesis of 2-(1-naphthoyl)-N-(3-(1-trityl-1H-imidazol-4-yl)propyl) hydrazine carbothioamide (14h)

Prepared according to the General Procedure 2A from compound 3h (412 mg, 2.2 mmol) and 1 (997 mg, 2.43 mmol) to afford 1.27 g (96%) of compound 14h as a white solid: $^1$H NMR (400 MHz, DMSO-d$_6$) δ 10.30 (s, 1H), 9.39 (s, 1H), 8.29 (m, 2H), 8.06 (d, J=8.3 Hz, 1H), 7.98 (d, J=7.8 Hz, 1H), 7.90 (d, J=6.9 Hz, 1H), 7.57-7.50 (m, 3H), 7.43-7.35 (m, 11H), 7.09 (m, 6H), 6.71 (s, 1H), 3.52 (m, 2H), 3.45-3.43 (m, 2H), 1.79 (m, 2H). $^{13}$C NMR (100 MHz, DMSO-d$_6$) δ 168.19, 142.19, 140.07, 128.27, 128.20, 128.04, 127.81, 127.58, 117.75, 74.66, 43.43, 28.31, 24.85.

Synthesis of 2-(5-fluoro-1H-indole-2-carbonyl)-N-(3-(1-trityl-1H-imidazol-4-yl)propyl)hydrazinecarbothioamide (14i)

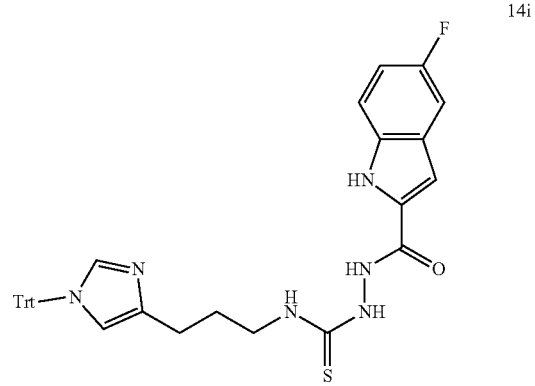

14i

Prepared according to the General Procedure 2A from compound 3i (434 mg, 2.25 mmol) and 1 (920 mg, 2.25 mmol) to afford 1.09 g (81%) of compound 14i as a white solid: $^1$H NMR (400 MHz, DMSO-d$_6$) δ 11.81 (s, 1H), 10.38 (s, 1H), 9.32 (s, 1H), 8.35 (s, 1H), 7.41-7.32 (m, 11H), 7.15 (s, 1H), 7.05 (m, 7H), 6.60 (s, 1H), 3.44 (m, 2H), 2.42 (m, 2H), 1.73 (m, 2H). $^{13}$C NMR (100 MHz, DMSO-d$_6$) δ 160.77, 158.34, 156.02, 142.37, 140.66, 137.61, 133.30, 131.37, 129.19, 128.20, 127.93, 127.01, 126.90, 117.39, 113.59, (d), 112.59 (d), 103.72, 74.34, 56.06, 54.96, 54.96, 43.62, 28.26, 25.29, 18.59.

Synthesis of 2-(3-(4-fluorophenyl)propanoyl)-N-(3-(1-trityl-1H-imidazol-4-yl)propyphydrazinecarbothioamide (14i)

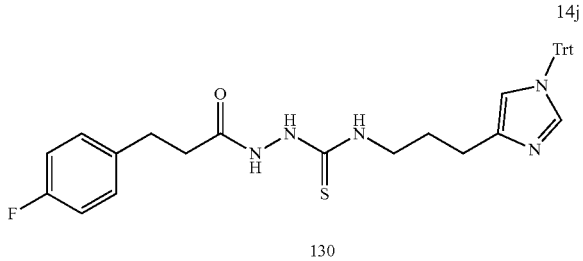

14j

130

Prepared according to the General Procedure 2A from compound 3j (356 mg, 1.95 mmol) and 1 (813 mg, 1.95 mmol) to afford 994 mg (85%) of compound 14j as a white solid: $^1$H NMR (400 MHz, DMSO-d$_6$) δ 9.64 (s, 1H), 9.08 (s, 1H), 7.83 (s, 1H), 7.37-7.30 (m, 9H), 7.22-7.16 (m, 3H), 7.04 (m, 7H), 6.59 (s, 1H), 3.33 (m, 2H, under H$_2$O), 2.75 (m, 2H), 2.36 (m, 2H), 1.67 (m, 2H). $^{13}$C NMR (100 MHz, DMSO-d$_6$) δ 171.20, 161.96, 159.56, 142.41, 140.68, 137.71, 137.23, 130.10, 130.02, 129.30, 128.29, 128.05, 117.63, 115.18, 114.93, 74.46, 43.39, 35.02, 29.55, 25.19.

Synthesis of 2-(1H-indole-2-carbonyl)-N-(3-(1-trityl-1H-imidazol-4-yl)propyl)hydrazinecarbothioamide (14k)

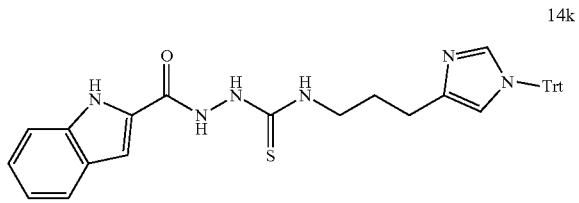

Prepared according to the General Procedure 2A from compound 3k (349 mg, 1.99 mmol) and 1 (815 mg, 1.99 mmol) to afford 815 mg (70% yield) of compound 14k as a white solid: $^1$H NMR (400 MHz, DMSO-d$_6$) δ 11.64 (s, 1H), 10.29 (s, 1H), 9.26 (s, 1H), 8.28 (s, 1H), 7.53 (d, J=7.8 Hz, 1H), 7.39-7.28 (m, 10H), 7.17-7.13 (m, 3H), 7.02-6.97 (m, 7H), 6.57 (s, 1H), 3.47 (m, 2H, under H$_2$O peak), 2.38 (m, 2H), 1.70 (m, 2H). $^{13}$C NMR (100 MHz, DMSO-d$_6$) δ 164.45, 163.95, 150.26, 150.22, 142.38, 140.64, 140.30, 139.62, 137.64, 129.25, 128.25, 128.01, 121.67, 121.06, 117.53, 74.41, 43.56, 28.36, 25.22.

Synthesis of 2-(2-(5-Fluoro-1H-indol-3-yl)acetyl)-N-(3-(1-trityl-1H-imidazol-4-yl)propyl)hydrazinecarbothioamide (14l)

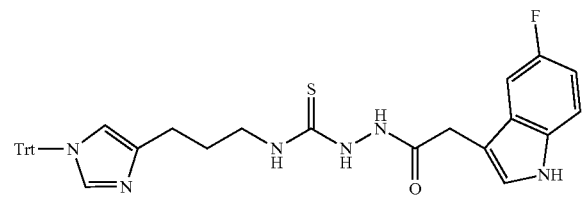

Prepared according to General Procedure 2A from compound 1 (1 g, 2.44 mmol) and hydrazide 3l (506 mg, 2.44 mmol) to afford 1.38 g (92%) of compound 14l as a yellow foam: $^1$H NMR (400 MHz, DMSO-d$_6$) δ 11.00 (s, 1H), 9.87 (s, 1H), 9.18 (s, 1H), 8.02 (s, 1H), 7.43-7.26 (m, 13H), 7.10-7.07 (m, 6H), 6.89 (m, 1H), 6.64 (s, 1H), 3.44 (m, 2H), 2.43 (m, 2H), 1.73 (m, 2H). $^{13}$C NMR (100 MHz, DMSO-d$_6$) δ 170.24, 157.86, 155.59, 142.40, 140.63, 137.67, 132.74, 129.25, 128.23, 127.98, 127.52 (d), 126.14, 117.55, 112.28, 109.22 (d), 108.34, 103.72 (d), 74.40, 67.05, 43.43, 30.59, 28.36, 25.17.

Synthesis of 2-(2-(6-fluoro-1H-indol-3-yl)acetyl-N-3-(1-trityl-1H-imidazol-4-yl)propyl)hydrazinecarbothioamide (14m)

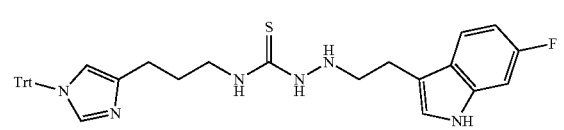

Prepared according to General Procedure A from compound 1 (1.12 g, 2.73 mmol) and hydrazide 3m (567 mg, 2.73 mmol) to afford 1.20 g (71%) of compound 14m as a yellow foam: $^1$H NMR (400 MHz, DMSO-d$_6$) δ 10.94 (s, 1H), 9.85 (s, 1H), 9.14 (s, 1H), 7.97 (s, 1H), 7.50 (m, 1H), 7.41-7.33 (m, 9H), 7.25 (d, J=1.4 Hz, 1H), 7.19 (d, J=2.3 Hz, 1H), 7.10-7.04 (m, 6H), 6.82-6.76 (m, 1H), 6.63 (s, 1H), 3.51 (s, 2H), 2.41 (m, 2H), 1.75 (m, 2H). $^{13}$C NMR (100 MHz, DMSO-d$_6$) δ 170.26, 160.01, 157.68, 142.39, 140.64, 137.68, 135.93 (d), 129.24, 128.22, 124.59 (d), 124.11, 119.93 (d), 117.55, 108.32, 106.90 (d), 97.36 (d), 74.40, 43.42, 30.58, 28.37, 25.21.

Synthesis of 2-(2-phenylacetyl)-N-(3-(1-trityl-1H-imidazol-4-yl)propyl) hydrazinecarbothioamide (14n)

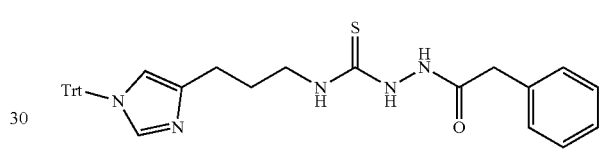

Prepared according to General Procedure A from compound 1 (1.10 g, 2.69 mmol) and hydrazide 3n (403 mg, 2.69 mmol) to afford 1.05 g (70%) of compound 14n as a white solid: $^1$H NMR (400 MHz, DMSO-d$_6$) δ 9.92 (s, 1H), 9.05 (s, 1H), 7.94 (s, 1H), 7.35-7.28 (m, 10H), 7.22 (m, 1H), 7.20-7.10 (m, 4H), 7.02-6.99 (m, 6H), 6.59 (s, 1H), 3.39 (s, 2H), 3.34 (m, 2H), 2.34 (m, 2H), 1.65 (m, 2H). $^{13}$C NMR (100 MHz, DMSO-d$_6$) δ 142.38, 140.65, 137.65, 135.49, 129.23, 128.20, 128.15, 127.95, 117.50, 74.37, 43.39, 33.37, 28.35, 25.19.

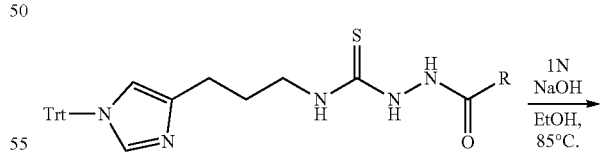

14a R = 3-indolylethyl
14b R = 2-quinolyl
14c R = 2-naphthalyl
14d R = phenylethyl
14e R = 3-indolyl
14f R = Ph
14g R = 3-indolylmethyl
14h R = 1-naphthalyl
14i R = 5-fluoro-2-indolyl
14j R = 4-fluoro-phenylethyl
14k R = 2-indolyl
14l R = 3-(5-fluoro)indolylmethyl

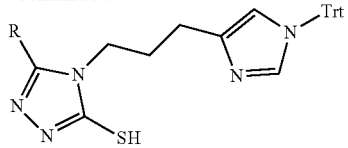

15a R = 3-indolylethyl
15b R = 2-quinolyl
15c R = 2-naphthalyl
15d R = phenylethyl
15e R = 3-indolyl
15f R = Ph
15g R = 3-indolylmethyl
15h R = 1-naphthalyl
15i R = 5-fluoro-2-indolyl
15j R = 4-fluoro-2-phenylethyl
15k R = 2-indolyl
15l R = 3-(5-fluoro)indolylmethyl Synthesis of 5-(2-(1H-indol-3-ynethyl)-4-(3-(1-trityl-1H-imidazol-4-yl)propyl)-4H-1,2,4-triazole-3-thiol (15a)

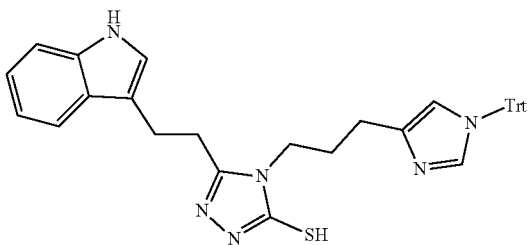

Prepared according to the General Procedure 2B from derivative 14a (2.41 g, 3.9 mmol). Flash chromatography on silica gel (gradient DCM/MeOH 9:1) afforded the desired product 15a as a yellow foam (1.78 g, 76%): $^1$H NMR (400 MHz, DMSO-$d_6$) δ 10.77 (s, 1H), 7.45 (d, J=7.8 Hz, 1H), 7.37-7.26 (m, 11H), 7.17 (d, J=1.4 Hz, 1H), 7.09 (s, 1H), 7.05-6.96 (m, 7H), 6.85 (t, J=6.9 Hz, 1H), 3.83 (t, J=8.2 Hz, 2H), 2.99 (m, 4H), 2.41 (t, J=6.9 Hz, 2H), 1.82 (m, 2H). $^{13}$C NMR (100 MHz, DMSO-$d_6$) δ 166.65, 152.61, 142.86, 140.37, 138.23, 136.69, 129.71, 128.70, 128.43, 127.35, 123.15, 121.48, 118.79, 118.70, 118.18, 113.27, 111.90, 74.87, 43.04, 27.80, 26.20, 25.39, 22.03. LCMS (25-95% acetonitrile in 0.05% TFA over 10 minutes) retention time=7.08 minutes, ESI m/z=595.41 [M+H]$^+$. HRMS (ESI+): m/z calculated for $C_{37}H_{35}N_6S$ (M+H)+595.2630, found 595.2638.

Synthesis of 5-(quinolin-2-yl)-4-(3-(1-trityl-1H-imidazol-4-yl)propyl)-4H-1,2,4-triazole-3-thiol (15b)

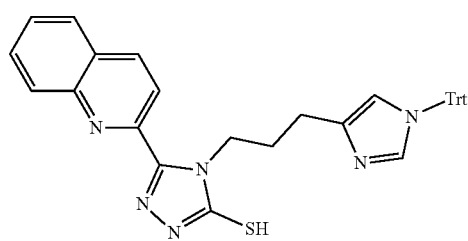

Prepared according to the General Procedure 2B from compound 14b (873 mg, 1.46 mmol) to afford 800 mg (94%) of compound 15b as a white solid: $^1$H NMR (400 MHz, DMSO-$d_6$) δ 8.56 (d, J=8.7 Hz, 1H), 8.13 (d, J=8.2 Hz, 1H), 8.08-8.02 (m, 2H), 7.77-7.68 (m, 2H), 7.38-7.34 (m, 9H), 7.23 (s, 1H), 7.05-7.03 (m, 6H), 6.69 (s, 1H), 4.69 (t, J=7.6 Hz, 2H), 2.63 (t, J=7.3 Hz, CH$_2$), 2.14-2.07 (m, 2H). $^{13}$C NMR (100 MHz, DMSO-$d_6$) δ 168.41, 148.57, 146.46, 145.85, 142.32, 140.13, 137.70, 130.55, 129.19, 128.13, 128.04, 127.90, 127.65, 119.76, 117.67, 74.36, 45.24, 27.99, 25.40.

Synthesis of 5-(naphthalen-2-yl)-4-(3-(1-trityl-1H-imidazol-4-yl)propyl)-4H-1,2,4-triazole-3-thiol (15c)

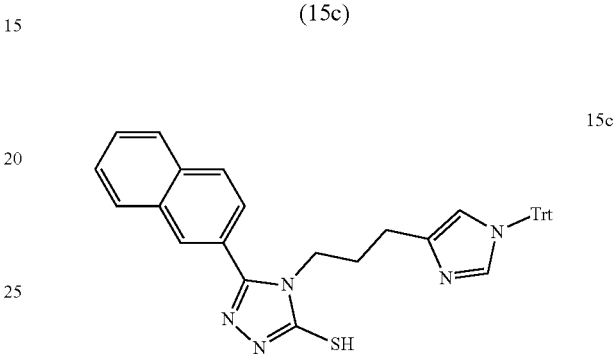

Prepared according to the General Procedure 2B from compound 14c (1.25 g, 2.1 mmol) to afford 996 mg (82%) of compound 15c as a white solid: $^1$H NMR (400 MHz, DMSO-$d_6$) δ 8.23 (d, J=0.9 Hz, 1H), 8.01 (d, J=8.2 Hz, 1H), 7.95 (d, J=8.2 Hz, 1H), 7.73 (dxd, J=8.2, 1.4 Hz, 1H), 7.63 (t, J=8.2 Hz, 1H), 7.55 (d, J=7.3 Hz, 1H), 4.07 (m, 2H), 2.39 (m, 2H), 1.94 (m, 2H). $^{13}$C NMR (100 MHz, DMSO-$d_6$) δ 167.25, 151.29, 137.67, 133.40, 132.33, 129.14, 128.73, 128.60, 128.49, 128.11, 127.89, 127.75, 127.70, 126.97, 125.17, 123.40, 118.01, 74.28, 56.07, 43.75, 27.31, 24.73, 18.59.

Synthesis of 5-phenethyl-4-(3-(1-trityl-1H-imidazol-4-yl) propyl)-4H-1,2,4-triazole-3-thiol (15d)

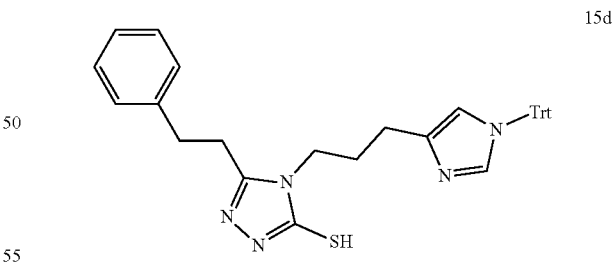

Prepared according to the General Procedure 2B from 14d (464 mg, 0.81 mmol) to afford 418 mg (93%) of compound 15d as a white solid: $^1$H NMR (400 MHz, DMSO-$d_6$) δ 10.82 (s, 1H), 8.76 (s, 1H), 7.47-7.43 (m, 10H), 7.32-7.24 (m, 5H), 7.21-7.15 (m, 8H), 3.91 (t, J=8.2 Hz, 2H), 3.01-2.93 (m, 4H), 2.68-264 (m, 2H), 1.95-1.88 (m, 2H). $^{13}$C NMR (100 MHz, DMSO-$d_6$) δ 166.33, 166.24, 151.75, 147.77, 140.68, 140.31, 136.62, 133.66, 132.55, 129.23, 128.61, 128.56, 128.46, 128.37, 128.33, 127.78, 127.55, 126.67, 126.25, 119.64, 115.56, 80.57, 41.94, 31.17, 26.49, 26.27, 21.24.

Synthesis of 5-(3a, 7a-dihydro-1H-indol-3-yl)-4-(3-(1-trityl-1H-imidazol-4-yl)propyl)-4H-1,2,4-triazole-3-thiol (15e)

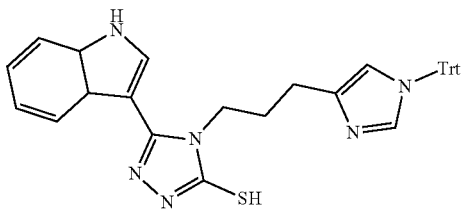

15e

Prepared according to the General Procedure 2B from compound 14e (1.09 g, 1.90 mmol) to afford 1.00 g (93%) of compound 15e as a white solid: $^1$H NMR (400 MHz, DMSO-d$_6$) δ 11.88 (s, 1H), 8.02 (d, J=2.8 Hz, 1H), 7.97 (d, J=8.2 Hz, 1H), 7.51 (d, J=7.8 Hz, 1H), 7.41-7.37 (m, 9H), 7.25-7.21 (m, 1H), 7.17-7.09 (m, 7H), 6.97 (s, 1H), 4.18 (m, 2H), 2.61 (m, 2H), 2.00 (m, 2H). $^{13}$C NMR (100 MHz, DMSO-d$_6$) δ 166.11, 147.48, 141.54, 137.38, 135.91, 129.19, 128.36, 128.19, 127.77, 127.54, 126.38, 125.28, 122.64, 120.60, 120.48, 118.89, 112.03, 100.46, 75.57, 43.24, 26.60, 23.46.

Synthesis of 5-phenyl-4-(3-(1-trityl-1H-imidazol-4-yl)propyl)-4H-1,2,4-triazole-3-thiol (15f)

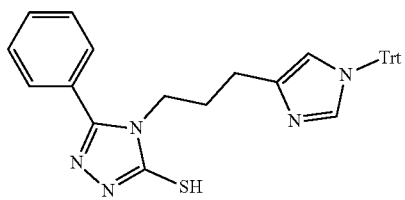

15f

Prepared according to the General Procedure 2B from compound 14f (890 mg, 1.63 mmol) to afford 851 mg (99%) of compound 15f as a white solid: $^1$H NMR (400 MHz, DMSO-d$_6$) δ 7.52 (m, 2H), 7.39-7.34 (m, 12H), 7.22 (s, 1H), 7.04-7.02 (m, 6H), 6.53 (s, 1H), 3.95 (t, J=7.8 Hz, 2H), 2.37 (t, J=7.3 Hz, 2H), 1.85 (m, 2H). $^{13}$C NMR (100 MHz, DMSO-d$_6$) δ 167.70, 150.66, 142.32, 140.02, 137.73, 129.25, 128.73, 128.64, 128.20, 127.99, 127.58, 117.83, 74.37, 43.16, 28.17, 25.05.

Synthesis of 5-((1H-indol-3-yl)methyl)-4-(3-(1-trityl-1H-imidazol-4-yl)propyl)-4H-1,2,4-triazole-3-thiol (15 g)

15g

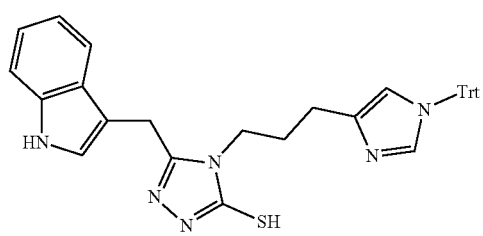

Prepared according to the General Procedure 2B from compound 14g (1.00 g, 1.67 mmol) to afford 829 mg (85%) of compound 15g as a white solid: $^1$H NMR (400 MHz, DMSO-d$_6$) δ 11.07 (s, 1H), 8.47 (s, 1H), 7.47-7.39 (m, 10H), 7.31-7.28 (m, 2H), 7.14-7.09 (m, 7H), 7.03 (m, 1H), 6.93 (m, 1H), 4.19 (m, 2H), 3.86 (t, J=7.3 Hz, 1H), 2.53 (m, 2H), 1.70 (m, 2H). $^{13}$C NMR (100 MHz, DMSO-d$_6$) δ 166.46, 151.36, 140.80, 136.62, 136.22, 134.76, 129.22, 128.56, 128.49, 127.78, 127.54, 126.65, 124.21, 121.29, 119.33, 118.66, 118.29, 111.62, 107.11, 76.68, 42.16, 26.44, 22.19, 21.92.

Synthesis of 5-(naphthalen-1-0-4-(3-(1-trityl-1H-imidazol-4-yl)propyl)-4H-1,2,4-triazole-3-thiol (15h)

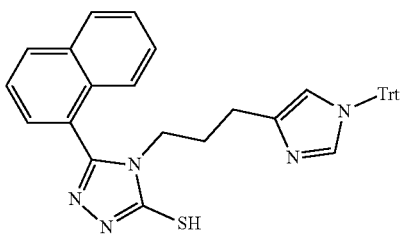

15h

Prepared according to the General Procedure 2B from compound 14h (1.11 g, 1.86 mmol) to afford 733 mg (69%) of 15h as a white solid: $^1$H NMR (400 MHz, DMSO-d$_6$) δ 8.76 (s, 1H), 8.11 (d, J=8.2 Hz, 1H), 8.04 (d, J=7.8 Hz, 1H) 7.80 (d, J=7.1 Hz, 1H), 7.62-7.54 (m, 4H), 7.41-7.37 (m, 10H), 7.08 (s, 1H), 7.02 (m, 6H), 3.70 (m, 2H), 2.44 (m, 2H), 1.74 (m, 2H). $^{13}$C NMR (100 MHz, DMSO-d$_6$) δ 166.84, 149.71, 140.16, 136.32, 132.98, 132.69, 131.30, 131.23, 129.33, 129.18, 128.71, 127.93, 126.98, 125.44, 124.28, 122.92, 120.22, 77.43, 42.55, 26.47, 20.87.

Synthesis of 5-(5-fluoro-1H-indol-2-0-4-(3-(1-trityl-1H-imidazol-4-yl)propyl)-4H-1,2,4-triazole-3-thiol (15I)

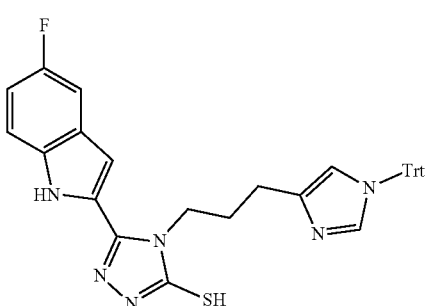

15i

Prepared according to the General Procedure 2B from compound 14i (1.09 g, 1.81 mmol) to afford 410 mg (39%) of 15i as a white solid: $^1$H NMR (400 MHz, DMSO-d$_6$) δ 11.96 (s, 1H), 7.44-7.41 (m, 1H), 7.36-7.34 (m, 10H), 7.19-7.16 (m, 1H), 7.09-7.05 (m, 8H), 6.95 (s, 1H), 6.72 (s, 1H), 4.23 (m, 2H), 2.58 (m, 2H), 2.02 (m, 2H). $^{13}$C NMR (100 MHz, DMSO-d$_6$) δ 166.84, 149.71, 140.16, 136.32, 132.98, 132.69, 131.30, 131.23, 129.33, 129.18, 128.71, 127.93, 126.98, 125.44, 124.28, 122.92, 120.22, 77.43, 42.55, 26.47, 20.87.

Synthesis of 5-(4-fluorophenethyl)-4-(3-(1-trityl-1H-imidazol-4-yl)propyl)-4H-1,2,4-triazole-3-thiol (15j)

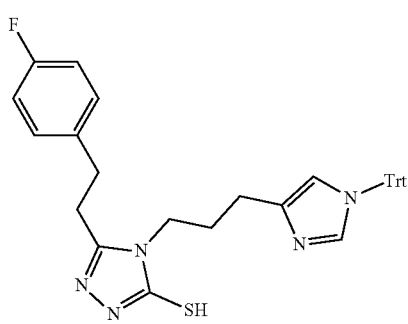

15j

Prepared according to the General Procedure 2B from compound 14j (893 mg, 1.51 mmol) to afford 790 mg (91%) of 15j as a white solid: $^1$H NMR (400 MHz, DMSO-$d_6$) δ 7.97 (s, 1H), 7.34-7.28 (m, 9H), 7.20-7.16 (m, 2H), 7.04-6.92 (m, 9H), 3.78 (m, 2H), 2.47 (m, 2H), 1.79 (m, 2H). $^{13}$C NMR (100 MHz, DMSO-$d_6$) δ 166.24, 162.05, 159.64, 151.61, 147.80, 141.21, 136.94, 136.43, 133.61, 132.38, 130.35 (d), 129.24, 128.50 (d), 127.81, 127.57, 126.68, 119.09, 115.09 (d), 76.14, 42.07, 30.26, 26.78, 26.33, 22.85.

Synthesis of 5-(1H-indol-2-0-4-(3-(1-trityl-1H-imidazol-4-yl)propyl)-4H-1,2,4-triazole-3-thiol (15k)

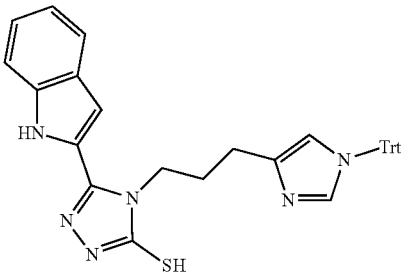

15k

Prepared according to the General Procedure 2B from 14k (735 mg, 1.26 mmol) to afford 610 mg (86%) of compound 15k as a white solid: $^1$H NMR (400 MHz, DMSO-$d_6$) δ 11.87 (s, 1H), 8.79 (s, 1H), 7.55 (d, J=8.3 Hz, 1H), 7.45-7.35 (m, 12H), 7.22-7.10 (m, 7H), 7.06-6.99 (m, 2H), 4.23 (m, 2H), 2.75 (m, 2H), 2.04 (m, 2H). $^{13}$C NMR (100 MHz, DMSO-$d_6$) δ 167.28, 147.80, 145.17, 140.51, 136.80, 136.56, 133.63, 129.25, 128.65, 127.81, 127.58, 127.48, 126.69, 123.71, 122.43, 120.20, 120.04, 112.05, 103.31, 77.16, 43.13, 26.54, 25.17.

Synthesis of 5-((5-Fluoro-1H-indol-3-yl)methyl)-4-(3-(1-trityl-1H-imidazol-4-yl)propyl)-4H-1,2,4-triazole-3-thiol (15l)

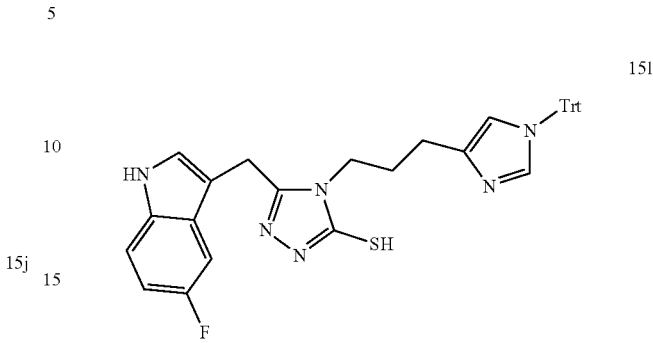

15l

Prepared according to General Procedure 2B from derivative 141 (1.23 g, 2.00 mmol). Evaporation of the organic phase afforded the desired product 151 as a yellow foam (860 mg, 72%): 1C NMR (400 MHz, DMSO-$d_6$) δ 11.19 (s, 1H), 7.48-7.39 (m, 10H), 7.32-7.21 (m, 3H), 7.17-7.14 (m, 6H), 6.90 (s, 1H), 4.17 (s, 2H), 3.86 (d, J=7.4 Hz, 2H), 2.61 (d, J=7.3 Hz, 2H), 1.76 (m, 2H). $^{13}$C NMR (100 MHz, DMSO-$d_6$) δ 166.49, 157.82, 155.52, 151.24, 147.78, 140.47, 136.39, 133.66, 132.89, 129.23, 128.66, 127.79, 127.55, 127.00 (d), 126.67, 126.34, 119.77, 112.71 (d), 109.58 (d), 107.40 (d), 103.21 (d), 77.20, 42.02, 26.36, 21.74, 21.62.

Synthesis of 5-((6-fluoro-1H-indol-3-yl)methyl)-4-(3-(1-trityl-1H-imidazol-4-yl)propyl)-4H-1,2,4-triazole-3-thiol (15m)

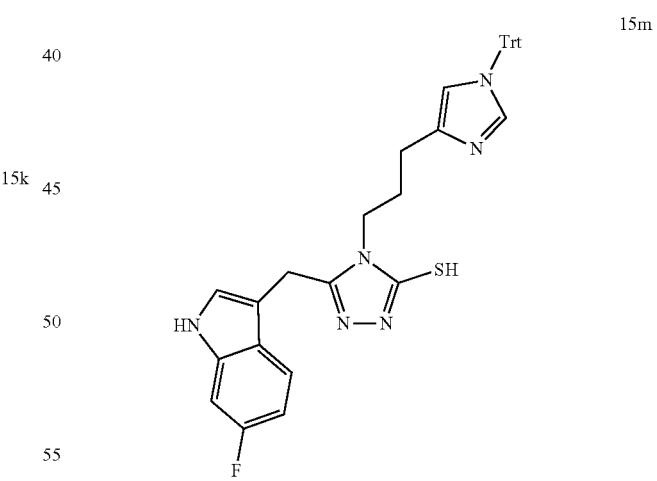

15m

Prepared according to General Procedure B from derivative 14m (1.50 g, 2.40 mmol) to afford the desired product 15m as a yellow foam (1.46 g, quantitative yield): $^1$H NMR (400 MHz, DMSO-$d_6$) δ 11.21 (s, 1H), 8.59 (s, 1H), 7.47-7.39 (m, 11H), 7.33 (s, 1H), 7.18-7.08 (m, 8H), 6.82 (s, 1H), 4.19 (s, 2H), 3.86 (m, 2H), 2.60 (m, 2H), 1.75 (m, 2H). $^{13}$C NMR (100 MHz, DMSO-$d_6$) δ 166.48, 160.05, 157.72, 151.21, 140.73, 136.58, 136.17 (d), 129.21, 128.58, 128.51, 124.86 (d), 123.55, 119.45 (d), 107.42, 107.34 (d), 97.70, 97.44, 76.80, 42.11, 26.41, 22.05, 21.81.

Synthesis of 5-benzyl-4-(3-(1-trityl-1H-imidazol-4-yl)propyl)-4H-1,2,4-triazole-3-thiol (15n)

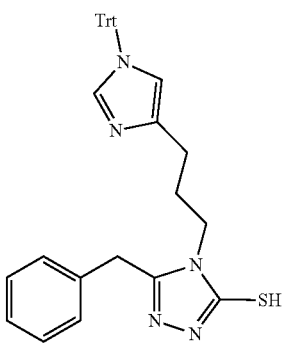

15n

Prepared according to General Procedure B from derivative 14n (879 mg, 1.55 mmol) to afford the desired product 15n as a yellow foam (703 mg, 84%): $^1$H NMR (400 MHz, DMSO-$d_6$) δ 8.09 (s, 1H), 7.45-7.39 (m, 9H), 7.27-7.22 (m, 4H), 7.17-7.11 (m, 7H), 6.92 (s, 1H), 4.10 (s, 2H), 3.83 (m, 2H), 2.53 (m, 2H), 1.68 (m, 2H). $^{13}$C NMR (100 MHz, DMSO-$d_6$) δ 166.60, 151.15, 141.30, 136.98, 135.07, 129.21, 128.73, 128.63, 128.44, 128.32, 127.02, 118.75, 42.40, 30.72, 26.58, 23.08.

Synthesis of 6-fluoro-345-(3-methylbenzylthio)-4-(3-(1-trityl-1H-imidazol-4-yl)propyl)-4H-1,2,4-triazol-3-yl)methyl)-JH-indole (16m)

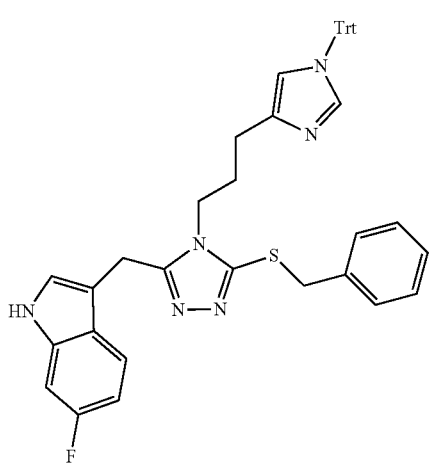

16m

Prepared according to General Procedure C from cyclized compound 15m (690 mg, 1.15 mmol) and benzyl bromide (138 μL, 1.15 mmol) to afford 500 mg (63%) of the desired product 16m as a yellow foam: $^1$H NMR (400 MHz, DMSO-$d_6$) δ 11.03 (s, 1H), 7.47-7.43 (m, 1H), 7.40-7.35 (m, 9H), 7.24 (s, 1H), 7.16-7.04 (m, 13H), 6.79 (m, 1H), 6.54 (s, 1H), 4.26 (s, 2H), 4.17 (s, 2H), 3.61 (t, J=7.8 Hz, 2H), 2.27 (t, J=7.1 Hz, 2H), 1.48 (m, 2H). $^{13}$C NMR (100 MHz, DMSO-$d_6$) δ 160.05, 157.73, 154.40, 148.36, 142.31, 139.56, 137.72, 137.21, 136.19, 136.07, 129.17, 128.73, 128.31, 128.16, 127.93, 127.32, 124.18, 123.60, 119.62 (d), 117.53, 108.76 (d), 107.14 (d), 97.51 (d), 74.35, 42.66, 37.60, 28.66, 24.59, 21.56.

Synthesis of 6-fluoro-345-(3-methylbenzylthio)-4-(3-(1-trityl-1H-imidazol-4-yl)propyl)-4H-1,2,4-triazol-3-yl)methyl)-1H-indole (17m)

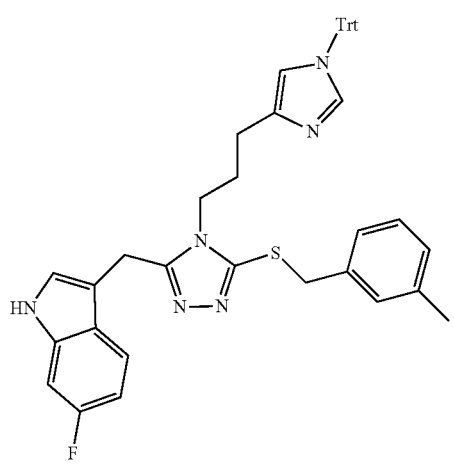

17m

Prepared according to General Procedure C from cyclized compound 15m (770 mg, 1.29 mmol) and 3-methylbenzyl bromide (174 μL, 1.29 mmol) to afford 545 mg (60%) of the desired product 17m as a yellow foam: $^1$H NMR (400 MHz, DMSO-$d_6$) δ 11.00 (s, 1H), 7.47-7.43 (m, 1H), 7.39-7.36 (m, 10H), 7.24 (m, 1H), 7.15 (m, 1H), 7.07-6.93 (m, 11H), 6.78 (m, 1H), 6.54 (s, 1H), 4.23 (s, 2H), 4.16 (s, 2H), 3.64 (t, J=7.8 Hz, 2H), 2.28 (t, J=6.9 Hz, 2H), 2.13 (s, 3H), 1.47 (m, 2H). $^{13}$C NMR (100 MHz, DMSO-$d_6$) δ 160.07, 157.75, 154.40, 148.50, 142.31, 139.53, 137.73 (d), 137.02, 136.21 (d), 129.35, 129.18, 128.25, 128.18, 128.03, 127.95, 125.85, 124.17 (d), 123.61, 119.63 (d), 117.56, 108.81, 107.16 (d), 97.54 (d), 74.40, 42.72, 37.53, 28.69, 24.59, 21.54, 20.79.

Synthesis of 3-benzyl-5-(benzylthio)-4-(3-(1-trityl-1H-imidazol-4-yl)propyl)-4H-1,2,4-triazole (17n)

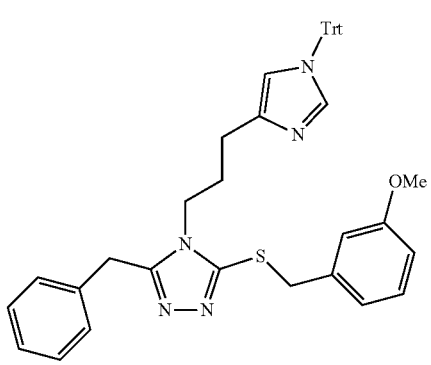

17n

Prepared according to General Procedure C from cyclized compound 15n (333 mg, 0.61 mmol) and 3-methoxybenzyl bromide (86 μL, 0.61 mmol) to afford 266 mg (65%) of the desired product 17n as a white foam: ¹H NMR (400 MHz, DMSO-d₆) δ 7.39-7.36 (m, 10H), 7.23-7.19 (m, 4H), 7.11-7.02 (m, 9H), 6.80-6.73 (m, 2H), 6.49 (s, 1H), 4.26 (s, 2H), 4.08 (s, 2H), 3.63 (s, 3H), 3.60 (m, 2H), 2.26 (m, 2H), 1.40 (m, 2H). ¹³C NMR (100 MHz, DMSO-d₆) δ 159.16, 154.31, 148.66, 142.32, 139.50, 138.67, 137.73, 136.27, 129.46, 129.18, 128.51, 128.37, 128.18, 127.97, 126.70, 120.97, 117.55, 114.26, 11305, 74.37, 42.80, 37.41, 30.39, 28.73, 24.64.

Synthesis of 3-(3-methoxybenzylthio)-5-phenethyl-4-(3-(1-trityl-1H-imidazol-4-yl)propyl)-4H-1,2,4-triazole (17d)

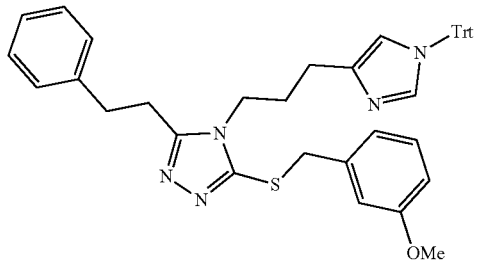

Prepared according to General Procedure C from cyclized compound 15d (401 mg, 0.72 mmol) and 3-methoxybenzyl bromide (101 μL, 0.72 mmol) to yield 420 mg (88%) of 17d as a white solid: ¹H NMR (400 MHz, DMSO-d₆) δ 7.39-7.33 (m, 9H), 7.21 (d, J=1.4 Hz, 1H), 7.20-7.11 (m, 6H), 7.04-7.02 (m, 6H), 6.81-6.75 (m, 3H), 6.58 (s, 1H), 4.25 (s, 2H), 3.66-3.62 (m, 2H), 3.65 (s, 3H), 2.97-2.86 (m, 4H), 2.36-2.33 (m, 2H), 1.67-1.63 (m, 2H). ¹³C NMR (100 MHz, DMSO-d₆) δ 159.17, 154.90, 148.11, 142.31, 140.62, 139.55, 138.71, 137.76, 129.50, 129.18, 128.37, 128.24, 128.19, 127.96, 126.11, 121.02, 117.74, 114.33, 113.00, 74.37, 42.42, 37.29, 32.47, 28.79, 26.21, 24.50.

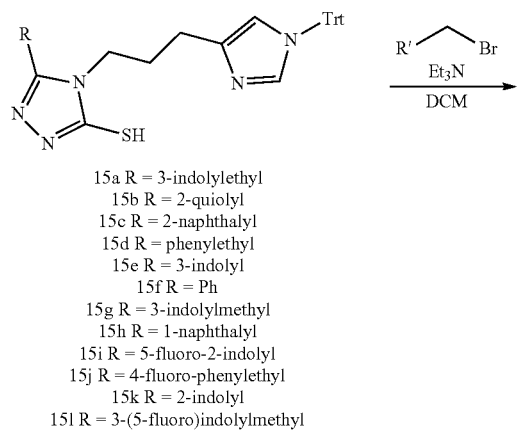

15a R = 3-indolylethyl
15b R = 2-quiolyl
15c R = 2-naphthalyl
15d R = phenylethyl
15e R = 3-indolyl
15f R = Ph
15g R = 3-indolylmethyl
15h R = 1-naphthalyl
15i R = 5-fluoro-2-indolyl
15j R = 4-fluoro-phenylethyl
15k R = 2-indolyl
15l R = 3-(5-fluoro)indolylmethyl

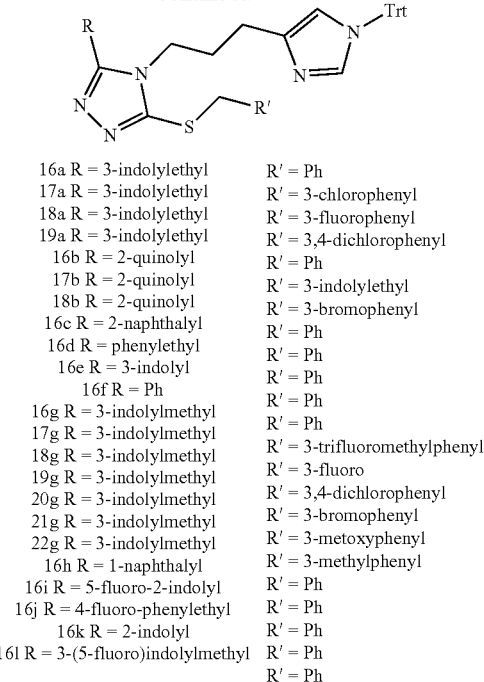

| | |
|---|---|
| 16a R = 3-indolylethyl | R' = Ph |
| 17a R = 3-indolylethyl | R' = 3-chlorophenyl |
| 18a R = 3-indolylethyl | R' = 3-fluorophenyl |
| 19a R = 3-indolylethyl | R' = 3,4-dichlorophenyl |
| 16b R = 2-quinolyl | R' = Ph |
| 17b R = 2-quinolyl | R' = 3-indolylethyl |
| 18b R = 2-quinolyl | R' = 3-bromophenyl |
| 16c R = 2-naphthyl | R' = Ph |
| 16d R = phenylethyl | R' = Ph |
| 16e R = 3-indolyl | R' = Ph |
| 16f R = Ph | R' = Ph |
| 16g R = 3-indolylmethyl | R' = Ph |
| 17g R = 3-indolylmethyl | R' = 3-trifluoromethylphenyl |
| 18g R = 3-indolylmethyl | R' = 3-fluoro |
| 19g R = 3-indolylmethyl | R' = 3,4-dichlorophenyl |
| 20g R = 3-indolylmethyl | R' = 3-bromophenyl |
| 21g R = 3-indolylmethyl | R' = 3-metoxyphenyl |
| 22g R = 3-indolylmethyl | R' = 3-methylphenyl |
| 16h R = 1-naphthalyl | R' = Ph |
| 16i R = 5-fluoro-2-indolyl | R' = Ph |
| 16j R = 4-fluoro-phenylethyl | R' = Ph |
| 16k R = 2-indolyl | R' = Ph |
| 16l R = 3-(5-fluoro)indolylmethyl | R' = Ph |

Synthesis of 3-(2-(5-(benzylthio)-4-(3-(1-trityl-1H-imidazol-4-yl)propyl)-4H-1,2,4-triazol-3-yl)ethyl)-1H-indole (S16a)

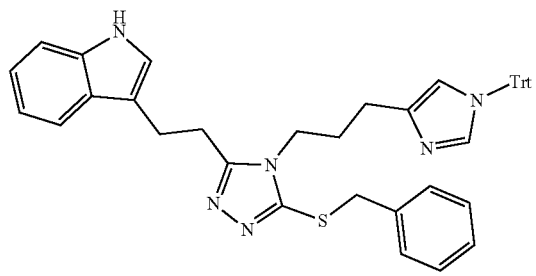

Prepared according to the General Procedure 2C from cyclized compound 15a (272 mg, 0.46 mmol) and benzyl bromide (55 μL, 0.46 mmol) to afford 218 mg (70%) of 16a as a yellow solid: ¹H NMR (400 MHz, DMSO-d₆) δ 10.78 (bs, 1H), 7.44 (d, J=7.8 Hz, 2H), 7.36-7.32 (m, 9H), 7.30 (d, J=8.2 Hz, 1H), 7.23-7.19 (m, 6H), 7.10 (m, 1H), 7.04-7.01 (m, 7H), 6.89 (t, J=7.6 Hz, 1H), 6.56 (s, 1H), 4.27 (s, 2H), 3.64 (t, J=7.8 Hz, 2H), 3.06-2.95 (m, 4H), 2.33 (t, J=6.8 Hz, 2H), 1.64 (m, 2H). ¹³C NMR (100 MHz, DMSO-d₆) δ 155.41, 147.03, 142.31, 139.50, 137.78, 137.22, 136.18, 129.18, 128.86, 128.42, 128.17, 127.94, 127.42, 126.89, 122.61, 120.93, 118.25, 117.66, 113.15, 111.35, 74.36, 42.51, 37.40, 28.87, 25.53, 24.59, 22.64. LCMS (50-95% acetonitrile in 0.05% TFA over 10 minutes) retention time=5.28 minutes, ESI m/z=685.44 [M+H]⁺.

Synthesis of 3-(2-(5-(3-chlorobenzylthio)-4-(3-(1-trityl-1H-imidazol-4-yl)propyl)-4H-1,2,4-triazol-3-yl)ethyl)-1H-indole (17a)

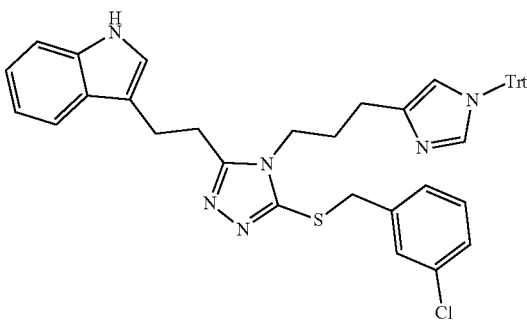

17a

Prepared according to the General Procedure 2C from cyclized compound 15a (323 mg, 0.54 mmol) and 3-chlorobenzyl bromide (71 µL, 0.54 mmol) to afford 320 mg (82%) of 17a as a white solid: $^1$H NMR (400 MHz, DMSO-$d_6$) δ 10.79 (s, 1H), 7.44 (d, J=8.2 Hz, 1H), 7.36-7.33 (m, 9H), 7.30-7.20 (m, 4H), 7.11 (d, J=3.5 Hz, 1H), 7.04-7.01 (m, 8H), 6.87 (m, 1H), 6.58 (s, 1H), 4.29 (s, 2H), 3.64 (m, 2H), 3.06-2.96 (m, 4H), 2.32 (m, 2H), 1.66 (m, 2H). $^{13}$C NMR (100 MHz, DMSO-$d_6$) δ 155.57, 147.82, 142.32, 140.05, 139.49, 137.83, 136.19, 132.89, 130.26, 129.19, 128.71, 128.19, 127.96, 127.61, 127.35, 126.89, 122.62, 120.94, 118.27, 118.15, 117.67, 113.16, 111.38, 74.37, 42.56, 36.42, 28.89, 25.55, 24.58, 22.65.

Synthesis of 3-(3-methoxybenzylthio)-5-phenethyl-4-(3-(1-trityl-1H-imidazol-4-yl)propyl)-4H-1,2,4-triazole (17d)

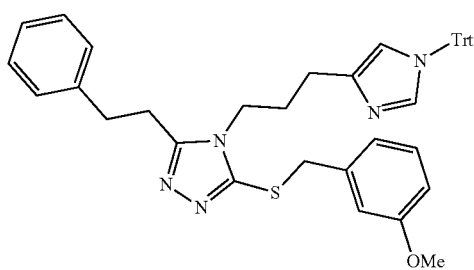

17d

Prepared according to General Procedure C from cyclized compound 15d (401 mg, 0.72 mmol) and 3-methoxybenzyl bromide (101 µL, 0.72 mmol) to yield 420 mg (88%) of 17d as a white solid: $^1$H NMR (400 MHz, DMSO-$d_6$) δ 7.39-7.33 (m, 9H), 7.21 (d, J=1.4 Hz, 1H), 7.20-7.11 (m, 6H), 7.04-7.02 (m, 6H), 6.81-6.75 (m, 3H), 6.58 (s, 1H), 4.25 (s, 2H), 3.66-3.62 (m, 2H), 3.65 (s, 3H), 2.97-2.86 (m, 4H), 2.36-2.33 (m, 2H), 1.67-1.63 (m, 2H). $^{13}$C NMR (100 MHz, DMSO-$d_6$) δ 159.17, 154.90, 148.11, 142.31, 140.62, 139.55, 138.71, 137.76, 129.50, 129.18, 128.37, 128.24, 128.19, 127.96, 126.11, 121.02, 117.74, 114.33, 113.00, 74.37, 42.42, 37.29, 32.47, 28.79, 26.21, 24.50.

Synthesis of 3-(2-(5-(3-fluorobenzylthio)-4-(3-(1-trityl-1H-imidazol-4-yl)propyl)-4H-1,2,4-triazol-3-ynethyl)-1H-indole (18a)

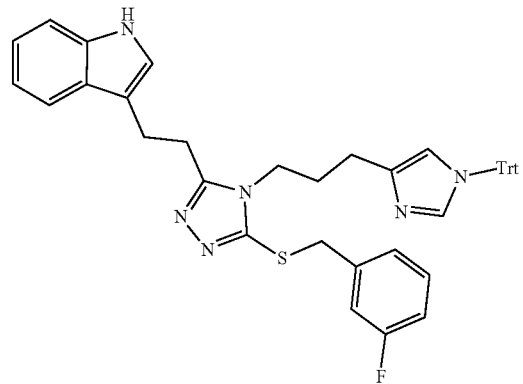

18a

Prepared according the General Procedure 2C from 15a (300 mg, 0.51 mmol) and 3-fluorobenzyl bromide (62 µL, 0.51 mmol) to afford 250 mg (73%) of compound 18a as a white solid: $^1$H NMR (400 MHz, DMSO-$d_6$) δ 10.75 (s, 1H), 7.41 (d, J=7.8 Hz, 1H), 7.34-7.19 (m, 12H), 7.18 (d, J=1.4 Hz, 1H), 7.10-7.04 (m, 2H), 7.01-6.96 (m, 8H), 6.85 (m, 1H), 6.54 (s, 1H), 4.27 (s, 2H), 3.64 (d, J=7.8 Hz, 2H), 3.05-2.83 (m, 4H), 2.31 (t, J=6.8 Hz, 2H), 1.64 (m, 2H). $^{13}$C NMR (100 MHz, DMSO-$d_6$) δ 207.10, 163.71, 161.24, 156.05, 148.36, 142.82, 140.76 (2), 140.00, 138.32, 136.69, 130.84 (2), 129.68, 128.68, 128.45, 127.39, 125.51, 123.11, 121.44, 118.76, 118.65, 118.18, 116.26, 116.04, 114.86, 114.65, 113.65, 111.88, 74.86, 43.06, 37.00, 31.23, 29.42, 26.05, 25.07, 23.15. LCMS (60-95% acetonitrile in 0.05% TFA over 10 minutes) retention time=2.77 minutes, ESI m/z=703.38 [M+H]$^+$.

Synthesis of 3-(2-(5-(3,4-dichlorobenzylthio)-4-(3-(1-trityl-1H-imidazol-4-yl)propyl)-4H-1,2,4-triazol-3-yl)ethyl)-1H-indole (19a)

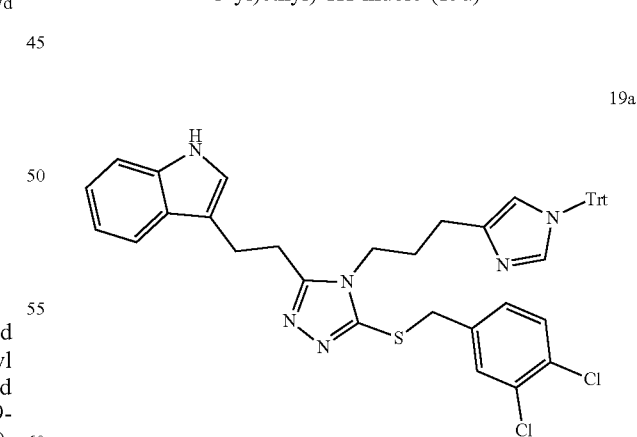

19a

Prepared according the General Procedure 2C from 15a (526 mg, 0.88 mmol) and 3,4-dichlorobenzyl bromide (128 µL, 0.88 mmol) to afford 218 mg (70%) of compound 19a as a white solid: $^1$H NMR (400 MHz, DMSO-$d_6$) δ 10.75 (s, 1H), 7.52 (d, J=1.8 Hz, 1H), 7.47 (d, J=8.2 Hz, 1H), 7.41 (d, J=7.8 Hz, 1H), 7.34-7.21 (m, 11H), 7.18 (d, J=1.4 Hz, 1H), 7.08 (d, J=2.3 Hz, 1H), 7.01-6.96 (m, 7H), 6.86 (t, J=7.3 Hz, 1H), 6.56 (s, 1H), 4.27 (s, 2H), 3.66 (t, J=7.3 Hz, 2H), 3.05-2.92 (m, 4H), 2.32 (t, J=6.8 Hz, 2H), 1.66 (m, 2H). $^{13}$C NMR (100 MHz, DMSO-d$_6$) δ 207.08, 156.14, 142.82, 139.99, 139.38*2, 138.34, 136.69, 131.34, 131.03, 130.51, 129.79, 129.72, 128.44, 128.16, 127.41*2, 123.15, 121.44, 118.78*2, 118.57, 118.19, 113.64, 74.87, 43.11, 36.10, 29.45, 26.02, 25.03, 23.10. LCMS (60-95% acetonitrile in 0.05% TFA over 10 minutes) retention time=2.67 minutes, ESI m/z=753.36 [M+H]$^+$.

Synthesis of 345-(4-bromobenzylthio)-4-(3-(1-trityl-1H-imidazol-4-yl)propyl)-4H-1,2,4-triazol-3-yl)methyl)-1H-indole (19o)

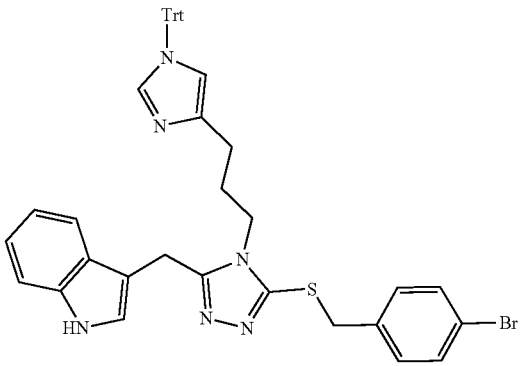

19o

Prepared according to General Procedure C from cyclized compound 15g (500 mg, 0.86 mmol) and 4-bromobenzyl bromide (215 mg, 0.86 mmol) to afford 506 mg (78%) of 19o as a yellow foam: $^1$H NMR (400 MHz, DMSO-d$_6$) δ 10.94 (s, 1H), 7.46 (d, J=7.8 Hz, 1H), 7.40-7.34 (m, 9H), 7.31 (d, J=7.8 Hz, 1H), 7.24-7.22 (m, 2H), 7.19 (m, 1H), 7.10-7.01 (m, 9H), 6.91 (t, J=7.8 Hz, 1H), 6.54 (s, 1H), 4.23 (s, 2H), 4.18 (s, 2H), 3.61 (t, J=7.5 Hz, 2H), 2.26 (t, J=6.8 Hz, 2H), 1.49 (m, 2H). $^{13}$C NMR (100 MHz, DMSO-d$_6$) δ 154.68, 148.11, 142.31, 139.54, 137.73, 136.85, 136.27, 131.18, 130.88, 129.18, 128.17, 127.93, 126.71, 123.64, 121.16, 120.52, 118.51, 118.47, 117.57, 111.50, 108.32, 74.36, 42.66, 36.65, 28.73, 24.57, 21.70.

Synthesis of Methyl 4-((5-((1H-indol-3-yl)methyl)-4-(3-(1-trityl-1H-imidazol-4-yl)propyl)-4H-1,2,4-triazol-3-ylthio)methyl)benzoate (20o)

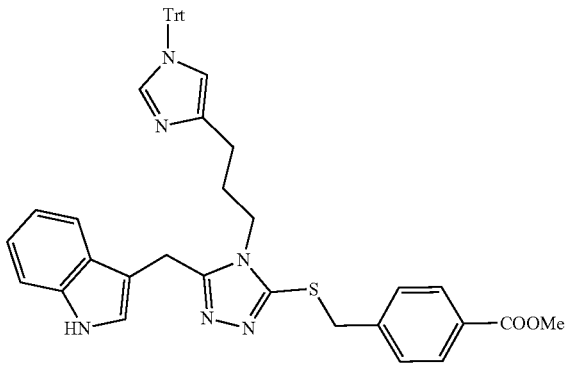

20o

Prepared according to General Procedure C from cyclized compound 15g (493 mg, 0.85 mmol) and methyl 4-(bromomethyl)benzoate (194 mg, 0.85 mmol) to afford 395 mg (64%) of 20o as a yellow foam: $^1$H NMR (400 MHz, DMSO-d$_6$) δ 10.87 (s, 1H), 7.65 (d, J=8.2 Hz, 2H), 7.40 (d, J=8.2 Hz, 1H), 7.35-7.31 (m, 9H), 7.26-7.23 (m, 3H), 7.18 (m, 1H), 7.14 (d, J=2.3 Hz, 1H), 7.03-6.96 (m, 7H), 6.85 (t, J=7.3 Hz, 1H), 6.49 (s, 1H), 4.29 (s, 2H), 4.13 (s, 2H), 3.78 (s, 3H), 3.58 (t, J=7.8 Hz, 2H), 2.21 (t, J=6.8 Hz, 2H), 1.44 (m, 2H). $^{13}$C NMR (100 MHz, DMSO-d$_6$) δ 165.87, 154.72, 148.02, 142.95, 142.32, 139.54, 137.71, 136.26, 129.21, 129.17, 129.05, 128.51, 128.16, 127.92, 126.69, 123.63, 121.16, 118.47, 117.57, 111.48, 108.30, 74.35, 52.10, 42.68, 38.87, 36.94, 28.75, 24.55, 21.68.

Synthesis of 3-benzyl-5-(benzylthio)-4-(3-(1-trityl-1H-imidazol-4-yl)propyl)-4H-1,2,4-triazole (16n)

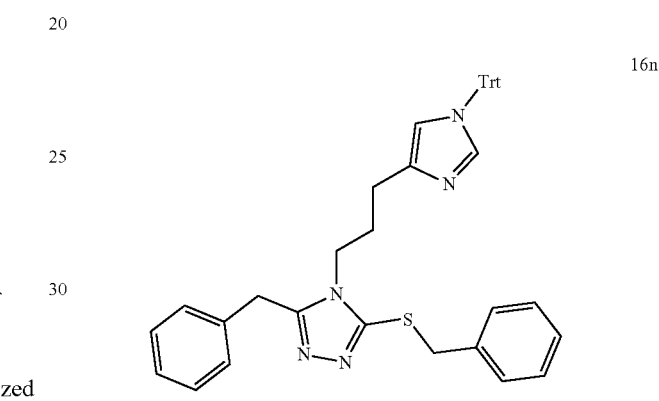

16n

Prepared according to General Procedure C from cyclized compound 15n (370 mg, 0.68 mmol) and benzyl bromide (82 μL, 0.68 mmol) to afford 252 mg (58%) of the desired product 16n as a white foam: $^1$H NMR (400 MHz, DMSO-d$_6$) δ 7.40-7.35 (m, 10H), 7.23-7.08 (m, 10H), 7.04-7.02 (m, 6H), 6.48 (s, 1H), 4.27 (s, 2H), 4.07 (s, 2H), 3.57 (t, J=7.6 Hz, 2H), 2.28 (t, J=7.2 Hz, 2H), 1.39 (m, 2H). $^{13}$C NMR (100 MHz, DMSO-d$_6$) δ 154.32, 148.65, 142.32, 139.50, 137.73, 137.21, 136.26, 129.20, 128.80, 128.53, 128.39, 128.20, 128.00, 127.39, 126.71, 117.57, 74.39, 42.76, 37.57, 30.40, 28.67, 24.64.

Synthesis of 2-(5-(benzylthio)-4-(3-(1-trityl-1H-imidazol-4-yl)propyl)-4H-1,2,4-triazol-3-yl)quinoline (16b)

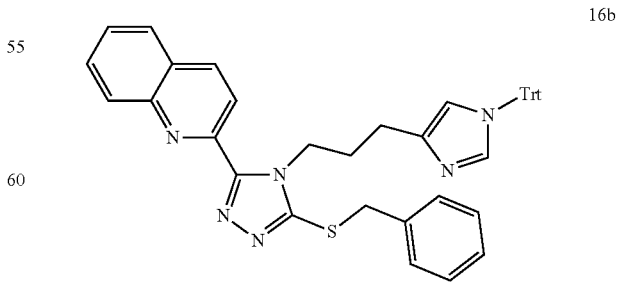

16b

Prepared according to the General Procedure 2C from 15b (550 mg, 0.95 mmol) to afford 460 mg (72%) of compound 16b as a white solid: $^1$H NMR (400 MHz, DMSO-d$_6$) δ 8.54 (d, J=8.7 Hz, 1H), 8.30 (d, J=8.7 Hz, 1H), 8.05 (d, J=6.9 Hz, 1H), 7.99 (d, J=8.3 Hz, 1H), 7.75-7.55 (m, 5H), 7.37-7.19 (m, 13H), 7.05-7.01 (m, 5H), 6.62 (s, 1H), 4.49 (m, 2H), 4.48 (m, 2H), 2.54 (m, 2H), 1.97 (m, 2H). $^{13}$C NMR (100 MHz, DMSO-d$_6$) δ 152.42, 152.26, 147.16, 146.59, 142.30, 139.77, 137.77, 137.42, 137.06, 130.33, 129.17, 128.97, 128.47, 128.11, 127.99, 127.92, 127.60, 127.53, 127.37, 119.93, 117.72, 74.35, 45.50, 36.80, 29.26, 25.13.

Synthesis of 2-(5-(2-(1H-indol-3-ynethylthio)-4-(3-(1-trityl-1H-imidazol-4-yl)propyl)-4H-1,2,4-triazol-3-yl)quinoline (17b)

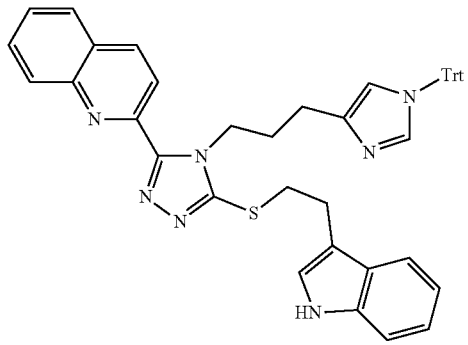

17b

The cyclized compound 15b (515 mg, 0.89 mmol) was dissolved in DMF (7.1 mL) followed by the addition of K2CO3 (123 mg, 0.89 mmol) and 3-(2-bromoethyl)-1H-indole (199 mg, 0.89 mmol). The reaction was stirred at 40° C. overnight and the precipitate was filtered and washed with cold diethyl ether to afford 496 mg (77%) of 17b as a brown solid: $^1$H NMR (400 MHz, DMSO-d$_6$) δ 10.91 (s, 1H), 8.53 (d, J=8.7 Hz, 1H), 8.29 (d, J=8.7 Hz, 1H), 8.04 (d, J=6.9 Hz, 1H), 7.99 (d, J=8.7 Hz, 1H), 7.74-7.60 (m, 3H) 7.35-7.32 (m, 10H), 7.25-7.23 (m, 2H), 7.08-6.95 (m, 8H), 6.66 (s, 1H), 4.57 (m, 2H), 3.55 (m, 2H), 3.16 (m, 2H), 2.59 (m, 2H), 2.10 (m, 2H). $^{13}$C NMR (100 MHz, DMSO-d$_6$) δ 152.66, 150.01, 147.78, 146.40, 143.79, 143.65, 138.67, 133.63, 133.53, 133.53, 132.13, 131.38, 129.50, 129.22, 128.27, 127.91, 127.79, 127.55, 127.00, 126.66, 124.40, 120.63, 120.32, 119.58, 115.80, 112.00, 105.17, 80.57, 48.00, 30.43, 27.94, 27.81, 21.12.

Synthesis of 2-(5-(3-Bromobenzylthio)-4-(3-(1-trityl-1H-imidazol-4-yl)propyl)-4H-1,2,4-triazol-3-Aquinoline (18b)

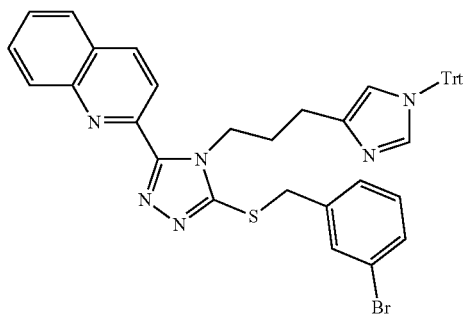

Prepared according to General Procedure 2C from cyclized compound 15b (480 mg, 0.83 mmol) and 3-bromobenzyl bromide (207 mg, 0.83 mmol) to afford 325 mg (52%) of 18b as a white foam: $^1$H NMR (400 MHz, DMSO-d$_6$) δ 8.54 (d, J=8.2 Hz, 1H), 8.30 (d, J=8.7 Hz, 1H), 8.06 (d, J=7.8 Hz, 1H), 7.99 (d, J=7.8 Hz, 1H), 7.75-7.64 (m, 2H), 7.60 (m, 1H), 7.41-7.32 (m, 11H), 7.25-7.20 (m, 2H), 7.05-7.01 (m, 6H), 6.64 (s, 1H), 4.49 (m, 4H), 2.55 (m, 2H), 1.99 (m, 2H). 13H NMR (100 MHz, DMSO-d$_6$) δ 152.51, 151.98, 147.11, 146.57, 142.29, 140.13, 139.73, 137.79, 137.40, 131.65, 130.54, 130.30, 129.16, 128.09, 127.96, 127.90, 127.58, 127.35, 121.52, 119.91, 117.70, 74.33, 45.53, 35.80, 29.26, 25.12.

Synthesis of 3-(benzylthio)-5-(naphthalen-2-yl)-4-(3-(1-trityl-1H-imidazol-4-yl)propyl)-4H-1,2,4-triazole (16c)

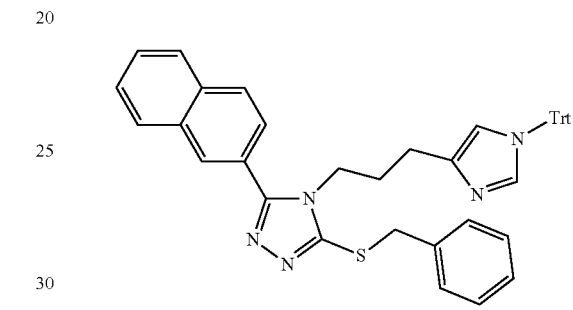

16c

Prepared according to the General Procedure 2C from compound 15b (417 mg, 0.72 mmol) to afford 270 mg (56%) of 16c as a white solid: $^1$H NMR (400 MHz, DMSO-d$_6$) δ 8.12 (s, 1H), 7.98 (d, J=8.7 Hz, 1H), 7.92 (d, J=8.2 Hz, 1H), 7.69 (dxd, J=8.2, 1.4 Hz, 1H), 7.59 (t, J=6.9 Hz, 1H), 7.51 (d, J=6.9 Hz, 1H), 7.34-7.19 (m, 14H), 7.14 (d, J=1.4 Hz, 1H), 7.14 (d, J=1.4 Hz, 1H), 6.92-6.90 (m, 6H), 6.45 (s, 1H), 4.42 (s, 2H), 3.88 (t, J=6.8 Hz, 2H), 2.31 (t, J=6.4 Hz, 2H), 1.75 (m, 2H). $^{13}$C NMR (100 MHz, DMSO-d$_6$) δ 154.95, 150.19, 142.20, 139.16, 137.85, 137.15, 133.11, 132.45, 129.19, 128.99, 128.58, 128.50, 128.10, 127.90, 127.66, 127.53, 127.40, 126.83, 125.39, 124.57, 117.97, 74.28, 43.82, 28.81, 24.50.

Synthesis of 3-(benzylthio)-5-phenethyl-4-(3-(1-trityl-1H-imidazol-4-yl)propyl)-4H-1,2,4-triazole (16d)

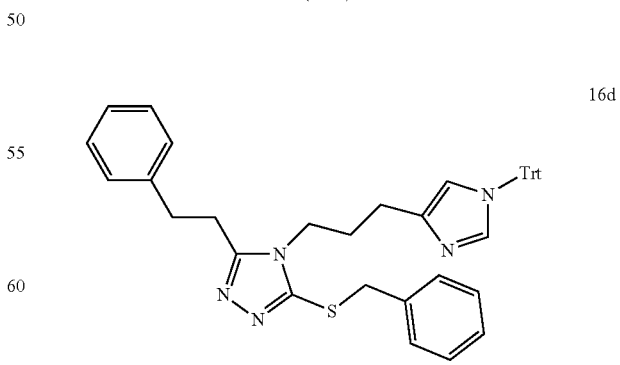

16d

Prepared according to the General Procedure 2C from compound 15d (388 mg, 0.70 mmol) to afford 335 mg (74%) of 16d as a white solid: $^1$H NMR (400 MHz, DMSO-d$_6$) δ

7.37 (m, 9H), 7.24-7.19 (m, 10H), 7.14 (m, 1H), 7.06-7.03 (m, 6H), 6.59 (s, 1H), 4.30 (s, 2H), 2.97-2.87 (m, 4H), 2.36 (m, 2H), 1.65 (m, 2H). $^{13}$C NMR (100 MHz, DMSO-$d_6$) δ 154.88, 148.11, 142.30, 140.62, 139.55, 137.76, 137.25, 129.18, 128.85, 128.40, 128.38, 128.23, 128.18, 127.96, 127.42, 126.10, 117.74, 74.38, 42.41, 37.34, 32.46, 28.76, 26.20, 24.51.

Synthesis of 3-(5-(benzylthio)-4-(3-(1-trityl-1H-imidazol-4-yl)propyl)-4H-1,2,4-triazol-3-yl)-1H-indole (16e)

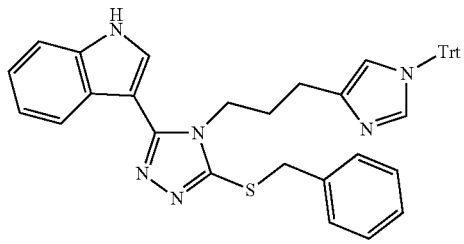

16e

Prepared according to the General Procedure 2C from compound 15e (457 mg, 0.81 mmol) to afford 423 mg (80%) of 16e as a white solid: $^1$H NMR (400 MHz, DMSO-$d_6$) δ 11.65 (s, 1H), 8.05 (d, J=7.8 Hz, 1H), 7.81 (d, J=2.8 Hz, 1H), 7.46 (d, J=8.2 Hz, 1H), 7.34-7.30 (m, 11H), 7.28 (s, 1H), 7.25-7.10 (m, 4H), 7.04-7.02 (m, 6H), 6.59 (s, 1H), 4.37 (s, 2H), 3.88 (t, J=8.2 Hz, 1H), 2.42 (t, J=6.8 Hz, 2H), 1.77 (m, 2H). $^{13}$C NMR (100 MHz, DMSO-$d_6$) δ 171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39.

Synthesis of 3-(benzylthio)-5-phenyl-4-(3-(1-trityl-1H-imidazol-4-yl)propyl)-4H-1,2,4-triazole (16f)

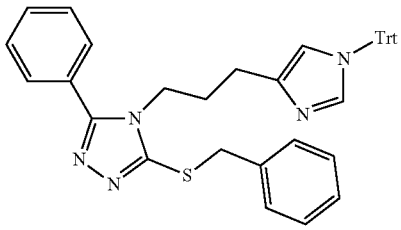

16f

Prepared according to the General Procedure 2C from 15f (810 mg, 1.53 mmol) to afford 440 mg (460%) of 16f as a white solid: $^1$H NMR (400 MHz, DMSO-$d_6$) δ 7.55 (m, 2H), 7.47-7.42 (m, 3H) 7.37-7.19 (m 15H), 7.04-7.00 (m, 6H), 6.48 (s, 1H), 4.41 (s, 2H), 3.81 (t, J=7.8 Hz, 2H), 2.30 (t, J=6.8 Hz, 2H), 1.70 (in, 2H). $^{13}$C NMR (100 MHz, DMSO-$d_6$) δ 154.95, 149.99, 142.27, 139.13, 137.87, 137.14, 129.99, 129.22, 129.00, 128.93, 128.51, 128.36, 128.20, 128.02, 127.56, 127.27, 117.92, 74.39, 43.60, 37.34, 28.82, 24.48.

Synthesis of 3-((5-(benzylthio)-4-(3-(1-trityl-1H-imidazol-4-yl)propyl)-4H-1,2,4-triazol-3-yl)methyl)-1H-indole (16 g)

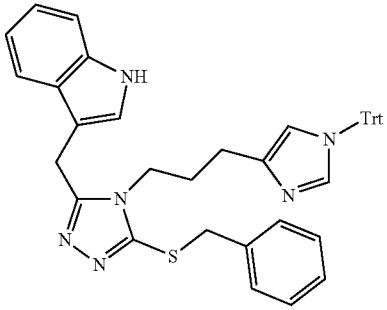

16g

Prepared according to the General Procedure 2C from 15 g (775 mg, 1.37 mmol) to afford 647 mg (720%) of compound 16g as a white solid: $^1$H NMR (400 MHz, DMSO-$d_6$) δ 10.93 (s, 1H), 7.47 (d, J=7.8 Hz, 1H), 7.40-7.35 (m, 9H), 7.30-7.25 (m, 2H), 7.15-7.01 (m, 13H), 6.91 (s, 1H), 6.53 (s, 1H), 4.25 (s, 2H), 4.17 (s, 2H), 3.59 (t, J=7.3 Hz, 2H), 2.24 (t, J=7.3 Hz, 2H), 1.45 (m, 2H). $^{13}$C NMR (100 MHz, DMSO-$d_6$) δ 154.62, 148.38, 142.30, 139.45, 137.72, 137.23, 136.30, 129.21, 128.75, 128.36, 128.22, 128.00, 127.36, 126.74, 123.61, 121.24, 118.53, 117.62, 111.47, 108.44, 74.45, 42.68, 37.68, 28.69, 24.57, 21.69.

Synthesis of 3-((5-(3-(trifluoromethyl)benzylthio)-4-(3-(J-trityl-1H-imidazol-4-yl)propyl)-4H-1,2,4-triazol-3-yl)methyl)-1H-indole (17 g

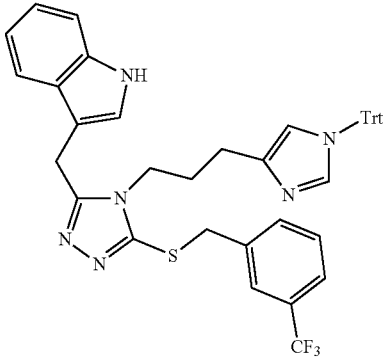

17g

Prepared according to the General Procedure 2C from compound 15g (468 mg, 0.81 mmol) and 3-trifluoromethylbenzyl bromide (123 μL, 0.81 mmol) to afford 474 mg (80%) of compound 17g as a pale yellow foam: $^1$H NMR (400 MHz, DMSO-$d_6$) δ 10.88 (d, J=2.3 Hz, 1H), 7.60 (s, 1H), 7.39-6.97 (m, 24H), 6.46 (d, 1H), 4.34 (s, 2H), 4.12 (s, 2H), 3.61 (t, J=7.4 Hz, 2H), 2.21 (t, J=7.1 Hz, 2H), 1.40 (m, 2H). $^{13}$C NMR (100 MHz, DMSO-$d_6$) δ 154.83, 148.13, 142.37, 139.55, 139.15, 137.81, 136.31, 132.97, 129.42, 129.24, 129.01, 128.25, 128.03, 126.76, 125.49 (d), 124.07 (d), 123.66, 122.76, 121.29, 118.53, 117.64, 111.53, 108.44, 74.45, 42.82, 36.46, 28.76, 24.61, 21.65.

Synthesis of 3-((5-(3-fluorobenzylthio)-4-(3-(1-trityl-1H-imidazol-4-yl)propyl)-4H-1,2,4-triazol-3-yl)methyl)-1H-indole (18d)

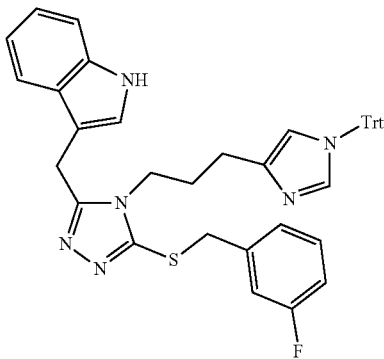

18g

Prepared according to the General Procedure 2C from compound 15g (529 mg, 0.91 mmol) and 3-fluorobenzyl bromide (112 µL, 0.91 mmol) to afford 610 mg (97%) of 18 g as a pale yellow foam: $^1$H NMR (400 MHz, DMSO-$d_6$) δ 10.93 (s, 1H), 7.45 (d, J=8.3 Hz, 1H), 7.40-7.34 (m, 10H), 7.29-7.23 (m, 2H), 7.14-6.98 (m, 12H), 6.90 (s, 1H), 6.53 (s, 1H), 4.30 (s, 2H), 4.18 (s, 2H), 3.66 (t, J=7.8 Hz, 2H), 2.26 (t, J=7.3 Hz, 2H), 1.48 (m, 2H). $^{13}$C NMR (100 MHz, DMSO-$d_6$) δ 163.11, 160.68, 154.68, 148.14, 142.32, 140.23 (d), 139.54, 137.72, 136.24, 130.26 (d), 129.17, 128.16, 127.92, 124.89, 123.57, 121.18, 118.47, 117.54, 115.69 (d), 114.29 (d), 111.43, 108.42, 74.35, 42.75, 36.56, 28.75, 24.58, 21.60.

Synthesis of 3-((5-(3,4-dichlorobenzylthio)-4-(3-(1-trityl-1H-imidazol-4-yl)propyl)-4H-1,2,4-triazol-3-yl)methyl)-1H-indole (19 g)

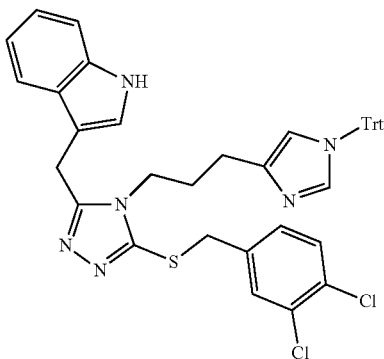

19g

Prepared according to the General Procedure 2C from 15 g (519 mg, 0.89 mmol) and 3,4-dichlorobenzyl bromide (130 µL, 0.89 mmol) to afford 538 mg (81%) of compound 19g as a pale yellow foam: $^1$H NMR (400 MHz, DMSO-$d_6$) δ 10.93 (s, 1H), 7.55 (d, J=1.8 Hz, 1H), 7.45-7.00 (m, 23H), 6.90 (m, 1H), 6.54 (s, 1H), 4.29 (s, 2H), 4.18 (s, 2H), 3.68 (t, J=7.6 Hz, 2H), 2.28 (t, J=6.9 Hz, 2H), 1.50 (m, 2H). $^{13}$C NMR (100 MHz, DMSO-$d_6$) δ 154.78, 147.98, 142.32, 139.54, 138.80, 137.75, 136.26, 130.83, 130.81, 130.38, 129.97, 129.19, 129.08, 128.16, 127.93, 126.71, 123.64, 121.18, 118.49, 117.58, 111.48, 108.36, 74.36, 42.77, 35.68, 28.78, 24.57, 21.64.

Synthesis of 3-((5-(3-bromobenzylthio)-4-(3-(1-trityl-1H-imidazol-4-yl)propyl)-4H-1,2,4-triazol-3-yl)methyl)-1H-indole (20 g)

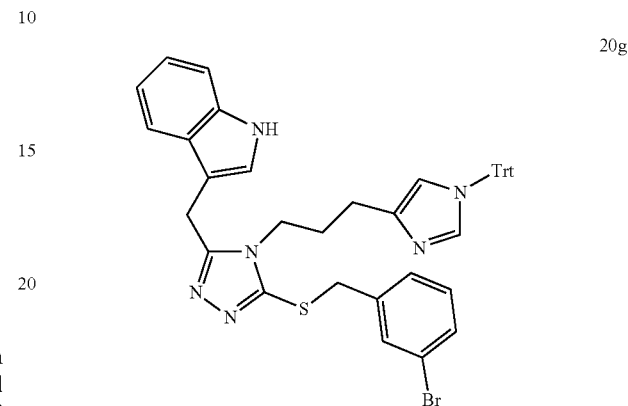

20g

Prepared according to the General Procedure 2C from 15 g (510 mg, 0.88 mmol) and 3-bromobenzyl bromide (219 mg, 0.88 mmol) to afford 544 mg (83%) of 20 g as a pale yellow foam: $^1$H NMR (400 MHz, DMSO-$d_6$) δ 10.92 (s, 1H), 7.48-7.00 (m, 24H), 6.92 (m, 1H), 6.53 (s, 1H), 4.28 (s, 2H), 4.17 (s, 2H), 3.68 (t, J=7.8 Hz, 2H), 2.27 (t, J=7.1 Hz, 2H), 1.47 (m, 2H). $^{13}$C NMR (100 MHz, DMSO-$d_6$) δ 154.71, 148.11, 142.32, 140.27, 139.52, 137.74, 136.25, 131.54, 130.41, 130.16, 129.19, 128.17, 127.94, 127.84, 126.71, 123.60, 121.49, 121.19, 118.49, 117.56, 111.45, 108.42, 74.36, 42.77, 36.40, 28.74, 24.60, 21.61.

Synthesis of 3-(benzylthio)-5-(naphthalen-1-yl)-4-(3-(1-trityl-1H-imidazol-4-yl)propyl)-4H-1,2,4-triazole (16h)

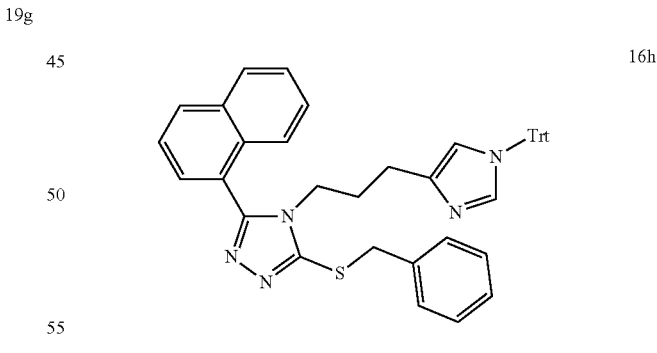

16h

Prepared according to the General Procedure 2C from 15h (733 mg, 1.3 mmol) to afford 310 mg (37%) of compound 16h as a white solid: $^1$H NMR (400 MHz, DMSO-$d_6$) δ 7.98-7.92 (m, 2H), 7.53-7.45 (m, 4H), 7.33-7.19 (m, 15H), 7.00 (m, 1H), 6.92-6.88 (m, 6H), 6.21 (s, 1H), 4.37 (s, 2H), 3.46 (m, 2H), 2.02 (m, 2H), 1.39 (m, 2H). $^{13}$C NMR (100 MHz, DMSO-$d_6$) δ 153.65, 149.32, 142.23, 139.04, 137.62, 137.32, 133.00, 131.46, 130.50, 129.16, 129.01, 128.69, 128.55, 128.48, 128.17, 127.98, 127.56, 127.34, 126.63, 125.28, 124.62, 124.55, 117.56, 74.29, 59.83, 43.43, 28.91, 24.32.

Synthesis of 2-(5-(benzylthio)-4-(3-(1-trityl-1H-imidazol-4-yl)propyl)-4H-1,2,4-triazol-3-yl)-5-fluoro-1H-indole (16i)

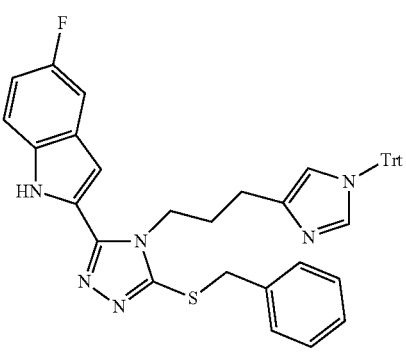

16i

Prepared according to the General Procedure 2C from 15i (340 mg, 0.58 mmol) to yield 156 mg (39%) of compound 16i as a pale yellow foam: $^1$H NMR (400 MHz, DMSO-d$_6$) δ 11.96 (s, 1H), 7.40-7.37 (m, 1H), 7.30-7.25 (m, 12H) 7.21-7.10 (m 4H), 7.01-6.99 (m, 7H), 6.74 (s, 1H), 6.58 (s, 1H), 4.38 (s, 2H), 3.96 (m, 2H), 2.43 (m, 2H), 1.78 (m, 2H). $^{13}$C NMR (100 MHz, DMSO-d$_6$) δ 158.31, 155.99, 150.44, 148.67, 142.30, 139.27, 138.02, 137.09, 133.31, 129.21, 128.97, 128.51, 128.19, 128.01, 127.58, 125.55, 118.23, 113.05, 112.94, 111.74, 111.49, 105.27, 105.04, 101.53, 74.44, 43.89, 37.49, 28.54, 24.59.

Synthesis of 3-(benzylthio)-5-(4-fluorophenethyl)-4-(3-(1-trityl-1H-imidazol-4-yl)propyl)-4H-1,2,4-triazole (16j)

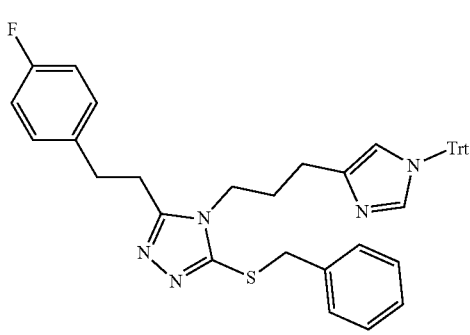

16j

Prepared according to the General Procedure 2C from compound 15j (740 mg, 1.29 mmol) and benzyl bromide (154 μL, 1.29 mmol) to afford 636 mg (74%) of 16j as a white solid: $^1$H NMR (400 MHz, DMSO-d$_6$) δ 7.39-7.35 (m, 9H), 7.25-7.19 (m, 8H) 7.05-6.97 (m, 8H), 6.59 (s, 1H), 4.28 (s, 2H), 3.65 (m, 2H), 2.96-2.84 (m, 4H), 2.35 (m, 2H), 1.65 (m, 2H). $^{13}$C NMR (100 MHz, DMSO-d$_6$) δ 161.99, 159.59, 154.79, 148.18, 142.33, 139.57, 137.81, 137.28, 136.78, 130.29, 130.21, 129.21, 128.89, 128.44, 128.22, 128.01, 128.47, 117.79, 115.02, 114.81, 74.40, 42.42, 37.33, 31.49, 28.80, 26.25, 24.51.

Synthesis of 2-(5-(benzylthio)-4-(3-(1-trityl-1H-imidazol-4-yl)propyl)-4H-1,2,4-triazol-3-yl)-1H-indole (16k)

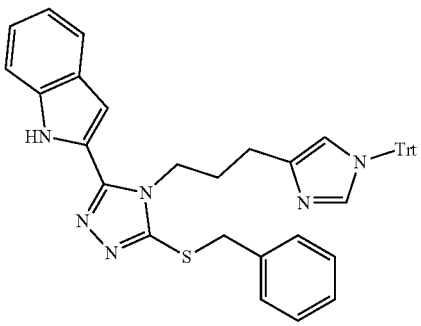

16k

Prepared according to the General Procedure 2C from compound 15k (590 mg, 1.04 mmol) and benzyl bromide (125 μL, 1.04 mmol) to afford 210 mg (31%) of 16k as a white solid: $^1$H NMR (400 MHz, DMSO-d$_6$) δ 11.86 (s, 1H), 7.44-7.38 (m, 2H), 7.34-7.28 (m, 12H) 7.25-7.14 (m 4H), 7.04-6.96 (m, 7H), 6.76 (s, 1H), 6.62 (s, 1H), 4.40 (s, 2H), 4.00 (m, 2H), 2.46 (m, 2H), 1.82 (m, 2H). $^{13}$C NMR (100 MHz, DMSO-d$_6$) δ 154.95, 150.19, 142.20, 139.16, 137.85, 137.15, 133.11, 132.45, 129.19, 128.99, 128.58, 128.50, 128.10, 127.90, 127.66, 127.53, 127.40, 126.83, 125.39, 124.57, 117.97, 74.28, 43.82, 28.81, 24.50.

Synthesis of 3-((5-(Benzylthio)-4-(3-(1-trityl-1H-imidazol-4-yl)propyl)-4H-1,2,4-triazol-3-yl)methyl)-5-fluoro-1H-indole (16l)

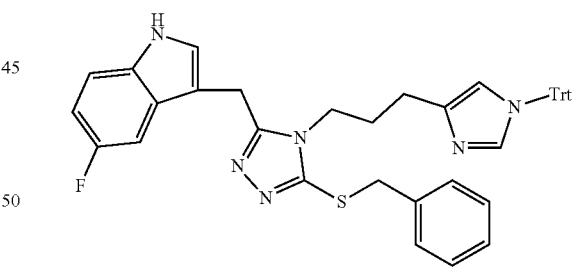

Prepared according to General Procedure 2C from cyclized compound 15l (460 mg, 0.77 mmol) and benzyl bromide (92 μL, 0.77 mmol) to afford 460 mg (87%) of the desired product 16l as a yellow foam: $^1$H NMR (400 MHz, DMSO-d$_6$) δ 11.05 (s, 1H), 7.41-7.36 (m, 10H), 7.30-7.21 (m, 1H), 7.23-7.20 (m, 2H), 7.15-7.04 (m, 11H), 6.91-6.85 (m, 1H), 6.56 (s, 1H), 4.26 (s, 2H), 4.15 (s, 2H), 3.61 (d, J=7.6 Hz, 2H), 2.27 (d, J=6.9 Hz, 2H), 1.46 (m, 2H). $^{13}$H NMR (100 MHz, DMSO-d$_6$) δ 157.74, 155.44, 154.41, 148.39, 142.22, 139.22, 137.66, 137.21, 132.93, 129.18, 128.73, 128.31, 128.21, 127.99, 127.33, 127.02 (d), 125.71, 117.65, 112.49 (d), 109.47 (d), 108.73 (d), 103.35 (d), 74.51, 42.66, 37.60, 28.63, 24.44, 21.48, 20.78.

Synthesis of 3-((5-(3-Methoxybenzylthio)-4-(3-(1-trityl-1H-imidazol-4-yl)propyl)-4H-1,2,4-triazol-3-yl)methyl)-1H-indole (21 g

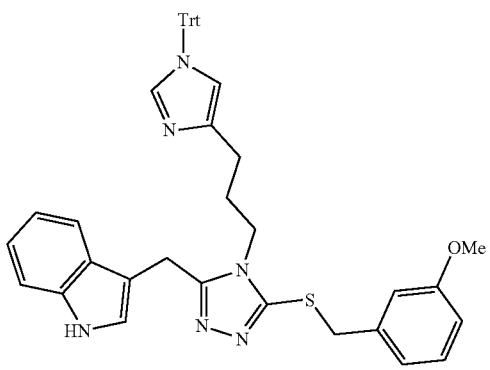

Prepared according to General Procedure 2C from cyclized compound 15g (500 mg, 0.86 mmol) and 3-methoxybenzyl bromide (121 μL, 0.86 mmol) to afford 441 mg (73%) of 21 g as a yellow foam: $^1$H NMR (400 MHz, DMSO-d$_6$) δ 10.93 (s, 1H), 7.47 (d, J=7.8 Hz, 1H), 7.39-7.34 (m, 9H), 7.29 (d, J=8.2 Hz, 1H), 7.23 (d, J=1.4 Hz, 1H), 7.14 (d, J=2.3 Hz, 1H), 7.05-7.00 (m, 8H), 6.90 (m, 1H), 6.82 (m, 1H), 6.74-6.71 (m, 2H), 6.52 (s, 1H), 4.25 (s, 2H), 4.17 (s, 2H), 3.65 (m, 2H), 3.62 (s, 3H), 2.25 (m, 2H), 1.47 (m, 2H). $^{13}$H NMR (100 MHz, DMSO-d$_6$) δ 159.16, 154.57, 148.37, 142.31, 139.53, 138.66, 137.71, 136.24, 129.40, 129.17, 128.16, 127.92, 126.71, 123.57, 121.17, 120.93, 118.47, 117.55, 114.22, 113.04, 111.43, 108.46, 74.36, 54.92, 42.74, 37.35, 28.75, 24.60, 21.60.

Synthesis of 3-((5-(3-Methylbenzylthio)-4-(3-(1-trityl-1H-imidazol-4-yl)propyl)-4H-1,2,4-triazol-3-yl)methyl)-JH-indole (22 g

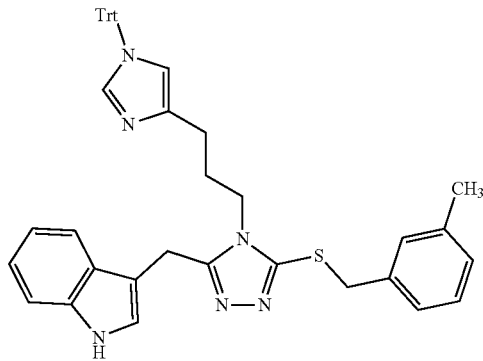

Prepared according to General Procedure 2C from cyclized compound 15g (513 mg, 0.88 mmol) and 3-methylbenzyl bromide (119 μL, 0.88 mmol) to afford 485 mg (80%) of 22 g as a yellow foam: $^1$H NMR (400 MHz, DMSO-d$_6$) δ 10.93 (s, 1H), 7.47 (d, J=7.8 Hz, 1H), 7.40-7.36 (m, 9H), 7.29 (d, J=8.2 Hz, 1H), 7.22 (d, J=1.4 Hz, 1H), 7.14 (d, J=2.3 Hz, 1H), 7.05-6.90 (m, 12H), 6.52 (s, 1H), 4.23 (s, 2H), 4.17 (s, 2H), 3.65 (t, J=7.6 Hz, 2H), 2.27 (t, J=6.9 Hz, 2H), 2.13 (s, 3H), 1.45 (m, 2H). $^{13}$H NMR (100 MHz, DMSO-d$_6$) δ 154.54, 148.41, 142.31, 139.56, 137.70, 137.56, 137.00, 136.25, 129.34, 129.17, 128.25, 128.16, 128.01, 127.92, 126.71, 125.84, 123.55, 121.17, 118.47, 117.53, 111.43, 108.46, 74.35, 42.71, 37.49, 28.72, 24.62, 20.79.

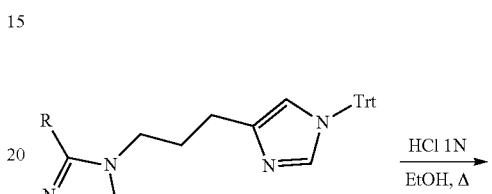

16a R = 3-indolylethyl
17a R = 3-indolylethyl
18a R = 3-indolylethyl
19a R = 3-indolylethyl
16b R = 2-quinolyl
17b R = 2-quinolyl
18b R = 2-quinolyl
16c R = 2-naphthalyl
16d R = phenylethyl
16e R = 3-indolyl
16f R = Ph
16g R = 3-indolylmethyl
17g R = 3-indolylmethyl
18g R = 3-indolylmethyl
19g R = 3-indolylmethyl
20g R = 3-indolylmethyl
21g R = 3-indolylmethyl
22g R = 3-indolylmethyl
16h R = 1-naphthalyl
16i- R = 5-fluoro-2-indolyl
16j R = 4-fluoro-phenylethyl
16k R = 2-indolyl 16l R = 3-(5-fluoro)indolylmethyl
R' = Ph
R' = 3-chlorophenyl
R' = 3-fluorophenyl
R' = 3,4-dichlorophenyl
R' = Ph
R' = 3-indolylethyl
R' = 3-bromophenyl
R' = Ph
R' = Ph
R' = Ph
R' = Ph
R' = Ph
R' = 3-trifluoromethylphenyl
R' = 3-fluoro
R' = 3,4-dichlorophenyl
R' = 3-bromophenyl
R' = 3-metoxyphenyl
R' = 3-methylphenyl
R' = Ph
R' = Ph
R' = Ph
R' = Ph
R' = Ph -continued

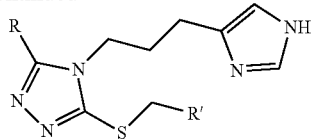

21a R = 3-indolylethyl
22a R = 3-indolylethyl
23a R = 3-indolylethyl
24a R = 3-indolylethyl
21b R = 2-quinolyl
22b R = 2-quinolyl
23b R = 2-quinolyl
21c R = 2-naphthalyl
21d R = phenylethyl
21e R = 3-indolyl
21f R = Ph
21g R = 3-indolylmethyl
22g R = 3-indolylmethyl
23g R = 3-indolylmethyl
24g R = 3-indolylmethyl
25g R = 3-indolylmethyl
26g R = 3-indolylmethyl
27g R = 3-indolylmethyl
21h R = 1-naphthalyl
21i- R = 5-fluoro-2-indolyl
21j R = 4-fluoro-phenylethyl
21k R = 2-indolyl
21l R = 3-(5-fluoro)indolylmethyl
R' = Ph
R' = 3-chlorophenyl
R' = 3-fluorophenyl
R' = 3,4-dichlorophenyl
R' = Ph
R' = 3-indolylethyl
R' = 3-bromophenyl
R' = Ph
R' = Ph
R' = Ph
R' = Ph
R' = Ph
R' = 3-trifluoromethylphenyl
R' = 3-fluoro
R' = 3,4-dichlorophenyl
R' = 3-bromophenyl
R' = 3-metoxyphenyl
R' = 3-methylphenyl
R' = Ph
R' = Ph
R' = Ph
R' = Ph
R' = Ph Synthesis of 3-(2-(4-(3-(1H-imidazol-4-yl)propyl)-5-(benzylthio)-4H-1,2,4-triazol-3-yl)ethyl)-1H-indole (AH-1-47)

AH-1-47

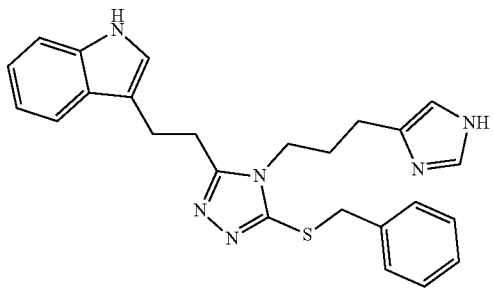

Prepared according to the General Procedure 2E from trityl protected 16a (218 mg g, 0.32 mmol) to afford 69 mg (49%) of AH-1-47 as a pale yellow solid: $^1$H NMR (400 MHz, DMSO-d$_6$) δ 11.79 (bs, 1H), 10.83 (bs, 1H), 7.48 (s, 1H), 7.47 (d, J=8.7 Hz, 1H), 7.35 (d, J=8.2 Hz, 2H), 7.29-7.24 (m, 5H), 7.14 (d, J=1.8 Hz, 1H), 7.08 (t, J=7.3 Hz, 1H), 6.99 (t, J=7.3 Hz, 1H), 6.76 (s, 1H), 4.31 (s, 2H), 3.65 (m, 2H), 3.10-2.97 (m, 4H), 1.72 (m, 2H). $^{13}$C NMR (100 MHz, DMSO-d$_6$) δ 155.47, 148.09, 137.26, 136.19, 134.69, 128.91, 128.47, 127.45, 126.92, 122.65, 120.97, 118.32, 118.15, 113.16, 111.38, 42.68, 37.45, 29.25, 25.55, 22.68. LCMS (05-95% acetonitrile in 0.05% TFA over 10 minutes) retention time=6.53 minutes, ESI m/z=443.42 [M+H]$^+$. HRMS (ESI+): m/z calculated for $C_{25}H_{27}N_6S$ (M+H)+ 443.2012, found 443.2000.

Synthesis of 3-(2-(4-(3-(1H-imidazol-4-yl)propyl)-5-(3-chlorobenzylthio)-4H-1,2,4-triazol-3-yl)ethyl)-1H-indole (AH-1-33)

AH-1-33

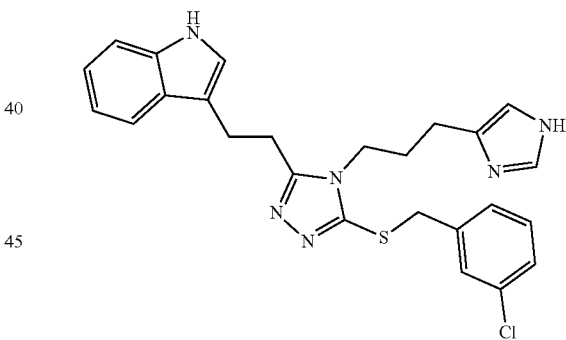

Prepared according to the General Procedure 2E from 17a (320 mg g, 0.44 mmol) to give 80 mg (38%) of AH-1-33 as a white solid: H NMR (400 MHz, DMSO-d$_6$) δ 10.81 (s, 1H), 7.47-7.42 (m, 2H), 7.36-7.23 (m, 5H), 7.13 (d, J=2.3 Hz, 1H), 7.07 (t, J=7.8 Hz, 1H), 6.96 (t, J=7.8 Hz, 1H), 6.70 (s, 1H), 4.30 (s, 2H), 3.66 (m, 2H), 3.08-3.04 (m, 2H), 2.99-2.95 (m, 2H), 2.37 (m, 2H), 1.71 (m, 2H). $^{13}$C NMR (100 MHz, DMSO-d$_6$) δ 156.12, 148.37, 140.64, 136.70, 135.21, 133.39, 130.80, 129.23, 128.15, 127.87, 127.41, 123.15, 121.48, 118.84, 118.64, 113.68, 111.90, 43.17, 36.94, 29.64, 26.02, 23.17. LCMS (25-95% acetonitrile in 0.05% TFA over 10 minutes) retention time=5.83 minutes, ESI m/z=477.34 [M+H]$^+$. HRMS (ESI+): m/z calculated for $C_{25}H_{26}C_1N_6S$ (M+H)+477.1623, found 477.1633.

Synthesis of 3-(2-(4-(3-(1H-imidazol-4-yl)propyl-5-(3-fluorobenzylthio)-4H-1,2,4-triazol-3-yl)ethyl)-1H-indole (AH-1-40)

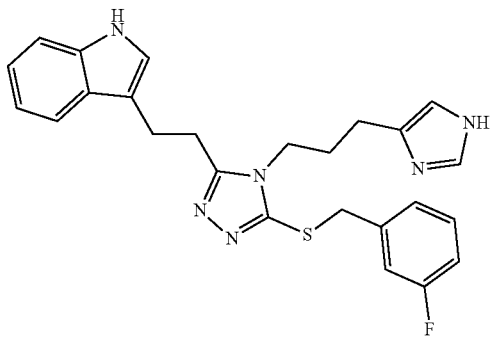

AH-1-40

Prepared according to the General Procedure 2E from 18a (250 mg, 0.36 mmol) to afford 80 mg (49%) of AH-1-40 as a white solid: $^1$H NMR (400 MHz, DMSO-d$_6$) δ 10.82 (s, 1H), 7.47 (s, 1H), 7.44 (d, J=7.8 Hz, 1H), 7.33-7.28 (m, 2H), 7.16-7.03 (m, 5H), 6.97 (t, J=7.3 Hz, 1H), 6.70 (s, 1H), 4.32 (s, 2H), 3.67 (m, 2H), 3.07 (m, 2H), 2.98 (m, 2H), 2.37 (m, 2H), 1.71 (m, 2H). $^{13}$C NMR (100 MHz, DMSO-d$_6$) J 156.10, 148.89, 140.89 (d), 136.71, 135.21, 130.92 (d), 127.42, 125.57, 125.54, 123.15, 121.47, 118.83 (d), 116.28 (d), 116.28 (d), 114.87 (d), 113.67, 111.90, 43.18, 37.04, 32.83, 29.64, 26.06, 23.18. LCMS (15-95% acetonitrile in 0.05% TFA over 10 minutes) retention time=6.27 minutes, ESI m/z=461.39 [M+H]$^+$. HRMS (ESI+): m/z calculated for C$_{25}$H$_{26}$FN$_6$S (M+H)+461.1918, found 461.1935.

Synthesis of 3-(2-(4-(3-(1H-imidazol-4-yl)propyl)-5-(3,4-dichlorobenzylthio)-4H-1,2,4-triazol-3-yl)ethyl)-1H-indole (AH-1-41)

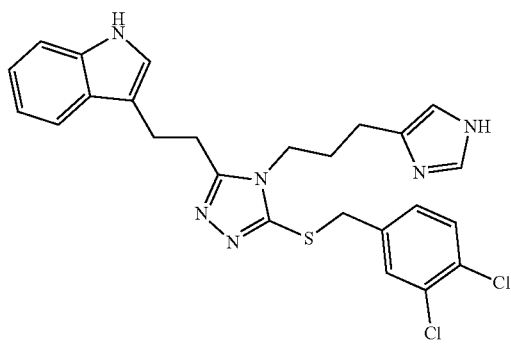

AH-1-41

Prepared according to the General Procedure 2E from compound 19a (450 mg g, 0.60 mmol) to afford 223 mg (73%) of AH-1-41 as a white solid: $^1$H NMR (400 MHz, DMSO-d$_6$) δ 10.82 (s, 1H), 7.57 (s, 1H), 7.53-7.43 (m, 3H), 7.34-7.24 (m, 2H), 7.13 (s, 1H), 7.05 (m, 1H), 6.95 (m, 1H), 6.71 (s, 1H), 4.31 (s, 2H), 3.69 (m, 2H), 3.05 (m, 2H), 2.98 (m, 2H), 2.37 (m, 2H), 1.72 (m, 2H). $^{13}$C NMR (100 MHz, DMSO-d$_6$) δ 155.67, 147.71, 139.00, 136.20, 134.71, 130.88, 130.81, 130.55, 129.98, 129.30, 127.78, 127.55, 126.91, 122.64, 120.97, 118.32, 118.15, 113.17, 111.40, 42.71, 35.68, 29.16, 25.56, 22.64. LCMS (15-95% acetonitrile in 0.05% TFA over 10 minutes) retention time=6.60 minutes, ESI m/z=511.30 [M+H]$^+$. HRMS (ESI+): m/z calculated for C$_{25}$H$_{25}$C$_{12}$N$_6$S (M+H)+511.1233, found 511.1246.

Synthesis of 2-(4-(3-(1H-imidazol-4-yl)propyl)-5-(benzylthio)-4H-1,2,4-triazol-3-yl)quinoline (AH-1-84)

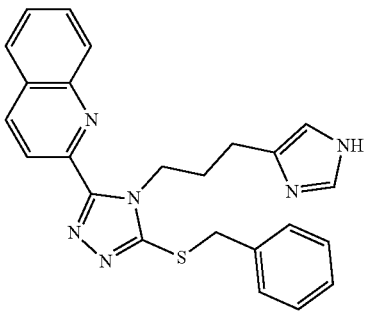

AH-1-84

Prepared according to the General Procedure 2E from compound 16b (310 mg, 0.46 mmol) to give 49 mg (25%) of AH-1-84 as a yellow solid: $^1$H NMR (400 MHz, DMSO-d$_6$) δ 8.53 (d, J=8.2 Hz, 1H), 8.30 (d, J=8.7 Hz, 1H), 8.05 (d, J=8.2 Hz, 1H), 7.93 (d, J=8.2 Hz, 1H), 7.84-7.80 (m, 1H), 7.69-7.65 (m, 1H), 7.46-7.39 (m, 2H), 7.33-7.18 (m, 5H), 6.72 (s, 1H), 4.56 (m, 2H), 4.51 (s, 2H), 2.57 (m, 2H), 1.99 (m, 2H). $^{13}$C NMR (100 MHz, DMSO-d$_6$) δ 171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39. IRMS (ESI+): m/z calculated for C$_{24}$H$_{23}$N$_6$S (M+H)+427.1693, found 427.1699.

Synthesis of 2-(4-(3-(1H-imidazol-4-yl)propyl)-5-(2-(1H-indol-3-yl)ethylthio)-4H-1,2,4-triazol-3-yl)quinoline (AH.2.132)

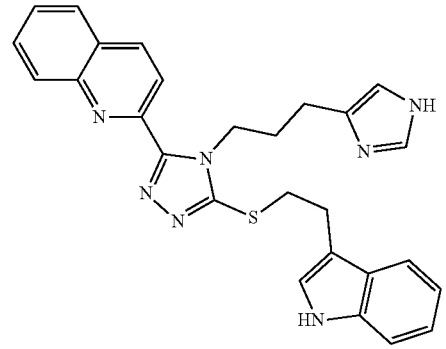

AH.2.132

Prepared according to the General Procedure 2E from compound 17b (400 mg, 0.55 mmol) to yield 31.2 mg (12%) of AH.2.132 as a yellow solid: $^1$H NMR (400 MHz, DMSO-d$_6$) δ 10.92 (s, 1H), 8.53 (d, J=8.7 Hz, 1H), 8.32 (d, J=8.7 Hz, 1H), 8.05 (d, J=8.2 Hz, 1H), 7.94 (d, J=8.7 Hz, 1H), 7.85

(m, 2H), 7.71-7.64 (m, 2H), 7.50 (s, 1H), 7.36 (d, J=8.4 Hz, 1H), 7.25 (d, J=2.3 Hz, 1H), 7.08 (m, 1H), 7.00 (m, 1H), 4.65 (s, 2H), 3.59 (m, 2H), 3.18 (m, 4H), 2.11 (m, 2H). $^{13}$C NMR (100 MHz, DMSO-d$_6$) δ 171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39. HRMS (ESI+): m/z calculated for $C_{24}H_{23}N_6S$ (M+H)+427.169345, found 427.169942.

Synthesis of 2-(4-(3-(1H-imidazol-4-yl)propyl)-5-(3-bromobenzylthio)-4H-1,2,4-triazol-3-yl)quinoline (AH.2.160)

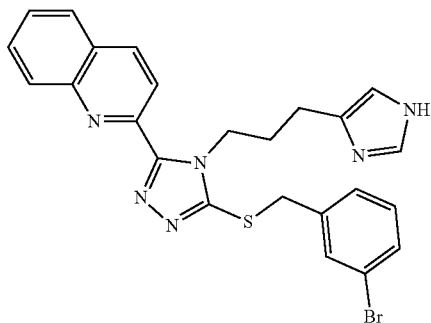

AH.2.160

Prepared according to General Procedure 2E from derivative 18b (265 mg, 0.35 mmol)) product AH.2.160 as a white foam (74 mg, 41%): $^1$H NMR (400 MHz, DMSO-d$_6$) δ 11.84 (s, 1H), 11.73 (s, 1H), 8.54 (d, J=8.7 Hz, 1H), 8.31 (d, J=8.7 Hz, 1H), 8.06 (d, J=7.8 Hz, 1H), 7.93 (m, 1H), 7.85 (t, J=6.8 Hz, 1H), 7.70 (d, J=6.8 Hz, 1H), 7.64 (s, 2H), 7.48-7.42 (m, 3H), 7.28 (m, 1H), 6.81 (s, 1H), 4.58 (m, 2H), 4.52 (s, 2H), 2.55 (m, 2H), 2.01 (m, 2H). 13H NMR (100 MHz, DMSO-d$_6$) δ 152.43, 152.09, 147.15, 146.58, 140.24, 137.43, 134.66, 131.71, 130.63, 130.42, 130.35, 129.13, 128.12, 127.99, 127.64, 127.38, 121.53, 119.90, 45.63, 35.79, 29.58. HRMS (ESI+): m/z calculated for $C_{37}H_{35}N_6S$ (M+H)+595.2630, found 595.2638.

Synthesis of 4-(3-(1H-imidazol-4-yl)propyl)-3-(benzylthio)-5-(naphthalen-2-yl)-4H-1,2,4-triazole (AH-1-75)

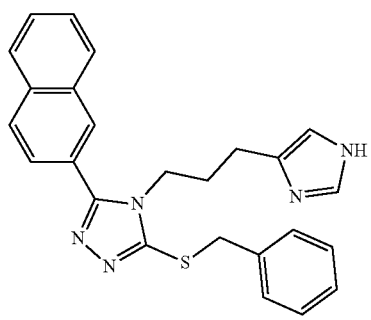

AH-1-75

Prepared according the General Procedure 2E from 16c (226 mg, 0.34 mmol) to afford 24 mg (32% yield) of AH-1-75 as a white solid: $^1$H NMR (400 MHz, DMSO-d$_6$) δ 8.12 (s, 1H), 8.01-7.95 (m, 3H), 7.67-7.65 (m, 1H), 7.59-7.57 (m, 2H), 7.39-7.16 (m, 6H), 6.63 (s, 1H), 6.41 (s, 1H), 4.41 (s, 2H), 3.93 (m, 2H), 2.27 (m, 2H), 1.75 (m, 2H). $^{13}$C NMR (100 MHz, DMSO-d$_6$) δ 171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39. HRMS (ESI+): m/z calculated for $C_{25}H_{24}N_5S$ (M+H)+426.1747, found 426.1747.

Synthesis of 4-(3-(1H-imidazol-4-yl)propyl)-3-(benzylthio)-5-phenethyl-4H-1,2,4-triazole (AH-1-81)

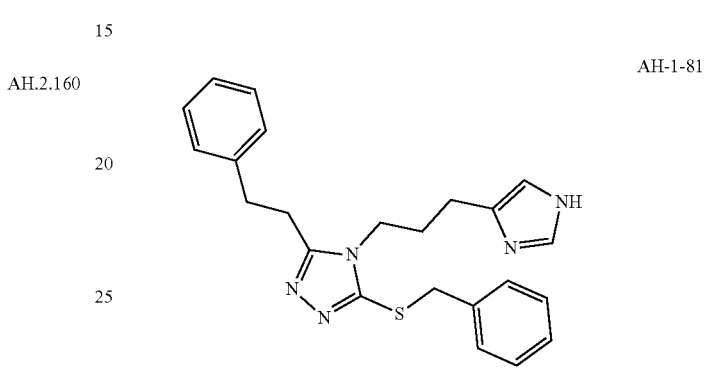

AH-1-81

Prepared according to the General Procedure 2E from 16d (300 mg, 0.46 mmol) to yield 83 mg (44%) of AH-1-81 as a white solid: $^1$H NMR (400 MHz, DMSO-d$_6$) δ 11.73 (s, 1H), 7.46 (s, 1H), 7.23-7.13 (m, 10H), 6.75 (s, 1H), 4.27 (s, 1H), 3.65 (m, 2H), 2.92-2.85 (m, 4H), 2.34 (m, 2H), 1.69 (m, 2H). $^{13}$C NMR (100 MHz, DMSO-d$_6$) δ 155.05, 148.30, 140.69, 137.32, 134.81, 128.95, 128.54, 128.49, 128.41, 127.55, 126.24, 42.62, 37.46, 32.60, 29.13, 26.29. HRMS (ESI+): m/z calculated for $C_{23}H_{26}N_5S$ (M+H)+404.1910, found 404.1903.

Synthesis of 3-(4-(3-(1H-imidazol-4-yl)propyl)-5-(benzylthio)-4H-1,2,4-triazol-3-yl)-1H-indole (AH-1-86)

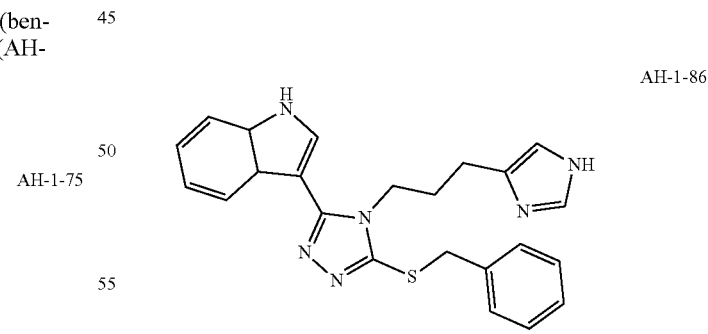

AH-1-86

Prepared according to the General Procedure 2E from compound 16e (390 mg, 0.6 mmol) to yield 154 mg (63%) of AH-1-86 as a white solid: $^1$H NMR (400 MHz, DMSO-d$_6$) δ 11.67 (s, 1H), 8.04 (d, J=7.8 Hz, 1H), 7.71 (s, 1H), 7.51 (s, 1H), 7.48-7.46 (d, J=7.8 Hz, 1H), 7.36-7.25 (m, 4H), 7.20 (t, J=8.2 Hz, 1H), 7.12 (t, J=8.3 Hz, 1H), 6.67 (s, 1H), 4.40 (s, 2H), 3.94 (m, 2H), 2.43 (m, 2H), 1.81 (m, 2H). $^{13}$C NMR (100 MHz, DMSO-d$_6$) δ 151.16, 148.37, 137.55, 135.93, 134.82, 129.01, 128.53, 127.52, 125.75, 125.02, 122.39, 120.91, 120.27, 111.85, 101.79, 43.63, 37.64, 28.89. HRMS (ESI+): m/z calculated for $C_{23}H_{23}N_6S$ (M+H)+415.1699, found 415.1699.

Synthesis of 4-(3-(1H-imidazol-4-yl)propyl)-3-(benzylthio)-5-phenyl-4H-1,2,4-triazole (AH-1-96)

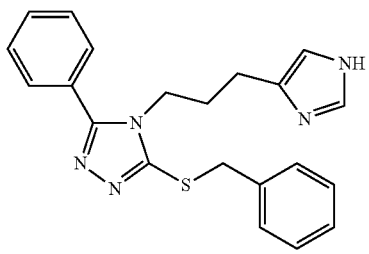

AH-1-96

Prepared according to the General Procedure 2E from 16f (400 mg, 0.65 mmol) to afford 113 mg (47%) of compound AH-1-96 as a white solid: $^1$H NMR (400 MHz, DMSO-$d_6$) δ 7.51-7.44 (m, 6H), 7.32-7.14 (m, 8H), 4.38 (s, 2H), 3.79 (m, 2H), 2.25 (m, 2H), 1.70 (m, 2H). $^{13}$C NMR (100 MHz, DMSO-$d_6$) δ 155.05, 150.10, 147.85, 137.20, 134.86, 130.11, 129.09, 129.05, 128.61, 128.41, 127.86, 127.65, 127.27, 126.76, 48.71, 43.79, 37.42, 29.14. HRMS (ESI+): m/z calculated for $C_{21}H_{22}N_5S$ (M+H)+376.1557, found 376.1590.

Synthesis of 3-((4-(3-(1H-imidazol-4-yl)propyl)-5-(benzylthio)-4H-1,2,4-triazol-3-yl)methyl)-1H-indole (AH-1-94)

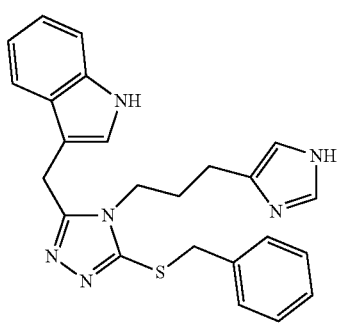

AH-1-94

Prepared according to the General Procedure 2E from compound 16g (605 mg, 0.9 mmol) to afford 305 mg (79%) of AH-1-94 as a yellow solid: $^1$H NMR (400 MHz, DMSO-$d_6$) δ 11.75 (s, 1H), 10.94 (s, 1H), 7.50 (s, 1H), 7.46 (d, J=7.8 Hz, 1H), 7.32 (d, J=7.8 Hz, 1H), 7.16-7.04 (m, 7H), 6.94 (t, J=7.8 Hz, 1H), 6.69 (s, 1H), 4.25 (s, 2H), 4.15 (s, 2H), 3.58 (m, 2H), 2.28 (m, 2H), 1.54 (m, 2H). $^{13}$C NMR (100 MHz, DMSO-$d_6$) δ 154.70, 148.56, 137.34, 136.41, 134.81, 128.83, 128.48, 127.45, 126.81, 123.68, 118.65, 111.59, 108.36, 42.78, 37.88, 29.01, 23.54, 21.82. HRMS (ESI+): m/z calculated for $C_{24}H_{25}N_6S$ (M+H)+429.1886, found 429, 1856.

Synthesis of 34(44341H-imidazol-4-yl)propyl)-5-(3-(trifluoromethyl)benzylthio)-4H-1,2,4-triazol-3-yl)methyl)-1H-indole (AH.1.109)

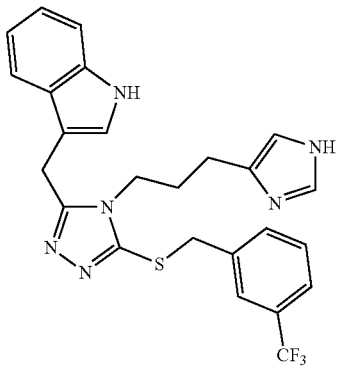

AH.1.109

Prepared according to the General Procedure 2E from compound 17g (400 mg, 0.54 mmol) to afford 106 mg (44%) of AH.1.109 as a white foam: $^1$H NMR (400 MHz, DMSO-$d_6$) δ 11.76 (s, 1H), 10.96 (s, 1H), 7.70 (s, 1H), 7.55-7.43 (m, 4H), 7.35-7.32 (m, 2H), 7.08-7.04 (m, 2H), 6.94 (m, 1H), 6.69 (s, 1H), 4.41 (s, 2H), 4.16 (s, 2H), 3.66 (m, 2H), 2.30 (m, 2H), 1.53 (m, 2H). $^{13}$C NMR (100 MHz, DMSO-$d_6$) δ 154.73, 148.08, 139.19, 136.30, 134.69, 132.93, 129.36, 126.71, 125.48, 124.02, 123.57, 121.23, 118.53, 111.49, 108.28, 42.77, 36.46, 28.93, 21.67. HRMS (ESI+): m/z calculated for $C_{25}H_{24}F_3N_6S$ (M+H)+497.1764, found 497.1730.

Synthesis of 3-((4-(3-(1H-imidazol-4-yl)propyl)-5-(3-fluorobenzylthio)-4H-1,2,4-triazol-3-yl)methyl)-1H-indole (AH.1.118)

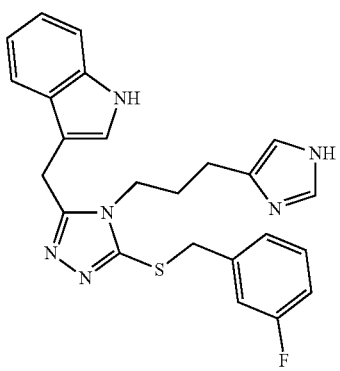

AH.1.118

Prepared according to the General Procedure 2E from compound 18g (500 mg, 0.73 mmol) to give 151 mg (47%) of AH.1.118 as a yellow foam: $^1$H NMR (400 MHz, DMSO-$d_6$) δ 11.75 (s, 1H), 10.94 (s, 1H), 7.49 (s, 1H), 7.42 (d, J=7.8 Hz, 1H), 7.31 (d, J=7.8 Hz, 1H), 7.15-6.91 (m, 7H), 6.69 (s, 1H), 4.30 (s, 2H), 4.16 (s, 2H), 3.66 (m, 2H), 2.28 (m, 2H), 1.55 (m, 2H). $^{13}$C NMR (100 MHz, DMSO-$d_6$) δ 163.16, 160.74, 154.73, 148.27, 140.36, 140.28, 136.33, 134.72, 130.32 (d), 126.73, 124.93, 123.59, 121.27, 118.58 (d), 115.74 (d), 114.35 (d), 111.52, 108.34, 42.81, 36.70, 28.97, 21.72. HRMS (ESI+): m/z calculated for $C_{24}H_{24}FN_6S$ (M+H)+447.1747, found 447.1762.

Synthesis of 3-((4-(3-(1H-imidazol-4-yl)propyl)-5-(3,4-dichlorobenzylthio)-4H-1,2,4-triazol-3-yl)methyl)-1H-indole (AH.1.116)

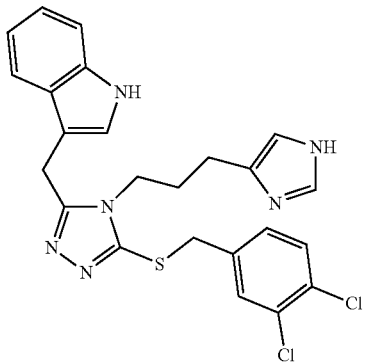

AH.1.116

Prepared according to the General Procedure 2E from 19 g (412 mg, 0.56 mmol) to afford 153 mg (41%) of compound AH.1.116 as a yellow foam: $^1$H NMR (400 MHz, DMSO-$d_6$) δ 11.76 (s, 1H), 10.95 (s, 1H), 7.57 (s, 1H), 7.51 (s, 1H), 7.45 (d, J=7.8 Hz, 1H), 7.34 (d, J=7.8 Hz, 1H), 7.27 (d, J=8.2 Hz, 1H), 7.11-7.10 (m, 2H), 7.06 (t, J=7.8 Hz, 1H), 6.93 (t, J=7.7 Hz, 1H), 6.69 (s, 1H), 4.28 (s, 2H), 4.17 (s, 2H), 3.67 (m, 2H), 2.29 (m, 2H), 1.54 (m, 2H). $^{13}$C NMR (100 MHz, DMSO-$d_6$) δ 154.78, 148.03, 138.96, 136.31, 134.68, 130.82, 130.38, 129.95, 129.06, 127.79, 127.55, 126.72, 123.60, 121.23, 118.55, 111.51, 108.26, 42.79, 35.83, 28.93, 21.72. HRMS (ESI+): m/z calculated for $C_{24}H_{23}Cl_2N_6S$ (M+H)+497.1077, found 497.1076.
169

Synthesis of 3-((4-(3-(1H-imidazol-4-yl)propyl)-5-(3-bromobenzylthio)-4H-1,2,4-triazol-3-yl)methyl)-1H-indole (AH. 1.112)

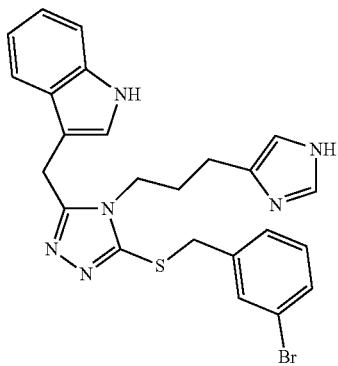

AH.1.112

Prepared according to the General Procedure 2E from compound 20g (440 mg, 0.59 mmol) to yield 261 mg (88%) of AH.1.112 as a white solid: $^1$H NMR (400 MHz, DMSO-$d_6$) δ 11.73 (s, 1H), 10.93 (s, 1H), 7.505-7.30 (m, 5H), 7.15 (m, 1H), 7.07-7.03 (m, 3H), 6.93 (m, 1H), 6.69 (s, 1H), 4.28 (s, 2H), 4.15 (s, 2H), 3.66 (m, 2H), 2.28 (m, 2H), 1.54 (m, 2H). $^{13}$C NMR (100 MHz, DMSO-$d_6$) δ 154.81, 148.30, 136.38, 134.78, 131.63, 130.54, 130.27, 127.93, 126.78, 123.64, 121.56 (d), 118.67 (d), 111.58, 108.37, 42.87, 36.56, 28.99, 21.75. HRMS (ESI+): m/z calculated for $C_{24}H_{24}BrN_6S$ (M+H)+507.0956, found 507.0961.

Synthesis of 4-(3-(1H-imidazol-4-yl)propyl)-3-(benzylthio)-5-(naphthalen-1-yl)-4H-1,2,4-triazole (AH.1.102)

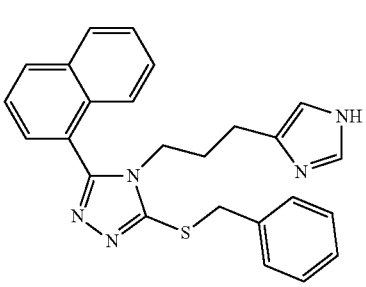

AH.1.102

Prepared according to the General Procedure 2E from compound 16h (264 mg, 0.40 mmol) to afford 77 mg (46%) of AH.1.102 as a white foam: $^1$H NMR (400 MHz, DMSO-$d_6$) δ 11.56 (s, 1H), 8.09 (d, J=8.4 Hz, 1H), 8.00 (d, J=7.8 Hz, 1H), 7.61-7.50 (m, 4H), 7.31-7.24 (m, 7H), 6.32 (s, 1H), 4.39 (s, 2H), 3.49 (m, 2H), 2.03 (m, 2H), 1.46 (m, 2H). $^{13}$C NMR (100 MHz, DMSO-$d_6$) δ 153.76, 149.41, 137.35, 134.62, 133.12, 131.44, 130.66, 129.08, 128.81, 128.63, 127.63, 127.46, 126.72, 125.42, 124.63, 124.55, 43.66, 38.12, 29.15. HRMS (ESI+): m/z calculated for $C_{25}H_{23}N_5S$ (M+H)+426.1774, found 426.1747.

Synthesis of 2-(4-(3-(1H-imidazol-4-yl)propyl)-5-(benzylthio)-4H-1,2,4-triazol-3-yl)-5-fluoro-1H-indole (AH.2.126)

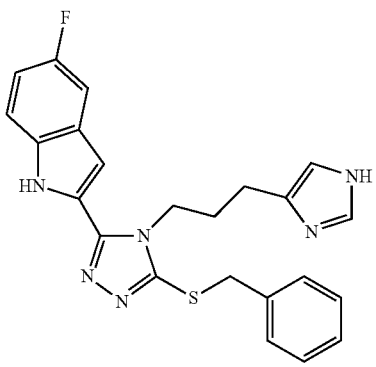

AH.1.126

Prepared according to the General Procedure 2E from 16i (123 mg, 0.18 mmol) to give 26 mg (33%) of compound AH.2.126 as a white solid: $^1$H NMR (400 MHz, DMSO-$d_6$) δ 12.06 (s, 1H), 9.04 (s, 1H), 7.47-7.25 (m, 8H), 7.07 (m, 1H), 6.81 (s, 1H), 4.46 (s, 2H), 4.09 (m, 2H), 2.68 (m, 2H), 1.93 (m, 2H). $^{13}$C NMR (100 MHz, DMSO-$d_6$) δ 171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39. HRMS (ESI+): m/z calculated for $C_{24}H_{23}N_6S$ (M+H)+427.169345, found 427.169942.

Synthesis of 4-(3-(1H-imidazol-4-yl)propyl)-3-(benzylthio)-5-(4-fluorophenethyl)-4H-1,2,4-triazole (AH.2.130)

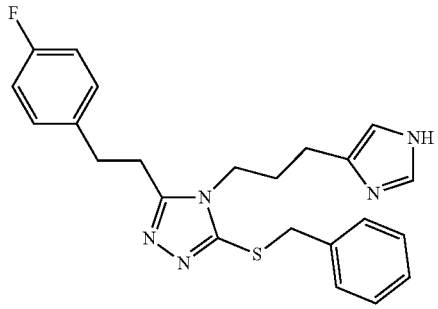

AH.2.130

Prepared according to the General Procedure 2E from compound 16j (585 mg, 0.88 mmol) to afford 84 mg (23% yield) of AH.2.130 as a white solid: $^1$H NMR (400 MHz, DMSO-$d_6$) δ 7.55 (m, 2H), 7.47-7.42 (m, 3H) 7.37-7.19 (m 15H), 7.04-7.00 (m, 6H), 6.48 (s, 1H), 4.41 (s, 2H), 3.81 (t, J=7.8 Hz, 2H), 2.30 (t, J=6.8 Hz, 2H), 1.70 (m, 2H). $^{13}$C NMR (100 MHz, DMSO-$d_6$) δ 154.95, 150.19, 142.20, 139.16, 137.85, 137.15, 133.11, 132.45, 129.19, 128.99, 128.58, 128.50, 128.10, 127.90, 127.66, 127.53, 127.40, 126.83, 125.39, 124.57, 117.97, 74.28, 43.82, 28.81, 24.50. HRMS (ESI+): m/z calculated for $C_{24}H_{23}N_6S$ (M+H)+ 427.169345, found 427.169942.

Synthesis of 2-(4-(3-(1H-imidazol-4-yl)propyl)-5-(benzylthio)-4H-1,2,4-triazol-3-yl)-1H-indole (AH.2.131)

AH.2.131

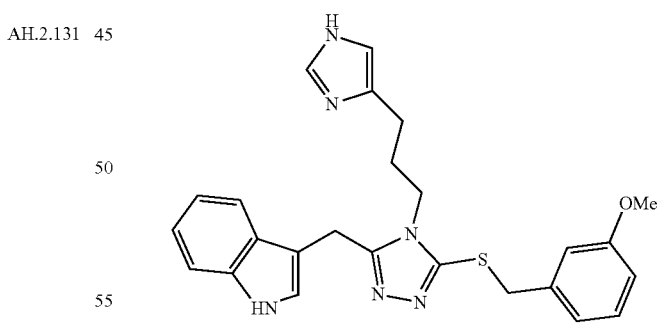

Prepared according to the General Procedure 2E from 16k (150 mg, 0.23 mmol) to yield 47.2 mg (50%) of compound AH.2.131 as a white solid: $^1$H NMR (400 MHz, DMSO-$d_6$) δ 11.89 (s, 1H), 7.73 (s, 1H), 7.57 (d, J=7.8 Hz, 1H), 7.43 (d, J=8.2 Hz, 1H), 7.37-7.24 (m, 5H), 7.21-7.16 (m, 2H), 7.05 (m, 1H), 6.85 (s, 1H), 6.62 (d, J=1.8 Hz, 1H), 4.44 (s, 2H), 4.08 (m, 2H), 2.55 (m, 2H), 1.87 (m, 2H). $^{13}$C NMR (100 MHz, DMSO-$d_6$) δ171.70, 142.38, 140.66, 137.65, 136.27, 129.24, 128.22, 127.96, 126.95, 122.23, 120.98, 118.31, 118.22, 117.53, 113.49, 111.38, 74.39, 43.32, 34.14, 28.40, 25.17, 20.39. LCMS (50-95% acetonitrile in 0.05% TFA over 10 minutes) retention time=2.10 minutes, ESI m/z=415.40 [M+H]+. HRMS (ESI+): m/z calculated for $C_{24}H_{23}N_6S$ (M+H)+427.169345, found 427.169942.

Synthesis of 3-((4-(3-(1H-Imidazol-4-yl)propyl)-5-(benzylthio)-4H-1,2,4-triazol-3-yl)methyl)-5-fluoro-1H-indole (AH.2.145)

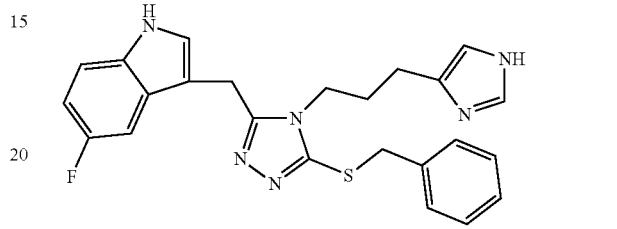

AH.2.145

Prepared according to General Procedure 2E from derivative 161 (400 mg, 0.58 mmol)) product AH.2.145 as a yellow foam (57 mg, 21%): $^1$H NMR (400 MHz, DMSO-$d_6$) δ 11.97 (s, 1H), 11.08 (s, 1H), 7.52 (s, 1H), 7.36-7.32 (m, 1H), 7.23-7.12 (m, 6H), 6.92 (m, 2H), 6.72 (s, 1H), 4.27 (s, 2H), 4.15 (s, 2H), 3.62 (m, 2H), 2.30 (m, 2H), 1.55 (m, 2H). $^{13}$H NMR (100 MHz, DMSO-$d_6$) δ 157.75, 155.46, 154.42, 148.46, 137.28, 134.68, 133.00, 128.77, 128.35, 127.36, 127.01 (d), 125.69, 112.55 (d), 109.52 (d), 108.63, 103.36 (d), 42.68, 37.69, 21.56. HRMS (ESI+): m/z calculated for $C_{24}H_{24}FN_6S$ (M+H)+447.1762, found 447.1787.

Synthesis of 3-((4-(3-(1H-imidazol-4-yl)propyl)-5-(3-methoxybenzylthio)-4H-1,2,4-triazol-3-yl)methyl)-1H-indole (AH.2.162)

AH.2.162

Prepared according to General Procedure 2E from derivative AH-1-94 (441 mg, 0.63 mmol)) product AH.2.162 as a yellow foam (151 mg, 53%): $^1$H NMR (400 MHz, DMSO-$d_6$) δ 11.76 (s, 1H), 10.95 (s, 1H), 7.51-7.46 (m, 2H), 7.35 (d, J=8.2 Hz, 1H), 7.08-7.02 (m, 3H), 6.97 (t, J=7.8 Hz, 1H), 6.85 (s, 1H), 6.77-6.70 (m, 3H), 4.27 (s, 2H), 4.17 (s, 2H), 3.65 (m, 5H), 2.31 (m, 2H), 1.56 (m, 2H). 13H NMR (100 MHz, DMSO-$d_6$) δ 159.18, 154.57, 148.44, 138.74, 136.29, 134.64, 129.43, 126.72, 123.52, 121.22, 120.95, 118.53, 114.22, 113.06, 111.46, 108.37, 54.93, 42.78, 37.45, 28.96, 24.57, 21.66. HRMS (ESI+): m/z calculated for $C_{37}H_{35}N_6S$ (M+H)+595.2630, found 595.2638.

Synthesis of 3-((4-(3-(1H-imidazol-4-yl)propyl)-5-(3-methylbenzylthio)-4H-1,2,4-triazol-3-yl)methyl)-1H-indole (AH.2.165)

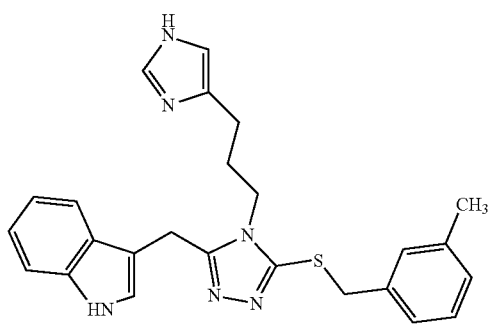

AH.2.165

Prepared according to General Procedure 2E from derivative AH.1.109 (421 mg, 0.61 mmol)) to yield AH.2.165 as a yellow foam (139 mg, 51%): $^1$H NMR (400 MHz, DMSO-$d_6$) δ 11.75 (s, 1H), 10.94 (s, 1H), 7.50-7.45 (m, 2H), 7.37-7.18 (m, 2H), 7.07-6.92 (m, 6H), 6.69 (s, 1H), 4.23 (s, 2H), 4.16 (s, 2H), 3.64 (m, 2H), 2.30 (m, 2H), 2.17 (s, 3H), 1.54 (m, 2H). $^{13}$H NMR (100 MHz, DMSO-$d_6$) δ 157.75, 155.46, 154.42, 148.46, 137.28, 134.68, 133.00, 128.77, 128.35, 127.36, 127.01 (d), 125.69, 112.55 (d), 109.52 (d), 108.63, 103.36 (d), 42.68, 37.69, 21.56. HRMS (ESI+): m/z calculated for $C_{37}H_{35}N_6S$ (M+H)+595.2630, found 595.2638.

Synthesis of 3-((4-(3-(1H-imidazol-4-yl)propyl)-5-(4-bromobenzylthio)-4H-1,2,4-triazol-3-yl)methyl)-1H-indole (MS.1.22)

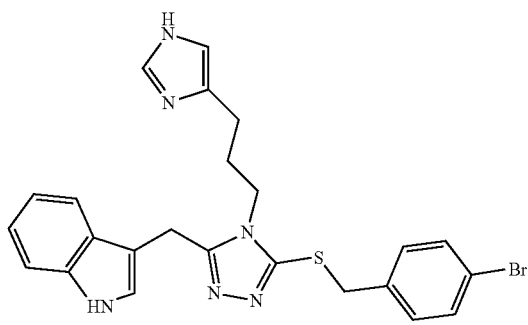

MS.1.22

Prepared according to General Procedure E from derivative 19o (491 mg, 0.65 mmol) to give product MS.1.22 as a yellow foam (169 mg, 51%): $^1$H NMR (400 MHz, DMSO-$d_6$) δ 11.75 (s, 1H), 10.95 (s, 1H), 7.50 (s, 1H), 7.45 (d, J=8 Hz, 1H), 7.34 (d, J=8.4 Hz, 1H), 7.30-7.17 (m, 3H), 7.10-7.04 (m, 4H), 6.94 (m, 1H), 4.21 (s, 2H), 4.16 (s, 2H), 3.59 (m, 2H), 2.28 (m, 2H), 1.53 (m, 2H). $^{13}$C NMR (100 MHz, DMSO-$d_6$) δ 154.69, 148.16, 147.78, 136.98, 136.33, 134.68, 131.21, 130.88, 128.14, 127.90, 127.79, 127.55, 126.73, 126.67, 123.61, 121.21, 120.52, 118.54, 111.55, 108.21, 42.65, 36.89, 28.90, 21.79. HRMS (ESI+): m/z calculated for $C_{24}H_{24}BrN_6S$ (M+H)$^+$ 507.0961, found 507.0974.

Synthesis of Methyl 4-((4-(3-(1H-imidazol-4-yl)propyl)-5-((1H-indol-3-yl)methyl)-4H-1,2,4-triazol-3-ylthio)methyl)benzoate (MS.1.27)

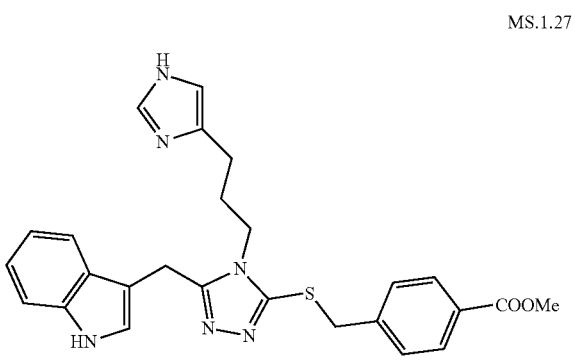 [SMILES: COC(=O)c1ccc(CSc2nnc(Cc3c[nH]c4ccccc34)n2CCCc2c[nH]cn2)cc1]

MS.1.27

Prepared according to General Procedure E from derivative 20o (395 mg, 0.54 mmol)) to yield MS.1.27 as a yellow foam (164 mg, 62%): $^1$H NMR (400 MHz, DMSO-$d_6$) δ 11.76 (s, 1H), 10.95 (s, 1H), 7.69-7.67 (m, 2H), 7.50 (s, 1H), 7.45 (m, 1H), 7.35-7.28 (m, 3H), 7.11-7.05 (m, 2H), 6.95 (m, 1H), 6.67 (bs, 1H), 4.34 (s, 2H), 4.17 (s, 2H), 3.8 (s, 3H), 3.60 (m, 2H), 2.29 (m, 2H), 1.53 (m, 2H). $^{13}$C NMR (100 MHz, DMSO-$d_6$) δ 165.90, 154.73, 148.08, 143.09, 136.32, 134.64, 129.24, 129.05, 128.51, 126.70, 123.59, 121.22, 118.51, 111.51, 108.20, 52.11, 42.69, 37.17, 28.90, 21.78. HRMS (ESI+): m/z calculated for $C_{26}H_{27}N_6O_2S$ (M+H)$^+$ 487.1911, found 487.1924.

Synthesis of 4-(3-(1H-imidazol-4-yl)propyl)-3-(3-methoxybenzylthio)-5-phenethyl-4H-1,2,4-triazole (MS.1.30)

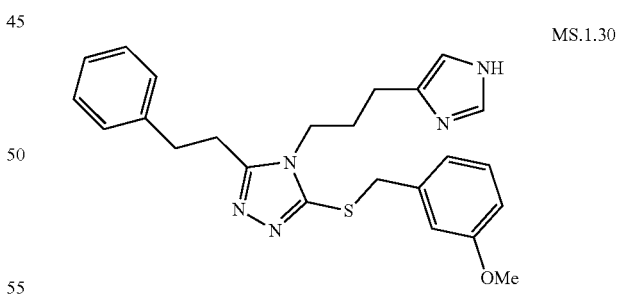

MS.1.30

Prepared according to General Procedure E from derivative 17d (441 mg, 0.63 mmol) to give product MS.1.30 as a yellow foam: H NMR (400 MHz, DMSO-$d_6$) δ 7.48 (s, 1H), 7.28-7.16 (m, 7H), 6.85-6.80 (m, 7H), 6.85-6.79 (m, 4H), 4.28 (s, 2H), 3.68 (m, 5H), 2.96-2.90 (m, 4H), 2.39 (m, 2H), 1.71 (m, 2H). $^{13}$C NMR (100 MHz, DMSO-$d_6$) δ 159.18, 154.57, 148.44, 138.74, 136.29, 134.64, 129.43, 126.72, 123.52, 121.22, 120.95, 118.53, 114.22, 113.06, 111.46, 108.37, 54.93, 42.78, 37.45, 28.96, 24.57, 21.66. HRMS (ESI+): m/z calculated for $C_{24}H_{28}N_5OS$ (M+H)$^+$ 434.2009, found 434.2009.

Synthesis of 3-((4-(3-(1H-imidazol-4-yl)propyl)-5-(3-methylbenzylthio)-4H-1,2,4-triazol-3-yl)methyl)-6-fluoro-1H-indole (AH2.182)

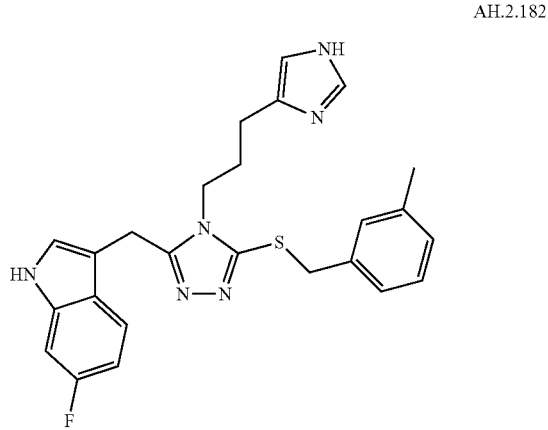 [SMILES: Cc1cccc(CSc2nnc(Cc3c[nH]c4cc(F)ccc34)n2CCCc2c[nH]cn2)c1]

AH.2.182

Prepared according to General Procedure E from derivative 17m (445 mg, 0.63 mmol) to afford product AH.2.182 as a yellow foam (129 mg, 44%): $^1$H NMR (400 MHz, DMSO-$d_6$) δ 11.76 (s, 1H), 11.03 (s, 1H), 7.51 (s, 1H), 7.45 (m, 1H), 7.13-6.95 (m, 7H), 6.81 (m, 1H), 4.25 (s, 2H), 4.16 (s, 2H), 3.65 (m, 2H), 2.31 (m, 2H), 1.55 (m, 2H). $^{13}$C NMR (100 MHz, DMSO-$d_6$) δ 160.16, 157.83, 154.50, 148.65, 137.71, 137.11, 136.30 (d), 134.75, 129.43, 128.33 (d), 127.84 (d), 126.74, 125.91, 124.24 (d), 123.65, 119.70 (d), 108.73, 107.28 (d), 97.62 (d), 42.81, 37.68, 28.95, 21.62, 20.96. HRMS (ESI+): m/z calculated for $C_{25}H_{26}FN_6S$ (M+H)+461.1918, found 461.1926.

Synthesis of 3-((4-(3-(1H-imidazol-4-yl)propyl)-5-(benzylthio)-4H-1,2,4-triazol-3-yl)methyl)-6-fluoro-1H-indole (AH.2.178)

AH.2.178

Prepared according to General Procedure E from derivative 16m (405 mg, 0.59 mmol) to give product AH.2.178 as a yellow foam (112 mg, 43%): $^1$H NMR (400 MHz, DMSO-$d_6$) δ 11.76 (s, 1H), 11.03 (s, 1H), 7.52 (s, 1H), 7.44 (m, 1H), 7.32-7.08 (m, 7H), 6.84 (m, 1H), 6.71 (s, 1H), 4.27 (s, 2H), 4.16 (s, 2H), 3.61 (m, 2H), 2.30 (m, 2H), 1.54 (m, 2H). $^{13}$C NMR (100 MHz, DMSO-$d_6$) δ 160.11, 157.78, 154.46, 148.47, 147.79, 137.28, 136.26 (d), 134.72, 128.78, 128.37, 127.80, 127.56, 127.37, 126.67, 124.20 (d), 123.61, 119.66 (d), 108.64, 107.21 (d), 97.58 (d), 42.68, 37.72, 28.94, 21.64. HRMS (ESI+): m/z calculated for $C_{24}H_{24}FN_6S$ (M+H)+447.1762, found 447.1757.

Synthesis of 4-(3-(1H-imidazol-4-yl)propyl)-3-benzyl-5-(benzylthio)-4H-1,2,4-triazole (AH.2.199)

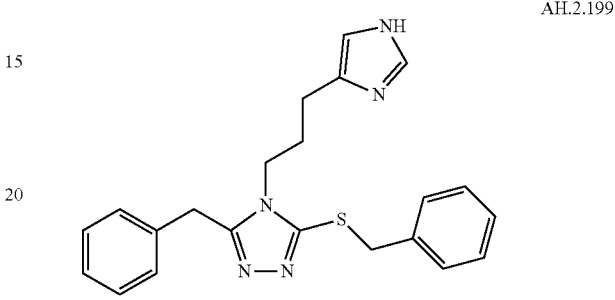

AH.2.199

Prepared according to General Procedure E from derivative 17n (200 mg, 0.32 mmol) to afford product AH.2.199 as a white solid (72 mg, 59%): $^1$H NMR (400 MHz, DMSO-$d_6$) δ 11.78 (s, 1H), 7.53 (s, 1H), 7.32-7.28 (m, 2H), 7.25-7.19 (m, 6H), 7.10 (m, 1H), 4.30 (s, 2H), 4.08 (s, 2H), 3.59 (m, 2H), 2.33 (m, 2H), 1.57 (m, 2H). $^{13}$C NMR (100 MHz, DMSO-$d_6$) δ 154.35, 148.67, 137.24, 136.17, 134.69, 128.83, 128.61, 128.44, 128.40, 127.42, 126.78, 42.74, 37.65, 30.44, 28.92. HRMS (ESI+): m/z calculated for $C_{25}H_{26}FN_6S$ (M+H)+ 461.1918, found 461.1926.

Synthesis of 4-(3-(1H-imidazol-4-yl)propyl)-3-benzyl-5-(benzylthio)-4H-1,2,4-triazole (AH.2.206)

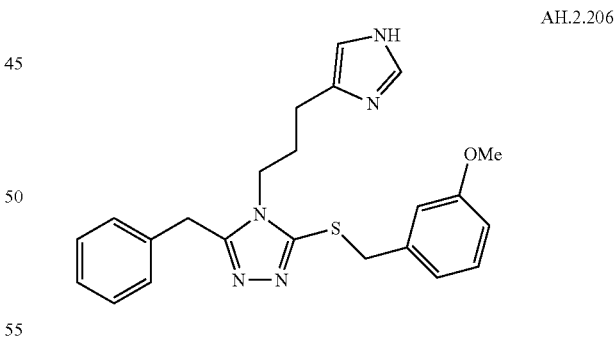

AH.2.206

Prepared according to General Procedure E from derivative 18n (200 mg, 0.30 mmol) to afford product AH.2.206 as a white solid (39 mg, 31%): $^1$H NMR (400 MHz, DMSO-$d_6$) δ 11.75 (s, 1H), 7.51 (s, 1H), 7.30-7.08 (m, 6H), 6.83-6.71 (m, 3H), 4.27 (s, 2H), 4.07 (s, 2H), 3.68 (s, 3H), 3.65 (m, 2H), 2.31 (m, 2H), 1.55 (m, 2H). $^{13}$C NMR (100 MHz, DMSO-$d_6$) δ 159.19, 154.34, 148.71, 138.73, 136.18, 134.69, 129.50, 128.60, 128.39, 126.77, 121.00, 114.27, 113.07, 54.98, 42.82, 37.51, 30.44, 28.93. HRMS (ESI+): m/z calculated for $C_{25}H_{26}FN_6S$ (M+H)+ 461.1918, found 461.1926.

General Procedure 2F: General Thiol Cross Coupling (to be Inserted after General Procedure 2E on page 89).

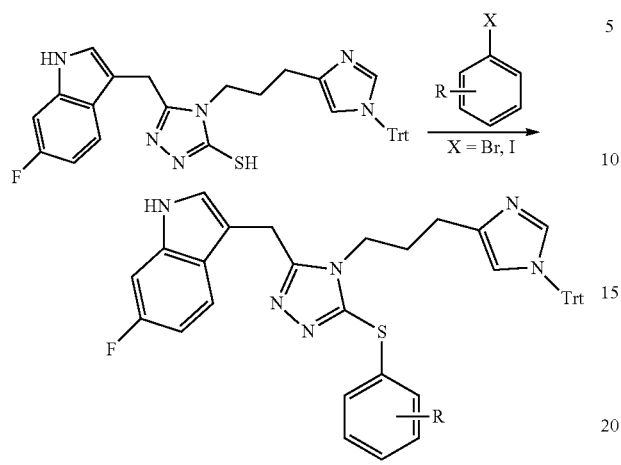

In the main reaction flask a mixture of cyclized derivative 15m-o (1 mmol), Zn(OAc)₂ (2 mmol), sodium dithionite (Na₂SO₄, 2 mmol), sodium t-butoxide (2.5 mmol), N-Xant-Phos (0.1 mmol) and Pd₂dba₃·CHCI₃ (0.05 mmol) was subjected to 3 vacuum/argon purge cycles and left under argon flow. In a separate flask, a mixture of DMSO (15 mL) and the aryl halide (3-5 mmol) were sparged with dry Argon for 15 min and the mixture was transferred to the main reaction flask with a pressurized cannula. The reaction was heated at 90° C. for 16 hours thereafter. The mixture was cooled and partitioned with EtOAc (150 mL) and water (100 mL). The layers were separated and the EtOAc solution was washed with water (2×50 mL) and brine (50 mL). The EtOAc layer was dried (Na₂SO₄), filtered and concentrated to afford the desired aryl sulfide product.

Synthesis of 6-fluoro-3-((5-(((4-fluorophenyl)thio)-4-(3-(1-trityl-1H-imidazol-4-yl)propyl)-4H-1,2,4-triazol-3-yl)methyl)-1H-indole (68a)

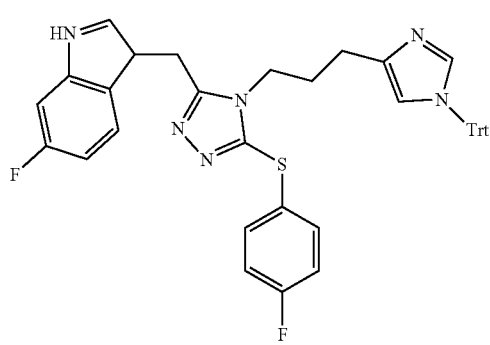

Prepared according to General Procedure 2F from 5-((6-fluoro-1H-indol-3-yl)methyl)-4-(3-(1-trityl-1H-imidazol-4-yl)propyl)-4H-1,2,4-triazole-3-thiol (15m) (216 mg, 0.36 mmol) and 1-fluoro-4-iodobenzene (208 μL, 400 mg, 1.80 mmol) using Zn(OAc)² (99 mg, 0.54 mmol), sodium dithionite (125 mg, 0.72 mmol), sodium t-butoxide (86 mg, 0.90 mmol), N-XantPhos (20 mg, 0.036 mmol) and Pd₂dba₃·CHCI₃ (10 mg, 0.018 mmol) to afford 307 mg of compound 68a as an orange oil (this material was used in the next step without further purification): ¹H NMR (400 MHz, DMSO-d₆) δ 10.94 (bs, 1H), 7.71 (dd, J=8.70, 5.10 Hz, 1H), 7.37-7.29 (complex overlapping m, 10H), 7.23-7.20 (m, 2H), 7.16 (d, J=1.80 Hz, 1H), 7.07 (t, J=8.70 Hz, 1H), 7.03-6.97 (m, 6H), 6.73 (dt, J=8.70, 2.30 Hz, 1H), 6.48 (bs, 1H), 4.19 (s, 2H), 3.84 (apparent t, J~7.00 Hz, 2H), 2.29 (t, J=6.90 Hz, 2H), 1.49 (quint., J=7.00 Hz, 2H). LCMS (40-95% acetonitrile in 0.05% TFA over 10 minutes) retention time=8.60 min, ESI m/z=693 [M+H]⁺.

Synthesis of 6-fluoro-3-((5-(p-tolylthio)-4-(3-(1-trityl-1H-imidazol-4-yl)propyl)-4H-1,2,4-triazol-3-yl)methyl)-JH-indole (68b)

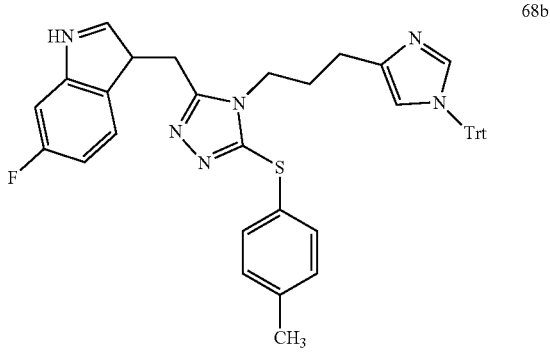

Prepared according to General Procedure 2F from 5-((6-fluoro-1H-indol-3-yl)methyl)-4-(3-(1-trityl-1H-imidazol-4-yl)propyl)-4H-1,2,4-triazole-3-thiol (15m) (300 mg, 0.50 mmol) and 4-iodotoluene (545 mg, 2.50 mmol) using Zn(OAc)₂ (138 mg, 0.75 mmol), sodium dithionite (174 mg, 1.00 mmol), sodium t-butoxide (120 mg, 1.25 mmol), N-XantPhos (28 mg, 0.05 mmol) and Pd₂dba₃·CHCI₃ (26 mg, 0.025 mmol). Purification by flash chromatography (SiO₂, 40:1 CH2CI2/MeOH to 20:1) afforded 247 mg (72% yield) of compound 68b as a tan solid: ¹H NMR (400 MHz, DMSO-d₆, t=100° C.) δ 10.70 (bs, 1H), 7.38-7.30 (complex overlapping m, 10H), 7.20 (bs, 1H), 7.11 (d, J=2.30 Hz, 1H), 7.08-7.02 (complex overlapping m, 11H), 7.01 (d, J=2.30 Hz, 1H), 6.71 (dt, J=9.00, 2.30 Hz, 1H), 6.50 (bs, 1H), 4.18 (s, 2H), 3.85 (apparent t, J~7.30 Hz, 2H), 2.23 (t, J=7.30 Hz, 2H), 1.63 (quint., J=7.80 Hz, 2H). LCMS (50-95% acetonitrile in 0.05% TFA over 10 minutes) retention time=5.55 min, ESI m/z=689 [M+H]⁺.

Synthesis of 6-fluoro-3-((5-((3-methoxyphenyn-thio)-4-(3-(1-trityl-1H-imidazol-4-yl)propyl)-4H-1,2,4-triazol-3-yl)methyl)-1H-indole (68c)

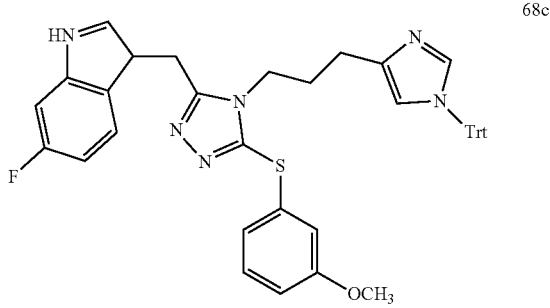

Prepared according to General Procedure 2F from 5-((6-fluoro-1H-indol-3-yl)methyl)-4-(3-(1-trityl-1H-imidazol-4-yl)propyl)-4H-1,2,4-triazole-3-thiol (15m) (300 mg, 0.50 mmol) and 3-bromoanisole (317 μL, 468 mg, 2.50 mmol) using Zn(OAc)$_2$ (138 mg, 0.75 mmol), sodium dithionite (174 mg, 1.00 mmol), sodium t-butoxide (120 mg, 1.25 mmol), N-XantPhos (28 mg, 0.05 mmol) and Pd$_2$dba$_3$·CHCl$_3$ (26 mg, 0.025 mmol). Purification by flash chromatography (SiO$_2$, 40:1 CH2Cl2/MeOH to 20:1) afforded 264 mg (75% yield) of compound 68c as a tan solid: $^1$H NMR (400 MHz, DMSO-d$_6$, t=25° C., peaks are broadened due to slow rotational interconversion) δ 10.96 (bs, 1H), 7.38-7.28 (complex overlapping m, 10H), 7.17 (bs, 2H), 7.07 (t, J=8.30 Hz, 1H), 7.03-6.97 (m, 7H), 6.74-6.67 (m, 2H), 6.58 (m, 2H), 6.43 (s, 1H), 4.21 (s, 2H), 3.84-3.81 (m, 2H), 3.52 (s, 3H), 2.27-2.24 (m, 2H), 1.51-1.43 (m, 2H). $^{13}$C NMR (100 MHz, DMSO-d$_6$) δ 160.21, 159.39 (d, $^1J_{CF}$=234 Hz), 156.35, 146.13, 142.82, 140.08, 138.20, 136.62 (d, $J_{CF}$=4.40 Hz), 134.55, 130.93, 129.67, 128.69, 128.46, 124.87 (d, $J_{CF}$=2.90 Hz), 124.05, 120.09, 119.99 (d, $J_{CF}$=9.50 Hz), 117.98, 113.71, 113.50, 109.00, 107.59 (d, $J_{CF}$=23.9 Hz), 97.95 ($J_{CF}$=24.9 Hz), 74.85, 55.59, 43.93, 29.51, 25.19, 22.38. LCMS (50-95% acetonitrile in 0.05% TFA over 10 minutes) retention time=5.67 min, ESI m/z=705 [M+H]$^+$.

Synthesis of 3-((4-(3-(1H-imidazol-4-yl)propyl)-5-((4-fluorophenyl)thio)-4H-1,2,4-triazol-3-yl)methyl)-6-fluoro-JH-indole (SK-I-128)

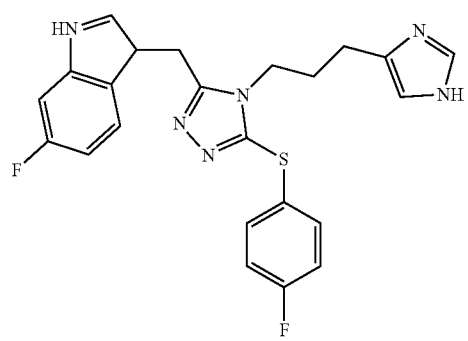

SK-I-128

Prepared according to General Procedure 1D from 6-fluoro-3-((4-fluorophenyl)thio)-4-(3-(1-trityl-1H-imidazol-4-yl)propyl)-4H-1,2,4-triazol-3-yl)methyl)-1H-indole (68a) (270 mg, 0.39 mmol) and afforded 77 mg (44% yield) of compound SK-I-128 as a white solid: $^1$H NMR (400 MHz, DMSO-d$_6$, t=30° C., peaks are broadened due to slow rotational interconversion and/or tautomeric equilibration) δ 11.73 (bs, 1H), 11.00 (bs, 1H), 7.48 (bs, 1H), 7.36 (apparent t, J~6.90 Hz, 1H), 7.27-7.22 (m, 2H), 7.16-7.12 (m, 3H), 7.06 (bd, J=10.0 Hz, 1H), 6.78 (bt, J=8.70 Hz, 1H), 6.64 (bs, 0.6H), 6.46 (bs, 0.4H), 4.19 (s, 2H), 3.867-3.75 (bm, 2H), 2.38-2.25 (bm, 2H), 1.54-1.46 (bm, 2H). LCMS (50-95% acetonitrile in 0.05% TFA over 10 minutes) retention time=2.05 min, ESI m/z=451 [M+H]$^+$.

Synthesis of 3-((4-(3-(1H-imidazol-4-yl)propyl)-5-(p-tolylthio)-4H-1,2,4-triazol-3-yl)methyl)-6-fluoro-1H-indole (SK-I-130)

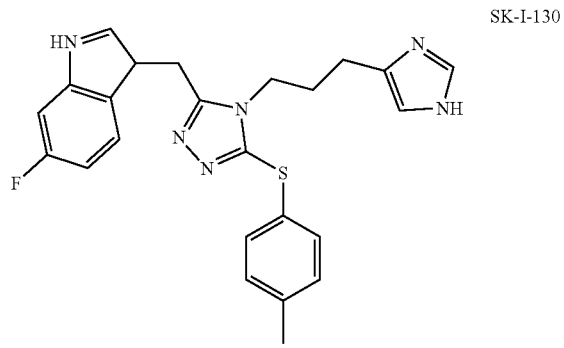 [SMILES: Cc1ccc(Sc2nnc(CC3C=Nc4cc(F)ccc43)n2CCCc2c[nH]cn2)cc1]

SK-I-130

Prepared according to General Procedure 1D from 6-fluoro-3-((5-(p-tolylthio)-4-(3-(1-trityl-1H-imidazol-4-yl)propyl)-4H-1,2,4-triazol-3-yl)methyl)-1H-indole (68b) (162 mg, 0.24 mmol) and afforded 94 mg (88% yield) of compound SK-I-130 as a white solid: $^1$H NMR (400 MHz, DMSO-d$_6$, t=100° C., peaks are broadened due to slow rotational interconversion and/or tautomeric equilibration) δ 11.43 (bs, 1H), 10.73 (bs, 1H), 7.41 (bs, 1H), 7.37 (dd, J=8.70, 5.50 Hz, 1H), 7.12-7.06 (complex overlapping m, 5H), 7.04 (d, J=2.30 Hz, 1H), 6.75 (dt, J=8.70, 2.30 Hz, 1H), 6.61 (bs, 0.6H), 6.47 (bs, 0.4H), 4.19 (s, 2H), 3.89-3.81 (bm, 2H), 2.38-2.31 (bm, 2H), 2.22 (s, 3H), 1.69-1.60 (bm, 2H). LCMS (50-95% acetonitrile in 0.05% TFA over 10 minutes) retention time=2.15 min, ESI m/z=447 [M+H]$^+$.

Synthesis of 3-((4-(3-(1H-imidazol-4-yl)propyl)-5-((3-methoxyphenyl)thio)-4H-1,2,4-triazol-3-yl)methyl)-6-fluoro-1H-indole (SK-I-132)

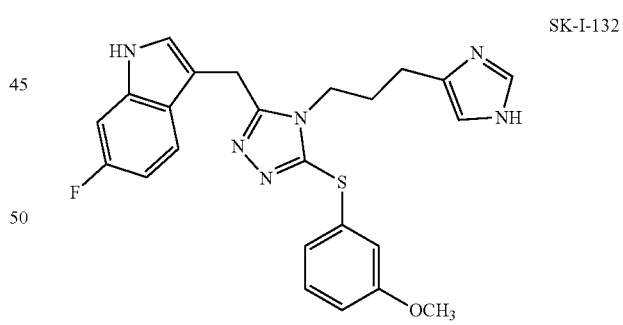

SK-I-132

Prepared according to General Procedure 1 D from 6-fluoro-3-((5-((3-methoxyphenyl)thio)-4-(3-(1-trityl-1H-imidazol-4-yl)propyl)-4H-1,2,4-triazol-3-yl)methyl)-1H-indole (68c) (82 mg, 0.12 mmol) and afforded 49 mg (91% yield) of compound SK-I-132 as a white solid: $^1$H NMR (400 MHz, CD$_3$OD) δ 7.51 (d, J=1.40 Hz, 1H), 7.29 (dd, J=8.70, 5.50 Hz, 1H), 7.14 (t, J=7.80 Hz, 1H), 7.00 (dd, J=10.0, 2.30 Hz, 1H) 6.98 (s, 1H), 6.75 (dd, J=8.70, 2.30 Hz, 2H), 6.71-6.67 (m, 1H), 6.64 (t, J=1.80 Hz, 1H), 6.55 (s, 1H), 4.30 (s, 2H), 3.82-3.78 (m, 2H), 3.61 (s, 3H), 2.34 (t, J=7.40 Hz, 2H), 1.53 (quint., J=7.80 Hz, 2H). $^{13}$C NMR (100 MHz, CD$_3$OD) δ 160.58, 159.99 (d, $^1J_{CF}$=235 Hz), 156.74, 148.15, 136.87 (d, $J_{CF}$=12.4 Hz), 134.64, 132.64, 130.25, 123.67 (d, $J_{CF}$=2.90 Hz), 123.35, 120.83, 118.80 (d, $J_{CF}$=9.50 Hz), 114.03, 113.45, 107.90, 107.45 (d, $J_{CF}$=24.9 Hz), 97.12 (d, $J_{CF}$=25.9 Hz), 54.44, 43.82, 28.86, 23.50 (broad), 22.08. LCMS (25-95% acetonitrile in 0.05% TFA over 10 minutes) retention time=5.67 min, ESI m/z=463 [M+H]$^+$.

Synthesis of 6-fluoro-3-((5-(pyridin-3-ylthio)-4-(3-(1-trityl-1H-imidazol-4-yl)propyl)-4H-1,2,4-triazol-3-yl)methyl)-1H-indole (BN-VII-95)

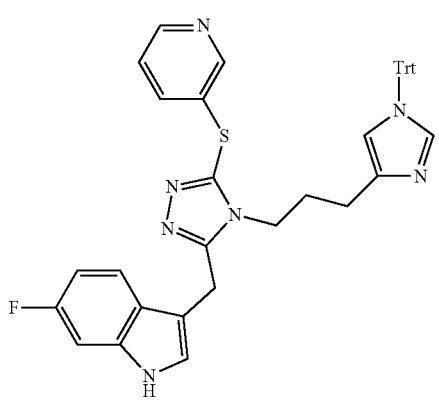

BN-VII-95

Prepared according to General Method 2F from 5-((6-fluoro-1H-indol-3-yl)methyl)-4-(3-(1-trityl-1H-imidazol-4-yl)propyl)-4H-1,2,4-triazole-3-thiol (15m) (300 mg, 0.50 mmol) and 3-iodopyridine (308 mg, 1.50 mmol) using Zn(OAc)$_2$ (138 mg, 0.75 mmol), sodium dithionite (174 mg, 1.00 mmol), sodium t-butoxide (120 mg, 1.25 mmol), N-XantPhos (28 mg, 0.05 mmol) and Pd$_2$dba$_3$·CHCl$_3$ (26 mg, 0.025 mmol). Trituration of the isolated residue with CH$_2$Cl$_2$ afforded ~350 mg of crude compound BN-VII-95 as a tan solid: LCMS (50-95% acetonitrile in 0.05% TFA over 10 minutes) retention time=3.38 min, ESI m/z=676 [M+H]$^+$. This material was taken on to the next step "as is."

Synthesis of 3-((4-(3-(1H-imidazol-4-yl)propyl)-5-(pyridin-3-ylthio)-4H-1,2,4-triazol-3-yl)methyl)-6-fluoro-1H-indole (BN-VII-97)

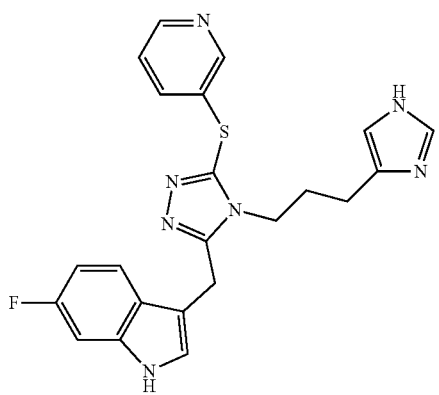

BN-VII-97

Prepared according to General Procedure 1D from 6-fluoro-3-((5-(pyridin-3-ylthio)-4-(3-(1-trityl-1H-imidazol-4-yl)propyl)-4H-1,2,4-triazol-3-yl)methyl)-1H-indole (BN-VII-95) (350 mg, <0.5 mmol) and afforded 97 mg (45% yield for two steps) of compound BN-VII-97 as a colorless glass: $^1$H NMR (400 MHz, CD$_3$OD) δ 8.43-8.41 (m, 2H), 7.69 (dd, J=2.30, 1.30 Hz, 1H), 7.67 (dd, J=2.30, 1.40 Hz, 1H), 7.54 (d, J=0.90 Hz, 1H), 7.34-7.32 (m, 1H), 7.30 (dd, J=8.70, 5.50 Hz, 1H), 7.01 (dd, J=9.60, 2.30 Hz, 1H), 7.01 (s, 1H), 6.77-6.72 (m, 1H), 6.60 (s, 1H), 4.31 (s, 2H), 3.89-3.85 (m, 2H), 2.38 (t, J=7.30 Hz, 2H), 1.55 (quint., J=7.60 Hz, 2H). $^{13}$C NMR (100 MHz, CD$_3$OD) δ 159.97 (d, $^1J_{CF}$=235.8 Hz), 156.76, 149.34, 148.34, 147.41, 138.23, 136.83 (J$_{CF}$=12.4 Hz), 134.75, 129.86, 124.71, 123.74 (d, J$_{CF}$=2.90 Hz), 123.36, 118.76 (d, J$_{CF}$=9.60 Hz), 107.81, 107.46 (d, J$_{CF}$=24.9 Hz), 97.14 (d, J$_{CF}$=25.8 Hz), 43.84, 29.09, 23.58, 21.98. LCMS (15-95% acetonitrile in 0.05% TFA over 10 minutes) retention time=5.63 min, ESI m/z=434 [M+H]$^+$.

Synthesis of 4-(3-(1H-imidazol-4-yl)propyl)-3-(naphthalene-1-ylmethyl)-5-(phenylsulfonyl)-4H-1,2,4-triazole (PSN-II-23)

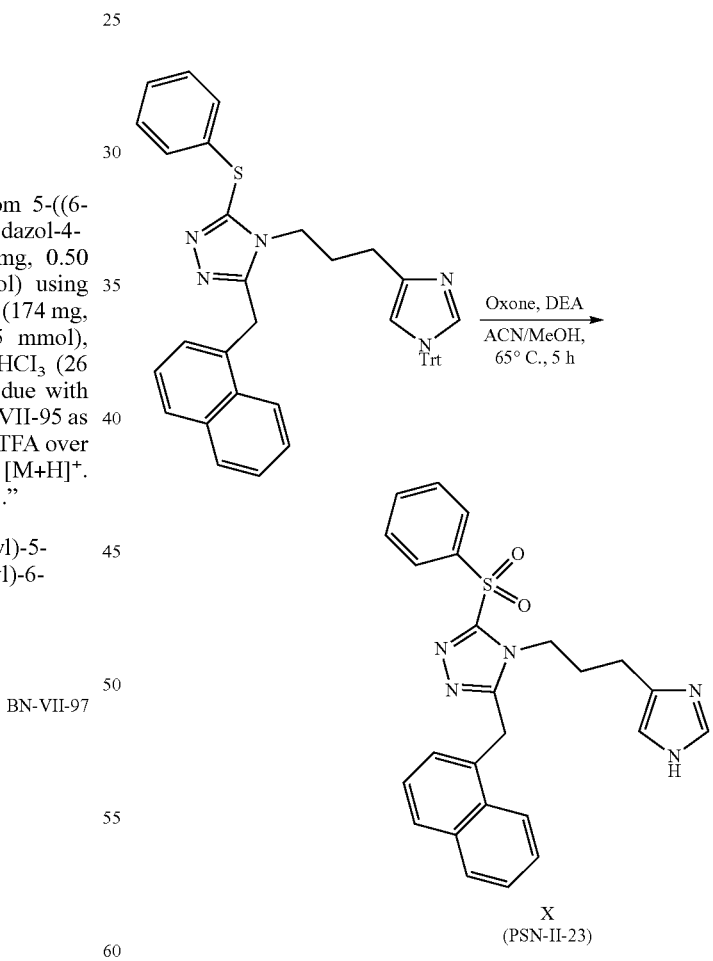

X
(PSN-II-23)

To a solution of 3-(naphthalen-1-ylmethyl)-5-(phenylthio)-4-(3-(1-trityl-1H-imidazol-4-yl)propyl)-4H-1,2,4-triazole (X) (250 mg, 0.37 mmol) in ACN (6 mL) and methanol (20 mL) was added diethylamine (8 μL, 0.08 mmol). To this mixture was added a solution of oxone (500 mg, 0.81 mmol) in H$_2$O (12 mL). The resulting reaction mixture was heated to 65° C. for 5 h. The reaction was cooled and partitioned with EtOAc (200 mL) and sat. NaHCO$_3$ (200 mL). The layers were separated and the aqueous was extracted (5×50 mL) with EtOAc. The combined extracts were dried (Na$_2$SO$_4$), filtered and concentrated. Purification by flash chromatography (10:1 CHCl3/MeOH) afforded 37 mg (22% yield) of compound X as a colorless glass: $^1$H NMR (400 MHz, CD$_3$OD) □ 8.04-7.98 (m, 1H), 7.96 (dt, J=8.1, 1.1 Hz, 2H), 7.90-7.83 (m, 1H), 7.82-7.70 (m, 2H), 7.66-7.59 (m, 2H), 7.54-7.44 (m, 3H), 7.35 (dd, J=8.3, 7.0 Hz, 1H), 7.11 (dd, J=7.0, 1.1 Hz, 1H), 6.65 (s, 1H), 4.21-4.09 (m, 2H), 2.44 (t, J=7.1 Hz, 2H), 1.70 (quint., J=7.1 Hz, 2H). $^{13}$C NMR (100 MHz, CD$_3$OD) Q 157.08, 153.13, 138.58, 135.01, 134.15, 131.71, 130.35, 129.57, 128.61, 128.25, 126.73, 125.88, 125.18, 123.12, 44.92, 29.47, 28.34, 23.24. LCMS (25-95% acetonitrile in 0.05% TFA over 10 minutes) retention time=6.00 min, ESI m/z=458 [M+H]$^+$. HRMS (ESI Q-TOF) m/z=458.1638 (458.1645 calc'd for C$_{25}$H$_{24}$N$_5$O$_2$S, [M+H]$^+$).

Example 3: Radioligand Binding Assay

Competitive radioligand binding experiments were performed using MEMBRANE TARGET Systems (Perkin-Elmer, Boston, MA) for human somatostatin receptors: SSTR1 (ES-520-M4000A), SSTR2A (ES-521-M400UA), SSTR3 (ES523-M400UA), SSTR4 (ES-524-M400UA) and SSTR5 (ES-522-M400UA) receptors. (See Table 1). Respective membrane receptor preparations were prepared in assay buffer (25 mM HEPES, 10 mM MgCl$_2$, 1 mM CaCl$_2$, 0.5% BSA, pH=7.4) at a 1:150 dilution. Binding assays were performed using 125I-Tyr-SRIF 14 (Perkin-Elmer, NEX 3890) dissolved in 1 mM HCl. Binding assays were performed in triplicate for each concentration of ligand in a total volume of 200 µL radioligand (25 µL ligand, 25 µL radioligand, 150 µL receptors) and incubated at room temperature for 90 minutes using a shaking table. Binding was terminated by filtration through GF/B glass fiber filters that were presoaked in 0.5% polyethyleneimine for a minimum of 4 hours. Filters were washed 9× with 1000 µL ice cold wash buffer (50 mM Tris-HCl, pH=7.4, 0.2% BSA). Filters were scored, transferred into plastic test tubes and counted in a gamma counter (Wizard2, Perkin-Elmer). Determination of the Ki for each compound was performed using non-linear regression with GraphPad PRISM-5 software (GraphPad Software, Inc., La Jolla, CA).

TABLE 1

Competitive Radioligand Binding Data
Compound SST1 (nM) SST2 (nM) SST3 (nM) SST4 (nM) SSTS (nM)

| Compound | SST1 (nM) | SST2 (nM) | SST3 (nM) | SST4 (nM) | SST5 (nM) |
|---|---|---|---|---|---|
| BN-VI-61 | >10000 | >10000 | >10000 | 7.738 9.325 | >10000 |
| BN-VI-56 | 6929 | >10000 | >10000 | 5.087 7.775 | >10000 |
| BN-VI-62 | | >10000 | | 37.52 47.28 | |
| BN-VI-87 | | >10000 | | 447.7 | |
| BN-VI-89 | | 6975 | | 51.70 | |
| BN-VI-97 | 5309 | >10000 | | 3.20 | >10000 |
| SM-I-26 | >10000 | >10000 | >10000 | 11.95 12.80 | >10000 |
| SM-I-29 | | >10000 | | 267.2 | |
| SM-I-38 | | >10000 | >10000 | 12.43 | >10000 |
| SM-I-50 | 4744 | >10000 | >10000 | 5.54 | >10000 |
| SM-I-55 | >10000 | >10000 | >10000 | 16.20 | >10000 |
| SM-I-60 | 3172 | >10000 | 6989 | 40.37 | >10000 |
| SM-I-76 | | >10000 | | 11.02 | |
| SM-I-92 | | >10000 | | 6.979 | |
| MM-I-17 | >10000 | >10000 | >10000 | 21.47 | >10000 |
| MM-I-21 | >10000 | >10000 | >10000 | 39.53 | >10000 |
| MM-I-26 | | >10000 | | 945.3 | |
| MM-I-36 | 4076 | >10000 | | 14.91 | |
| MM-I-43 | | >10000 | | 36.60 | |
| MM-I-53 | | >10000 | | 386.6 | |
| MM-I-63 | | >10000 | | 30.33 | |
| MM-I-66 | 587.6 | >10000 | 2335 | 0.8250 0.8383 | >10000 |
| MM-I-72 | 660.7 | >10000 | | 1.023 | |
| MM-I-83 | | 2080 | | 1.036 | |
| MM-I-87 | | 3278 | | 0.6726 | |
| MM-I-89 | | >10000 | | 2.966 | |
| SK-I-16 | | >10000 | | 1.719 | |
| SK-I-22 | | 7693 | | 1.422 | |
| SK-I-23 | 2576 | >10000 | >10000 | 2.219 | >10000 |
| SK-I-25 | | >10000 | | 1.695 | |
| SK-I-53 | 1716 | 7103 | >10000 | 3.107 | >10000 |
| SK-I-55 | 1032 | 5,434 | >10000 | 2.791 | >10000 |
| SK-I-56 | 1011 | >10000 | >10000 | 3.326 | >10000 |
| SK-I-57 | 365.3 | 1693 | 1129 | 1.759 | >10000 |
| SK-I-91 | 468.0 | 3,969 | >10000 | 0.9025 | >10000 |
| SK-I-105 | 1,080 | 5,304 | >10000 | 5.133 | >10000 |
| SK-I-119 | 4,336 | >10000 | >10000 | 57.05 | >10000 |
| SK-I-124 | 97.82 | 639.7 | 1736 | 0.7070 | >10000 |
| AH-1-33 | | >10000 | | 92.84 | |
| AH-1-40 | | >10000 | | 90.18 | |
| AH-1-41 | | >10000 | | 78.80 | |
| AH-1-47 | 4076 (3435-4835) | >10000 | 2414 | 31.05 | >10000 |
| AH-1-75 | | >10000 | | 1347 | |
| AH-1-81 | | >10000 | | 213.6 | |
| AH-1-84 | | >10000 | | 959.2 | |
| AH-1-86 | >10000 | >10000 | | 76.14 | >10000 |
| AH-1-94 | | >10000 | | 20.87 | >10000 |
| AH-1-96 | | >10000 | | 563.3 | |
| AH.1.102 | | >10000 | | 916.2 | |
| AH.1.109 | | >10000 | | 26.37 | |
| AH.1.112 | | >10000 | | 16.18 | |
| AH.1.116 | | >10000 | | 53.12 | |
| AH.1.118 | | >10000 | | 19.30 | |
| AH.2.126 | | >10000 | | 775.7 | |
| AH.2.130 | | >10000 | | 306.0 | |
| AH.2.131 | | >10000 | | 140.8 | |
| AH.2.132 | 2134 | >10000 | >10000 | 27.32 | >10000 |
| AH.2.145 | | >10000 | | 59.32 | |
| AH.2.160 | | >10000 | | 326.8 | |
| AH.2.162 | 2250 | >10000 | >10000 | 16.51 | >10000 |
| AH.2.165 | 1644 | >10000 | >10000 | 13.76 | >10000 |
| MS.1.22 | 4645 | 7695 | >10000 | 129.6 | >10000 |
| MS.1.27 | >10000 | >10000 | >10000 | 152.2 | >10000 |
| MS.1.30 | 6,633 | >10000 | >10000 | 151.8 | >10000 |
| AH.2.178 | | >10000 | | 12.29 | |
| AH.2.182 | 2451 | 8094 | 5934 | 8.390 | >10000 |
| AH.2.199 | | >10000 | | 80.75 | |
| AH.2.206 | | 301.4 | | 596.7 | |
| SK-I-128 | 314.6 | 2937 | >10000 | 0.6318 | >10000 |
| SK-I-130 | 732.7 | 3918 | 5553 | 3.723 | >10000 |
| SK-I-132 | 655.7 | 2876 | 2912 | 0.6464 | >10000 |

Example 4: Activity Assays

Measurement of forskolin stimulated inhibition of cAMP was performed via time-resolved fluorescence resonance energy transfer (TR-FRET) LANCE assay (AD0262, PerkinElmer Life Science, Inc., Boston MA). Recombinant Chinese hamster ovary (CHO-Ki) cells expressing human somatostatin SSTR4 cells (ES-524-CF, PerkinElmer Life Science, Inc., Boston MA) were thawed (37° C.), resuspended in 10 mL 187 Hanks' balanced salt solution no phenol red (HIBSS, Invitrogen, Carlsbad CA), and then centrifuged (150×g, 5 minutes). Cellular pellet resuspended in stimulation buffer containing HIBSS 1×, HEPES 5 mM, Protease free BSA 0.1% (PerkinElmer), and 3-Isobutyl-1-methylxanthine 0.5 mM (pH 7.4) and seeded in 96-well plates at 4000 cells/well. LANCE cAMP assay was performed per manufacture instruction with assessment of respective compound, somatostatin-28 (Sigma-Aldrich Co., St. Louis, MO) as control agonist, against 5 µM forskolin, performed in triplicate across concentration curve. Fluorescence signal was measured at 20 hours (excitation 340 nm and emission 665 nm, 400-µs delay) via TR-FRET (FLUOSTAR Omega-F, BMG Labtech, Inc., Cary, NC). Data was calculated via GraphPad PRISM-5 software.

Measurement of β-arrestin was conducted with use of the PATHHUNTER eXpress SSTR4 CHO-K1 β-Arrestin GPCR Assay (93-0308E2, Discover Rx). PathHunter EXPRESS β-Arrestin SSTR4 cells (CHO-K1, DiscoverX) are engineered to co-express the PROLINK (PK) and the Enzyme Acceptor (EA) tagged β-Arrestin. Activation of the SSTR4-PK induces β-Arrestin-EA recruitment, forcing complementation of the two β-galactosidase enzyme fragments (EA and PK). Cells were thawed and diluted in cell-plating reagent, with subsequent plating in 96-well plate (100 µL/well) and incubated at 37° C./5% $CO_2$ for 48 hours. Serial dilutions of control curve (somatostatin-28, Sigma-Aldrich Co., St. Louis, MO) and compound(s) being tested are added after 48 hours incubation. After subsequent incubation with control/compounds for 90 minutes, detection reagent is added followed by a 1 hour incubation. The resulting functional enzyme hydrolyzes substrate to generate a chemiluminescent signal which is measured (FLUOSTAR Omega-F, BMG Labtech, Inc., Cary, NC). Data was calculated via GraphPad PRISM-5 software.

TABLE 2

Activity Assay Data

| Compound | $EC_{50}$ cAMP (nM) |
|---|---|
| BN-VI-61 | 15.62 |
| BN-VI-56 | 7.264 |
| BN-VI-62 | 19.28 |
| BN-VI-87 | 691.7 |
| BN-VI-89 | 17.01 |
| BN-VI-97 | 6.083 |
| SM-1-26 | 16.51 |
| | 23.48 |
| SM-1-38 | 21.02 |
| SM-1-50 | 4.35 |
| SM-1-55 | 8.811 |
| SM-1-60 | 21.31 |
| SM-1-76 | 10.69 |
| SM-1-92 | 22.72 |
| MM-I-17 | 17.31 |
| MM-I-21 | 28.88 |
| MM-I-36 | 54.96 |
| MM-I-43 | 98.42 |
| MM-I-53 | 254.5 |
| MM-I-63 | 75.75 |
| MM-I-66 | 0.5851 |
| MM-I-72 | 3.324 |
| MM-I-83 | 0.2756 |
| MM-I-87 | 0.2495 |
| MM-I-89 | 2.799 |
| SK-I-16 | 1.756 |
| SK-I-22 | 1.280 |

TABLE 2-continued

Activity Assay Data

| Compound | $EC_{50}$ cAMP (nM) |
|---|---|
| SK-I-23 | 7.271 |
| SK-I-25 | 2.032 |
| SK-I-53 | 5.972 |
| SK-I-55 | 6.021 |
| SK-I-56 | 5.630 |
| SK-I-57 | 1.003 |
| SK-I-91 | 3.173 |
| SK-I-105 | 6.650 |
| SK-I-119 | 77.72 |
| SK-I-124 | 0.7253 |
| AH-1-33 | 130.2 |
| AH-1-40 | 213.5 |
| AH-1-41 | 35.00 |
| AH-1-47 | 85.19 |
| AH-1-81 | 969.9 |
| AH-1-86 | 104.6 |
| AH-1-94 | 21.89 |
| AH-1-96 | 3778 |
| AH.1.109 | 38.49 |
| AH.1.112 | 25.17 |
| AH.1.116 | 44.02 |
| AH.1.118 | 52.77 |
| AH.2.126 | 1128 |
| AH.2.130 | 2708 |
| AH.2.131 | 142.8 |
| AH.2.132 | 89.27 |
| AH.2.145 | 46.94 |
| AH.2.160 | 1399 |
| AH.2.162 | 13.96 |
| AH.2.165 | 8.410 |
| MS.1.22 | 165.5 |
| MS.1.27 | 612.8 |
| MS.1.30 | 289.6 |
| AH.2.178 | 17.46 |
| AH.2.182 | 10.00 |
| AH.2.199 | 143.9 |
| AH.2.206 | 301.4 |
| SK-I-128 | 0.6186 |
| SK-I-130 | 3.086 |
| SK-I-132 | 0.9915 |

What is claimed is:
1. A compound of Formula (II):

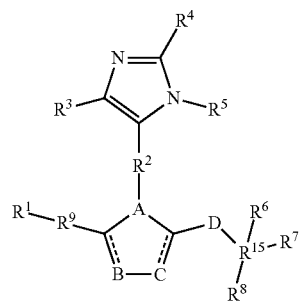

(II)

wherein
⁎⁎ are independently a single bond or is absent;
A is C(H) or N;
B and C are independent C(H), N, N(H), O, or S, provided that when B or C is C(H) or N, ⁎⁎ is a single bond, and when B or C is N(H), O, or S, ⁎⁎ is absent;
D is S, O, $NR^{16}$, P, sulfone, or sulfoxide, wherein $R^{16}$ is hydrogen, $C_1$-$C_6$ alkyl, aryl, or benzyl;
$R^1$ and $R^7$ are independently hydrogen, substituted or unsubstituted aryl, substituted or unsubstituted heteroaryl, substituted or unsubstituted $C_1$-$C_6$ alkyl, substituted or unsubstituted cycloalkyl or substituted or unsubstituted fused ring system;

$R^2$ is substituted or unsubstituted $C_1$-$C_6$ alkyl;

$R^3$, $R^4$, and $R^5$ are independently hydrogen, F, Cl, Br, I, substituted or unsubstituted alkyl, substituted or unsubstituted alkoxy, substituted or unsubstituted amine, thiosulfinate, thiosulfonate, thioamide, sulfimide, sulfoximide, sulfonediimine, or sulfur halide;

$R^6$ and $R^8$ are independently hydrogen, F, Cl, Br, I, substituted or unsubstituted $C_1$-$C_6$ alkyl, substituted or unsubstituted aryl, substituted or unsubstituted heteroaryl, or substituted or unsubstituted cycloalkyl; and $R^9$ and $R^{15}$ are independently substituted or unsubstituted $C_1$-$C_6$ alkyl, substituted or unsubstituted aryl, substituted or unsubstituted heteroaryl, or substituted or unsubstituted cycloalkyl;

or a pharmaceutically acceptable salt thereof.

2. The compound of claim 1, wherein ⌇ are each a single bond and A, B, and C are N.

3. The compound of claim 1, wherein D is S, sulfone, or sulfoxide.

4. The compound of claim 1, wherein $R^9$ is substituted or unsubstituted $C_1$-$C_3$ alkyl.

5. The compound of claim 1, wherein $R^{15}$ is unsubstituted $C_1$-$C_3$ alkyl.

6. The compound of claim 1, wherein $R^6$ and $R^8$ are independently hydrogen or substituted or unsubstituted $C_1$-$C_3$ alkyl.

7. The compound of claim 1, wherein $R^1$ and $R^7$ are independently substituted or unsubstituted aryl or a substituted or unsubstituted fused ring system.

8. The compound of claim 7, wherein $R^1$ is a substituted or unsubstituted fused ring system.

9. The compound of claim 8, wherein $R^1$ is substituted or unsubstituted indole, substituted or unsubstituted naphthalene, or substituted or unsubstituted quinolone.

10. The compound of claim 7, wherein $R^7$ is substituted or unsubstituted aryl or substituted or unsubstituted indole.

11. The compound of claim 10, wherein $R^7$ is

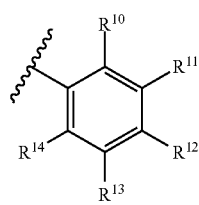

and $R^{10}$, $R^{11}$, $R^{12}$, $R^{13}$ and $R^{14}$ are independently hydrogen, F, Cl, Br, I, substituted or unsubstituted alkyl, substituted or unsubstituted alkoxy, substituted or unsubstituted amine, thiosulfinate, thiosulfonate, thioamide, sulfimide, sulfoximide, sulfonediimine, or sulfur halide.

12. The compound of claim 10, wherein $R^7$ is

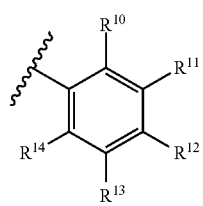

and $R^{10}$, $R^{11}$, $R^{12}$, $R^{13}$, and $R^{14}$ are independently hydrogen, F, Cl, Br, I, $CF_3$, $OCH_3$, $NO_2$, $OCH_2(C_6H_4)$, $C_6H_4$, $SO_2CH_3$, or $OCF_3$.

13. The compound of claim 1, wherein $R^2$ is substituted or unsubstituted $C_1$-$C_3$ alkyl.

14. The compound of claim 1, wherein $R^3$, $R^4$, and $R^5$ are independently hydrogen, F, Cl, Br, I, or substituted or unsubstituted alkyl.

15. The compound of claim 14, wherein $R^3$, $R^4$, and $R^5$ are hydrogen.

16. The compound of claim 1, wherein $R^{15}$ is unsubstituted $C_1$-$C_6$ alkyl.

17. The compound of claim 1, wherein the compound is selected from the group consisting of:

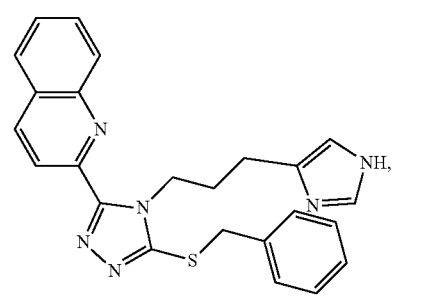

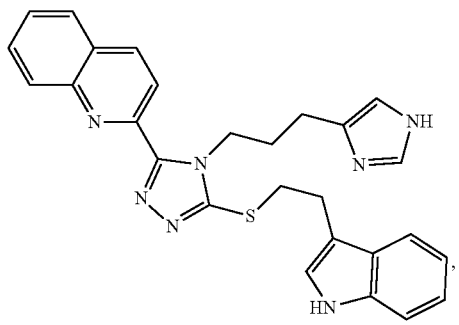

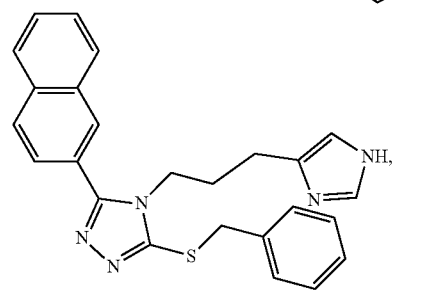

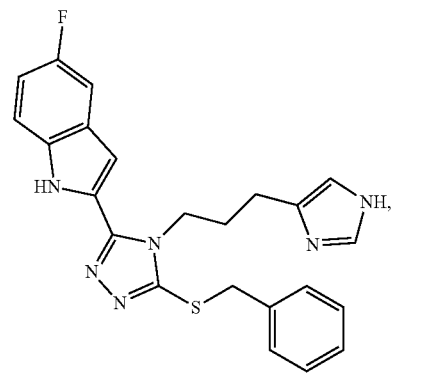

-continued
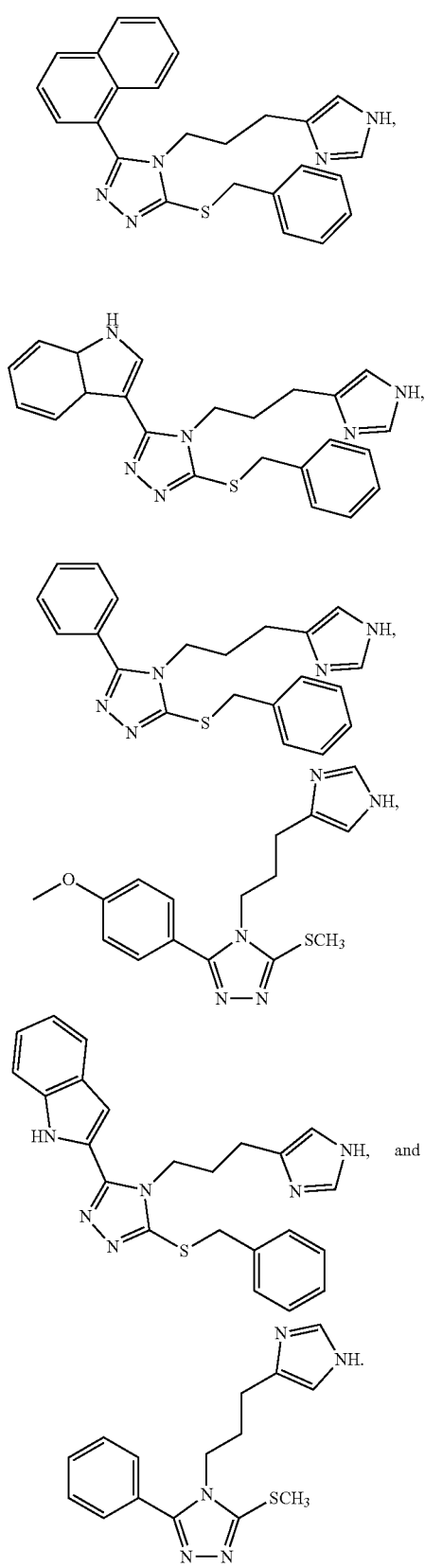
18. The compound of claim 1, wherein the compound is selected from the group consisting of:
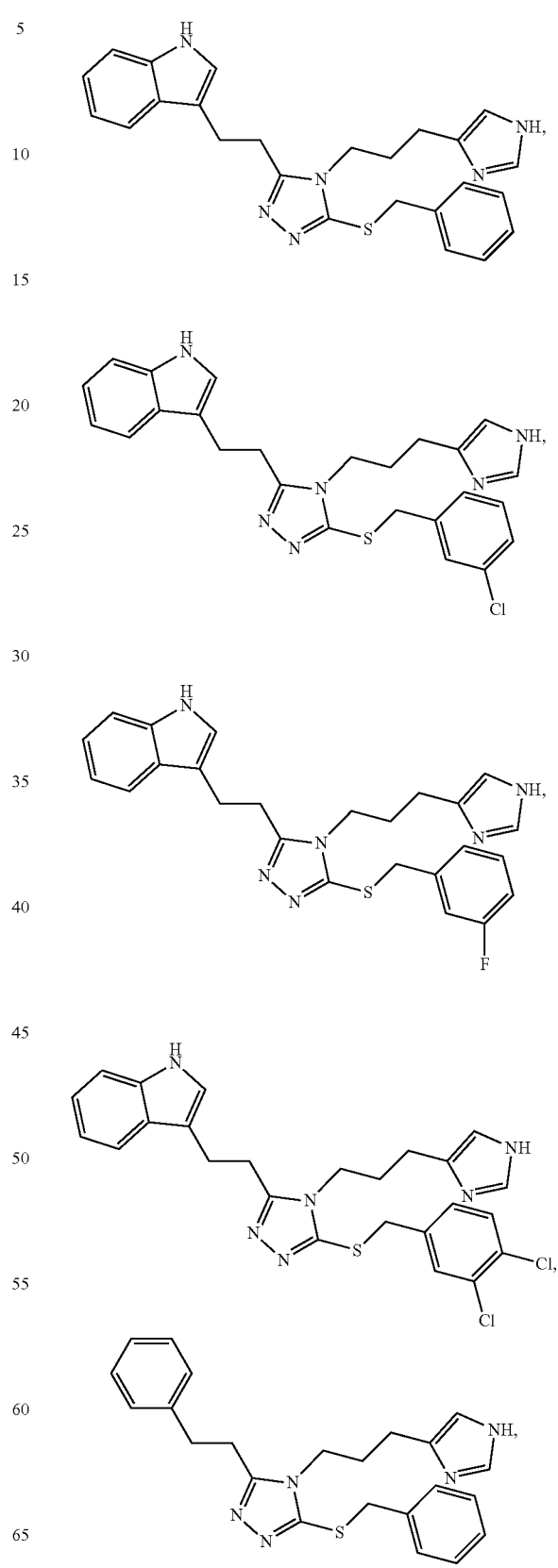

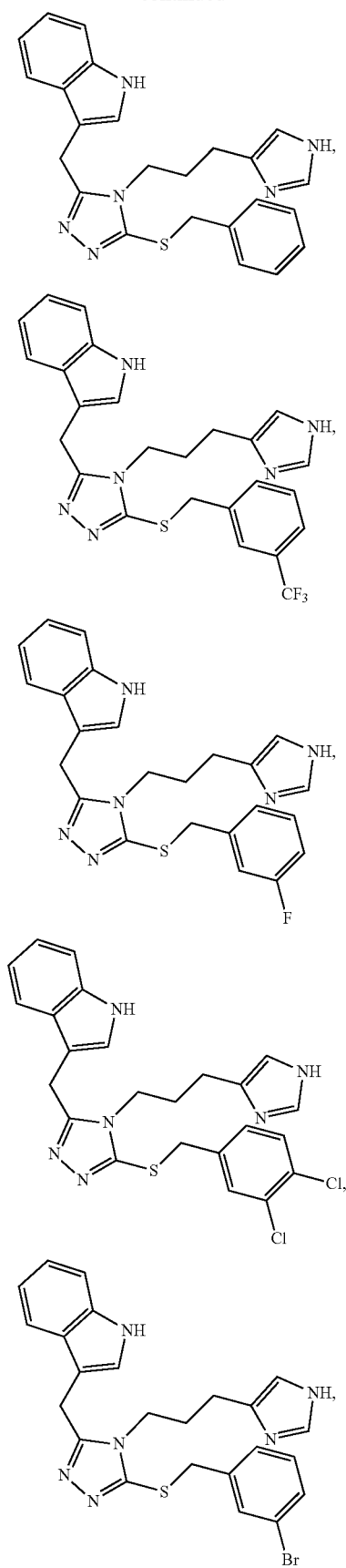
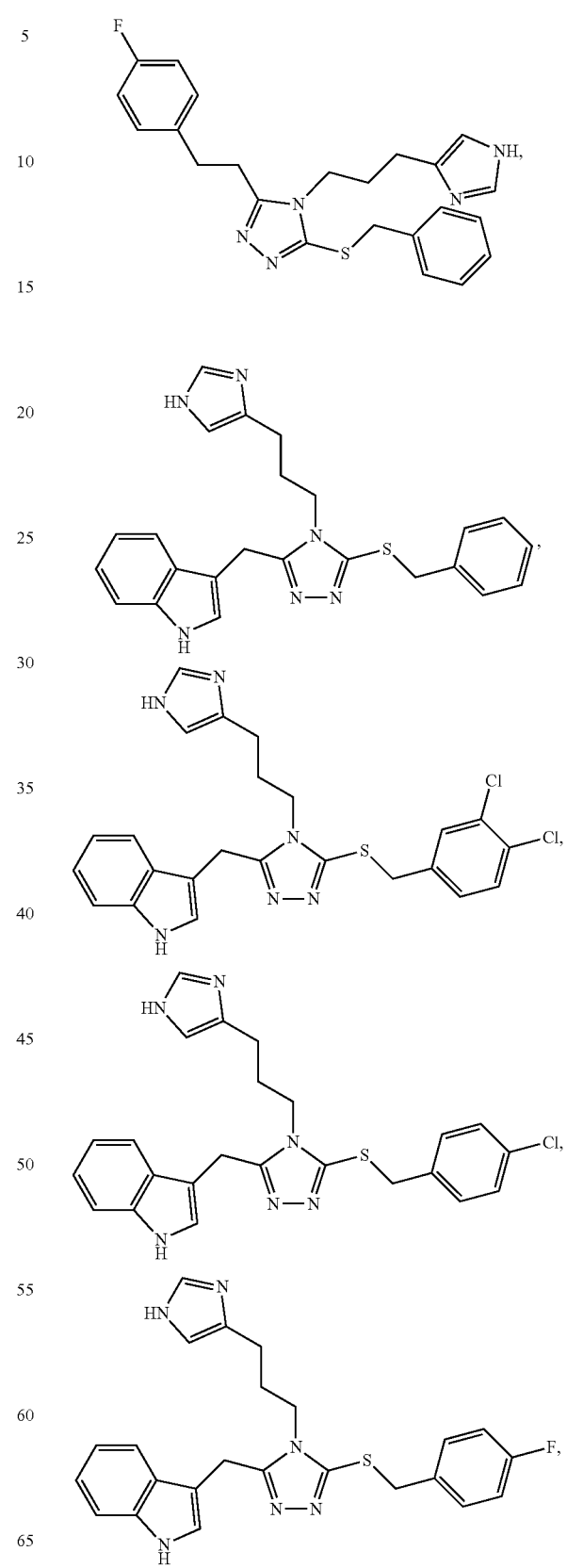

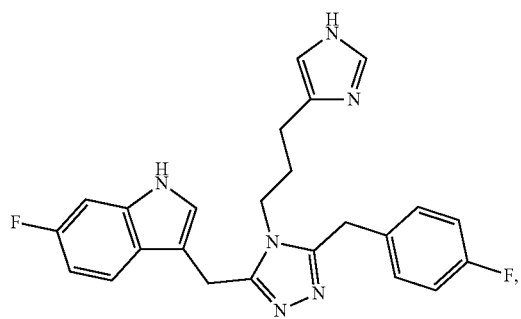
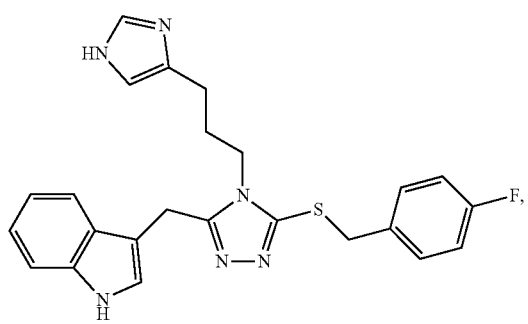
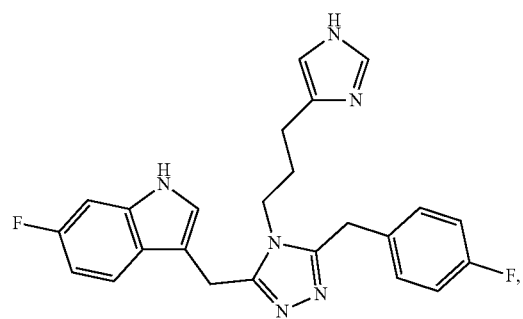
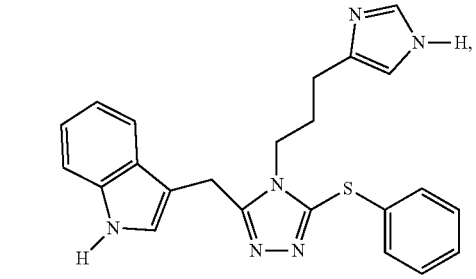
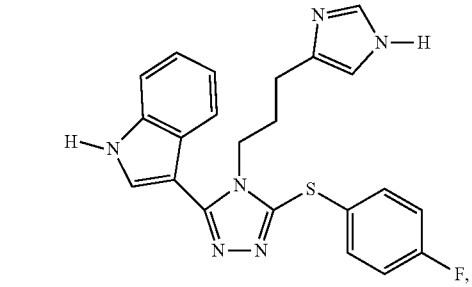
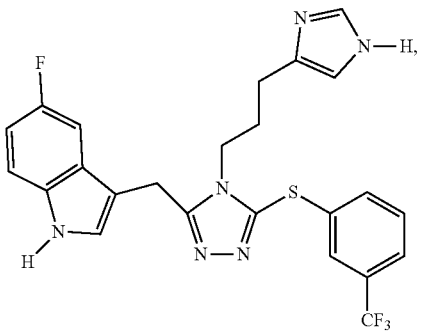
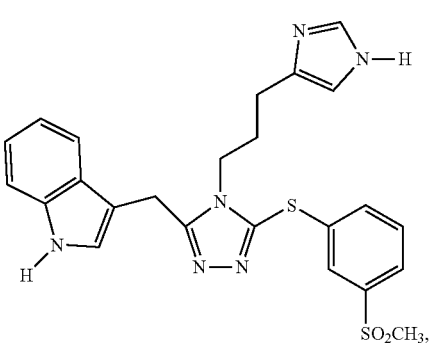
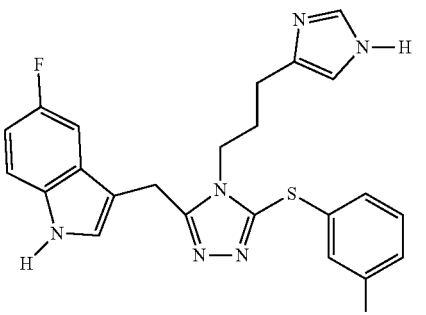
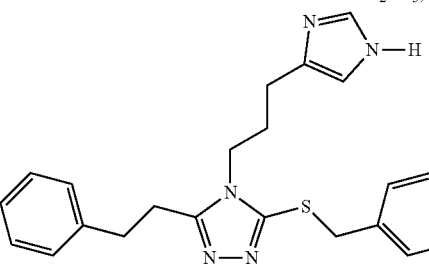
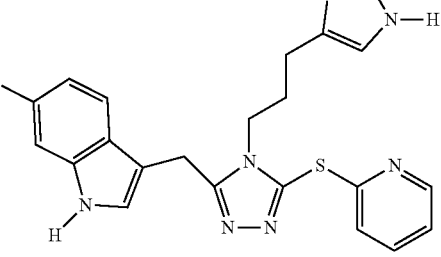

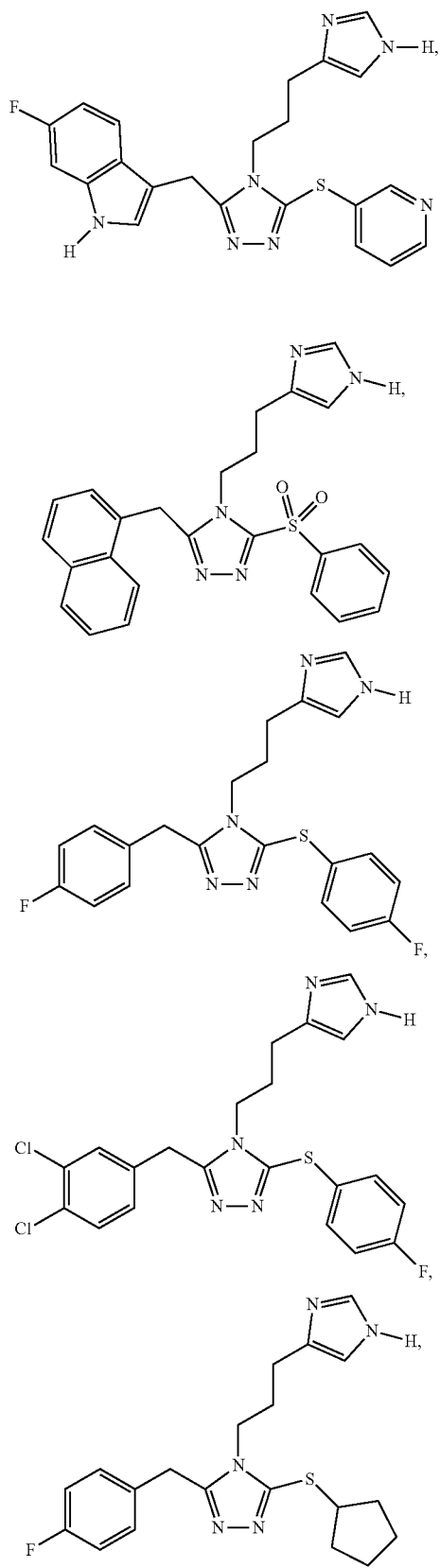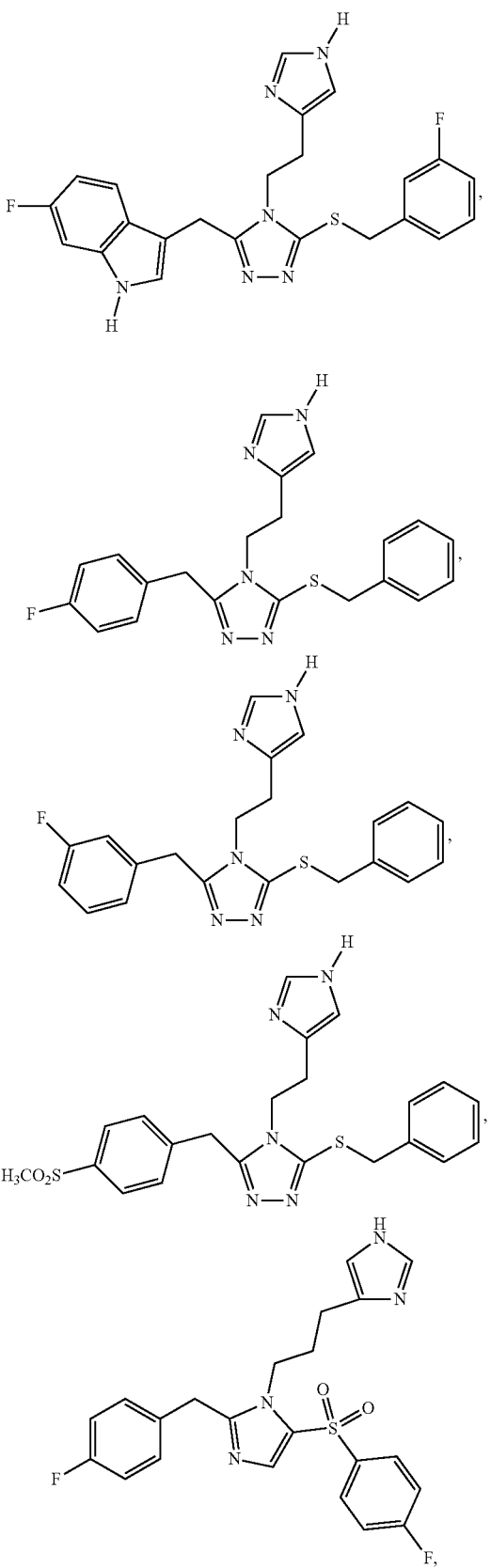

187
-continued
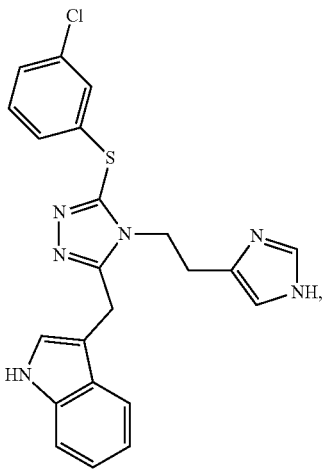
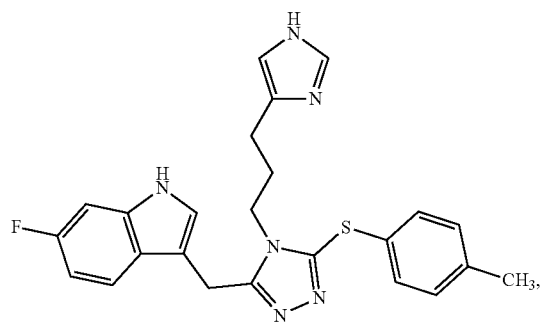
188
-continued
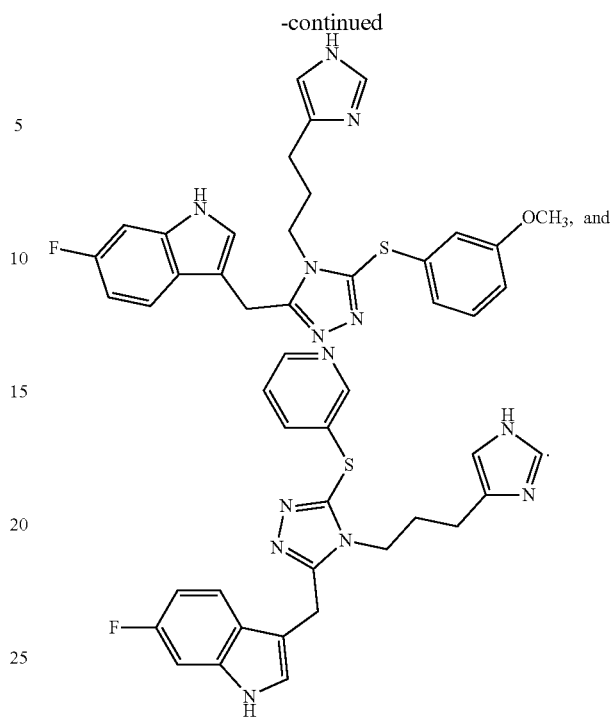
19. A method for the treatment of pain or inflammation which comprises administering to a subject in need thereof a therapeutically effective amount of a compound according to claim 1.
20. A pharmaceutical composition containing a compound according to claim 1 and a pharmaceutically acceptable carrier.
* * * * *